US012799085B2

(12) United States Patent
Wu et al.

(10) Patent No.: US 12,799,085 B2
(45) Date of Patent: Nov. 17, 2026

(54) BENZOXAZINONE DERIVATIVES

(71) Applicants: CHIA TAI TIANQING PHARMACEUTICAL GROUP CO., LTD., Lianyungang (CN); MEDSHINE DISCOVERY INC., Nanjing (CN)

(72) Inventors: Lingyun Wu, Shanghai (CN); Zheming Xiao, Shanghai (CN); Yi Chen, Shanghai (CN); Xiongbin Xu, Shanghai (CN); Wei Xia, Shanghai (CN); Tangyang Guo, Shanghai (CN); Lan Cao, Shanghai (CN); Chi-Chung Chan, Shanghai (CN); Qiu Li, Shanghai (CN); Jian Li, Shanghai (CN); Shuhui Chen, Shanghai (CN)

(73) Assignees: CHIA TAI TIANQING PHARMACEUTICAL GROUP CO., LTD., Jiangsu (CN); MEDSHINE DISCOVERY INC., Jiangsu (CN)

( * ) Notice: Subject to any disclaimer, the term of this patent is extended or adjusted under 35 U.S.C. 154(b) by 362 days.

(21) Appl. No.: 18/569,867

(22) PCT Filed: Jun. 14, 2022

(86) PCT No.: PCT/CN2022/098750

§ 371 (c)(1),
(2) Date: Dec. 13, 2023

(87) PCT Pub. No.: WO2022/262736

PCT Pub. Date: Dec. 22, 2022

(65) Prior Publication Data

US 2025/0034099 A1 Jan. 30, 2025

(30) Foreign Application Priority Data

Jun. 15, 2021 (CN) ......................... 202110661381.8
Nov. 12, 2021 (CN) ......................... 202111341577.5
Apr. 20, 2022 (CN) ......................... 202210421052.0
Jun. 2, 2022 (CN) ......................... 202210626997.6

(51) Int. Cl.
*C07D 265/36* (2006.01)
*A61K 31/538* (2006.01)
*A61P 13/12* (2006.01)
*C07D 413/14* (2006.01)

(52) U.S. Cl.
CPC .......... *C07D 265/36* (2013.01); *A61K 31/538* (2013.01); *A61P 13/12* (2018.01); *C07D 413/14* (2013.01)

(58) Field of Classification Search
CPC ............................ C07D 265/36; C07D 413/14
See application file for complete search history.

(56) References Cited

U.S. PATENT DOCUMENTS

| | | | |
|---|---|---|---|
| 2009/0054417 | A1 | 2/2009 | Michellys et al. |
| 2015/0376170 | A1 | 12/2015 | O'Mahony et al. |
| 2017/0217945 | A1 | 8/2017 | O'Mahony et al. |

FOREIGN PATENT DOCUMENTS

| | | | |
|---|---|---|---|
| CN | 101365696 | A | 2/2009 |
| JP | 2008508314 | A | 3/2008 |
| JP | 2017522300 | A | 8/2017 |
| WO | 2016/001631 | A1 | 1/2016 |

OTHER PUBLICATIONS

Granberg et al.; "Identification of Mineralocorticoid Receptor Modulators with Low Impact on Electrolyte Homeostasis but Maintained Organ Protection;" Journal of Medicinal Chemistry; 2018; 73 pages.
Whittaker et al.; "Safety, Tolerability, and Pharmacokinetics of the Mineralocorticoid Receptor Modulator AZD9977 in Healthy Men: A Phase 1 Multiple Ascending Dose Study;" Clin Trans Sci; 2020; 25 pages; vol. 13.
Sep. 14, 2022 Search Report issued in International Patent Application No. PCT/CN2022/098750.

*Primary Examiner* — Matthew P Coughlin
(74) *Attorney, Agent, or Firm* — Oliff PLC

(57) ABSTRACT

A class of benzoxazinone derivatives and a preparation method therefor, specifically related to a compound shown in formula (II), or a stereoisomer or a pharmaceutically acceptable salt thereof.

(II)

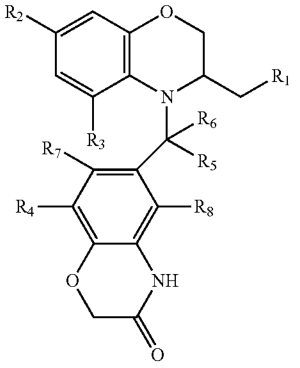

19 Claims, No Drawings

BENZOXAZINONE DERIVATIVES

CROSS-REFERENCE TO RELATED APPLICATIONS

CN202110661381.8, Jun. 15, 2021;
CN202111341577.5, Nov. 12, 2021;
CN202210421052.0, Apr. 20, 2022; and
CN202210626997.6, Jun. 2, 2022.

TECHNICAL FIELD

The present application relates to a class of benzoxazinone derivatives and a preparation method therefor, and in particular to a compound of formula (II), a stereoisomer thereof or a pharmaceutically acceptable salt thereof.

BACKGROUND

Aldosterone, a mineralocorticoid hormone secreted mainly by the zona glomerulosa of the adrenal cortex, is an important substance for regulating the balance of water and sodium and maintaining homeostasis in vivo. Recent studies have found that excessive aldosterone can promote inflammation and cause myocardial remodeling and fibrosis, and can also directly cause damage to kidney tissues and thus lead to an increase in proteinuria, thereby participating in the occurrence and development processes of various diseases such as chronic kidney disease, hypertension, heart failure, and the like. Mineralocorticoid receptor antagonists antagonize the binding of aldosterone to mineralocorticoid receptors (MRs) so as to prevent excessive activation of aldosterone-MR complexes, thereby delaying disease progression. Although early clinical trials have demonstrated that the MR antagonists can improve the prognosis and survival rate of patients with heart failure and have kidney protection effects in addition to a hypotensive effect, spironolactone as the first-generation medicament has poor nuclear receptor selectivity, and can cause adverse events such as mammary development and impotence in males, menstrual disorders in females, and the like after long-term administration, and eplerenone as the second-generation medicament, although it has improved nuclear receptor selectivity, is weakly active and difficult to synthesize. Both spironolactone and eplerenone may pose a risk of hyperkalemia in clinical use, thus limiting the application of MR antagonists.

AZD9977 (WO2016001631) is a mineralocorticoid receptor regulator developed by AstraZeneca. The research shows that AZD9977 has partial antagonistic activity on mineralocorticoid receptors, and the completed phase I clinical trial in healthy individuals demonstrates that AZD9977 has almost no influence on the sodium-to-potassium excretion ratio in urine and almost no influence on potassium in blood, potentially being capable of avoiding the critical clinical risk of hyperkalemia. Currently, AstraZeneca is conducting a phase II clinical trial of the combination of AZD9977 and the SGLT-2 inhibitor dapagliflozin for the treatment of heart failure and chronic kidney disease.

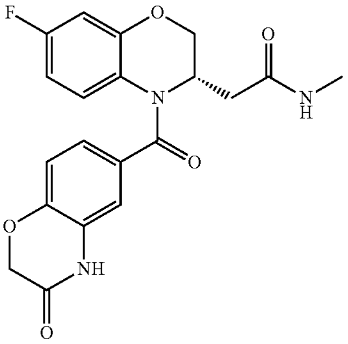

AZD9977

SUMMARY

In one aspect, the present application provides a compound of formula (II), a stereoisomer thereof or a pharmaceutically acceptable salt thereof:

(II)

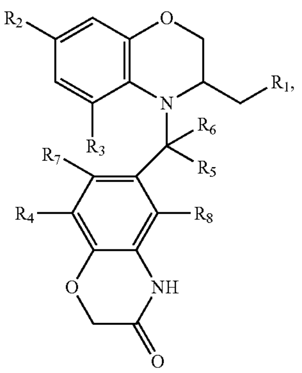

wherein $R_1$ is selected from the group consisting of $R_{11}$ and $R_{12}$;

$R_{11}$ is selected from the group consisting of —$OR_a$, —C(═O)$NR_bR_c$, and —S(═O)$_2C_{1-4}$ alkyl, wherein the $C_{1-4}$ alkyl is optionally substituted with 1, 2, or 3 $R_{aa}$;

$R_{12}$ is selected from 5-membered heteroaryl, wherein the 5-membered heteroaryl is optionally substituted with 1, 2, or 3 $R_d$;

$R_2$, $R_3$, and $R_4$ are each independently selected from the group consisting of H, F, Cl, Br, I, —CN, —$NH_2$, —OH, and $C_{1-4}$ alkyl;

$R_5$ and $R_6$ are each independently selected from the group consisting of H, D, F, Cl, Br, and $C_{1-4}$ alkyl, wherein the $C_{1-4}$ alkyl is optionally substituted with 1, 2, or 3 $R_{ab}$;

$R_7$ and $R_8$ are each independently selected from the group consisting of H, F, Cl, Br, I, —CN, —$NH_2$, —OH, and $C_1$_4 alkyl;

$R_a$, $R_b$, and $R_c$ are each independently selected from the group consisting of H, $C_{1-4}$ alkyl, and $C_{3-4}$ cycloalkyl, wherein the $C_{1-4}$ alkyl and the $C_{3-4}$ cycloalkyl are each independently and optionally substituted with 1, 2, or 3 R;

each $R_d$ is independently selected from the group consisting of H, F, Cl, Br, I, —CN, —$NH_2$, —OH, and $C_{1-4}$ alkyl, wherein the $C_{1-4}$ alkyl is optionally substituted with 1, 2, or 3 $R_{ac}$;

$R_{aa}$, $R_{ab}$, and $R_{ac}$ are each independently selected from the group consisting of D, F, Cl, Br, I, —CN, —$NH_2$, and —OH;

each R is independently selected from the group consisting of F, Cl, Br, I, —CN, —$NH_2$, and —OH; and the "hetero" in the 5-membered heteroaryl means 1, 2, 3, or 4 heteroatoms or heteroatom groups each independently selected from the group consisting of —O—, —NH—, —S—, and —N—.

In one aspect, the present application provides a compound of formula (II), a stereoisomer thereof or a pharmaceutically acceptable salt thereof:

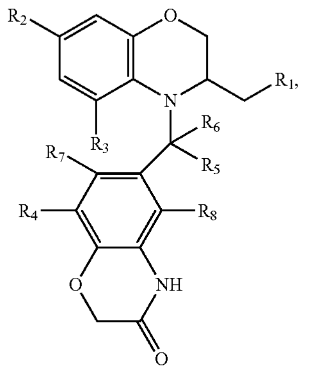

(II)

wherein $R_1$ is selected from the group consisting of $R_{11}$ and $R_{12}$;

$R_{11}$ is selected from the group consisting of —$OR_a$, —C(═O)$NR_bR_c$, and —S(═O)$_2C_{1-4}$ alkyl, wherein the $C_{1-4}$ alkyl is optionally substituted with 1, 2, or 3 $R_{aa}$;

$R_{12}$ is selected from 5-membered heteroaryl, wherein the 5-membered heteroaryl is optionally substituted with 1, 2, or 3 $R_d$;

$R_2$, $R_3$, and $R_4$ are each independently selected from the group consisting of H, F, Cl, Br, I, —CN, —$NH_2$, —OH, and $C_{1-4}$ alkyl;

$R_5$ and $R_6$ are each independently selected from the group consisting of H, D, F, Cl, Br, and $C_{1-4}$ alkyl, wherein the $C_{1-4}$ alkyl is optionally substituted with 1, 2, or 3 $R_{ab}$;

$R_7$ and $R_8$ are each independently selected from the group consisting of H, F, Cl, Br, I, —CN, —$NH_2$, and —OH;

$R_a$, $R_b$, and $R_c$ are each independently selected from the group consisting of H, $C_{1-4}$ alkyl, and $C_{3-4}$ cycloalkyl, wherein the $C_{1-4}$ alkyl and the $C_{3-4}$ cycloalkyl are each independently and optionally substituted with 1, 2, or 3 R;

each $R_d$ is independently selected from the group consisting of H, F, Cl, Br, I, —CN, —$NH_2$, —OH, and $C_{1-4}$ alkyl, wherein the $C_{1-4}$ alkyl is optionally substituted with 1, 2, or 3 $R_{ac}$;

$R_{aa}$, $R_{ab}$, and $R_{ac}$ are each independently selected from the group consisting of D, F, Cl, Br, I, —CN, —$NH_2$, and —OH;

each R is independently selected from the group consisting of F, Cl, Br, I, —CN, —$NH_2$, and —OH; and the "hetero" in the 5-membered heteroaryl means 1, 2, 3, or 4 heteroatoms or heteroatom groups each independently selected from the group consisting of —N—, —O—, —S—, and —NH—.

In another aspect, the present application provides a compound of formula (I), a stereoisomer thereof or a pharmaceutically acceptable salt thereof:

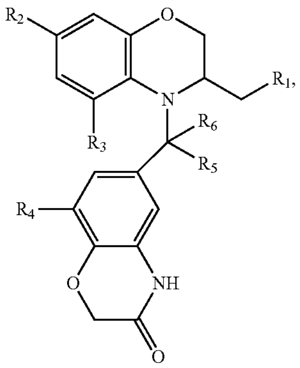

(I)

wherein $R_1$ is selected from the group consisting of $R_{11}$ and $R_{12}$;

$R_{11}$ is selected from the group consisting of —$OR_a$, —C(═O)$NR_bR_c$, and —S(═O)$_2C_{1-4}$ alkyl, wherein the $C_{1-4}$ alkyl is optionally substituted with 1, 2, or 3 $R_{aa}$;

$R_{12}$ is selected from 5-membered heteroaryl, wherein the 5-membered heteroaryl is optionally substituted with 1, 2, or 3 $R_d$;

$R_2$, $R_3$, and $R_4$ are each independently selected from the group consisting of H, F, Cl, Br, I, —CN, —$NH_2$, —OH, and $C_{1-4}$ alkyl;

$R_5$ and $R_6$ are each independently selected from the group consisting of H, F, Cl, Br, and $C_{1-4}$ alkyl, wherein the $C_{1-4}$ alkyl is optionally substituted with 1, 2, or 3 $R_{ab}$;

$R_a$, $R_b$, and $R_c$ are each independently selected from the group consisting of H, $C_{1-4}$ alkyl, and $C_{3-4}$ cycloalkyl, wherein the $C_{1-4}$ alkyl and the $C_{3-4}$ cycloalkyl are each independently and optionally substituted with 1, 2, or 3 R;

each $R_d$ is independently selected from the group consisting of H, F, Cl, Br, I, —CN, —$NH_2$, —OH, and $C_{1-4}$ alkyl, wherein the $C_{1-4}$ alkyl is optionally substituted with 1, 2, or 3 $R_{ac}$;

$R_{aa}$, $R_{ab}$, and $R_{ac}$ are each independently selected from the group consisting of F, Cl, Br, I, —CN, —$NH_2$, and —OH;

each R is independently selected from the group consisting of F, Cl, Br, I, —CN, —$NH_2$, and —OH; and the "hetero" in the 5-membered heteroaryl means 1, 2, 3, or 4 heteroatoms or heteroatom groups each independently selected from the group consisting of —N—, —O—, —S—, and —NH—.

In some embodiments of the present application, the compound described above has a structure of formula (II-1) or (II-2):

(II-1)

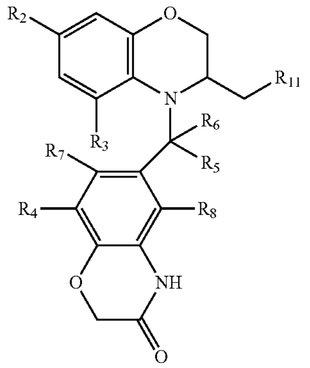

or (II-2)

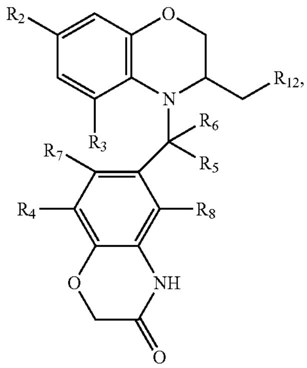

, wherein $R_2$, $R_3$, $R_4$, $R_5$, $R_6$, $R_7$, $R_8$, $R_{11}$, and $R_{12}$ are as defined herein.

In some embodiments of the present application, the compound described above has a structure of formula (I-1) or (I-1)

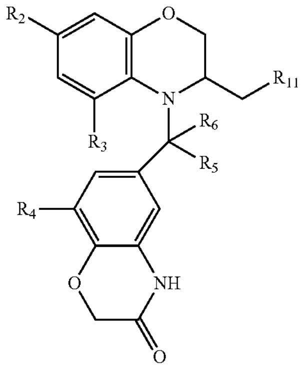

or

-continued (I-2)

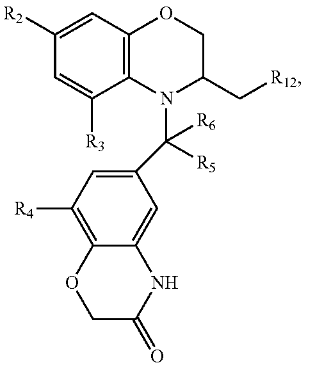

, wherein $R_2$, $R_3$, $R_4$, $R_5$, $R_6$, $R_{11}$, and $R_{12}$ are as defined herein.

In some embodiments of the present application, the compound described above has a structure of formula (II-3), (II-4), (II-5), or (II-6):

(II-3)

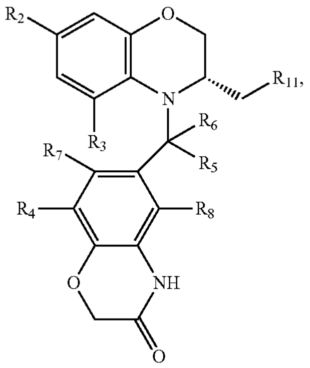

, (II-4)

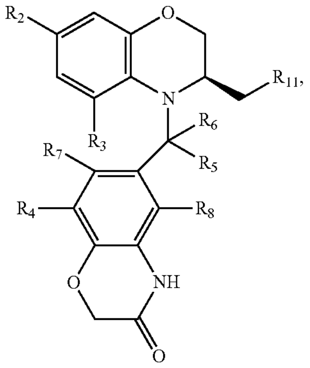

,

-continued (II-5)

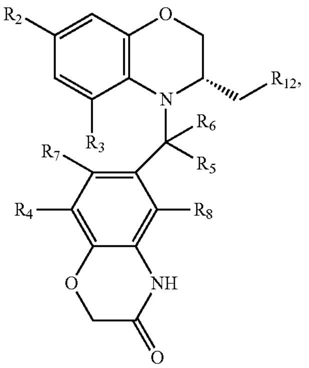

or (II-6)

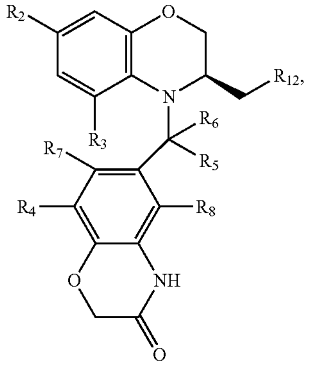

wherein $R_2$, $R_3$, $R_4$, $R_5$, $R_6$, $R_7$, $R_8$, $R_{11}$, and $R_{12}$ are as defined herein.

In some embodiments of the present application, the compound described above has a structure of formula (I-3), (I-4), (I-5), or (I-6):

(I-3)

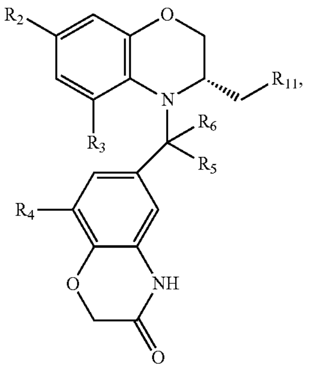

-continued (I-4)

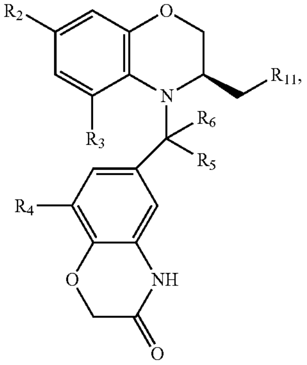

(I-5)

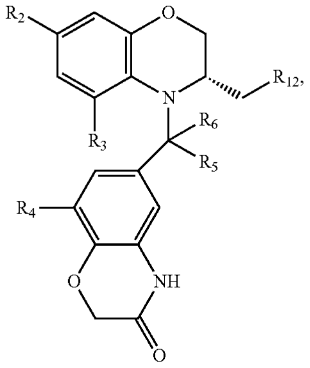

or (I-6)

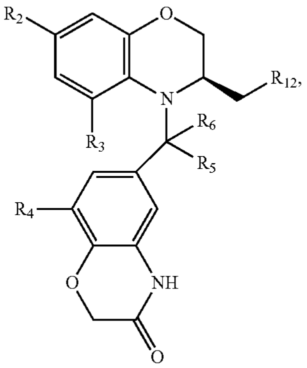

wherein $R_2$, $R_3$, $R_4$, $R_5$, $R_6$, $R_{11}$, and $R_{12}$ are as defined herein.

In some embodiments of the present application, $R_a$ described above is selected from H, while the other variables are as defined herein.

In some embodiments of the present application, $R_b$ and $R_e$ described above are each independently selected from the group consisting of H, —$CH_3$, —$CH_2CH_3$, and

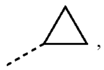

while the other variables are as defined herein.

In some embodiments of the present application, each $R_d$ described above is independently selected from the group consisting of H, F, Cl, Br, and $C_{1-4}$ alkyl, wherein the $C_{1-4}$ alkyl is optionally substituted with 1, 2, or 3 $R_{ac}$, while $R_{ac}$ and the other variables are as defined herein.

In some embodiments of the present application, each $R_d$ described above is independently selected from the group consisting of H, F, Cl, Br, and —$CH_3$, wherein the —$CH_3$ is optionally substituted with 1, 2, or 3 $R_ac$, while $R_ac$ and the other variables are as defined herein.

In some embodiments of the present application, $R_{ac}$ described above is selected from the group consisting of D and —OH, while the other variables are as defined herein.

In some embodiments of the present application, each $R_d$ described above is independently selected from the group consisting of H, F, Cl, Br, —$CH_3$,

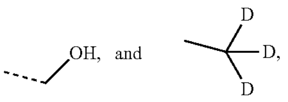, while the other variables are as defined herein.

In some embodiments of the present application, each $R_d$ described above is independently selected from the group consisting of H, F, Cl, Br, and —$CH_3$, while the other variables are as defined herein.

In some embodiments of the present application, each $R_d$ described above is independently selected from the group consisting of H, —$CH_3$,

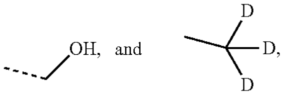, while the other variables are as defined herein.

In some embodiments of the present application, $R_{11}$ described above is selected from the group consisting of —OH, —C(═O)$NH_2$, —C(═O)$NHCH_3$, —C(═O)$NHCH_2CH_3$,

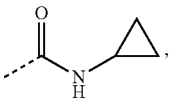, and —S(═O)$_2CH_3$, while the other variables are as defined herein.

In some embodiments of the present application, $R_{11}$ described above is selected from the group consisting of —OH, —C(═O)$NHCH_3$, —C(═O)$NHCH_2CH_3$,

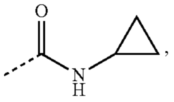, and —S(═O)$_2CH_3$, while the other variables are as defined herein.

In some embodiments of the present application, $R_{12}$ is selected from 5-membered heteroaryl, wherein the "hetero" in the 5-membered heteroaryl means 1, 2, 3, or 4 heteroatoms or heteroatom groups each independently selected from the group consisting of —N—, —O—, and —NH—, and the 5-membered heteroaryl is optionally substituted with 1, 2, or 3 $R_d$, while the other variables are as defined herein.

In some embodiments of the present application, $R_{12}$ is selected from 5-membered heteroaryl, wherein the "hetero" in the 5-membered heteroaryl means 3 or 4 heteroatoms or heteroatom groups each independently selected from the group consisting of —N—, —O—, and —NH—, and the 5-membered heteroaryl is optionally substituted with 1, 2, or 3 $R_d$, while the other variables are as defined herein.

In some embodiments of the present application, $R_{12}$ described above is selected from the group consisting of

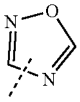, 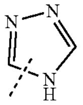, 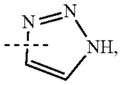, 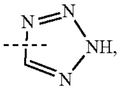, 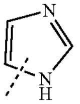, 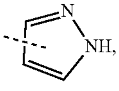, 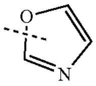, 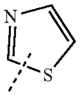, 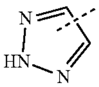, and 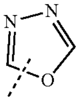, wherein the

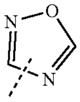, 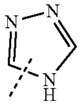, 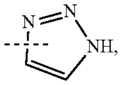, 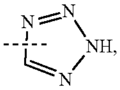, 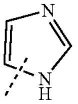, 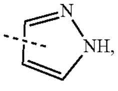, 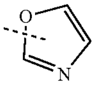, 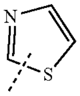, 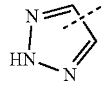 and 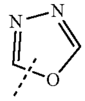

are each independently and optionally substituted with 1, 2, or 3 $R_d$, while $R_d$ and the other variables are as defined herein.

In some embodiments of the present application, $R_{12}$ described above is selected from the group consisting of

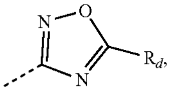, 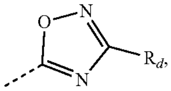, 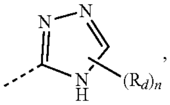, 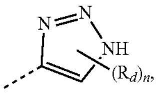, 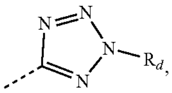, 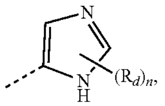, 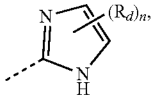, 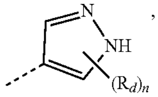, 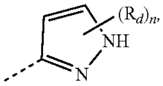, 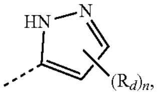, 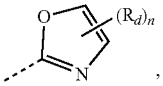, 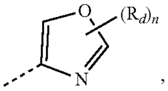, 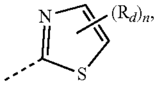, 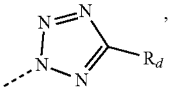, 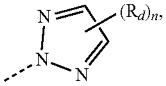, and 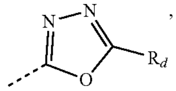, wherein n is selected from the group consisting of 1, 2, and 3, while $R_d$ and the other variables are as defined herein.

In some embodiments of the present application, $R_{12}$ described above is selected from the group consisting of

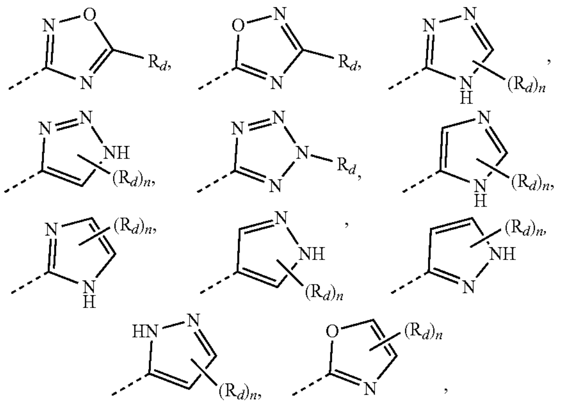

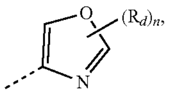

and

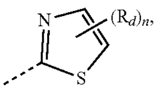

wherein n is selected from the group consisting of 1, 2, and 3, while $R_d$ and the other variables are as defined herein.

In some embodiments of the present application, $R_{12}$ described above is selected from the group consisting of

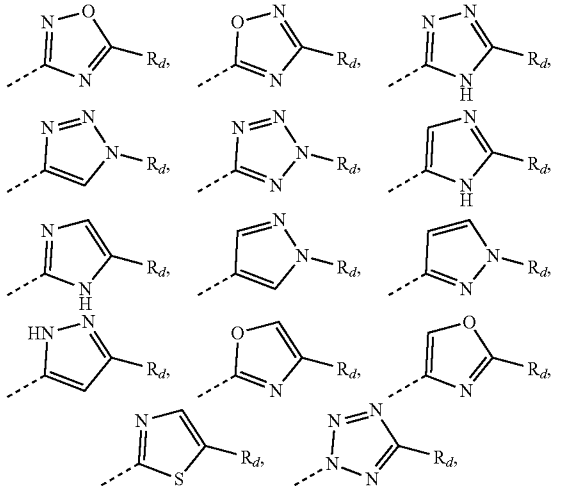

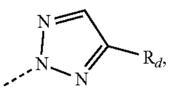

and

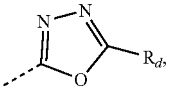

while $R_d$ and the other variables are as defined herein.

In some embodiments of the present application, $R_{12}$ described above is selected from the group consisting of

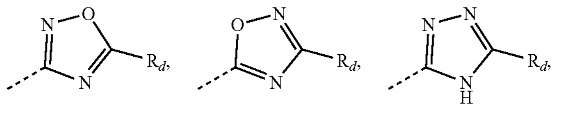

-continued

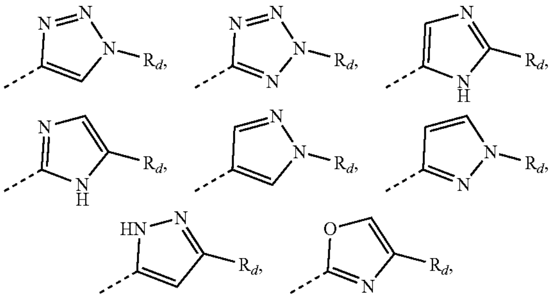

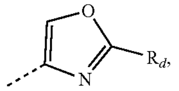

and

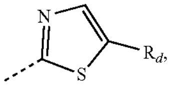

while $R_d$ and the other variables are as defined herein.

In some embodiments of the present application, $R_{12}$ described above is selected from the group consisting of

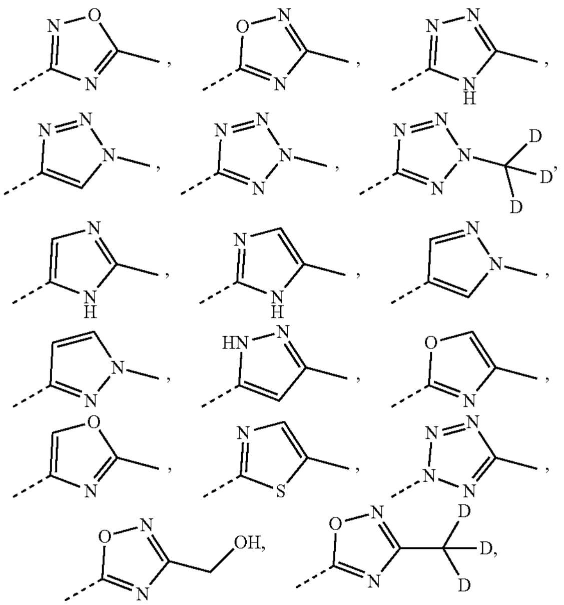

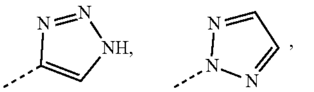

and

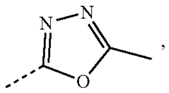

while the other variables are as defined herein.

In some embodiments of the present application, $R_{12}$ described above is selected from the group consisting of

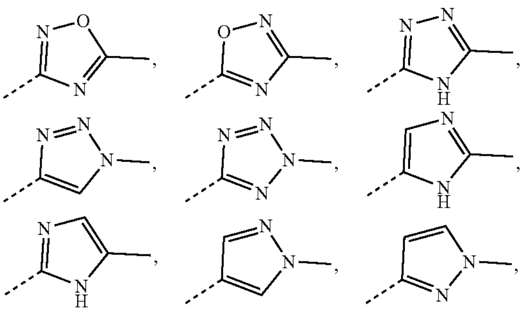

-continued

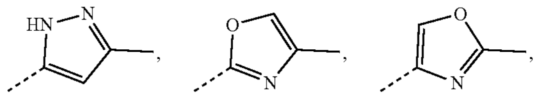

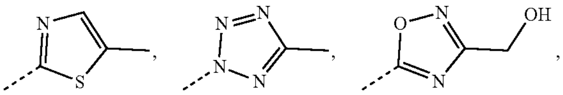

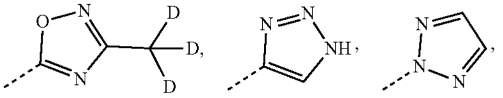 and

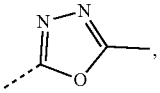

while the other variables are as defined herein.

In some embodiments of the present application, $R_{12}$ described above is selected from the group consisting of

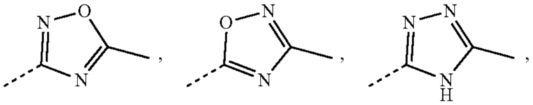

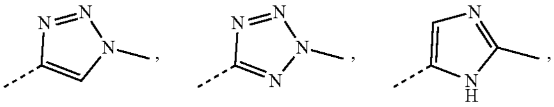

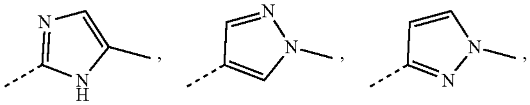

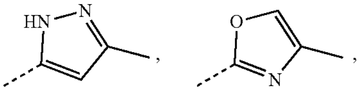

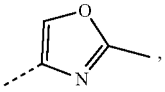 and 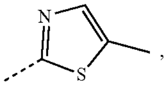

while the other variables are as defined herein.

In some embodiments of the present application, $R_1$ described above is selected from the group consisting of —OH, —C(=O)$NH_2$, —C(=O)$NHCH_3$, —C(=O)$NHCH_2CH_3$,

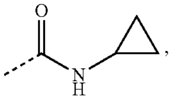

S(=O)$_2CH_3$,

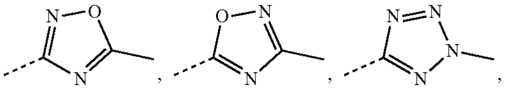

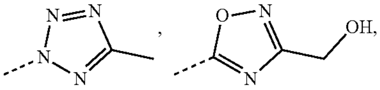

-continued

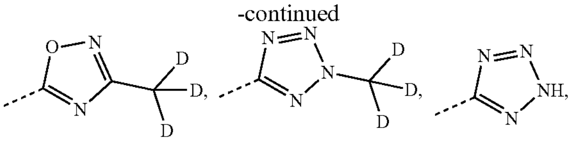

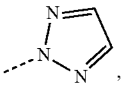 and 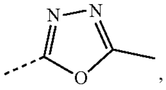

while the other variables are as defined herein.

In some embodiments of the present application, $R_1$ described above is selected from the group consisting of —OH, —C(=O)$NHCH_3$, —C(=O)$NHCH_2CH_3$,

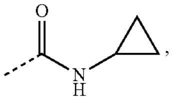

—S(=O)$_2CH_3$,

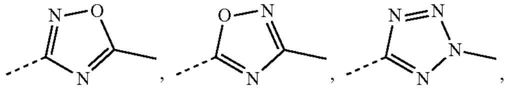

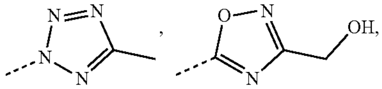

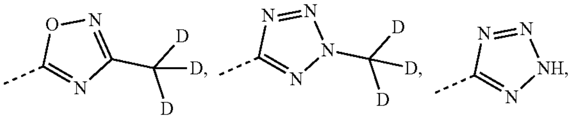

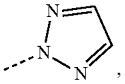 and 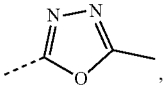

while the other variables are as defined herein.

In some embodiments of the present application, $R_1$ described above is selected from the group consisting of —OH, —C(=O)$NH_2$, —C(=O)$NHCH_3$, —C(=O)$NHCH_2CH_3$,

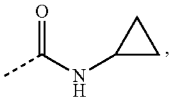

—S(=O)$_2CH_3$,

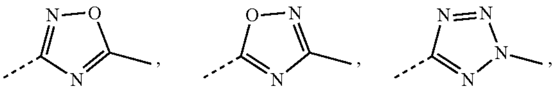

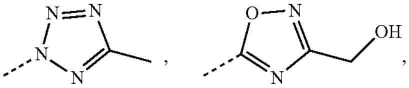

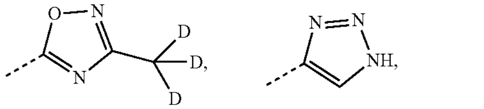

-continued

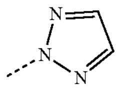, and 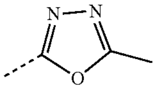, while the other variables are as defined herein.

In some embodiments of the present application, $R_1$ described above is selected from the group consisting of —OH, —C(=O)NHCH$_3$, —C(=O)NHCH$_2$CH$_3$,

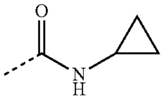,

—S(=O)$_2$CH$_3$,

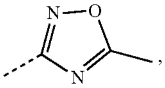, 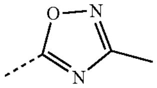, 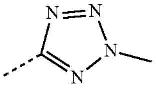, 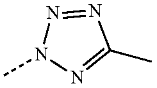, 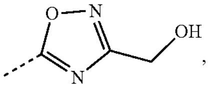, 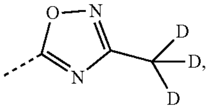 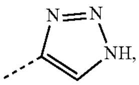 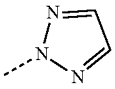, and 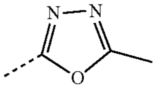, while the other variables are as defined herein.

In some embodiments of the present application, $R_1$ described above is selected from the group consisting of —OH, —C(=O)NHCH$_3$, —C(=O)NHCH$_2$CH$_3$,

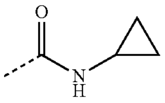,

—S(=O)$_2$CH$_3$, and

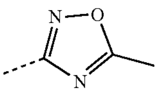, while the other variables are as defined herein.

In some embodiments of the present application, $R_2$ and $R_3$ described above are each independently selected from the group consisting of H, F, and Cl, while the other variables are as defined herein.

In some embodiments of the present application, $R_2$ described above is selected from F, and $R_3$ is selected from the group consisting of H and F, while the other variables are as defined herein.

In some embodiments of the present application, $R_2$ described above is selected from F, while the other variables are as defined herein.

In some embodiments of the present application, $R_3$ described above is selected from the group consisting of H and F, while the other variables are as defined herein.

In some embodiments of the present application, $R_4$ described above is selected from the group consisting of H, F, Cl, and $C_{1-4}$ alkyl, while the other variables are as defined herein.

In some embodiments of the present application, $R_4$ described above is selected from the group consisting of H, F, Cl, and —CH$_3$, while the other variables are as defined herein.

In some embodiments of the present application, $R_4$ described above is selected from H, while the other variables are as defined herein.

In some embodiments of the present application, $R_5$ and $R_6$ described above are each independently selected from the group consisting of H, D, and $C_{1-4}$ alkyl, wherein the $C_{1-4}$ alkyl is optionally substituted with 1, 2, or 3 $R_{ab}$, while $R_{ab}$ and the other variables are as defined herein.

In some embodiments of the present application, $R_5$ described above is selected from the group consisting of H, D, and $C_{1-4}$ alkyl, wherein the $C_{1-4}$ alkyl is optionally substituted with 1, 2, or 3 $R_{ab}$, while $R_{ab}$ and the other variables are as defined herein.

In some embodiments of the present application, $R_5$ and $R_6$ described above are each independently selected from the group consisting of H, D, and —CH$_3$, while the other variables are as defined herein.

In some embodiments of the present application, $R_5$ described above is selected from the group consisting of H, D, and —CH$_3$, while the other variables are as defined herein.

In some embodiments of the present application, $R_6$ described above is selected from the group consisting of H and D, while the other variables are as defined herein.

In some embodiments of the present application, $R_5$ and $R_6$ described above are each independently selected from the group consisting of H and —CH$_3$, while the other variables are as defined herein.

In some embodiments of the present application, $R_5$ described above is selected from the group consisting of H and —CH$_3$, while the other variables are as defined herein.

In some embodiments of the present application, $R_6$ described above is selected from H, while the other variables are as defined herein.

In some embodiments of the present application, $R_7$ described above is selected from the group consisting of H and F, while the other variables are as defined herein.

In some embodiments of the present application, $R_7$ described above is selected from H, while the other variables are as defined herein.

In some embodiments of the present application, $R_8$ described above is selected from the group consisting of H, F, Cl, and $C_{1-4}$ alkyl, while the other variables are as defined herein.

In some embodiments of the present application, $R_8$ described above is selected from the group consisting of H, F, Cl, and —CH$_3$, while the other variables are as defined herein.

Some other embodiments of the present application are derived from any combination of the variables described above.

The present application further provides compounds of the following formulas, stereoisomers thereof or pharmaceutically acceptable salts thereof:

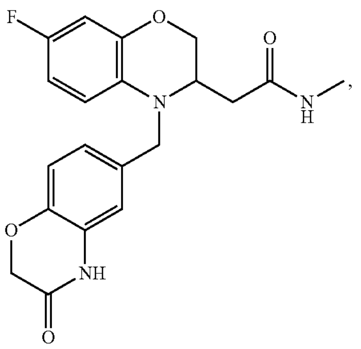
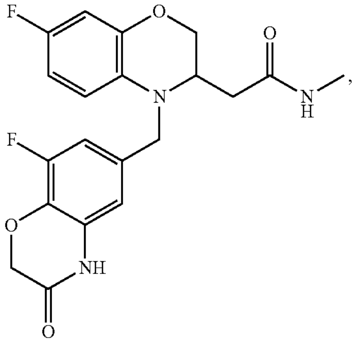
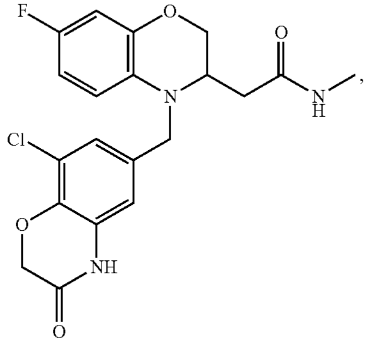
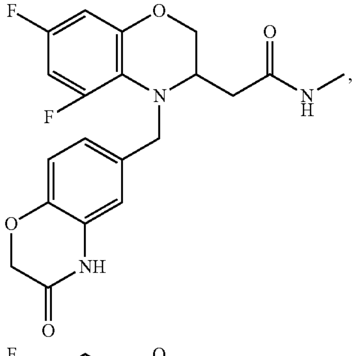
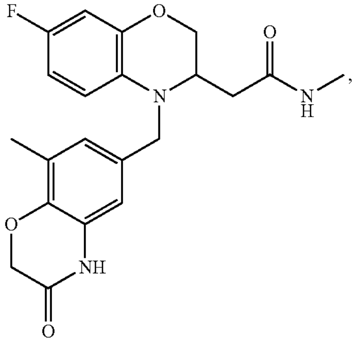
-continued
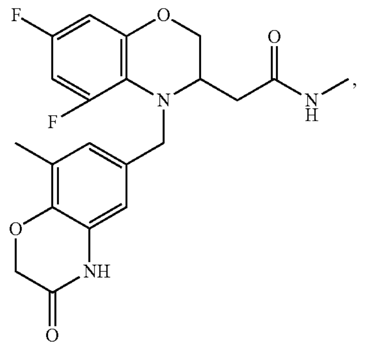
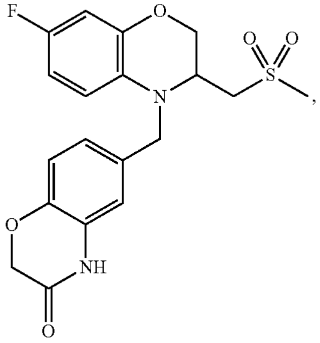
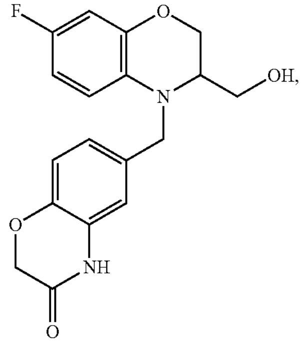
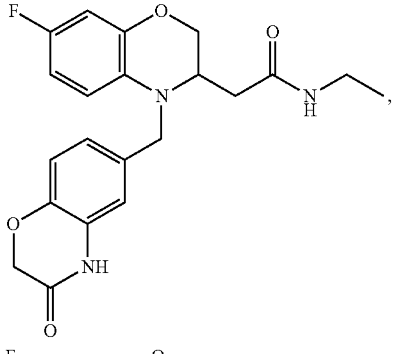
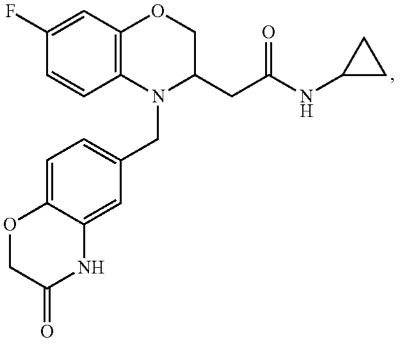

-continued
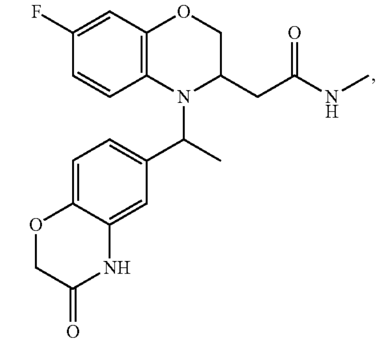
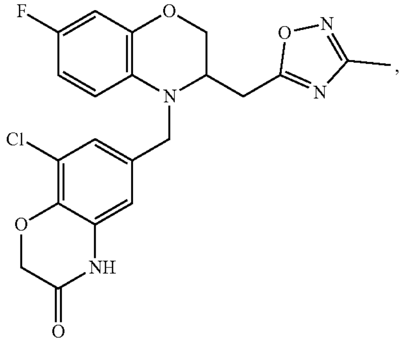
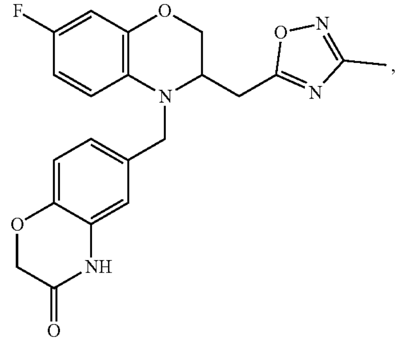
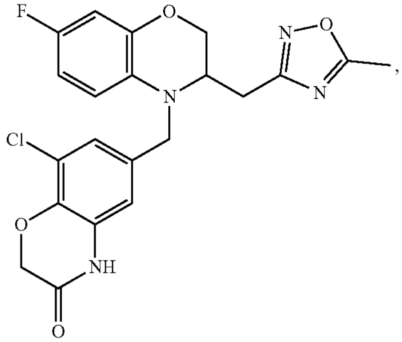
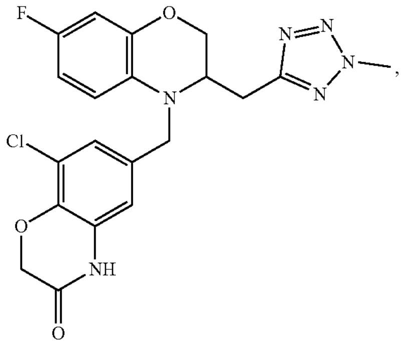
-continued
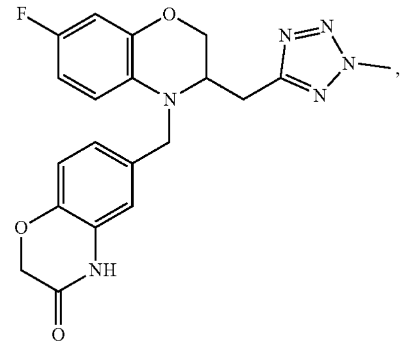
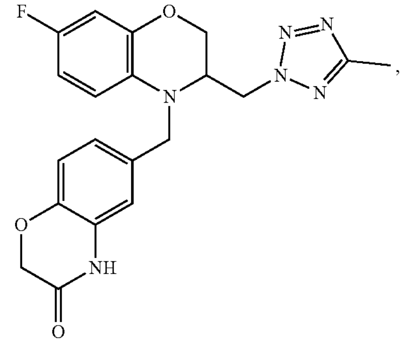
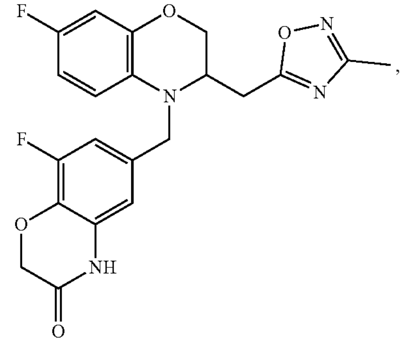
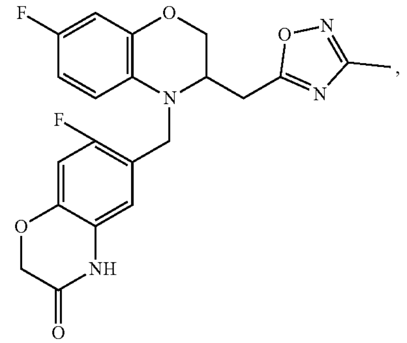
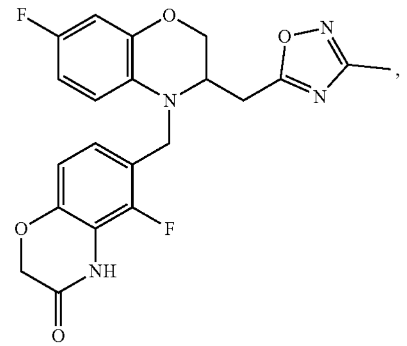

-continued
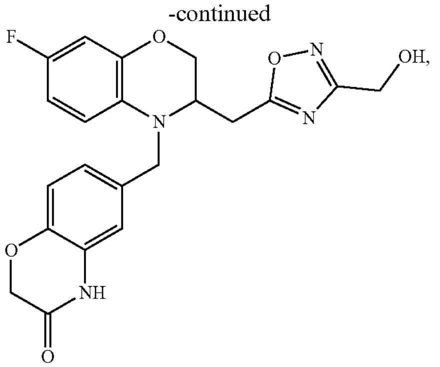
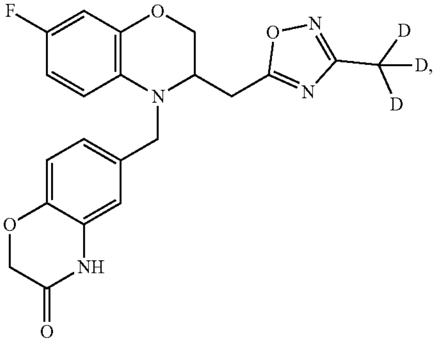
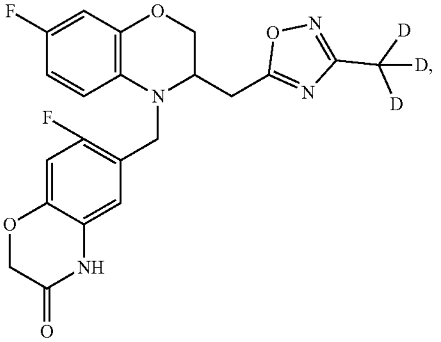
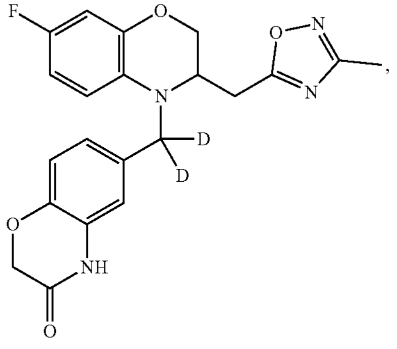
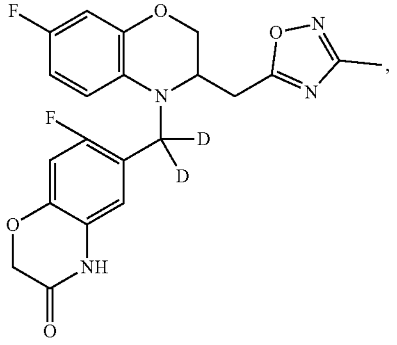
-continued
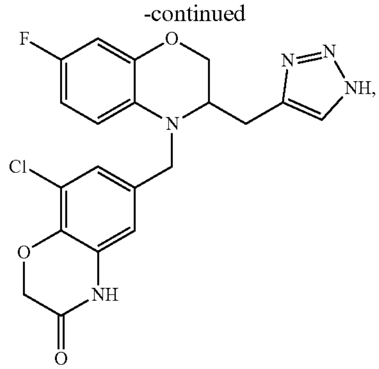
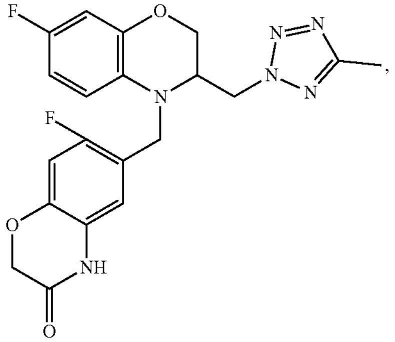
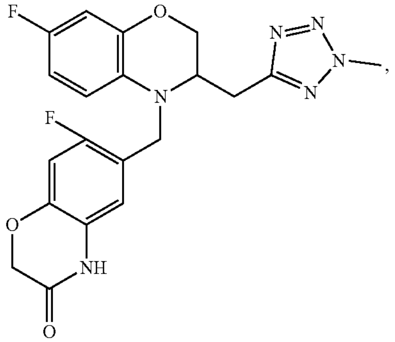
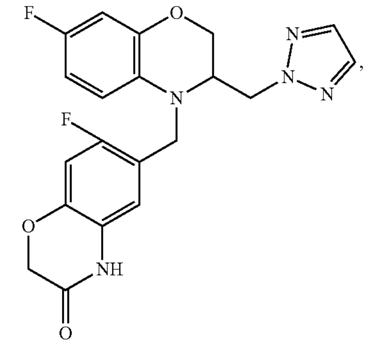
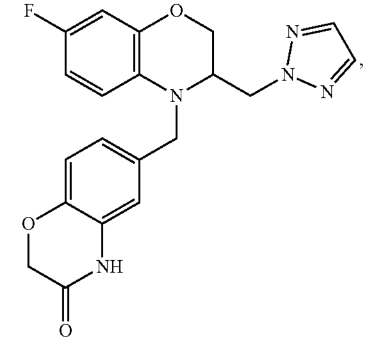

-continued
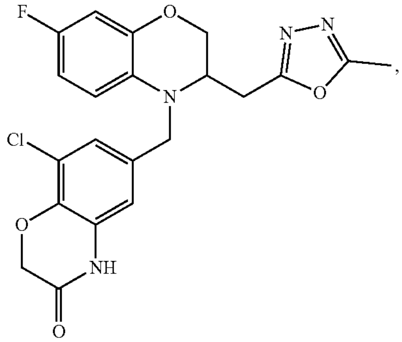,
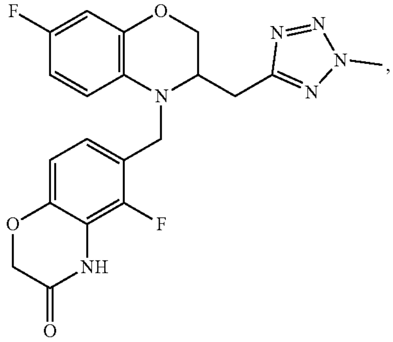,
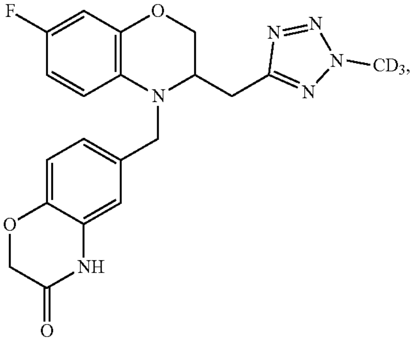,
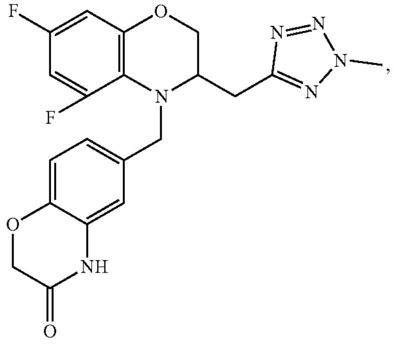,
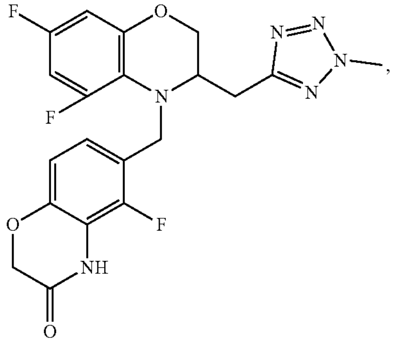,
-continued
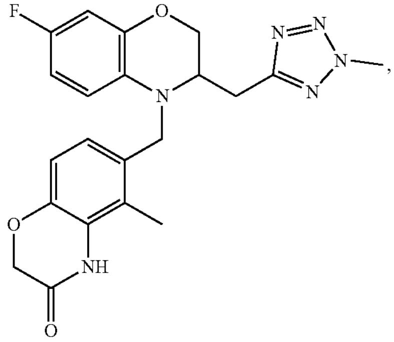,
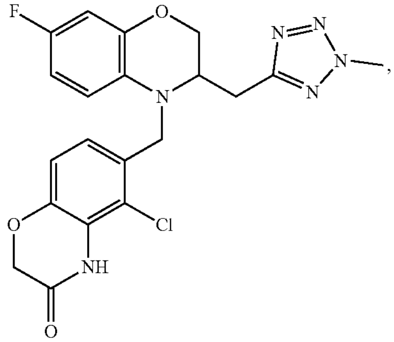,
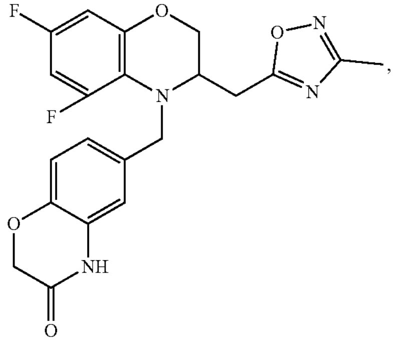,
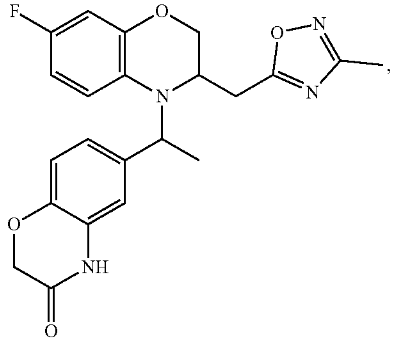,
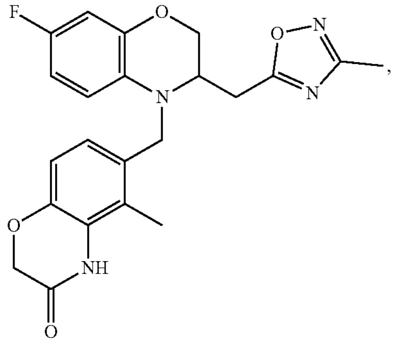, -continued
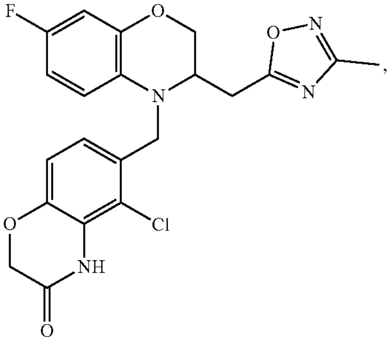,
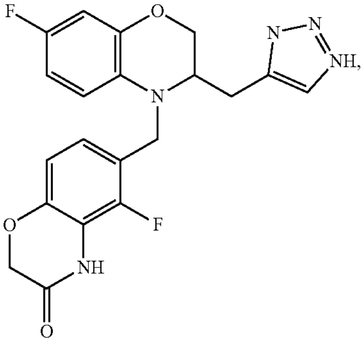,
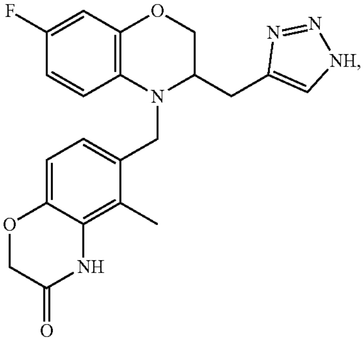,
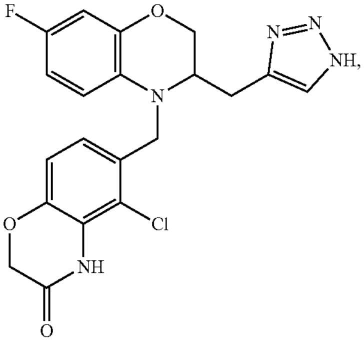,
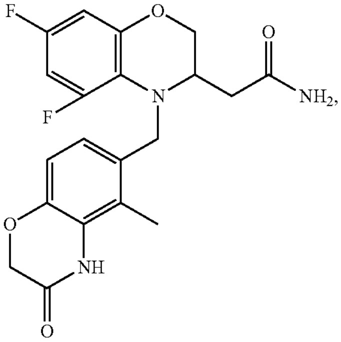, and
-continued
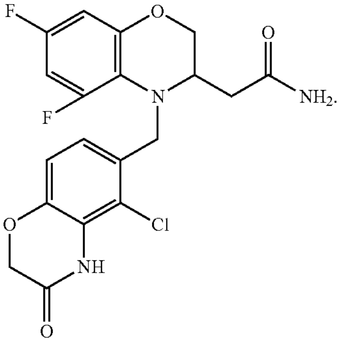 [SMILES: NC(=O)CC1COc2cc(F)cc(F)c2N1Cc1ccc2c(c1Cl)NC(=O)CO2].
The present application further provides compounds of the following formulas, stereoisomers thereof or pharmaceutically acceptable salts thereof:
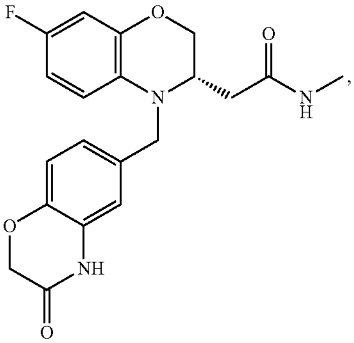,
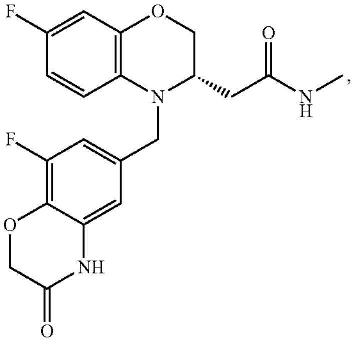,
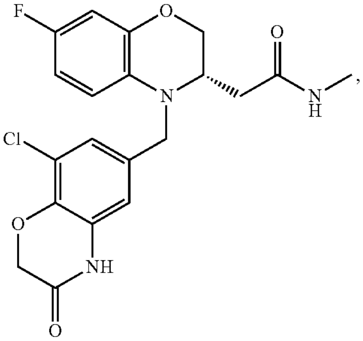, -continued
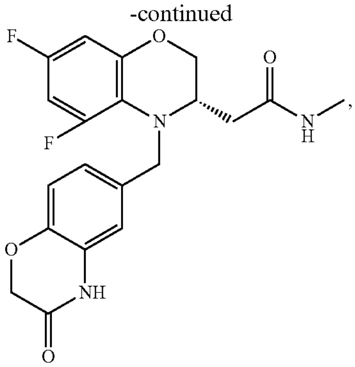
,
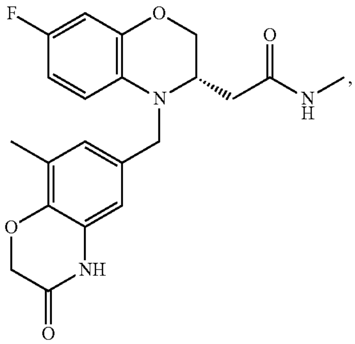
,
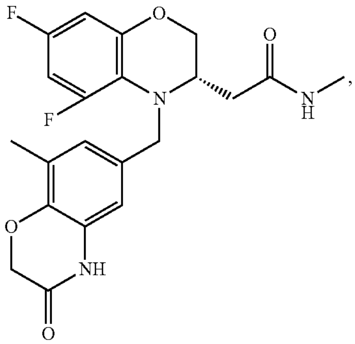
,
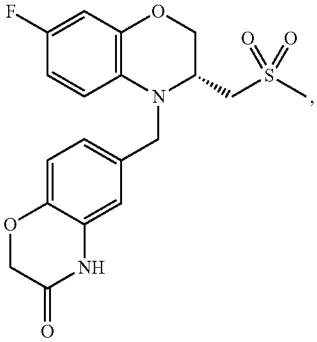
,
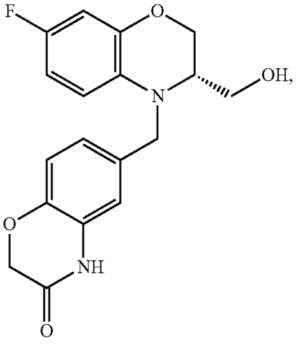
-continued
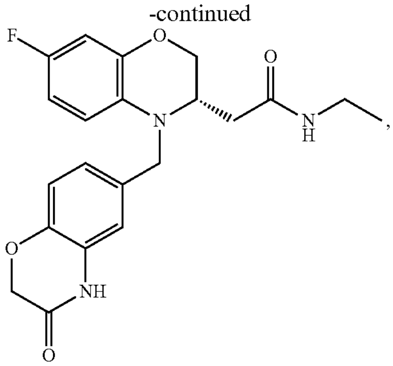
,
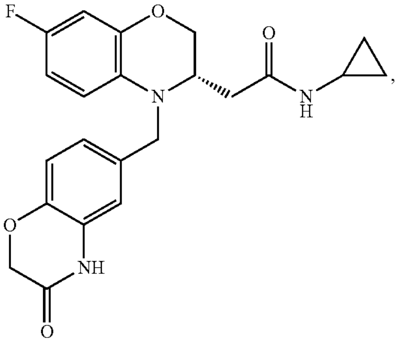
,
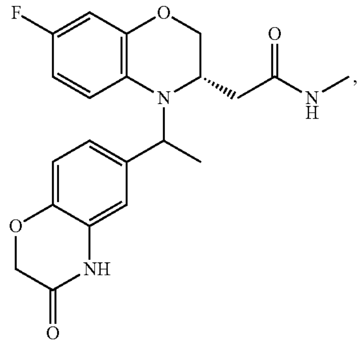
,
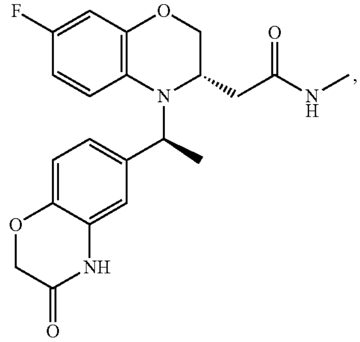
,
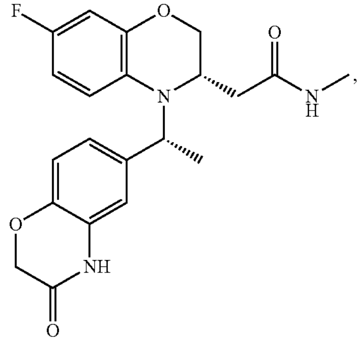

-continued
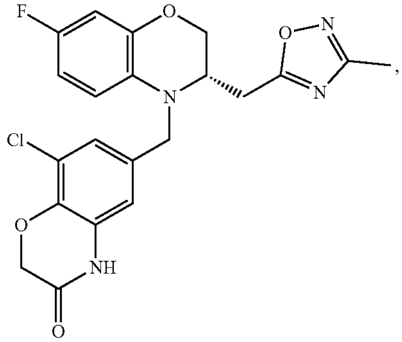,
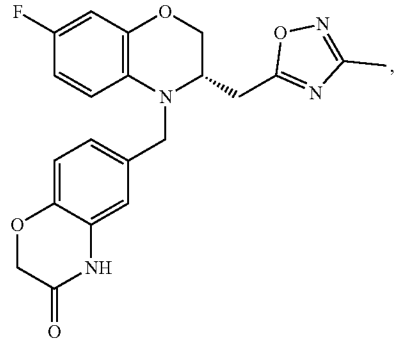,
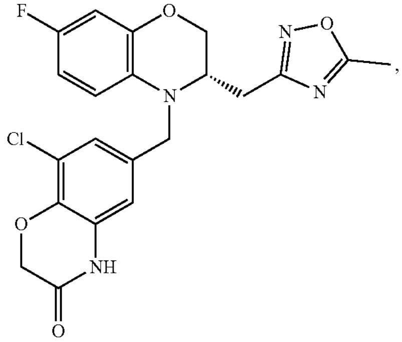,
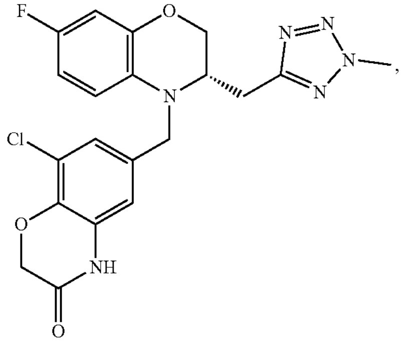,
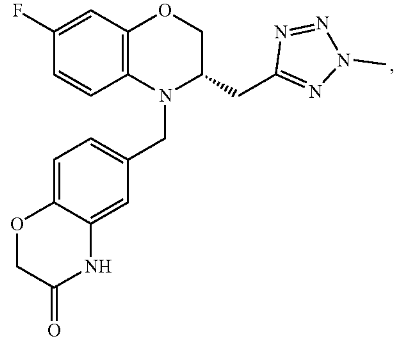,
-continued
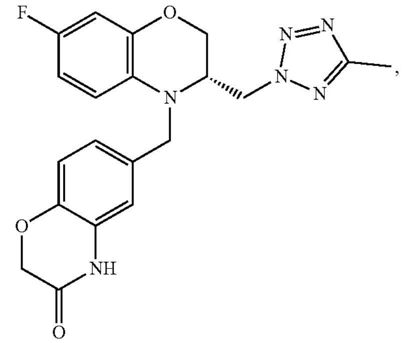,
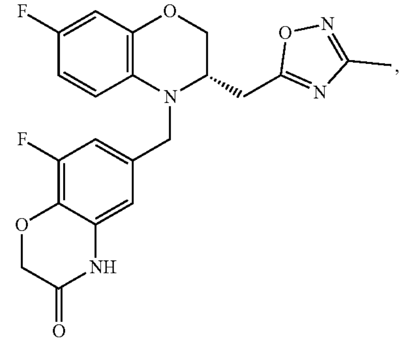,
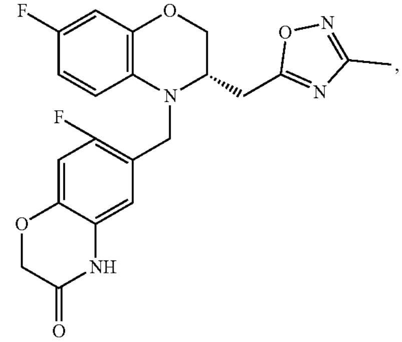,
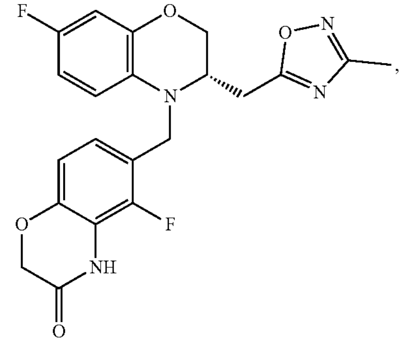,
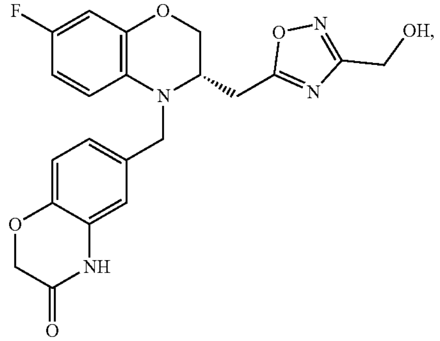

-continued
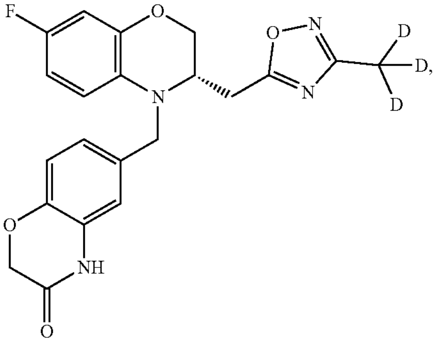,
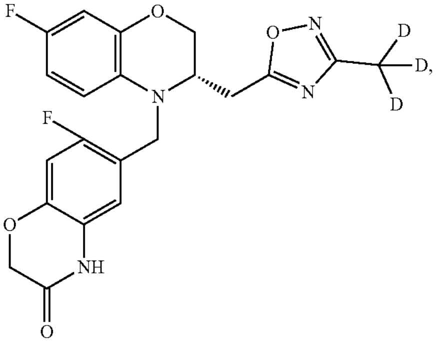,
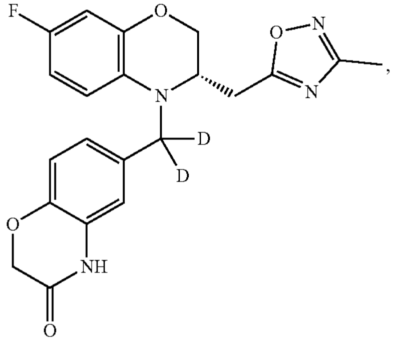,
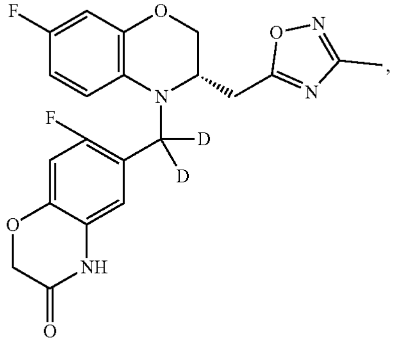,
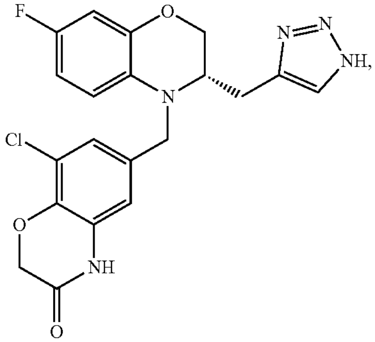,
-continued
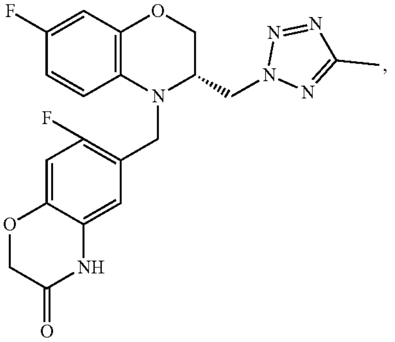,
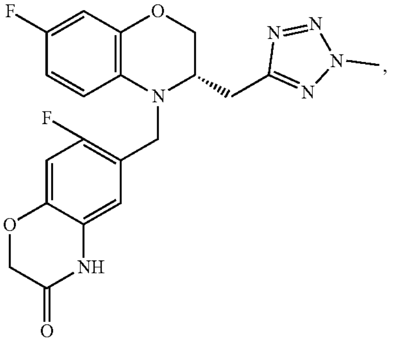,
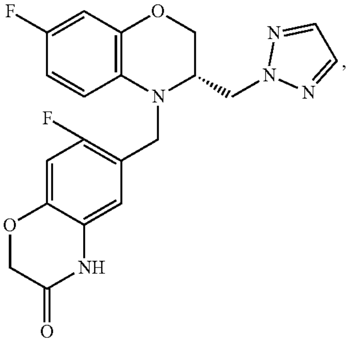,
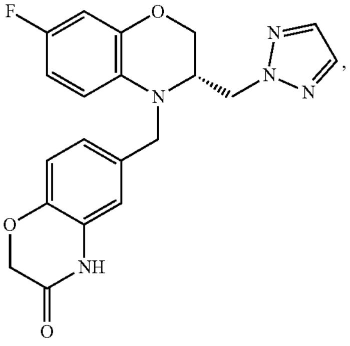,
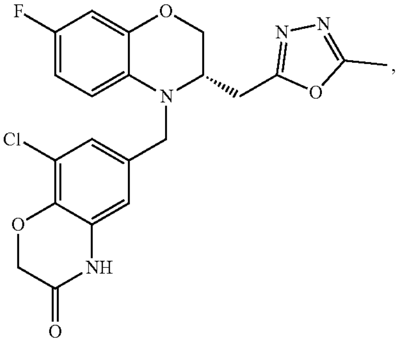, -continued
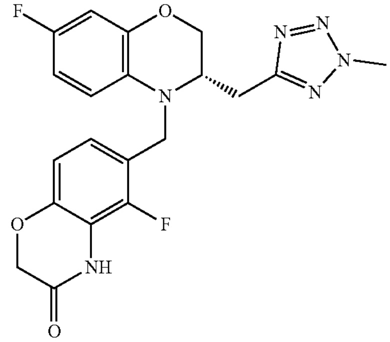
,
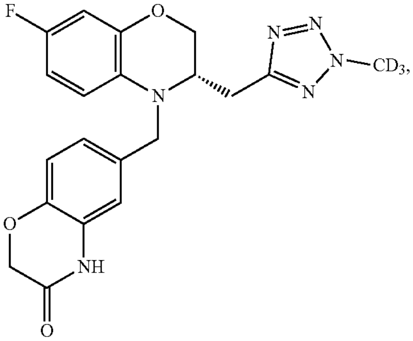
,
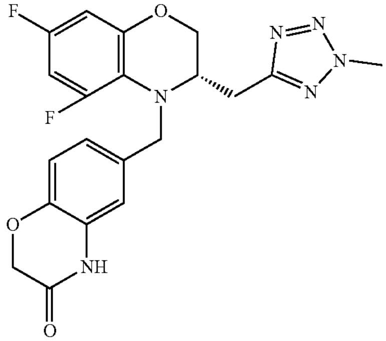
,
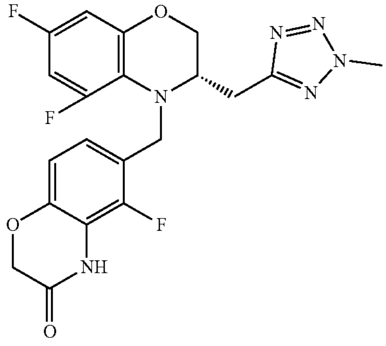
,
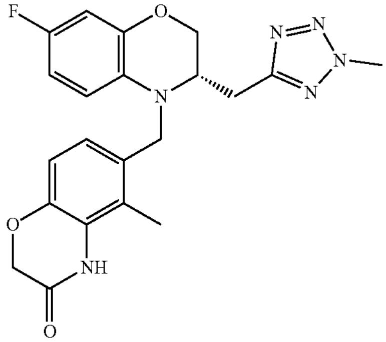
,
-continued
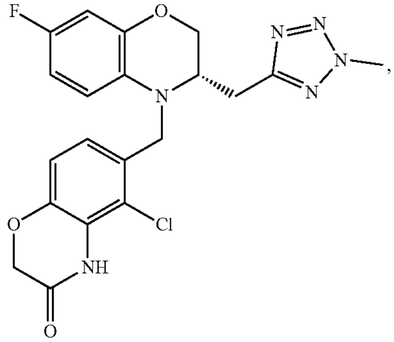
,
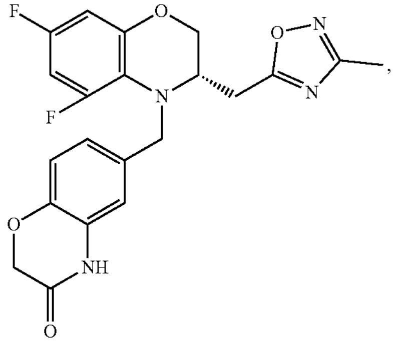
,
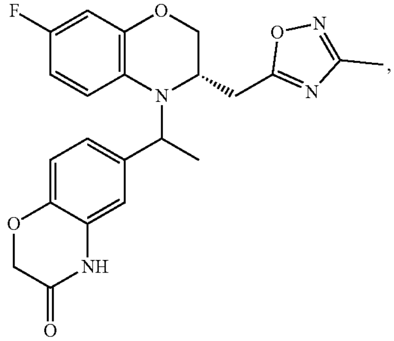
,
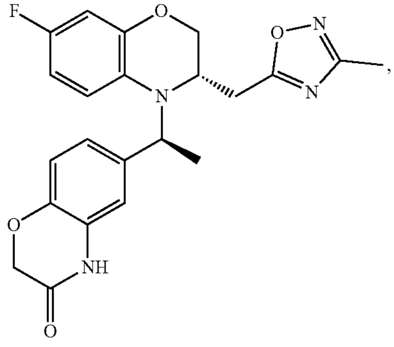
,
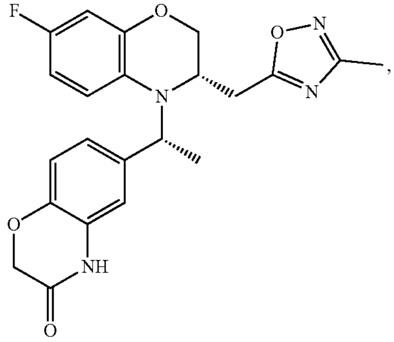
, -continued
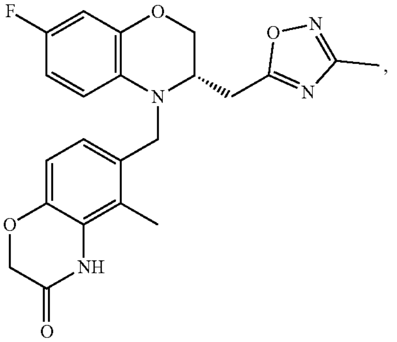
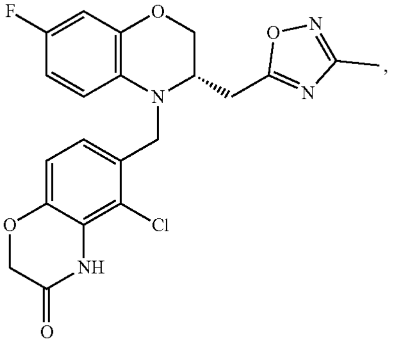
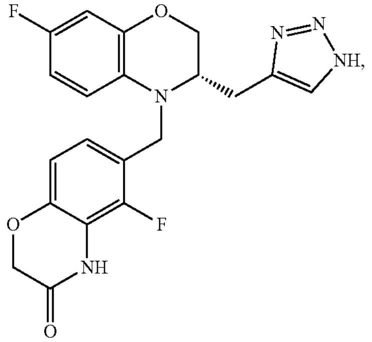
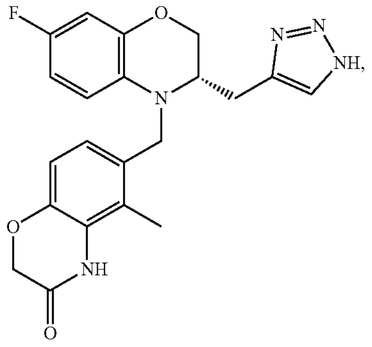
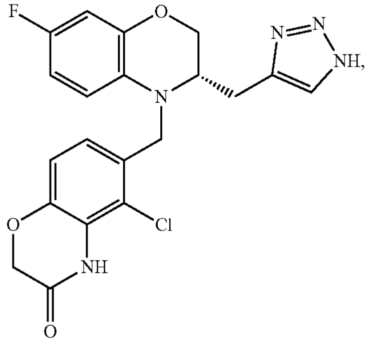
-continued
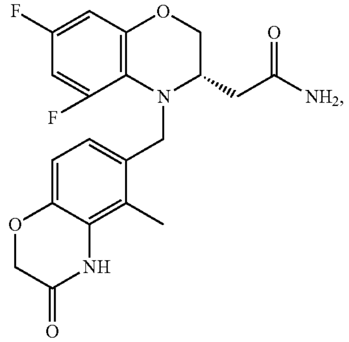
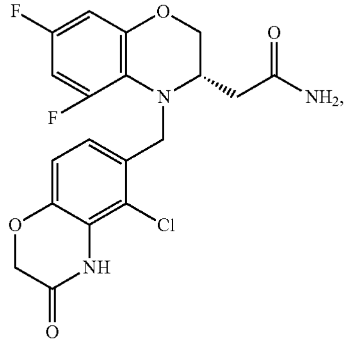
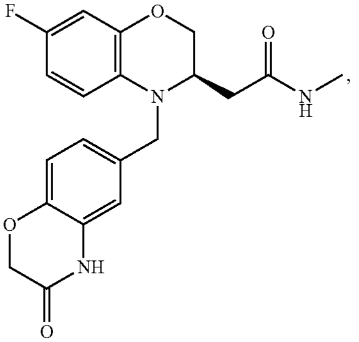
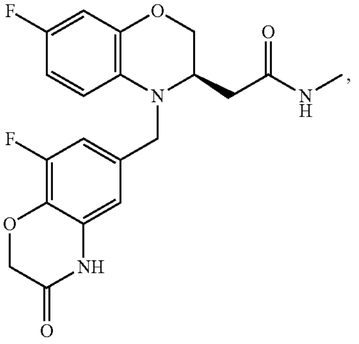
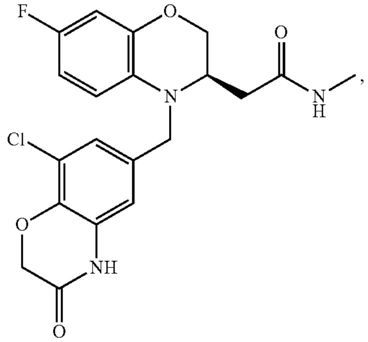

-continued
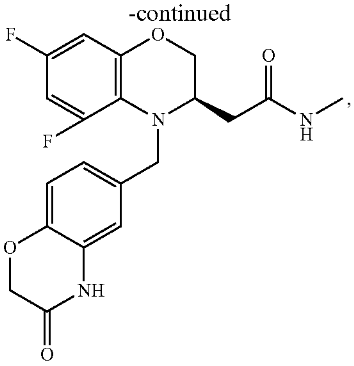,
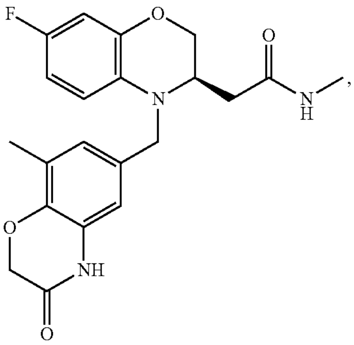,
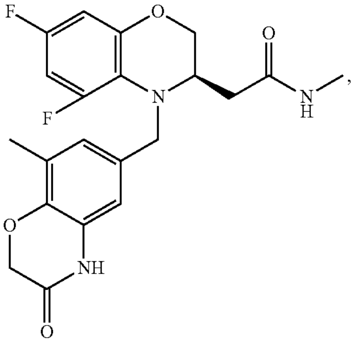,
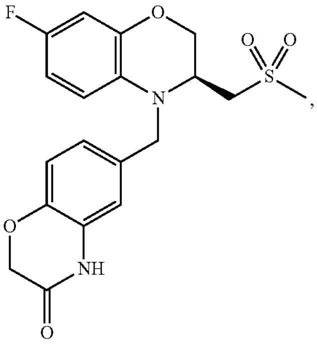,
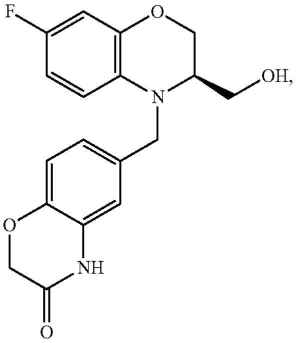
-continued
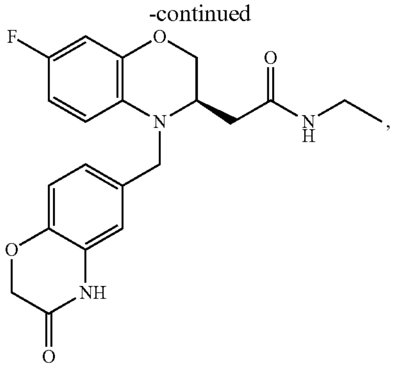,
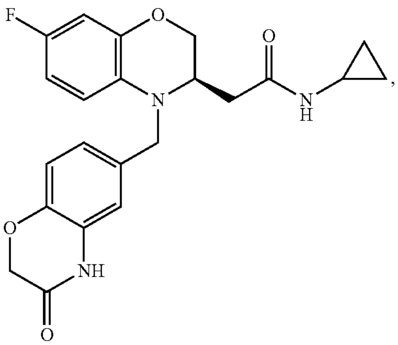,
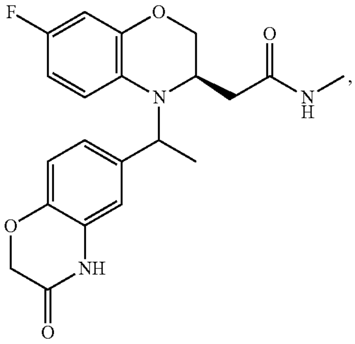,
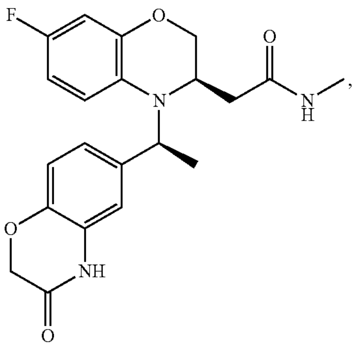,
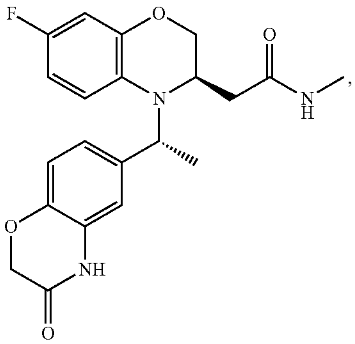, -continued
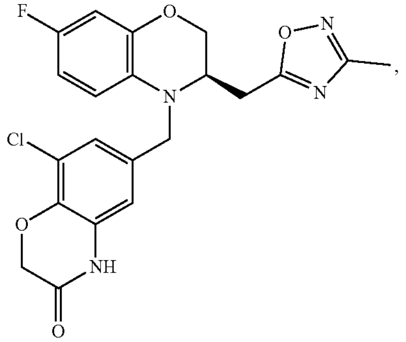
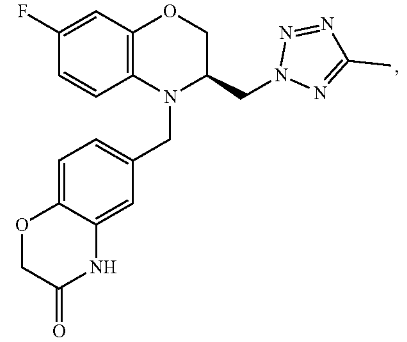
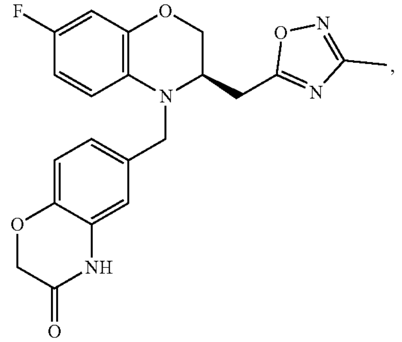
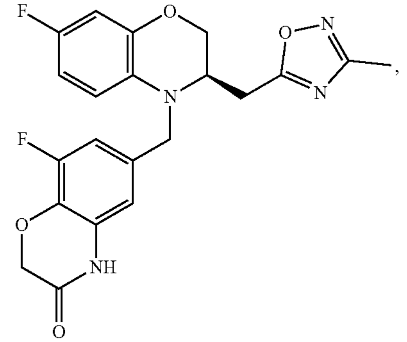
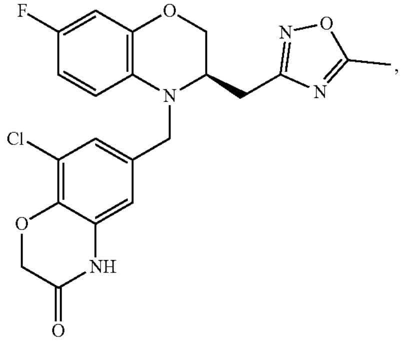
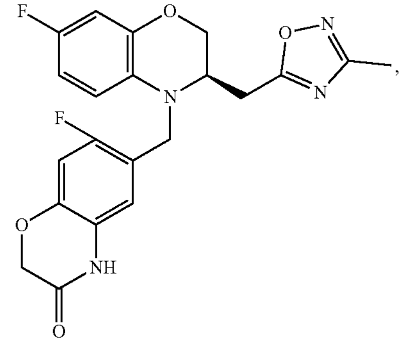
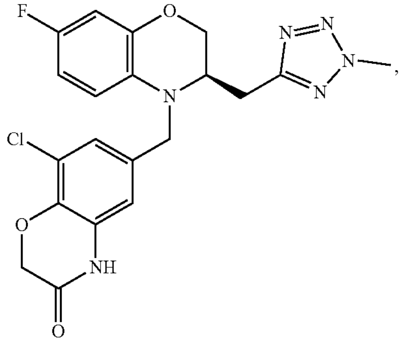
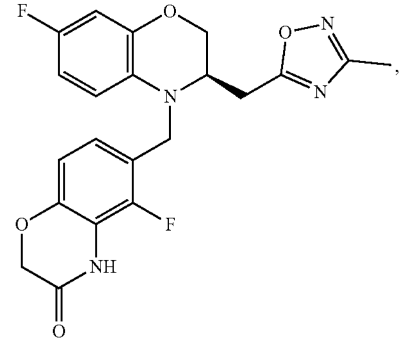
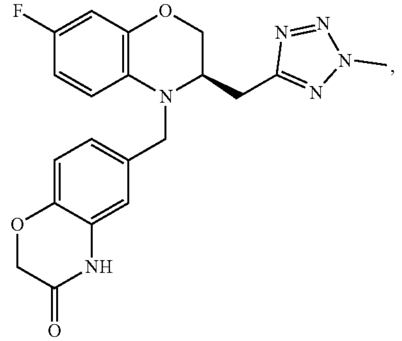
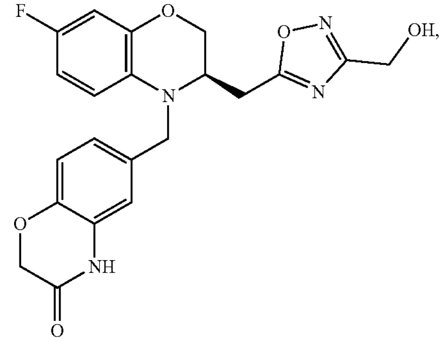
-continued -continued
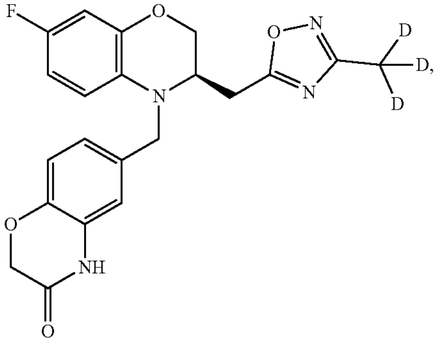
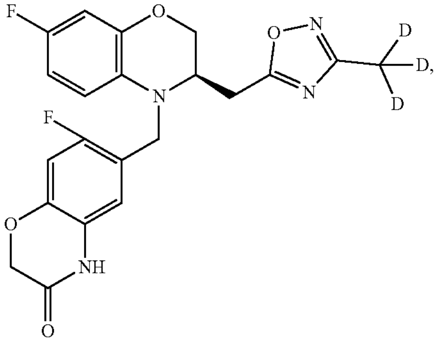
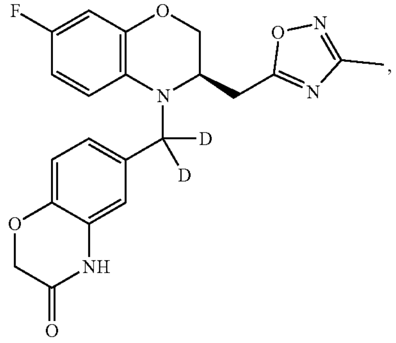
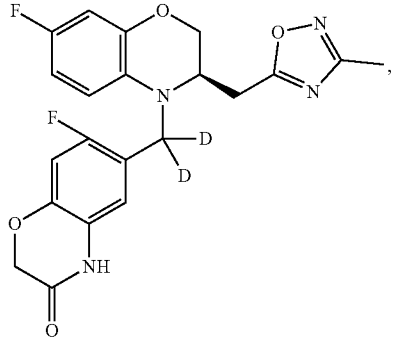
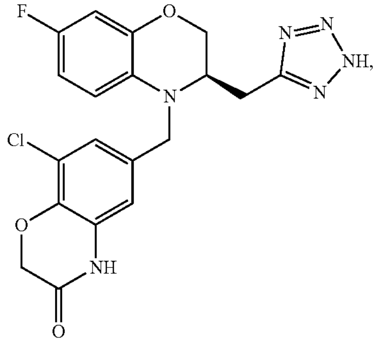
-continued
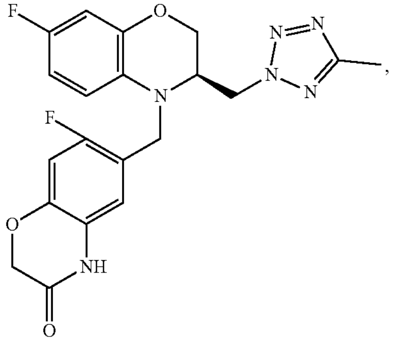
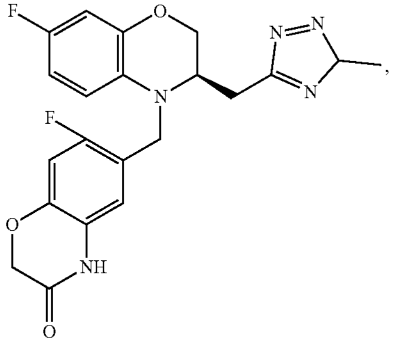
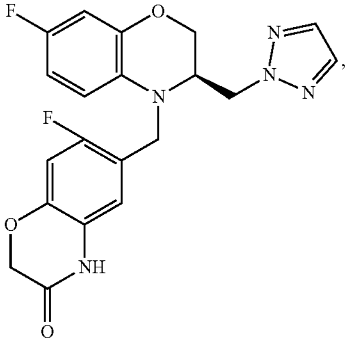
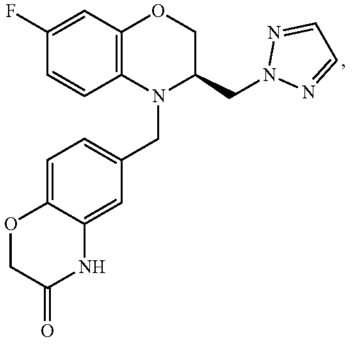
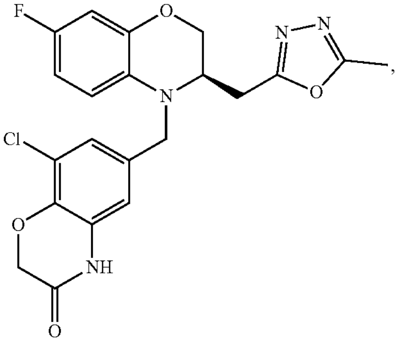

-continued
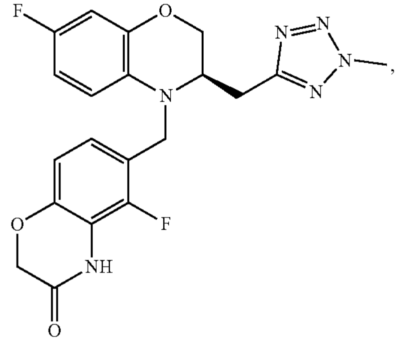
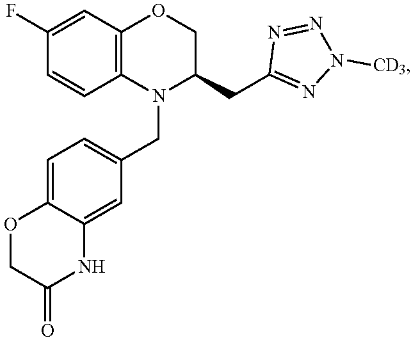
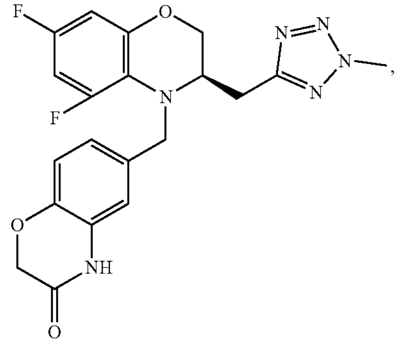
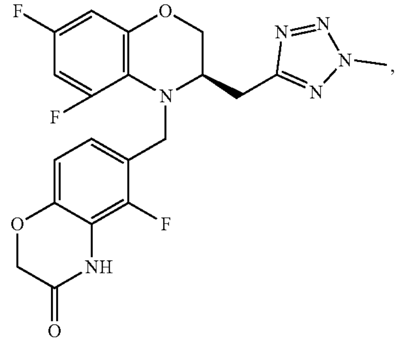
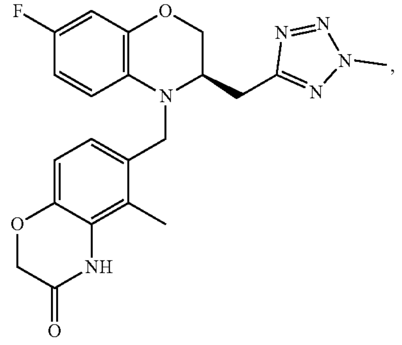
-continued
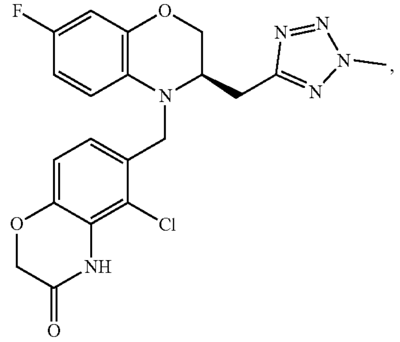
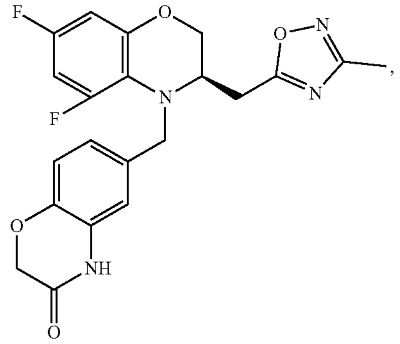
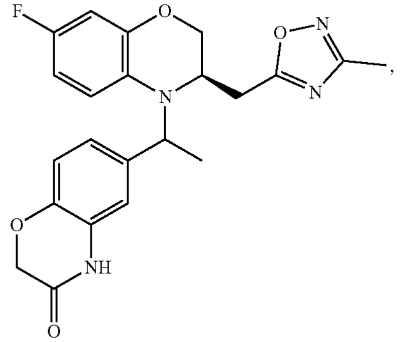
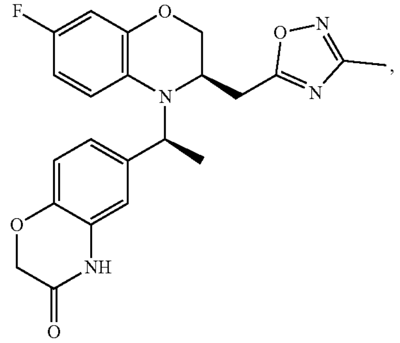
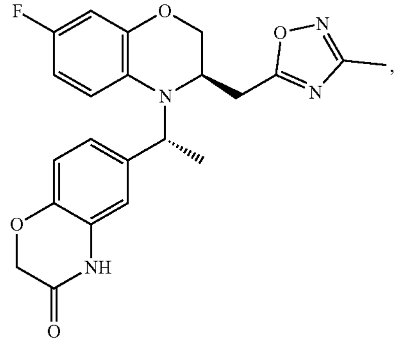

-continued

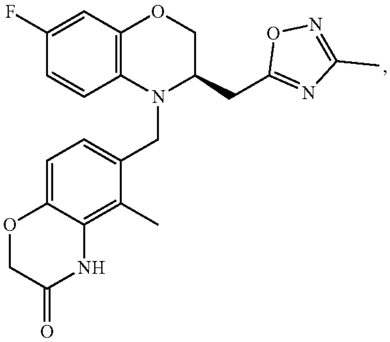

,

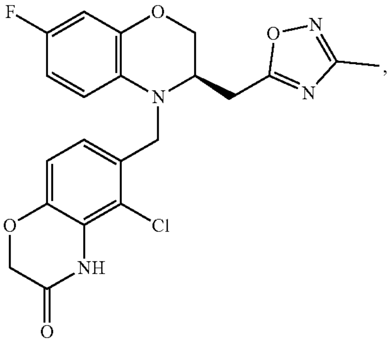

,

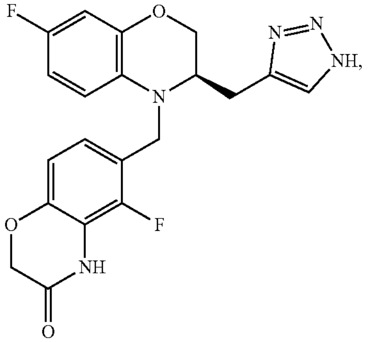

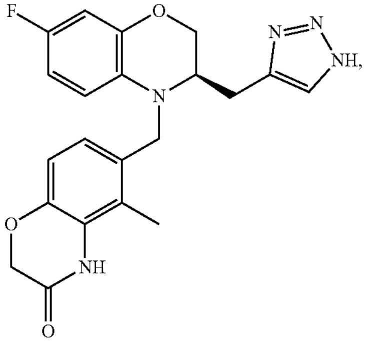

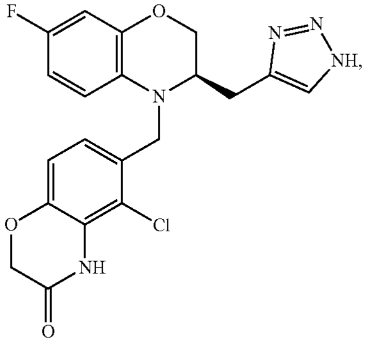

-continued

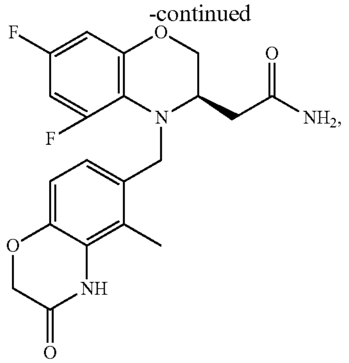

and

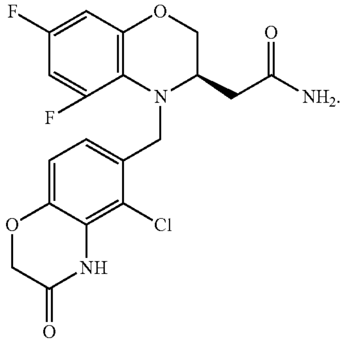

The present application further provides a pharmaceutical composition comprising a therapeutically effective amount of the compound, the stereoisomer thereof or the pharmaceutically acceptable salt thereof disclosed herein, and a pharmaceutically acceptable carrier.

The present application further provides use of the compound, the stereoisomer thereof or the pharmaceutically acceptable salt thereof described above or the pharmaceutical composition described above for preparing a medicament for treating a mineralocorticoid receptor antagonist-related disease.

The present application further provides use of the compound, the stereoisomer thereof or the pharmaceutically acceptable salt thereof described above or the pharmaceutical composition described above for preparing a medicament for treating diabetic nephropathy.

The present application further provides a method for treating a mineralocorticoid receptor antagonist-related disease in a subject in need thereof, comprising providing an effective dose of the compound, the stereoisomer thereof or the pharmaceutically acceptable salt thereof described above or the pharmaceutical composition described above to the subject.

The present application further provides use of the compound, the stereoisomer thereof or the pharmaceutically acceptable salt thereof described above or the pharmaceutical composition described above for treating a mineralocorticoid receptor antagonist-related disease.

The present application further provides the compound, the stereoisomer thereof or the pharmaceutically acceptable salt thereof described above or the pharmaceutical composition described above for use in treating a mineralocorticoid receptor antagonist-related disease.

In some embodiments of the present application, the mineralocorticoid receptor antagonist-related disease is selected from diabetic nephropathy.

The present application further provides a biological experimental test method for the compound described above.

Technical Effects

The compound of the present application has good antagonistic activity on mineralocorticoid receptors. In addition, the compound exhibits excellent pharmacokinetic and pharmacodynamic properties, while having good membrane permeability and solubility.

Definitions and Explanations

Unless otherwise stated, the following terms and phrases used herein are intended to have the following meanings. A particular term or phrase, unless otherwise specifically defined, should not be considered as indefinite or unclear, but construed according to its common meaning. When referring to a trade name, it is intended to refer to its corresponding commercial product or its active ingredient.

The term "pharmaceutically acceptable" is used herein for those compounds, materials, compositions, and/or dosage forms that are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" refers to a salt of the compound of the present application, which is prepared from the compound having particular substituents discovered by the present application and a relatively non-toxic acid or base. When the compound of the present application contains a relatively acidic functional group, a base addition salt can be obtained by making such a compound in contact with a sufficient amount of a base in a pure solution or a suitable inert solvent. Pharmaceutically acceptable base addition salts include sodium, potassium, calcium, ammonium, organic amine or magnesium salts, or similar salts. When the compound of the present application contains a relatively basic functional group, an acid addition salt can be obtained by making such a compound in contact with a sufficient amount of an acid in a pure solution or a suitable inert solvent. Certain specific compounds disclosed herein contain both basic and acidic functional groups that allow the compounds to be converted into either base or acid addition salts.

The pharmaceutically acceptable salts of the present application can be synthesized from a parent compound having an acidic or basic group using conventional chemical methods. In general, such salts are prepared by subjecting the free acid or base form of the compound to a reaction with a stoichiometric amount of the appropriate base or acid in water or an organic solvent or a mixture thereof.

The compounds of the present application can be in the form of a geometric isomer or stereoisomer. All such compounds are contemplated herein, including cis- and trans-isomers, (−)- and (+)-enantiomers, (R)- and (S)-enantiomers, diastereoisomers, (D)-isomers, (L)-isomers, and racemic mixtures and other mixtures thereof, such as an enantiomer or diastereoisomer enriched mixture, all of which are encompassed within the scope of the present application. The substituents such as alkyl may have an additional asymmetric carbon atom. All these isomers and mixtures thereof are encompassed within the scope of the present application.

Unless otherwise stated, the term "enantiomer" or "optical isomer" refers to stereoisomers that are mirror images of each other.

Unless otherwise stated, the term "cis-trans isomer" or "geometric isomer" results from the inability of a single bond of a ring carbon atom or a double bond to rotate freely.

Unless otherwise stated, the term "diastereoisomer" refers to stereoisomers whose molecules have two or more chiral centers and are not mirror images of each other.

Unless otherwise stated, "(+)" stands for dextrorotation, "(−)" stands for levorotation, and "(±)" stands for racemization.

Unless otherwise stated, the absolute configuration of a stereogenic center is represented by a wedged solid bond ( ) and a wedged dashed bond ( ), and the relative configuration of a stereogenic center is represented by a straight solid bond ( ) and a straight dashed bond ( ). A wavy line ( ) represents a wedged solid bond ( ) or a wedged dashed bond ( ), or a wavy line ( ) represents a straight solid bond ( ) and a straight dashed bond ( ). For example,

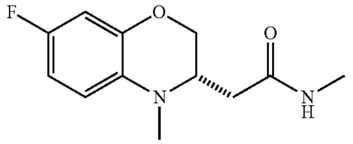

represents

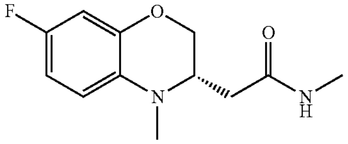

or

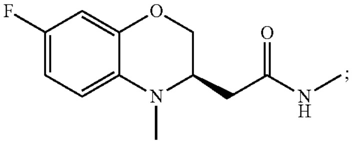

;

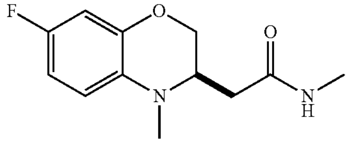

represents

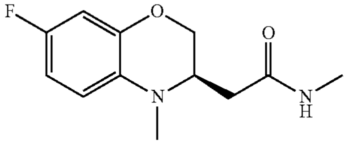

or

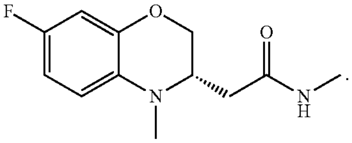

.

Unless otherwise stated, the term "tautomer" or "tautomeric form" means that different functional isomers are in dynamic equilibrium at room temperature and can be rapidly converted into each other. If tautomers are possible (e.g., in a solution), the chemical equilibrium of the tautomers can be achieved. For example, a proton tautomer, also known as a prototropic tautomer, includes the interconversion by proton transfer, such as keto-enol isomerization and imine-enamine isomerization. A valence isomer includes the interconversion by recombination of some bonding electrons. A specific example of the keto-enol tautomerization is the interconversion between tautomers pentane-2,4-dione and 4-hydroxypent-3-en-2-one.

Unless otherwise stated, the term "enriched in one isomer", "isomer enriched", "enriched in one enantiomer", or "enantiomer enriched" means that the content of one of the isomers or enantiomers is less than 100% and more than or equal to 60%, 70%, 80%, 90%, 95%, 96%, 97%, 98%, 99%, 99.5%, 99.6%, 99.7%, 99.8% or 99.9%.

Unless otherwise stated, the term "isomeric excess" or "enantiomeric excess" refers to the difference between the relative percentages of two isomers or enantiomers. For example, if the content of one of the isomers or enantiomers is 90% and the content of the other isomer or enantiomer is 10%, the isomeric or enantiomeric excess (ee) is 80%.

Optically active (R)- and (S)-isomers and D and L isomers can be prepared by chiral synthesis or chiral reagents or other conventional techniques. An enantiomer of a certain compound disclosed herein can be prepared by asymmetric synthesis or derivatization using a chiral additive, wherein the resulting diastereoisomeric mixture is separated and the auxiliary group is cleaved so as to provide the desired pure enantiomer. Alternatively, when the molecule contains a basic functional group (such as amino) or an acidic functional group (such as carboxyl), the compound reacts with an appropriate optically active acid or base to form a salt of the diastereoisomer, which is then subjected to diastereomeric resolution through conventional methods in the art to give the pure enantiomer. Furthermore, the enantiomer and the diastereoisomer are generally isolated through chromatography using a chiral stationary phase, optionally in combination with chemical derivatization (e.g., carbamate generated from amines). The compound of the present application may contain an unnatural proportion of atomic isotope at one or more of the atoms that constitute the compound. For example, the compound may be labeled with a radioisotope, such as tritium ($^{3}H$), iodine-125 ($^{125}I$), or C-14 ($^{14}C$). For another example, hydrogen can be substituted by deuterium to form a deuterated drug, and the bond formed by deuterium and carbon is firmer than that formed by common hydrogen and carbon. Compared with an un-deuterated drug, the deuterated drug has the advantages of reduced toxic side effects, increased stability, enhanced efficacy, prolonged biological half-life, and the like. All isotopic variations of the compound of the present application, whether radioactive or not, are encompassed within the scope of the present application.

The term "optional" or "optionally" means that the subsequently described event or circumstance may, but not necessarily, occur, and the description includes instances where the event or circumstance occurs and instances where it does not.

The term "substituted" means that one or more hydrogen atoms on a specific atom are substituted by substituents, wherein the substituents may include deuterium and hydrogen variants, as long as the valence of the specific atom is normal and the substituted compound is stable. When the substituent is oxygen (i.e., =O), it means that two hydrogen atoms are substituted. Substitution by oxygen does not occur on aromatic groups. The term "optionally substituted" means that an atom can be or cannot be substituted by a substituent. Unless otherwise specified, the type and number of the substituent may be arbitrary as long as being chemically achievable.

When any variable (e.g., R) occurs once or more in the constitution or structure of a compound, the definition of the variable in each case is independent. Thus, for example, if a group is substituted with 0-2 R, the group can be optionally substituted with up to two R, and the definition of R in each case is independent. Furthermore, a combination of the substituent and/or the variant thereof is permissible only if the combination can result in a stable compound.

When the number of a connecting group is 0, for example, $-(CRR)_0-$, it means that the connecting group is a single bond.

When one of the variables is selected from a single bond, it means that the two groups linked by the single bond are connected directly. For example, in A-L-Z, when L represents a single bond, it means that the structure is actually A-Z.

When a substituent is absent, it means that the substituent does not exist. For example, when X is absent in A-X, the structure of A-X is actually A. When it is not specified by which atom the listed substituent is linked to the group to be substituted, the substituent can be linked via any atom of the group. For example, pyridinyl as a substituent can be linked to the group to be substituted through any carbon atom on the pyridine ring.

When the direction for connection of the listed connecting group is not specified, the direction for connection is arbitrary. For example, when the connecting group L contained in

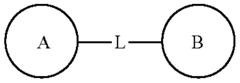

is -M-W—, -M-W— can either connect ring A and ring B in a direction same as left-to-right reading order to form

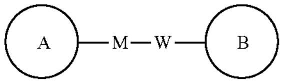, or connect ring A and ring B in a direction opposite to the left-to-right reading order to form

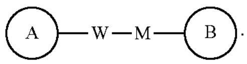.

A combination of the connecting group, the substituent and/or the variant thereof is permissible only if the combination can result in a stable compound.

Unless otherwise specified, when a group has one or more connectable sites, any one or more of the sites of the group may be connected to other groups by chemical bonds. If there is no designated connecting mode for chemical bonds and H atoms are present at a connectable site, when the connectable site is connected to chemical bonds, the number of the H atoms at the connectable site is correspondingly reduced based on the number of the connected chemical bonds, and a number of groups corresponding to the valence number are thus formed. The chemical bond that connects the site and another group may be represented by a straight solid bond (), a straight dashed bond (), or a wavy line (().). For example, the straight solid bond in $-OCH_3$ indicates that the group is connected to another group through the oxygen atom; in

, the straight dashed bond indicates that the group is connected to another group through the two ends of the nitrogen atom;

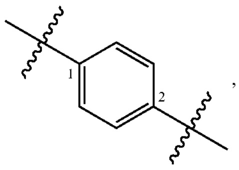 [SMILES: *c1ccc(*)cc1], the wavy line indicates that the phenyl group is connected to another group through the carbon atoms on positions 1 and 2.

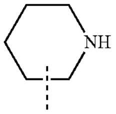

indicates that any connectable site on the piperidinyl can be connected to another group through 1 bond in at least 4 connecting modes:

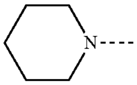, 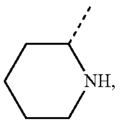, 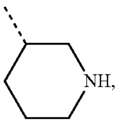, and

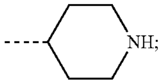;

even if —N— is connected with a H atom,

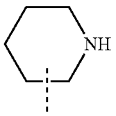

includes the connection mode of

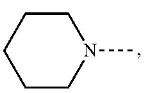, but when 1 chemical bond is connected to a site, the number of H at that site is correspondingly reduced by 1 and a monovalent piperidinyl is thus formed.

When a chemical bond of a substituent intersects a chemical bond between two atoms on a connecting ring, it means that the substituent may be bonded to any atom on the ring. When the atom to which a substituent is connected is not specified, the substituent may be bonded to any atom, and if the atom to which the substituent is connected is in a bicyclic or tricyclic ring system, it means that the substituent may be bonded to any atom on any ring in the system. A combination of substituents and/or variables is permissible only if the combination results in a stable compound. For example, structural unit

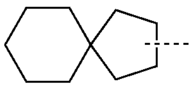 or 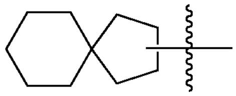

represents that substitution may occur at any one position of cyclohexyl or cyclopentyl.

Unless otherwise specified, the term "$C_{1-4}$ alkyl" refers to a linear or branched saturated hydrocarbon group consisting of 1 to 4 carbon atoms. The $C_{1-4}$ alkyl includes, but is not limited to, $C_{1-2}$ alkyl, $C_{1-3}$ alkyl, $C_{2-3}$ alkyl, and the like, and may be monovalent (e.g., methyl), divalent (e.g., methylene) or polyvalent (e.g., methenyl). Examples of $C_{1-4}$ alkyl include, but are not limited to, methyl (Me), ethyl (Et), propyl (including n-propyl and isopropyl), butyl (including n-butyl, isobutyl, s-butyl, t-butyl), and the like.

Unless otherwise specified, the term "$C_{3-4}$ cycloalkyl" refers to any stable cyclic alkyl group containing 3 to 4 carbon atoms, which is a monocyclic ring system and may be monovalent, divalent, or polyvalent. Examples of $C_{3-4}$ cycloalkyl include cyclopropyl and cyclobutyl.

Unless otherwise specified, the terms "5-membered heteroaromatic ring" and "5-membered heteroaryl" are used interchangeably, and the term "5-membered heteroaryl" refers to a monocyclic group consisting of 5 ring atoms with a conjugated it-electron system, of which 1, 2, 3, or 4 ring atoms are heteroatoms independently selected from the group consisting of O, S, and N, and the rest are carbon atoms. The nitrogen atom is optionally quaternized, and the nitrogen and sulfur heteroatoms can be optionally oxidized (i.e., NO and $S(O)_p$, wherein p is 1 or 2). The 5- to 6-membered heteroaryl can be connected to the rest of the molecule through a heteroatom or a carbon atom. Examples of the 5-membered heteroaryl include, but are not limited to, pyrrolyl (including N-pyrrolyl, 2-pyrrolyl, 3-pyrrolyl, and the like), pyrazolyl (including 2-pyrazolyl, 3-pyrazolyl, and the like), imidazolyl (including N-imidazolyl, 2-imidazolyl, 4-imidazolyl, 5-imidazolyl, and the like), oxazolyl (including 2-oxazolyl, 4-oxazolyl, 5-oxazolyl, and the like), triazolyl (including 1H-1,2,3-triazolyl, 2H-1,2,3-triazolyl, 1H-1,2,4-triazolyl, 4H-1,2,4-triazolyl, and the like), tetrazolyl, isoxazolyl (including 3-isoxazolyl, 4-isoxazolyl, 5-isoxazolyl, and the like), thiazolyl (including 2-thiazolyl, 4-thiazolyl, 5-thiazolyl, and the like), furanyl (including 2-furanyl, 3-furanyl, and the like), and thienyl (including 2-thienyl, 3-thienyl, and the like).

Unless otherwise specified, $C_{n-n+m}$ or $C_n$—$C_{n+m}$ includes any one of the specific cases of n to n+m carbon atoms. For example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$. Also, any range within n to n+m may be included. For example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$ and $C_{9-12}$, etc. Similarly, n– to n+m-membered represents that the number of atoms on the ring is n to n+m. For example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring. n– to n+m-membered also represents any range within n to n+m. For example, 3- to 12-membered ring includes 3- to 6-membered ring, 3- to 9-membered ring, 5- to 6-membered ring, 5- to 7-membered ring, 6- to 7-membered ring, 6- to 8-membered ring, 6- to 10-membered ring, and the like.

The term "leaving group" refers to a functional group or atom that can be replaced by another functional group or atom through a substitution reaction (e.g., nucleophilic substitution). For example, representative leaving groups include triflate; chlorine, bromine and iodine; sulfonate groups, such as mesylate, tosylate, p-bromobenzenesulfonate, and p-toluenesulfonate; and acyloxy groups, such as acetoxy and trifluoroacetoxy.

The term "protecting group" includes, but is not limited to, "amino protecting group", "hydroxy protecting group" or "sulfydryl protecting group". The term "amino protecting group" refers to a protecting group suitable for preventing side reactions at the nitrogen atom of the amino. Representative amino protecting groups include, but are not limited to: formyl; acyl, such as alkanoyl (such as acetyl, trichloroacetyl, or trifluoroacetyl); alkoxycarbonyl, such as tert-butoxycarbonyl (Boc); arylmethoxycarbonyl, such as carbobenzoxy (Cbz) and 9-fluorenylmethoxycarbonyl (Fmoc); arylmethyl, such as benzyl (Bn), trityl (Tr), 1,1-di-(4'-methoxyphenyl)methyl; and silyl, such as trimethylsilyl (TMS), 2-(trimethylsilyl)ethoxymethyl (SEM), and tert-butyldimethylsilyl (TBS), etc. The term "hydroxy protecting group" refers to a protecting group suitable for preventing side reactions of the hydroxy group. Representative hydroxy protecting groups include, but are not limited to: alkyl, such as methyl, ethyl, and tert-butyl; acyl, such as alkanoyl (such as acetyl); arylmethyl, such as benzyl (Bn), p-methoxybenzyl (PMB), 9-fluorenylmethyl (Fm) and diphenylmethyl (DPM); and silyl, such as trimethylsilyl (TMS) and tert-butyldimethylsilyl (TBS), etc.

The compounds of the present application can be prepared using a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples of the present application.

The compound of the present application may be structurally confirmed by conventional methods well known to those skilled in the art; if the present application relates to the absolute configuration of the compound, this absolute configuration may be confirmed by means of conventional techniques in the art. For example, in single crystal X-ray diffraction (SXRD), intensity data of diffraction of the single crystal grown are collected with a Bruker D8 venture diffractometer, with the light source being Cu-Kα radiation and the scanning mode being p/o scanning; after related data are collected, a direct method (Shelxs97) is further employed to analyze the crystal structure, and thus the absolute configuration can be confirmed.

The solvents used herein are commercially available.

The present application employs the following abbreviations: MR for mineralocorticoid receptor; ACEI for angiotensin-converting enzyme inhibitor; ARB for angiotensin receptor blocker; UACR for urine albumin-to-creatinine ratio; RAAS for renin-angiotensin-aldosterone system; g for gram; mg for milligram; L for microliter; mL for milliliter; mol for mole; mmol for millimole; μmol for micromole; M for mole/liter; mM for millimole/liter; M for micromole/liter; nM for nanomole/liter; Me for methyl; Boc for tert-butyloxycarbonyl; DMSO-$d_6$ for deuterated dimethyl sulfoxide; $CD_3OD$ for deuterated methanol; $CDCl_3$ for deuterated chloroform; DEA for diethanolamine; SFC for supercritical fluid chromatography.

DETAILED DESCRIPTION

The present application is described in detail below by way of examples. However, this is by no means disadvantageously limiting the scope of the present application. Although the present application has been described in detail herein and specific examples have also been disclosed, it will be apparent to those skilled in the art that various changes and modifications can be made to the specific examples without departing from the spirit and scope of the present application.

Intermediate A

Synthetic Route:

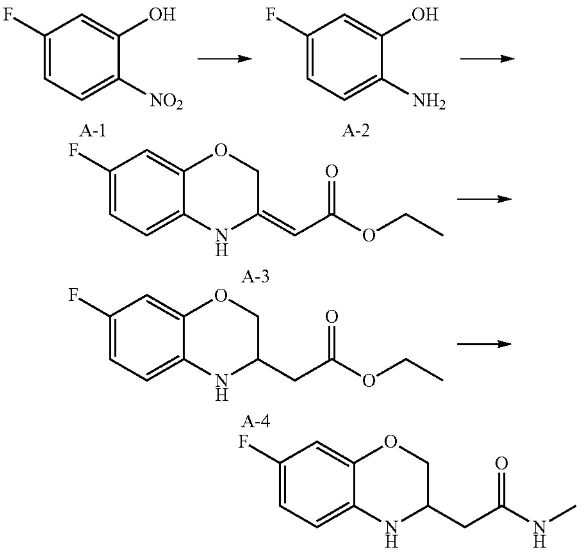

A-1 A-2 A-3 A-4 Intermediate A

Step 1

Compound A-1 (50.0 g, 318 mmol) was dissolved in methanol (500 mL), and palladium on carbon (6.00 g, 10% purity) was added to the reaction solution under nitrogen atmosphere. The reaction mixture was purged several times with hydrogen, then stirred under 50 psi hydrogen atmosphere at 20° C. for 24 h, and filtered. The filtrate was concentrated under reduced pressure to give crude compound A-2. MS-ESI calcd. $[M+H]^+$ 128, found 128.

Step 2

Ethyl 4-chloroacetoacetate (47.0 g, 286 mmol) was dissolved in tetrahydrofuran (340 mL), and compound A-2 (33.0 g, 260 mmol) was added to the reaction solution. The reaction mixture was heated to 50° C. N,N-Diisopropylethylamine (33.6 g, 260 mmol) was added to the reaction mixture at 50° C., and the mixture was stirred at 50° C. for 12 h, then diluted with water (200 mL), and extracted with ethyl acetate (300 mL×3). The organic phases were combined, washed with saturated brine (200 mL×2), dried over anhydrous sodium sulfate, and filtered. The filtrate was concentrated under reduced pressure. The resulting crude product was separated by silica gel column chromatography (eluent: petroleum ether/ethyl acetate, 20/1-10/1, V/V) to give compound A-3. MS-ESI calcd. $[M+H]^+$ 238, found 238.

Step 3

Compound A-3 (15.0 g, 63.2 mmol) was dissolved in ethanol (200 mL), and palladium on carbon (2.00 g, 10% purity) was added to the reaction solution under nitrogen atmosphere. The reaction mixture was purged several times with hydrogen, then stirred under 50 psi hydrogen atmosphere at 20° C. for 12 h, and filtered. The filtrate was concentrated under reduced pressure, and the resulting crude product was separated by silica gel column chromatography (eluent: petroleum ether/ethyl acetate, 50/1-2/1, V/V) to give compound A-4. MS-ESI calcd. $[M+H]^+$ 240, found 240.

Step 4

Compound A-4 (12.0 g, 50.2 mmol) was dissolved in ethanol (50 mL), and a solution of methylamine in ethanol (35.5 g, 343 mmol) was added to the reaction solution. The reaction mixture was stirred at 25° C. for 12 h, then diluted with water (100 mL), and extracted with ethyl acetate (200 mL×3). The organic phases were combined, washed with saturated brine (200 mL), dried over anhydrous sodium sulfate, and filtered. The filtrate was concentrated under reduced pressure to give intermediate A. MS-ESI calcd. $[M+H]^+$ 225, found 225.

Intermediate B

Synthetic Route:

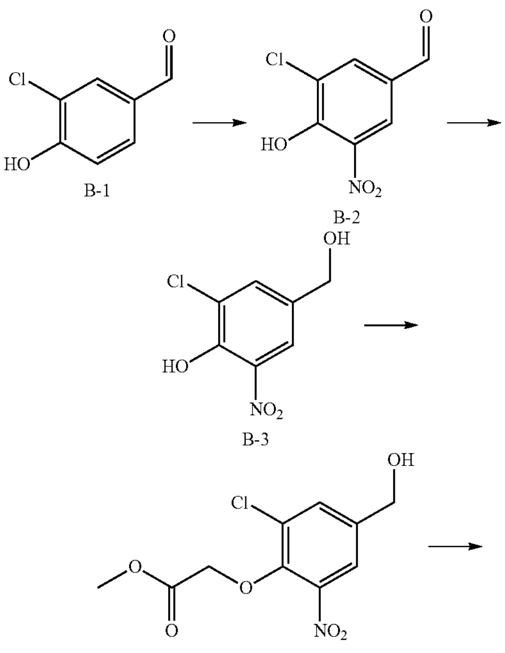

B-1

B-2

B-3

B-4

-continued

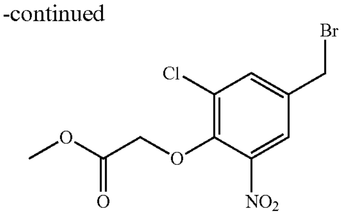

Intermediate B

Step 1

Compound B-1 (25.0 g, 160 mmol) was dissolved in glacial acetic acid (200 mL), and a 60% nitric acid solution (22.5 g, 232 mmol) was added slowly and dropwise to the reaction solution at 0° C. The reaction mixture was stirred at 25° C. for 5 h. 400 mL of ice water was added to the reaction mixture, and the resulting mixture was filtered. The filter cake was collected and dried to give crude compound B-2.

Step 2

Compound B-2 (17.1 g, 84.8 mmol) was dissolved in methanol (150 mL), and sodium borohydride (6.42 g, 170 mmol) was added slowly and portionwise to the reaction solution at 0° C. The reaction mixture was stirred at 25° C. for 1 h. Water (200 mL) was added to the reaction mixture, and the resulting mixture was adjusted to pH 4 with 12 M hydrochloric acid, stirred for 1 h, and extracted with ethyl acetate (200 mL×5). The organic phases were combined, washed with saturated brine (200 mL), dried over anhydrous sodium sulfate, and filtered. The filtrate was concentrated under reduced pressure to give crude compound B-3.

Step 3

Compound B-3 (22.0 g, 108 mmol) and methyl bromoacetate (19.8 g, 130 mmol) were dissolved in N,N-dimethylformamide (200 mL), and potassium carbonate (22.0 g, 162 mmol) was added to the reaction solution. The reaction mixture was stirred at 80° C. for 1.5 h, then diluted with water (500 mL), and extracted with ethyl acetate (200 mL×3). The organic phases were combined, washed with saturated brine (300 mL×3), dried over anhydrous sodium sulfate, and filtered. The filtrate was concentrated under reduced pressure to give crude compound B-4. MS-ESI calcd. $[M+H]^+$ 276, found 276.

Step 4

Compound B-4 (22.1 g, 80.2 mmol) was dissolved in anhydrous dichloromethane (200 mL), and phosphorus tribromide (32, 6 g, 120 mmol) was added slowly and dropwise to the reaction solution at 0° C. The reaction mixture was stirred at 25° C. for 2 h, then diluted with ice water (500 mL), and extracted with ethyl acetate (400 mL×3). The organic phases were combined, washed with saturated brine (50 mL), dried over anhydrous sodium sulfate, and filtered. The filtrate was concentrated under reduced pressure. The crude product was separated by silica gel column chromatography (eluent: petroleum ether/ethyl acetate, 3/1, V/V) to give intermediate B. $^1H$ NMR (400 MHz, $CDCl_3$) δ 7.79 (d, J=2.4 Hz, 1H), 7.68 (d, J=2.4 Hz, 1H), 4.81 (s, 2H), 4.43 (s, 2H), 3.83 (s, 3H) ppm.

Intermediate C

Synthetic Route:

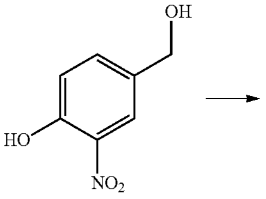

C-1

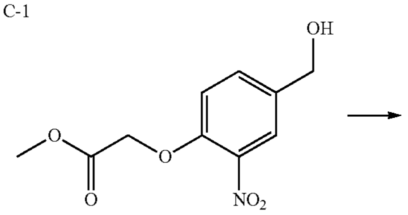

C-2

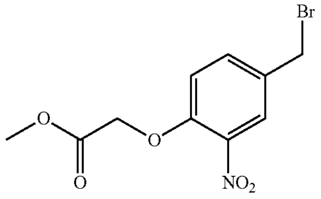

Intermediate C

Step 1

Compound C-1 (0.5 g, 2.96 mmol) and methyl bromoacetate (543 mg, 3.55 mmol) were dissolved in N,N-dimethylformamide (7.5 mL), and potassium carbonate (613 mg, 4.43 mmol) was added to the reaction solution. The reaction mixture was stirred at 80° C. for 0.5 h. Water (10 mL) was added to the reaction mixture, and the resulting mixture was extracted with ethyl acetate (10 mL×3). The organic phases were combined, washed with saturated brine (50 mL), dried over anhydrous sodium sulfate, and filtered. The filtrate was concentrated under reduced pressure to give crude compound C-2.

Step 2

Compound C-2 (0.72 g, 2.99 mmol) was dissolved in anhydrous dichloromethane (11 mL), and phosphorus tribromide (889 mg, 3.28 mmol) was added slowly and dropwise to the reaction solution at 0° C. The reaction mixture was stirred at 20° C. for 1 h and then slowly poured into a saturated aqueous sodium bicarbonate solution (20 mL). The resulting mixture was extracted with dichloromethane (10 mL×2), and the organic phase was washed with saturated brine (50 mL), dried over anhydrous sodium sulfate, and filtered. The filtrate was concentrated under reduced pressure, and the resulting crude product was separated and purified by silica gel column chromatography (eluent: petroleum ether/ethyl acetate, 5/1, V/V) to give intermediate C. $^1H$ NMR (400 MHz, $CDCl_3$) δ 7.93 (d, J=2.4 Hz, 1H), 7.60-7.54 (m, 1H), 6.96 (d, J=8.8 Hz, 1H), 4.81 (s, 2H), 4.47 (s, 2H), 3.82 (s, 3H) ppm.

Intermediate D

Synthetic Route:

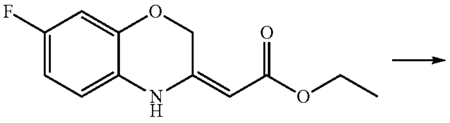

A-3

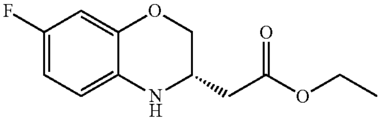

Intermediate D

Step 1

Compound A-3 (30.0 g, 126 mmol) and (+)-1,2-bis ((2S, 5S)-2,5-diphenylphospholano)ethane(1,5-cyclooctadiene) rhodium(I) tetrafluoroborate (2.24 g, 2.78 mmol) were dissolved in ethanol (300 mL), and zinc trifluoromethanesulfonate (4.60 g, 12.7 mmol) was added to the reaction solution under nitrogen atmosphere. The reaction mixture was purged several times with hydrogen, then stirred under 50 psi hydrogen atmosphere at 60° C. for 16 h, and filtered. The filtrate was concentrated under reduced pressure, and the resulting crude product was separated by silica gel column chromatography (eluent: petroleum ether/ethyl acetate, 200/1-2/1, V/V) to give intermediate D. MS-ESI calcd. $[M+H]^+$ 240, found 240.

Intermediate E

Synthetic Route:

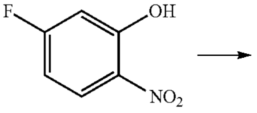

A-1

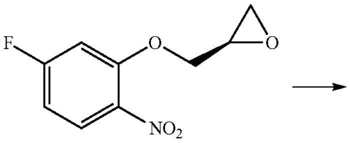

E-1

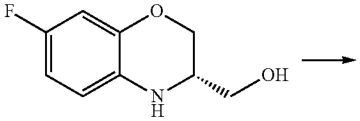

E-2

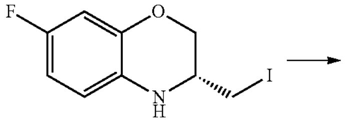

E-3

-continued

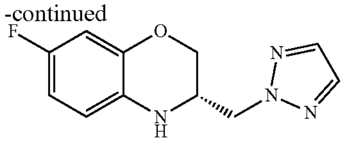

Intermediate E

Step 1

(S)-Glycidol (10.6 g, 143 mmol, 9.47 mL) was dissolved in tetrahydrofuran (150 mL), and triphenylphosphine (37.6 g, 143 mmol) and compound A-1 (15.0 g, 95.5 mmol) were added. The mixture was cooled to 0° C., and diethyl azodicarboxylate (24.9 g, 143 mmol, 26.0 mL) was added slowly. The reaction mixture was stirred at 20° C. for 14 h and then concentrated under reduced pressure. The crude product resulting from the concentration was separated and purified by silica gel column chromatography (petroleum ether/ethyl acetate, 5/1-1/1, V/V) to give compound E-1.

Step 2

E-1 (5.00 g, 23.5 mmol) was dissolved in ethanol (920 mL), water (154 mL) and glacial acetic acid (12.7 g, 211 mmol, 12.1 mL), and iron powder (7.86 g, 141 mmol) was added. The reaction mixture was stirred at 80° C. for reaction for 14 h and then filtered. The filtrate was concentrated under reduced pressure. A saturated aqueous sodium carbonate solution (100 mL) was added to the crude product resulting from the concentration, and the mixture was extracted with ethyl acetate (100 mL×3). The organic phases were combined, dried over anhydrous sodium sulfate, and filtered, and the filtrate was concentrated under reduced pressure. The crude product resulting from the concentration was separated and purified by silica gel column chromatography (dichloromethane/methanol, 100/0-20/1, V/V) to give compound E-2. MS-ESI calcd. $[M+H]^+$ 184, found 184.

Step 3

E-2 (25.0 g, 136 mmol), imidazole (16.7 g, 24.6 mmol), and triphenylphosphine (50.1 g, 191 mmol) were dissolved in dichloromethane (250 mL), and iodine (52.0 g, 205 mmol) was added to the reaction solution at 0° C. The reaction mixture was stirred at 20° C. for 0.5 h. A saturated sodium sulfite solution (300 mL) was added to the reaction mixture, and the resulting mixture was extracted with dichloromethane (500 mL×2). The organic phases were combined, washed with saturated brine, dried over anhydrous sodium sulfate, and filtered. The filtrate was concentrated under reduced pressure, and the crude product was stirred with methyl tert-butyl ether (1 L). The mixture was filtered, and the filter cake was collected and then separated by silica gel column chromatography (eluent: petroleum ether/ethyl acetate, 10/1-10/1, V/V) to give compound intermediate E-3.

Step 4

Compound intermediate E-3 (20 g, 68.2 mmol) and 1H-1,2,3-triazole (18.9 g, 273 mmol) were dissolved in acetonitrile (400 mL), and potassium carbonate (18.9 g, 136 mmol) was added to the reaction solution. The reaction mixture was stirred at 80° C. for 18 h and then filtered. The filtrate was concentrated under reduced pressure. The crude product resulting from the concentration was separated by silica gel column chromatography (eluent: petroleum ether/ethyl acetate, 15/1-8/1, V/V) to give intermediate E. MS-ESI calcd. $[M+H]^+$ 235, found 235.

Intermediate F

Synthetic Route:

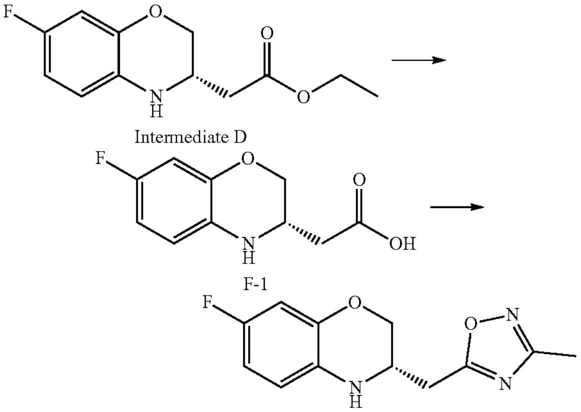

Intermediate D

F-1

Intermediate F

Step 1

Intermediate D (20 g, 83.6 mmol) was dissolved in methanol (200 mL), and a solution of lithium hydroxide monohydrate (17.5 g, 418 mmol) in water (50 mL) was added to the reaction solution. The reaction mixture was stirred at 20° C. for 12 h. The reaction solution was adjusted to about pH 4 with 12 M hydrochloric acid, and water (200 mL) was added. The mixture was extracted with ethyl acetate (200 mL×2), and the organic phases were combined, washed with saturated brine (300 mL), dried over anhydrous sodium sulfate, and filtered. The filtrate was concentrated under reduced pressure to give crude compound F-1. MS-ESI calcd. $[M+H]^+$ 212, found 212.

Step 2

Compound F-1 (17.5 g, 82.9 mmol) was dissolved in N,N-dimethylformamide (200 mL), and 1,1'-carbonyldiimidazole (16.1 g, 99.4 mmol) was added to the reaction solution. The reaction mixture was stirred at 20° C. for 1 h. N-Hydroxyacetamidine (7.37 g, 99.4 μmol) was added to the reaction solution, and the reaction mixture was stirred at 20° C. for 1 h. The reaction mixture was then stirred at 80° C. for 24 h. Water (500 mL) was added to the reaction mixture, and the resulting mixture was extracted with ethyl acetate (500 mL×3). The organic phases were combined, washed with saturated brine (500 mL), dried over anhydrous sodium sulfate, and filtered. The filtrate was concentrated under reduced pressure, and the crude product resulting from the concentration was separated by silica gel column chromatography (eluent: petroleum ether/ethyl acetate, 20/1-3/1, V/V) to give intermediate F. MS-ESI calcd. $[M+H]^+$ 250, found 250.

Intermediate G

Synthetic Route:

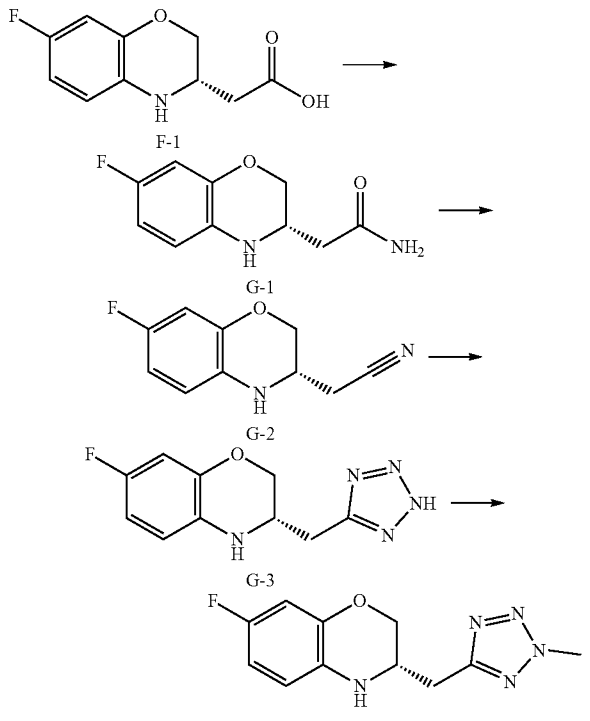

Intermediate G

Step 1

F-1 (3.00 g, 14.2 mmol) was dissolved in N,N-dimethylformamide (30 mL), and 1,1'-carbonyldiimidazole (3.46 g, 21.3 mmol) was added to the reaction solution. The reaction mixture was stirred at 25° C. for 0.5 h. Ammonium chloride (2.28 g, 42.6 mmol) and N,N-diisopropylethylamine (5.51 g, 42.6 mmol) were then added to the reaction solution, and the reaction mixture was stirred at 25° C. for 12 h, then diluted with water (200 mL), and extracted with ethyl acetate (150 mL×2). The organic phases were combined, washed with saturated brine, dried over anhydrous sodium sulfate, and filtered. The filtrate was concentrated under reduced pressure to give compound G-1. MS-ESI calcd. $[M+H]^+$ 211, found 211.

Step 2

Palladium dichloride (1.05 g, 5.95 mmol) was added to a mixed solution of compound G-1 (2.50 g, 1.13 mmol) in acetonitrile (10 mL) and water (10 mL), and the reaction mixture was stirred at 50° C. for reaction for 12 h, then diluted with water (100 mL), and extracted with ethyl acetate (100 mL×2). The organic phases were combined, washed with saturated brine, dried over anhydrous sodium sulfate, and filtered. The filtrate was concentrated under reduced pressure, and the resulting crude product was separated by silica gel column chromatography (petroleum ether/ethyl acetate, 3:1-3:1, V/V) to give compound G-2. MS-ESI calcd. $[M+H]^+$ 193, found 193.

Step 3

Compound G-2 (1.30 g, 6.76 mmol), azidotrimethylsilane (3.28 g, 27.1 mmol, 3.75 mL), and dibutyltin oxide (1.04 g, 4.19 mmol) were dissolved in toluene (5 mL), and the reaction solution was stirred at 100° C. under nitrogen atmosphere for reaction for 2.5 h. A saturated aqueous KF solution (100 mL) was first added to the reaction solution, and the mixture was stirred for at least one hour. A saturated sodium bicarbonate solution (100 mL) was then added, and the mixture was extracted with ethyl acetate (100 mL×2). The organic phases were combined, washed with saturated brine, dried over anhydrous sodium sulfate, and filtered. The filtrate was concentrated under reduced pressure to give compound G-3. MS-ESI calcd. $[M+H]^+$ 236, found 236.

Step 4

Compound G-3 (200 mg, 505 mol) was dissolved in tetrahydrofuran (3 mL) and methanol (10 mL), and diazomethyl(trimethyl)silane (2 M, 11.1 mmol, 5.53 mL) was added to the reaction solution. The reaction mixture was stirred at 25° C. for reaction for 1.5 h, then diluted with water (100 mL), and extracted with ethyl acetate (100 mL×2). The organic phases were combined, washed with saturated brine, dried over anhydrous sodium sulfate, and filtered. The filtrate was concentrated under reduced pressure, and the resulting crude product was separated by silica gel column chromatography (petroleum ether/ethyl acetate, 5:1-1:1, V/V) to give intermediate G. MS-ESI calcd. $[M+H]^+$ 250, found 250. $^1H$ NMR (400 MHz, $CDCl_3$) δ ppm 6.66-6.44 (m, 3H), 4.41-4.22 (m, 5H), 4.09-3.98 (m, 1H), 3.89-3.79 (m, 1H), 3.20-2.99 (m, 2H).

Intermediate H

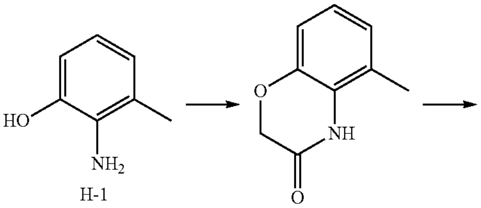

H-1 H-2

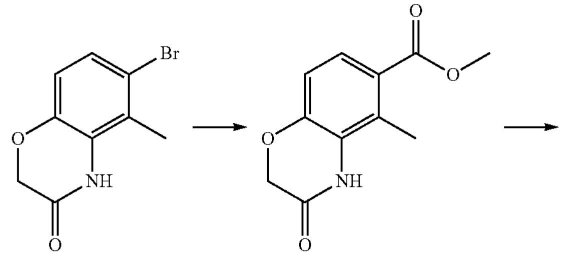

H-3 H-4

-continued

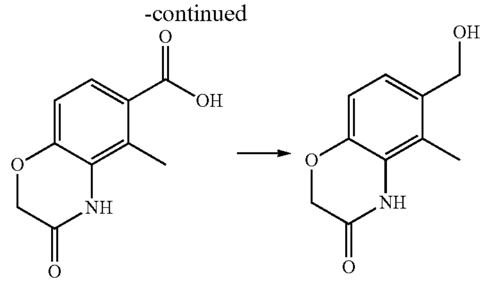

H-5 Intermediate H

Step 1

Compound H-1 (25 g, 203 mmol) and potassium carbonate (84.2 g, 609 mmol) were dissolved in N,N-dimethylformamide (200 mL). Chloroacetyl chloride (17.0 mL, 213 mmol) was added at 0° C., and the mixture was allowed to react at 20° C. for 2 h. Water (1.5 L) was added to the reaction mixture, and the resulting mixture was stirred for 20 min and then filtered. The filter cake was dried to give compound H-2. MS-ESI calcd. $[M+H]^+$ 164, found 164.

Step 2

Compound H-2 (25.6 g, 157 mmol) was dissolved in N,N-dimethylformamide (250 mL). N-Bromosuccinimide (30.7 g, 173 mmol) was added, and the mixture was stirred at 20° C. for 0.5 h. Water (1500 mL) was added to the reaction mixture, and the resulting mixture was stirred for 30 min and then filtered. The filter cake was dried under reduced pressure to give compound H-3. MS-ESI calcd. $[M+H]^+$ 242/244, found 242/244.

Step 3

Compound H-3 (1 g, 4.13 mmol) and [1,1-bis(diphenylphosphino)ferrocene]palladium chloride (302 mg, 413 μmol) were dissolved in methanol (20 mL) and N,N-dimethylformamide (10 mL). Triethylamine (1.25 g, 12.4 mmol, 1.72 mL) was added, and the reaction mixture was stirred at 80° C. under carbon monoxide atmosphere (50 psi) for 16 h and then concentrated under reduced pressure to give a crude product, which was then separated and purified by silica gel column chromatography (eluent: petroleum ether/ethyl acetate, 5/1-1/1, V/V) to give compound H-4. MS-ESI calcd. $[M+H]^+$ 222, found 222.

Step 4

Compound H-4 (500 mg, 2.26 mmol) was dissolved in methanol (5 mL) and tetrahydrofuran (5 mL), and a solution of lithium hydroxide monohydrate (948 mg, 22.6 mmol) in water (2 mL) was added to the reaction solution. The reaction mixture was stirred at 65° C. for 1 h. Water (20 mL) was added to the reaction mixture, and the mixture was adjusted to about pH 5 with concentrated hydrochloric acid and then filtered. The filter cake was dried to give crude compound H-5. MS-ESI calcd. $[M+H]^+$ 208, found 208.

Step 5

Compound H-5 (400 mg, 1.93 mmol) was dissolved in acetonitrile (15 mL), and 1,1'-carbonyldiimidazole (626 mg, 3.86 mmol) was added to the reaction solution. The reaction mixture was stirred at 20° C. for 1 h. A solution of sodium borohydride (361 mg, 9.54 mmol) in water (5 mL) was added to the reaction mixture, and the reaction mixture was stirred at 20° C. for 0.5 h and then adjusted to pH 2 with 2 M hydrochloric acid. Water (20 mL) was added, and the mixture was extracted with ethyl acetate (30 mL×2). The organic phases were combined, washed with saturated brine, dried over anhydrous sodium sulfate, and filtered. The filtrate was concentrated under reduced pressure to give intermediate H. MS-ESI calcd. $[M+H]^+$ 194, found 194. $^1H$ NMR (400 MHz, DMSO-$d_6$) δ ppm 10.25-10.06 (m, 1H), 7.02-6.85 (m, 1H), 6.83-6.70 (m, 1H), 5.06-4.88 (m, 1H), 4.50-4.33 (m, 4H), 2.22-2.06 (m, 3H).

Intermediate I

Synthetic Route:

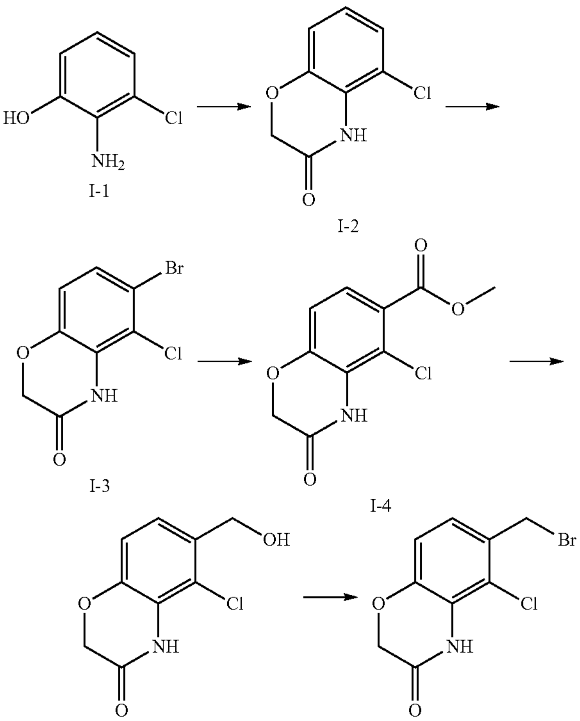

I-1 I-2 I-3 I-4 I-5 I

Step 1

Compound I-1 (3 g, 20.9 mmol) and potassium carbonate (8.66 g, 62.69 mmol) were dissolved in N,N-dimethylformamide (540 mL), and chloroacetyl chloride (2 mL, 25.15 mmol) was added at 0° C. The reaction mixture was allowed to react at 50° C. for 16 h and then concentrated under reduced pressure. A saturated aqueous sodium bicarbonate solution (50 mL) was then added to the reaction mixture, and the resulting mixture was extracted with ethyl acetate (50 mL×2). The organic phases were combined, washed with saturated brine (50 mL×2), and filtered. The filter cake was dried under reduced pressure to give compound I-2. MS-ESI calcd. $[M+H]^+$ 184, found 184.

Step 2

Compound I-2 (3.7 g, 20.15 mmol) was dissolved in acetonitrile (80 mL), and N-bromosuccinimide (3.95 g, 20.17 mmol) was added. The mixture was stirred at 30° C. for 14 h and then filtered. The filter cake was dried under reduced pressure to give compound I-3. MS-ESI calcd. $[M+H]^+$ 262/264, found 262/264.

Step 3

Compound I-3 (4 g, 15.24 mmol) and [1,1-bis(diphenylphosphino)ferrocene]palladium chloride (1.12 g, 1.53 mmol) were dissolved in methanol (120 mL). Triethylamine (4.65 g, 45.98 mmol, 6.4 mL) was added, and the reaction mixture was stirred at 80° C. under carbon monoxide atmosphere (50 psi) for 16 h and then concentrated under reduced pressure to give compound I-4. MS-ESI calcd. $[M+H]^+$ 242, found 242.

Step 4

Lithium aluminum hydride (314.16 mg, 8.28 mmol) was dissolved in tetrahydrofuran (5 mL), and a solution of compound I-4 (800 mg, 3.31 mmol) in tetrahydrofuran (5 mL) was added to the reaction solution under nitrogen atmosphere at 0° C. The reaction mixture was stirred at 20° C. for 2 h and then cooled to 0° C. Water (10 mL) and an aqueous sodium hydroxide solution (1 M, 4 mL) were added sequentially to quench the reaction, and the mixture was adjusted to about pH 5 with concentrated hydrochloric acid and then filtered. The filter cake was dried to give crude compound I-5. MS-ESI calcd. $[M+H]^+$ 214, found 214.

Step 5

Compound I-5 (50 mg, 234.06 μmol) was dissolved in dichloromethane (5 mL), and phosphorus tribromide (76.03 mg, 280.88 μmol) was added dropwise to the reaction solution at 0° C. The reaction mixture was stirred at 20° C. for 1 h. Water (5 mL) was added to the reaction mixture, and the resulting mixture was adjusted to pH 8 with saturated sodium bicarbonate and then extracted with ethyl acetate (30 mL×3). The organic phases were combined, washed with saturated brine (20 mL×2), dried over anhydrous sodium sulfate, and filtered. The filtrate was concentrated under reduced pressure to give crude intermediate I. MS-ESI calcd. $[M+H]^+$ 276/278, found 276/278.

Intermediate J

Synthetic Route:

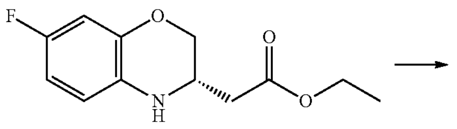

Intermediate D

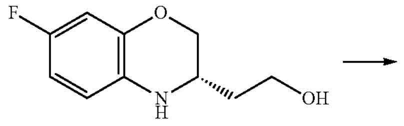

J-1

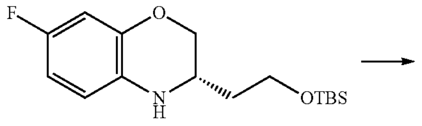

J-2

-continued

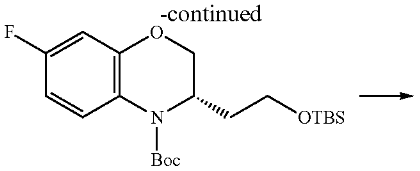

J-3

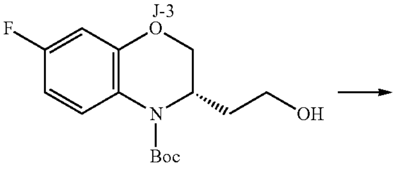

J-4

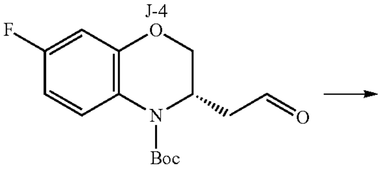

J-5

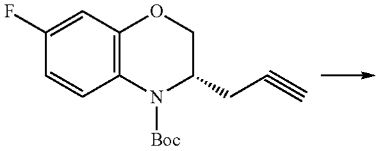

J-6

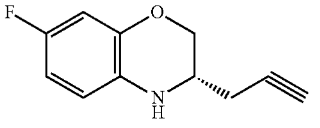

Intermediate J

Step 1

Lithium aluminum hydride (7.14 g, 188.09 mmol) was dispersed in tetrahydrofuran (200 mL). Intermediate D (30 g, 125.40 mmol) was dissolved in 100 mL of tetrahydrofuran in an ice-water bath, and the solution was added dropwise to the lithium aluminum hydride dispersion system. After the addition was completed, the reaction mixture was warmed to 25° C. and stirred for 2 h at 25° C. Water (7 mL) and a 15% aqueous sodium hydroxide solution (7 mL) were added to the reaction mixture, and the resulting mixture was diluted with water (21 mL) and then filtered. The filtrate was concentrated under reduced pressure to give compound J-1. MS-ESI calcd. $[M+H]^+$ 198, found 198.

Step 2

Dimethyl tert-butyl chlorosilane (82.54 g, 547.65 mmol) and imidazole (49.71 g, 730.20 mmol) were added to a solution of compound J-1 (72 g, 365.10 mmol) in N,N-dimethylformamide (500 mL). The reaction mixture was stirred at 25° C. for reaction for 3 h, then diluted with water (5000 mL), and extracted with ethyl acetate (800 mL×3), and the organic phases were combined, washed with saturated brine, dried over anhydrous sodium sulfate, and filtered. The filtrate was concentrated under reduced pressure, and the resulting crude product was separated by silica gel column chromatography (petroleum ether/ethyl acetate, 100/0-100/5, V/V) to give compound J-2. MS-ESI calcd. $[M+H]^+$ 312, found 312.

Step 3

Compound J-2 (50 g, 160.53 mmol) and Boc anhydride (210.21 g, 963.19 mmol) were dissolved in tetrahydrofuran (300 mL), and 4-dimethylaminopyridine (58.84 g, 481.59 mmol) was added. The reaction mixture was stirred at 70° C. under nitrogen atmosphere for reaction for 4 h and then concentrated under reduced pressure. The resulting crude product was separated by silica gel column chromatography (petroleum ether/ethyl acetate, 100/0-100/3, V/V) to give compound J-3. MS-ESI calcd. $[M-56+H]^+$356, found $[M-56+H]^+$356.

Step 4

Compound J-3 (60 g, 145.78 mmol) was dissolved in tetrahydrofuran (700 mL), and tetrabutylammonium fluoride (a 1 M solution in tetrahydrofuran, 145.78 mmol, 145.78 mL) was added to the reaction solution. The reaction mixture was stirred at 25° C. for reaction for 1 h and then concentrated under reduced pressure. The resulting crude product was separated by silica gel column chromatography (petroleum ether/ethyl acetate, 100/0-5/1, V/V) to give compound J-4. MS-ESI calcd. $[M-56+H]^+$242, found $[M-56+H]^+$242.

Step 5

Compound J-4 (40 g, 134.53 mmol) was dissolved in dichloromethane (450 mL), and Dess-Martin reagent (74.18 g, 174.90 mmol) was added portionwise. The reaction mixture was stirred at 25° C. for reaction for 1 h. The reaction was quenched with a saturated sodium sulfite solution (450 mL), and the reaction mixture was diluted with a saturated sodium bicarbonate solution (300 mL). The mixture was extracted with ethyl acetate (200 mL×3), and the organic phases were combined, washed with saturated brine, dried over anhydrous sodium sulfate, and filtered. The filtrate was concentrated under reduced pressure to give compound J-5. MS-ESI calcd. [M−56+H]+240, found $[M-56+H]^+$240.

Step 6

Compound J-5 (33 g, 111.75 mmol) was dissolved in methanol (85 mL), and dimethyl (1-diazo-2-oxopropyl) phosphonate (42.94 g, 223.50 mmol) and potassium carbonate (46.33 g, 335.25 mmol) were added. The reaction mixture was allowed to react at 25° C. for 1 h, then diluted with water (100 mL), and extracted with ethyl acetate (80 mL×3). The organic phases were combined, washed with saturated brine, dried over anhydrous sodium sulfate, and filtered. The filtrate was concentrated under reduced pressure, and the resulting crude product was separated by silica gel column chromatography (petroleum ether/ethyl acetate, 100/0-10/1, V/V) to give compound J-6. MS-ESI calcd. $[M-56+H]^+$236, found $[M-56+H]^+$236.

Step 7

Compound J-6 (37 g, 127.01 mmol) was dissolved in dichloromethane (370 mL), and trifluoroacetic acid (113.96 g, 999.44 mmol, 74.00 mL) was added dropwise. The reaction solution was allowed to react at 25° C. for 2 h. The reaction was quenched with saturated sodium bicarbonate (300 mL), and the reaction solution was diluted with water (500 mL). The mixture was extracted with ethyl acetate (80 mL×3), and the organic phases were combined, washed with saturated brine, dried over anhydrous sodium sulfate, and filtered. The filtrate was concentrated under reduced pressure to give intermediate J. MS-ESI calcd. $[M+H]^+$ 192, found 192.

Example 1

Synthetic Route:

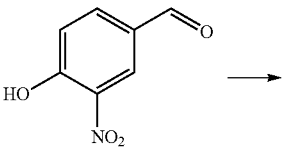

1-1

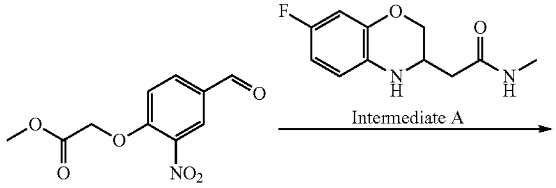

1-2

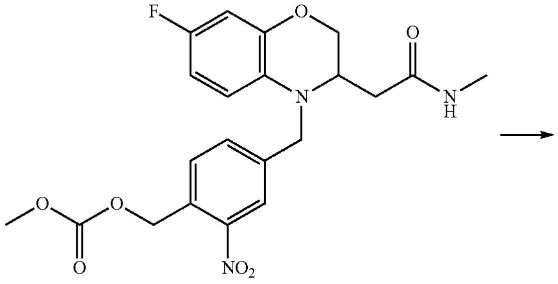

1-3

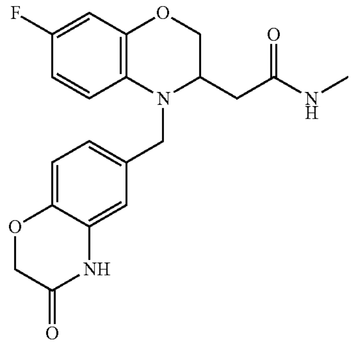

1

Step 1

Compound 1-1 (1.00 g, 5.98 mmol) and methyl bromoacetate (1.10 g, 7.18 mmol) were dissolved in N,N-dimethylformamide (10 mL), and potassium carbonate (1.24 g, 8.97 mmol) was added to the reaction solution. The reaction mixture was stirred at 80° C. for 2 h. Water (100 mL) was added to the reaction mixture, and the resulting mixture was extracted with ethyl acetate (100 mL×2). The organic phases were combined, washed with saturated brine (100 mL), dried over anhydrous sodium sulfate, and filtered. The filtrate was concentrated under reduced pressure to give crude compound 1-2. MS-ESI calcd. [M+H]+ 240, found 240.

Step 2

Compound 1-2 (250 mg, 1.05 mmol) and intermediate A (260 mg, 1.10 mmol) were dissolved in 1,2-dichloroethane (3 mL), and acetic acid (126 mg, 2.10 mmol) was added to the reaction solution. The reaction mixture was stirred at 20° C. for 0.5 h, and then sodium triacetoxyborohydride (267 mg, 1.26 mmol) was added. The reaction mixture was stirred at 20° C. for another 12 h, then diluted with water (50 mL), and extracted with ethyl acetate (50 mL×2). The organic phases were combined, washed with saturated brine (50 mL), dried over anhydrous sodium sulfate, and filtered. The filtrate was concentrated under reduced pressure. The crude product resulting from the concentration was separated by thin layer chromatography (developing solvent: dichloromethane/methanol, 15/1, V/V) to give compound 1-3. MS-ESI calcd. [M+H]+ 448, found 448.

Step 3

Compound 1-3 (120 mg, 0.268 mmol) was dissolved in acetic acid (3 mL), and iron powder (74.9 mg, 1.34 mmol) was added to the reaction solution. The reaction mixture was stirred at 80° C. for 1 h, then diluted with water (10 mL), and extracted with ethyl acetate (20 mL×3). The organic phases were combined, washed with saturated brine (20 mL), dried over anhydrous sodium sulfate, and filtered. The filtrate was concentrated under reduced pressure. The crude product resulting from the concentration was separated by preparative high performance liquid chromatography (chromatographic column: Waters Xbridge 150×25 mm×10 Wm; mobile phase: 0.225% aqueous formic acid solution-acetonitrile; gradient:acetonitrile 27%-57%, 10 min) to give compound 1. MS-ESI calcd. [M+H]+ 386, found 386. $^1$H NMR (400 MHz, DMSO-$d_6$) δ 10.62 (s, 1H), 7.99-7.81 (m, 1H), 6.94-6.76 (m, 3H), 6.70-6.62 (m, 1H), 6.60-6.51 (m, 1H), 6.51-6.38 (m, 1H), 4.53 (s, 2H), 4.39 (d, J=16.4 Hz, 1H), 4.28 (d, J=16.4 Hz, 1H), 4.23-4.14 (m, 1H), 4.09-3.91 (m, 1H), 3.86-3.75 (m, 1H), 2.56 (d, J=4.4 Hz, 3H), 2.41-2.22 (m, 2H) ppm.

Example 2

Synthetic Route:

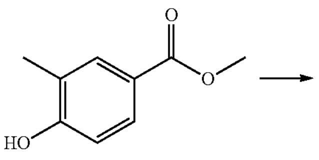

2-1

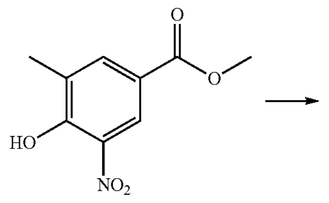

2-2

-continued

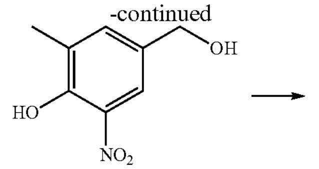

2-3

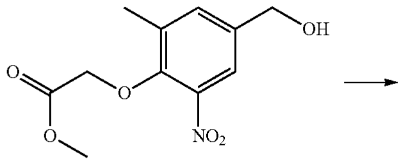

2-4

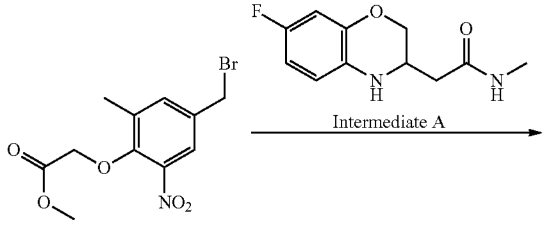

2-5

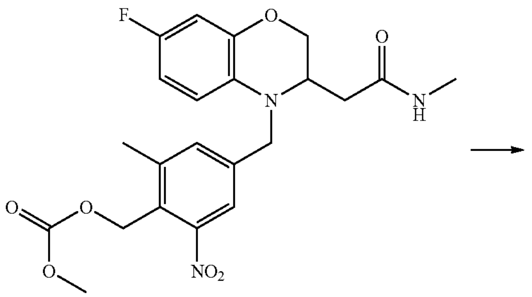

2-6

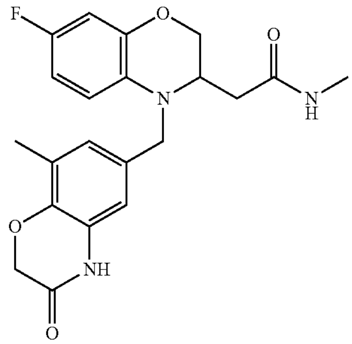

2

Step 1

Compound 2-1 (4.00 g, 24.1 mmol) was dissolved in acetic acid (40 mL), and nitric acid (2.36 g, 37.5 mmol) was added to the reaction solution at 0° C. The reaction mixture was stirred at 20° C. for 2 h. Water (400 mL) was added to the reaction mixture, and the resulting mixture was filtered. The filter cake was collected and dried to give crude compound 2-2. MS-ESI calcd. [M+H]+ 212, found 212.

Step 2

Compound 2-2 (2.20 g, 10.4 mmol) was dissolved in dichloromethane (30 mL), and a solution of diisobutylaluminum hydride in toluene (1 M, 31.3 mL) was added slowly to the reaction solution at −65° C. The reaction mixture was stirred at −65 to 20° C. for 5 h. 1 M hydrochloric acid (100 mL) was added to the reaction mixture, and the resulting mixture was extracted with ethyl acetate (100 mL×3). The organic phases were combined, dried over anhydrous sodium sulfate, and filtered. The filtrate was concentrated under reduced pressure. The crude product was separated by silica gel column chromatography (eluent: petroleum ether/ethyl acetate, 100/1-10/1, V/V) to give compound 2-3.

Step 3

Compound 2-3 (2.50 g, 13.7 mmol) and methyl bromoacetate (2.51 g, 16.4 mmol) were dissolved in N,N-dimethylformamide (25 mL), and potassium carbonate (2.45 g, 17.7 mmol) was added to the reaction solution. The reaction mixture was stirred at 80° C. for 1 h, then diluted with water (100 mL), and extracted with ethyl acetate (100 mL×2). The organic phases were combined, washed once with saturated brine (100 mL), dried over anhydrous sodium sulfate, and filtered. The filtrate was concentrated under reduced pressure to give crude compound 2-4. MS-ESI calcd. $[M+H]^+$ 256, found 256.

Step 4

Compound 2-4 (3.10 g, 12.2 mmol) was dissolved in dichloromethane (30 mL), and phosphorus tribromide (3.62 g, 13.4 mmol) was added to the reaction solution at 0° C. The reaction mixture was stirred at 20° C. for 1 h. The reaction solution was adjusted to pH 7 with a saturated sodium bicarbonate solution, and the mixture was extracted with dichloromethane (100 mL×2). The organic phases were combined, washed with saturated brine (100 mL), dried over anhydrous sodium sulfate, and filtered. The filtrate was concentrated under reduced pressure to give crude compound 2-5. MS-ESI calcd. $[M+H]^+$ 318/320, found 318/320.

Step 5

Intermediate A (1.20 g, 5.35 mmol) and compound 2-5 (2.04 g, 6.42 mmol) were dissolved in acetonitrile (12 mL), and sodium iodide (802 mg, 5.35 mmol) and potassium carbonate (2.22 g, 16.1 mmol) were added to the reaction solution. The reaction mixture was stirred at 80° C. for 12 h and then filtered. The filtrate was concentrated under reduced pressure to give a crude product, which was then separated by silica gel column chromatography (eluent: petroleum ether/ethyl acetate, 10/1-1/2, V/V) to give compound 2-6. MS-ESI calcd. $[M+H]^+$ 462, found 462.

Step 6

Compound 2-6 (1.80 g, 3.90 mmol) was dissolved in acetic acid (18 mL), and iron powder (1.09 g, 19.50 mmol) was added to the reaction solution. The reaction mixture was stirred at 80° C. for 2 h. Water (200 mL) and a saturated sodium bicarbonate solution (100 mL) were added to the reaction mixture, and the resulting mixture was extracted with ethyl acetate (200 mL×2). The organic phases were combined, washed with saturated brine (100 mL), dried over anhydrous sodium sulfate, and filtered. The filtrate was concentrated under reduced pressure. The resulting crude product was separated by silica gel column chromatography (eluent: ethyl acetate) to give compound 2. MS-ESI calcd. $[M+H]^+$ 400, found 400. $^1H$ NMR (400 MHz, DMSO-$d_6$) δ 10.53 (s, 1H), 7.93-7.84 (m, 1H), 6.73 (s, 1H), 6.69-6.60 (m, 2H), 6.60-6.52 (m, 1H), 6.51-6.42 (m, 1H), 4.54 (s, 2H), 4.39-4.30 (m, 1H), 4.29-4.15 (m, 2H), 4.15-4.01 (m, 1H), 3.86-3.74 (m, 1H), 2.56 (d, J=4.4 Hz, 3H), 2.40-2.33 (m, 1H), 2.32-2.25 (m, 1H), 2.13 (s, 3H) ppm.

Example 3

Synthetic Route:

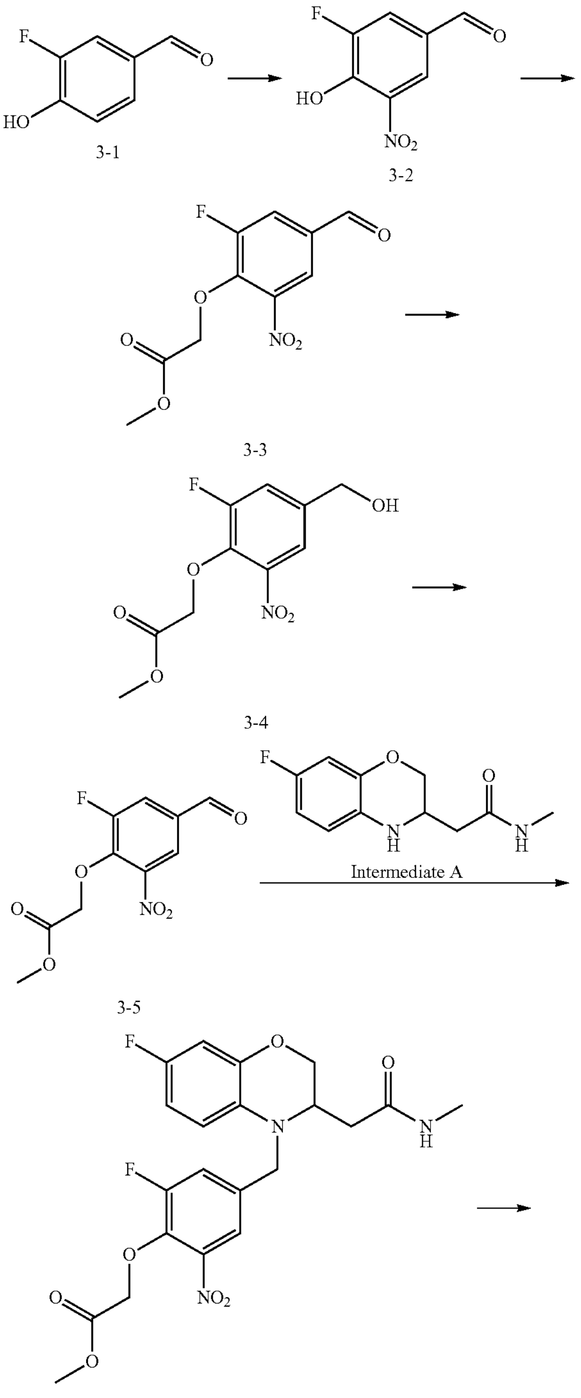

3-1 3-2 3-3 3-4 3-5 3-6

-continued

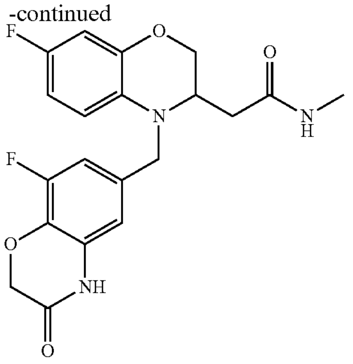

3

Step 1

Compound 3-1 (5.60 g, 40 mmol) and acetic acid (65 mL) were added to a reaction flask, and the mixture was purged three times with nitrogen. Nitric acid (8.09 g, 128 mmol, 5.78 mL) was added slowly and dropwise with stirring, and the reaction mixture was stirred at 20° C. for reaction for 1 h and then poured into ice water (30 mL). The resulting mixture was filtered, and the filter cake was washed with water (50 mL) and then collected to give crude compound 3-2.

Step 2

Compound 3-2 (2.00 g, 10.8 mmol), methyl bromoacetate (1.98 g, 13.0 mmol, 1.22 mL), potassium carbonate (2.24 g, 16.2 mmol), and N,N-dimethylformamide (20 mL) were added to a reaction flask. The reaction mixture was slowly heated to 80° C., stirred for reaction for 1 h, and then slowly poured into water (20 mL). The resulting mixture was extracted with ethyl acetate (20 mL×3), and the organic phases were combined, washed with saturated brine (50 mL), dried over anhydrous sodium sulfate, and filtered. The filtrate was concentrated under reduced pressure to give crude compound 3-3.

Step 3

3-3 (0.8 g, 3.11 mmol) was dissolved in acetonitrile (1 mL), and the solution was purged three times with nitrogen and then cooled to −78° C. Sodium borohydride (235 mg, 6.22 mmol) was added, and the mixture was allowed to react at 78° C. for 2 h and then slowly poured into a saturated ammonium chloride solution (20 mL). The resulting mixture was extracted with ethyl acetate (20 mL×3), and the organic phases were combined, dried over anhydrous sodium sulfate, and filtered. The filtrate was concentrated under reduced pressure to give compound 3-4.

Step 4

3-4 (0.75 g, 2.89 mmol) and dichloromethane (11.5 mL) were added to a reaction flask, and the mixture was purged three times with nitrogen and then cooled to 0° C. Phosphorus tribromide (3.15 g, 11.64 mmol) was added. The reaction mixture was heated to 20° C., stirred for reaction for 1 h, and then slowly poured into a saturated sodium bicarbonate solution (20 mL). The resulting mixture was extracted with dichloromethane (20 mL×3), and the organic phases were combined, washed with saturated brine (20 mL), dried over anhydrous sodium sulfate, and filtered. The filtrate was concentrated under reduced pressure. The resulting crude product was subjected to silica gel column chromatography (eluent: petroleum ether/ethyl acetate, 1/1, V/V) to give compound 3-5.

Step 5

Intermediate A (50.0 mg, 223 μmol), compound 3-5 (108 mg, 335 μmol), sodium iodide (33.4 mg, 223 μmol), potassium carbonate (92.5 mg, 669 μmol), and acetonitrile (1.5 mL) were added to a reaction flask. The reaction mixture was purged three times with nitrogen, heated to 80° C., stirred for reaction for 1 h, and then concentrated under reduced pressure to give crude compound 3-6.

Step 6

3-6 (350 mg, 752 mol), reduced iron powder (420 mg, 7.52 mmol), and glacial acetic acid (8 mL) were added to a reaction flask. The mixture was purged three times with nitrogen, heated to 80° C., and stirred for reaction for 1 h. The reaction mixture was filtered through diatomite. The filter cake was washed with methanol (20 mL), and the filtrate was concentrated under reduced pressure. The crude product resulting from the concentration under reduced pressure was dissolved in ethyl acetate (50 mL) and washed with water (30 mL). The organic phase was dried over anhydrous sodium sulfate and filtered, and the filtrate was concentrated under reduced pressure. The crude product resulting from the concentration was separated and purified by preparative high performance liquid chromatography (chromatographic column: Phenomenex Gemini-NX C18 75×30 mm×3 μm; mobile phase: [10 mM aqueous ammonium bicarbonate solution-acetonitrile]; gradient:acetonitrile 20%-45%, 6 min) to give compound 3. MS-ESI calcd. $[M+H]^+$ 404, found 404. $^1H$ NMR (400 MHz, DMSO-$d_6$) δ 10.80 (s, 1H), 7.89 (d, J=4.4 Hz, 1H), 6.90-6.78 (m, 1H), 6.71-6.62 (m, 2H), 6.62-6.51 (m, 1H), 6.49-6.41 (m, 1H), 4.63 (s, 2H), 4.38-4.27 (m, 2H), 4.23-4.17 (m, 1H), 4.10-4.02 (m, 1H), 3.84-3.77 (m, 1H), 2.56 (d, J=4.4 Hz, 3H), 2.40-2.25 (m, 2H) ppm.

Example 4

Synthetic Route:

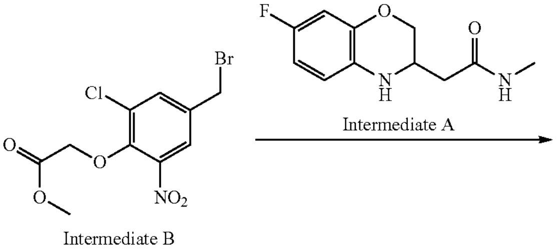

-continued

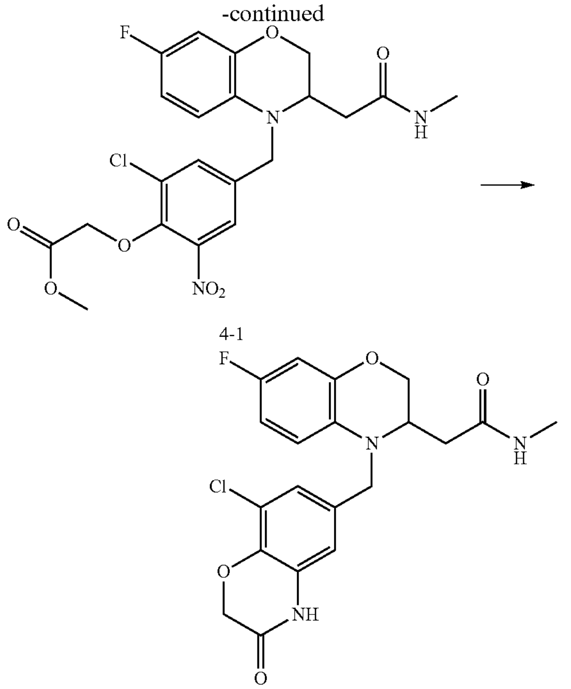

4-1

4

Step 1

Intermediate A (0.700 g, 3.12 mmol) and intermediate B (2.05 g, 6.06 mmol) were dissolved in acetonitrile (10 mL), and sodium iodide (468 mg, 3.12 mmol) and potassium carbonate (1.29 g, 9.36 mmol) were added to the reaction solution. The reaction mixture was stirred at 80° C. for 12 h and then filtered. The filtrate was concentrated under reduced pressure to give compound 4-1. MS-ESI calcd. $[M+H]^+$ 482, found 482.

Step 2

Compound 4-1 (1.30 g, 2.70 mmol) was dissolved in acetic acid (10 mL), and iron powder (1.51 g, 27.0 mmol) was added to the reaction solution. The reaction mixture was stirred at 80° C. for 0.5 h. Water (100 mL) and a saturated sodium bicarbonate solution (100 mL) were added to the reaction mixture to quench the reaction, and the mixture was extracted with ethyl acetate (100 mL×2). The organic phases were combined, washed once with saturated brine (100 mL), dried over anhydrous sodium sulfate, and filtered. The filtrate was concentrated under reduced pressure. The crude product was separated by silica gel column chromatography (eluent: ethyl acetate), and then separated by preparative high performance liquid chromatography (chromatographic column: Phenomenex Luna C18 250×50 mm×10 Wm; mobile phase: 0.225% aqueous formic acid solution-acetonitrile; gradient:acetonitrile 35%-65%, 14 min) to give compound 4. MS-ESI calcd. $[M+H]^+$ 420, found 420. $^1H$ NMR (400 MHz, DMSO-$d_6$) δ 10.79 (s, 1H), 7.93-7.83 (m, 1H), 6.97 (d, J=1.6 Hz, 1H), 6.77 (d, J=1.6 Hz, 1H), 6.69-6.63 (m, 1H), 6.60-6.54 (m, 1H), 6.49-6.43 (m, 1H), 4.66 (s, 2H), 4.41-4.26 (m, 2H), 4.23-4.16 (m, 1H), 4.11-4.01 (m, 1H), 3.81 (d, J=1.6 Hz, 1H), 2.56 (d, J=4.4 Hz, 3H), 2.46-2.25 (m, 2H) ppm.

Example 5

Synthetic Route:

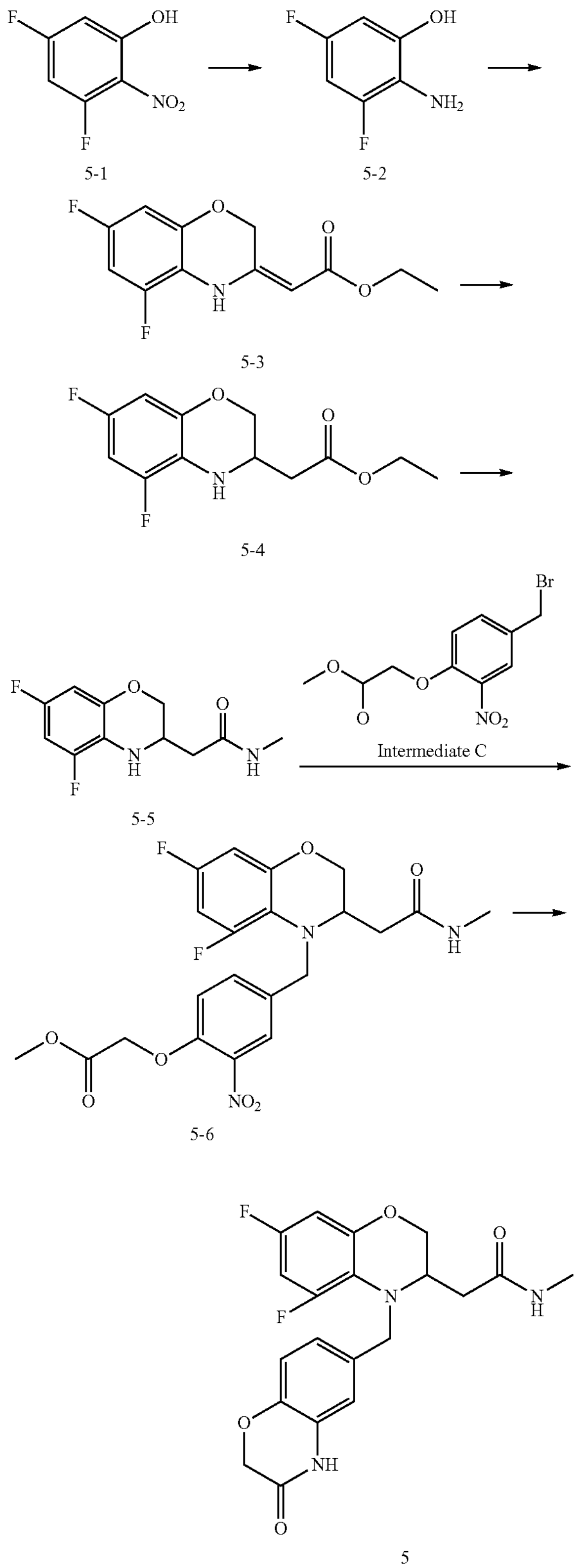

5-1

5-2

5-3

5-4

5-5

5-6

5

Step 1

Compound 5-1 (1.00 g, 5.71 mmol) was dissolved in ethanol (5 mL), and palladium on carbon (100 mg, 10% purity) was added. The reaction mixture was stirred under hydrogen atmosphere (15 psi) at 20° C. for 4 h and then filtered. The filtrate was concentrated under reduced pressure to give compound 5-2. MS-ESI calcd. $[M+H]^+$ 146, found 146.

Step 2

Compound 5-2 (820 mg, 5.65 mmol) and ethyl 4-chloroacetoacetate (1.12 g, 6.78 mmol) were dissolved in tetrahydrofuran (10 mL), and the solution was heated to 50° C. Triethylamine (787 μL, 5.65 mmol) was added to the reaction solution, and the mixture was stirred at 50° C. for 4 h. After the reaction was completed, the reaction mixture was extracted with ethyl acetate (50 mL), and the organic phase was washed with water (50 mL), washed with saturated brine (50 mL), dried over anhydrous sodium sulfate, and filtered. The filtrate was concentrated under reduced pressure. The resulting crude product was separated and purified by column chromatography (eluent: petroleum ether/ethyl acetate, 100/1-10/1, V/V) to give compound 5-3. MS-ESI calcd. $[M+H]^+$ 256, found 256.

Step 3

Compound 5-3 (500 mg, 1.96 mmol) was dissolved in ethanol (5 mL), and palladium on carbon (100 mg, 10% purity) was added to the reaction solution. The reaction mixture was stirred under hydrogen atmosphere (15 psi) at 20° C. for 14 h and then filtered. The filtrate was concentrated under reduced pressure, and the resulting crude product was dissolved in ethanol (10 mL). Palladium on carbon (200 mg, 10% purity) was added, and the reaction mixture was stirred under hydrogen atmosphere (15 psi) at 20° C. for 14 h and then filtered. The filtrate was concentrated under reduced pressure to give compound 5-4. MS-ESI calcd. $[M+H]^+$ 258, found 258.

Step 4

Compound 5-4 (400 mg, 1.56 mmol) was dissolved in ethanol (10 mL), and a solution of methylamine (4.78 g, 46.2 mmol) in ethanol was added to the reaction solution. The reaction mixture was stirred at 20° C. for 14 h, then diluted with water (20 mL), and extracted with ethyl acetate (20 mL×3). The organic phases were combined, dried over anhydrous sodium sulfate, and filtered. The filtrate was concentrated under reduced pressure to give compound 5-5. MS-ESI calcd. $[M+H]^+$ 243, found 243.

Step 5

Compound 5-5 (150 mg, 619 μmol) and intermediate C (188 mg, 619 mol) were dissolved in acetonitrile (5 mL), and sodium iodide (93 mg, 619 μmol) and potassium carbonate (257 mg, 1.86 mmol) were added to the reaction solution. The reaction mixture was stirred at 80° C. for 12 h and then filtered. The filtrate was concentrated under reduced pressure. The resulting crude product was separated by column chromatography (eluent: dichloromethane/methanol, 200/1-20/1, V/V) to give compound 5-6. MS-ESI calcd. $[M+H]^+$ 466, found 466.

Step 6

Compound 5-6 (75.0 mg, 161 mol) was dissolved in acetic acid (2 mL), and iron powder (90.0 mg, 1.61 mmol) was added to the reaction solution. The reaction mixture was stirred at 80° C. for 14 h and then concentrated under reduced pressure. The crude product resulting from the concentration was subjected to preparative high performance liquid chromatography (chromatographic column: Waters Xbridge 150×25 mm×5 Wm; mobile phase: 10 mM aqueous ammonium bicarbonate solution-acetonitrile; gradient:acetonitrile: 26%-56%, 9 min) to give compound 5. MS-ESI calcd. $[M+H]^+$ 404, found 404. $^1H$ NMR (400 MHz, DMSO-$d_6$) δ 10.68 (s, 1H), 7.69 (d, J=4.4 Hz, 1H), 6.95 (s, 1H), 6.90 (s, 2H), 6.87-6.79 (m, 1H), 6.69-6.61 (m, 1H), 4.55 (s, 2H), 4.15-4.01 (m, 2H), 3.97-3.78 (m, 2H), 3.51-3.48 (m, 1H), 2.52-2.50 (m, 3H), 2.16-1.92 (m, 2H) ppm.

Example 6

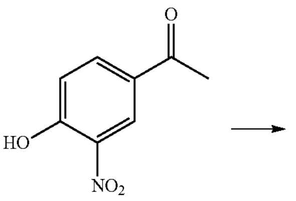

6-1

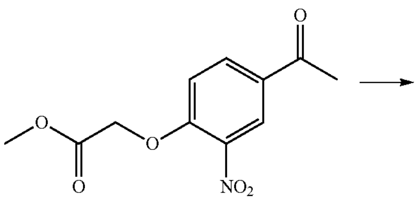

6-2

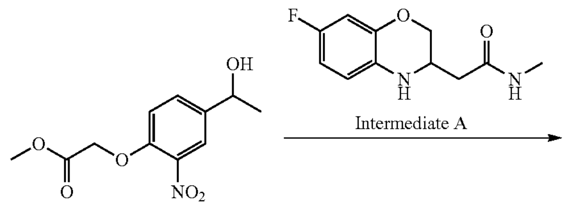

6-3

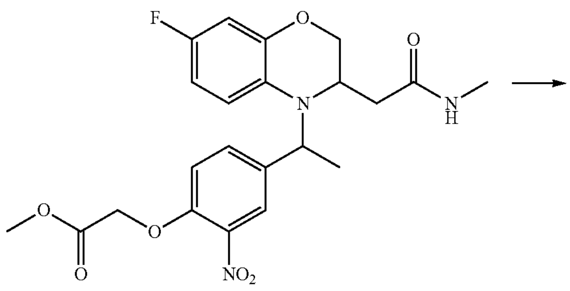

6-4

-continued

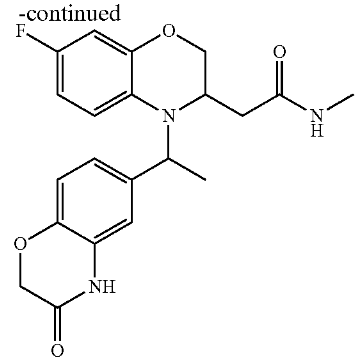

6

Step 1

Compound 6-1 (2.23 g, 12.3 mmol) and methyl bromoacetate (1.88 g, 12.3 mmol) were dissolved in acetonitrile (10 mL), and potassium carbonate (1.70 g, 12.3 mmol) was added to the reaction solution. The reaction mixture was stirred at 80° C. for 4 h and then filtered. The filtrate was concentrated under reduced pressure to give compound 6-2. MS-ESI calcd. $[M+H]^+$ 254, found 254.

Step 2

Compound 6-2 (2.70 g, 10.7 mmol) was dissolved in methanol (30 mL), and sodium borohydride (448 mg, 11.9 mmol) was added slowly to the reaction solution at −20° C. The reaction mixture was stirred at −20° C. for 2 h. After the reaction was completed, a saturated aqueous ammonium chloride solution (150 mL) was added to the reaction mixture to quench the reaction, and the mixture was extracted with ethyl acetate (60 mL×3). The organic phases were combined and concentrated under reduced pressure. The crude product was separated and purified by silica gel column chromatography (eluent: petroleum ether/ethyl acetate, 10/1-1/1, V/V) to give compound 6-3. MS-ESI calcd. $[M-H]^-$ 254, found 254.

Step 3

Compound 6-3 (428 mg, 1.68 mmol) and intermediate A (220 mg, 932 μmol) were dissolved in toluene (5 mL), and ferrous bromide (10.1 mg, 46.6 mol) and potassium hydrogen sulfate (127 mg, 932 μmol) were added to the reaction solution. The reaction mixture was stirred at 120° C. for 16 h. After the reaction was completed, the reaction mixture was filtered, and the filtrate was concentrated under reduced pressure to give a crude product. The crude product was separated and purified by silica gel column chromatography (eluent: dichloromethane/methanol, 200/1-20/1, V/V) to give compound 6-4. MS-ESI calcd. $[M+H]^+$ 462, found 462.

Step 4

Compound 6-4 (150 mg, 325 mol) was dissolved in ethanol (3 mL) and water (3 mL), and iron powder (182 mg, 3.25 mmol) and ammonium chloride (348 mg, 6.50 mmol) were added to the reaction solution. The reaction mixture was stirred at 80° C. for 2 h and then concentrated. The resulting residue was stirred in a mixed solution of methanol/ethyl acetate (1/10, 50 mL, V/V) at 25° C. for 0.5 h. The mixture was filtered, and the filtrate was concentrated under reduced pressure. The crude product resulting from the concentration was separated by preparative high performance liquid chromatography (chromatographic column: Waters Xbridge 150×25 mm×5 mu; mobile phase: [10 mM aqueous ammonium bicarbonate solution-acetonitrile]; gradient:acetonitrile: 26%-56%) to give compound 6. MS-ESI calcd. $[M+H]^+$ 400, found 400. $^1H$ NMR (400 MHz, DMSO-$d_6$) δ 10.59 (s, 1H), 7.98-7.52 (m, 1H), 6.99-6.78 (m, 4H), 6.70-6.58 (m, 2H), 4.98-4.81 (m, 1H), 4.61-4.48 (m, 2H), 4.15-3.98 (m, 1H), 3.81-3.72 (m, 1.5H), 3.38-3.35 (m, 0.5H), 2.60-2.52 (m, 3H), 2.36-2.10 (m, 1.5H), 1.96-1.85 (m, 0.5H), 1.52-1.37 (m, 3H) ppm.

Example 7

Synthetic Route:

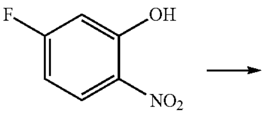

A-1

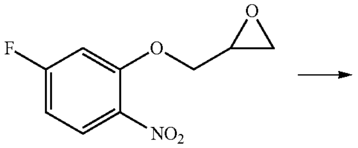

7-1

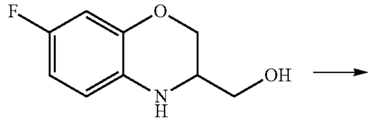

7-2

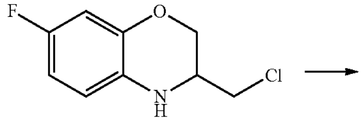

7-3

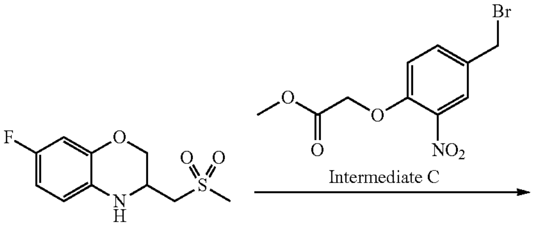

7-4

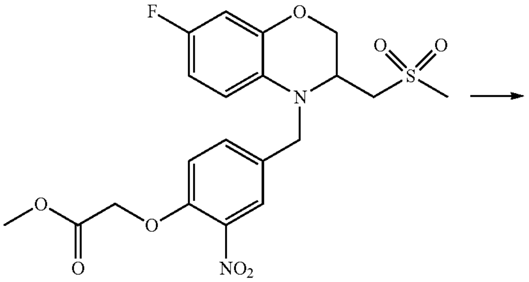

7-5

-continued

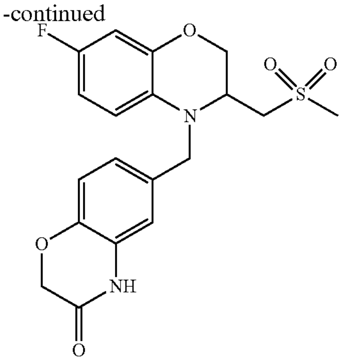

7

Step 1

Glycidol (2.59 g, 35.0 mmol) was dissolved in tetrahydrofuran (50 mL), and triphenylphosphine (8.35 g, 31.8 mmol) and compound A-1 (5.00 g, 31.8 mmol) were added. The temperature was lowered to 0° C., and diethyl azodicarboxylate (5.54 g, 31.8 mmol) was added slowly. The reaction mixture was stirred at 15° C. for 2 h. A saturated aqueous ammonium chloride solution (20 mL) was added, and the mixture was extracted with ethyl acetate (50 mL). The organic phase was dried over anhydrous sodium sulfate and filtered. The filtrate was concentrated under reduced pressure to give a crude product. The crude product was separated and purified by silica gel column chromatography (eluent: petroleum ether/ethyl acetate, 1/1, V/V) to give compound 7-1. MS-ESI calcd. $[M+H]^+$ 214, found 214.

Step 2

Compound 7-1 (4 g, 18.8 mmol) was dissolved in ethanol (20 mL) and water (40 mL), and iron powder (5.24 g, 93.8 mmol) and acetic acid (20 mL) were added under nitrogen atmosphere. The reaction mixture was stirred at 80° C. for 16 h and then filtered. Water (20 mL) and ethyl acetate (30 mL) were added to the filtrate for extraction, and the organic phase was dried over anhydrous sodium sulfate and filtered. The filtrate was concentrated under reduced pressure. The crude product was separated and purified by silica gel column chromatography (eluent: petroleum ether/ethyl acetate, 1/1, V/V) to give compound 7-2. MS-ESI calcd. $[M+H]^+$ 184, found 184.

Step 3

Compound 7-2 (1.40 g, 7.64 mmol) was dissolved in dichloromethane (15 mL), and triethylamine (2.13 mL, 15.3 mmol) and methanesulfonyl chloride (887 μL, 11.5 mmol) were added. The mixture was stirred at 25° C. for 16 h. A saturated aqueous ammonium chloride solution (10 mL) was added to quench the reaction, and the mixture was extracted with dichloromethane (10 mL). The organic phase was dried over anhydrous sodium sulfate and filtered, and the filtrate was concentrated under reduced pressure. The crude product resulting from the concentration was separated and purified by silica gel column chromatography (eluent: petroleum ether/ethyl acetate, 1/1, V/V) to give compound 7-3. MS-ESI calcd. $[M+H]^+$ 202, found 202.

Step 4

Potassium iodide (395 mg, 2.38 mmol) and sodium methylsulfinyl salt (486 mg, 4.76 mmol) were added to a solution of compound 7-3 (0.48 g, 2.38 mmol) in N,N-dimethylformamide (4 mL), and the mixture was microwaved for reaction at 100° C. for 1 h. A saturated ammonium chloride solution (10 mL) was added to quench the reaction, and the mixture was extracted with water (10 mL) and ethyl acetate (10 mL). The organic phase was dried over anhydrous sodium sulfate and filtered, and the filtrate was concentrated under reduced pressure. The crude product resulting from the concentration was separated and purified by silica gel column chromatography (eluent: petroleum ether/ethyl acetate, 1/1, V/V) to give compound 7-4. MS-ESI calcd. $[M+H]^+$ 246, found 246.

Step 5

Compound 7-4 (0.2 g, 815 μmol), intermediate C (372 mg, 1.22 mmol), sodium iodide (122 mg, 815 μmol), potassium carbonate (338 mg, 2.45 mmol), and acetonitrile (3 mL) were added to a reaction flask. The reaction mixture was purged three times with nitrogen, heated to 80° C., stirred for reaction for 16 h, and then directly concentrated under reduced pressure to give compound 7-5.

Step 6

7-5 (0.50 g, 1.07 mmol), reduced iron powder (596 mg, 10.7 mmol), and glacial acetic acid (5 mL) were added to a reaction flask. The reaction mixture was purged three times with nitrogen, heated to 80° C., stirred for reaction for 1 h, and then filtered through diatomite. The filter cake was washed with ethyl acetate (20 mL), and the filtrate was concentrated under reduced pressure. The resulting crude product was dissolved in ethyl acetate (10 mL) and washed with water (10 mL×3), and the organic phase was dried over anhydrous sodium sulfate and filtered. The filtrate was concentrated under reduced pressure. The crude product resulting from the concentration was separated and purified by preparative high performance liquid chromatography (chromatographic column: Phenomenex Gemini-NX C18 75×30 mm×3 M; mobile phase: [10 mM aqueous ammonium bicarbonate solution-acetonitrile]; gradient:acetonitrile 25%-45%, 6 min) to give compound 7. MS-ESI calcd. $[M+H]^+$ 407, found 407. $^1H$ NMR (400 MHz, DMSO-$d_6$) δ 10.61 (s, 1H), 6.92-6.88 (m, 1H), 6.88-6.85 (m, 1H), 6.84 (s, 1H), 6.70 (d, J=9.2 Hz, 1H), 6.63-6.58 (m, 2H), 4.53 (s, 2H), 4.52-4.46 (m, 1H), 4.44-4.38 (m, 1H), 4.32-4.24 (m, 1H), 4.10-4.05 (m, 1H), 4.04-3.97 (m, 1H), 3.40-3.36 (m, 2H), 3.05 (s, 3H) ppm.

Example 8

Synthetic Route:

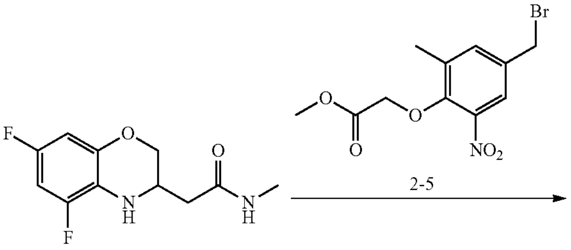

5-5

-continued

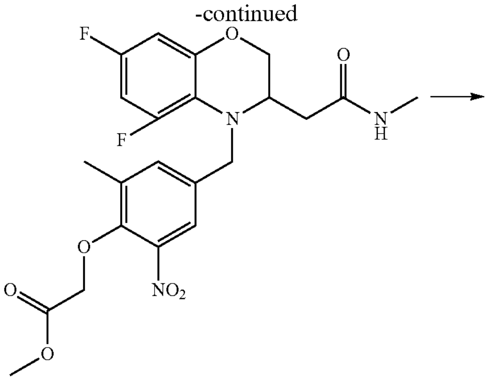

8-1

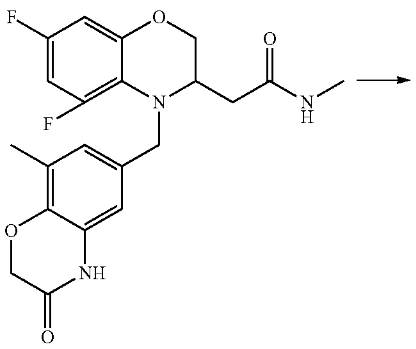

8

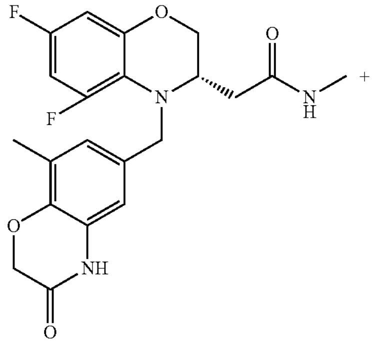

8a or 8b

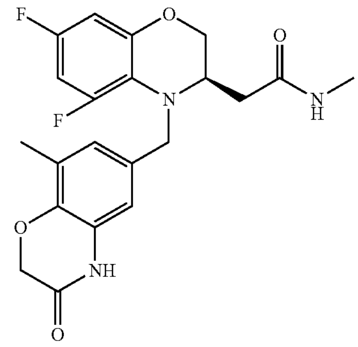

8b or 8a

Step 1

Compound 2-5 (0.220 g, 0.692 mmol) and compound 5-5 (0.168 g, 0.692 mmol) were dissolved in acetonitrile (10 mL), and sodium iodide (149 mg, 0.691 mmol) and anhydrous potassium carbonate (286 mg, 2.07 mmol) were added to the reaction solution. The reaction mixture was stirred at 80° C. for 12 h and then filtered. The filtrate was concentrated under reduced pressure, and the crude product resulting from the concentration was separated by silica gel column chromatography (eluent: petroleum ether/ethyl acetate, 1:1, V/V) to give compound 8-1. Calcd. $[M+H]^+$ 480, found 480.

Step 2

Compound 8-1 (250 mg, 2.70 mmol) was dissolved in acetic acid (6 mL), and iron powder (582 mg, 10.4 mmol) was added to the reaction solution. The reaction mixture was stirred at 80° C. for 14 h, then filtered, and concentrated. Water (100 mL) and a saturated sodium bicarbonate solution (100 mL) were added to quench the reaction, and the mixture was extracted with ethyl acetate (100 mL×2). The organic phases were combined, washed with saturated brine (100 mL), dried over anhydrous sodium sulfate, and filtered. The filtrate was concentrated under reduced pressure to give a crude product. The crude product was purified by preparative high performance liquid chromatography (chromatographic column: Waters Xbridge 150×25 mm×5 Wm; mobile phase: 10 mM aqueous ammonium bicarbonate solution-acetonitrile; gradient:acetonitrile: 33%-63%, 10 min) to give a compound. The compound was then separated by SFC (chromatographic column: DAICEL CHIRALPAK AS (250 mm×30 mm×10 M); mobile phase: [supercritical $CO_2$-methanol]; gradient: methanol 60%-60%, 4.1 min, 30 min) to give compounds 8a (first main peak) and 8b (second main peak). The compounds were tested for e.e. % value by SFC (chromatographic column: Chiralpak AS-3 50×4.6 mm I.D., 3 μm; mobile phase: supercritical $CO_2$-solution of 0.05% diethylamine in methanol; gradient: solution of 0.05% diethylamine in methanol: 5%-40%; flow rate: 3 mL/min; detector: DAD; chromatographic column temperature: 35° C.; back pressure: 100 Bar).

Compound 8a: MS-ESI calcd. $[M+H]^+$ 418, found 418. e.e. %=100%, RT=1.477 min. $^1$H NMR (400 MHz, $CD_3OD$) δ 6.83-6.81 (m, 1H), 6.80-6.78 (m, 1H), 6.61-6.51 (m, 1H), 6.49-6.42 (m, 1H), 4.54 (s, 2H), 4.16 (d, J=14.4 Hz, 1H), 4.09-4.02 (m, 1H), 3.87-3.80 (m, 1H), 3.77 (d, J=14.4 Hz, 1H), 3.49-3.42 (m, 1H), 2.56 (s, 3H), 2.17 (s, 3H), 2.09 (d, J=7.6 Hz, 2H) ppm.

Compound 8b: MS-ESI calcd. $[M+H]^+$ 418, found 418. e.e. %=100%, RT=2.443 min. $^1$H NMR (400 MHz, $CD_3OD$) δ 6.88-6.85 (m, 1H), 6.84-6.81 (m, 1H), 6.63-6.56 (m, 1H), 6.52-6.46 (m, 1H), 4.58 (s, 2H), 4.20 (d, J=14.4 Hz, 1H), 4.13-4.06 (m, 1H), 3.91-3.84 (m, 1H), 3.81 (d, J=14.4 Hz, 1H), 3.52-3.46 (m, 1H), 2.60 (s, 3H), 2.21 (s, 3H), 2.13 (d, J=7.6 Hz, 2H) ppm.

Example 9

Synthetic Route:

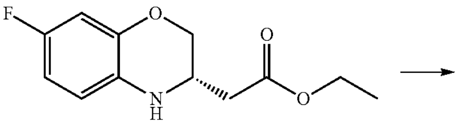

Intermediate D

-continued

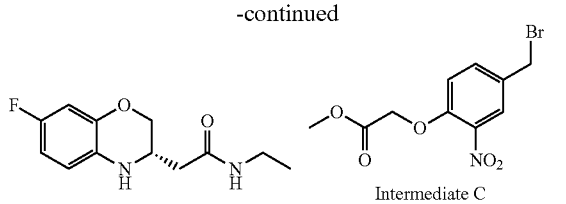

9-1

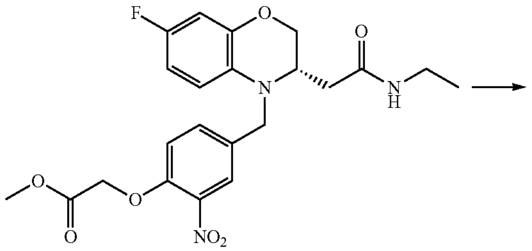

9-2

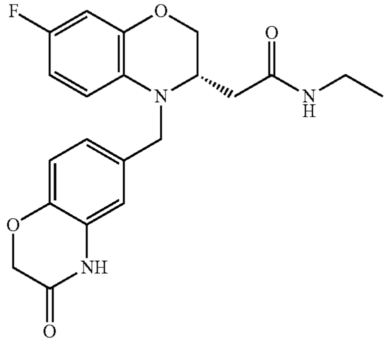

9

Step 1

Intermediate D (0.50 g, 2.09 mmol) was dissolved in methanol (3 mL), and ethylamine (471 mg, 10.5 mmol) was added to the reaction solution. The reaction mixture was stirred at 25° C. for 12 h and then diluted with water (100 mL), and extracted with ethyl acetate (100 mL×3). The organic phases were combined, washed with saturated brine (200 mL), dried over anhydrous sodium sulfate, and filtered. The filtrate was concentrated under reduced pressure to give crude compound 9-1. MS-ESI calcd. $[M+H]^+$ 239, found 239.

Step 2

Compound 9-1 (200 mg, 839 mol) and intermediate C (306 mg, 1.01 mmol) were dissolved in acetonitrile (5 mL), and sodium iodide (126 mg, 839 μmol) and potassium carbonate (348 mg, 2.52 mmol) were added to the reaction solution. The reaction mixture was stirred at 80° C. for 12 h and then filtered. The filtrate was concentrated under reduced pressure to give compound 9-2. MS-ESI calcd. $[M+H]^+$ 462, found 462.

Step 3

Compound 9-2 (300 mg, 650 mol) was dissolved in acetic acid (3 mL), and iron powder (363 mg, 6.50 mmol) was added to the reaction solution. The reaction mixture was stirred at 80° C. for 2 h. Water (10 mL) and a saturated sodium bicarbonate solution (20 mL) were added to the reaction mixture to the quench the reaction, and the mixture was extracted with ethyl acetate (50 mL×2). The organic phases were combined, washed once with saturated brine (100 mL), dried over anhydrous sodium sulfate, and filtered. The filtrate was concentrated under reduced pressure. The crude product resulting from the concentration was separated and purified by high performance liquid chromatography (chromatographic column: Waters Xbridge 150×25 mm×5 Wm; mobile phase: 10 mM aqueous ammonium bicarbonate solution-acetonitrile; gradient:acetonitrile: 32%-62%, 10 min) to give compound 9. MS-ESI calcd. $[M+H]^+$ 400, found 400. $^1H$ NMR (400 MHz, DMSO-$d_6$) δ 10.62 (s, 1H), 8.02-7.93 (m, 1H), 6.97-6.76 (m, 3H), 6.72-6.62 (m, 1H), 6.61-6.51 (m, 1H), 6.51-6.41 (m, 1H), 4.53 (s, 2H), 4.45-4.25 (m, 2H), 4.19 (d, J=9.8 Hz, 1H), 4.11-3.97 (m, 1H), 3.87-3.74 (m, 1H), 3.15-2.96 (m, 2H), 2.42-2.20 (m, 2H), 0.99 (t, J=7.2 Hz, 3H) ppm.

Example 10

Synthetic Route:

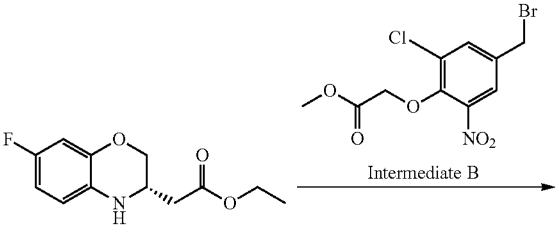

Intermediate D

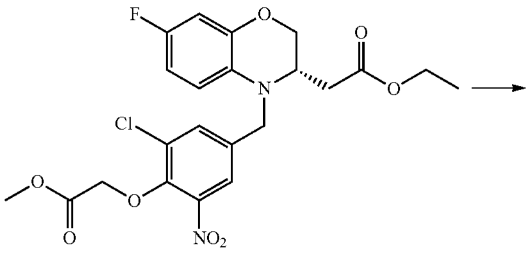

10-1

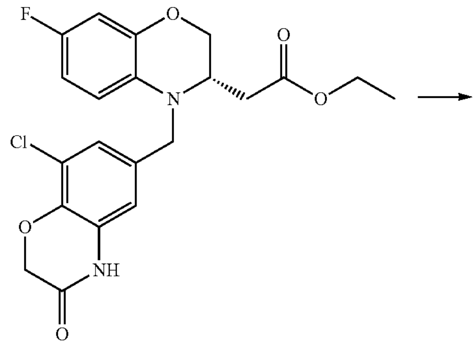

10-2

-continued

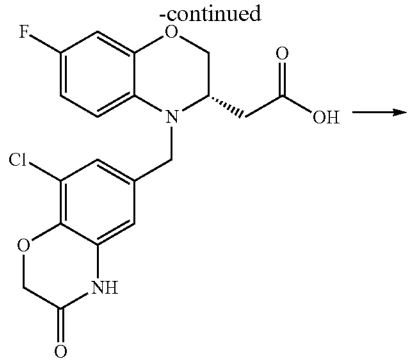

10-3

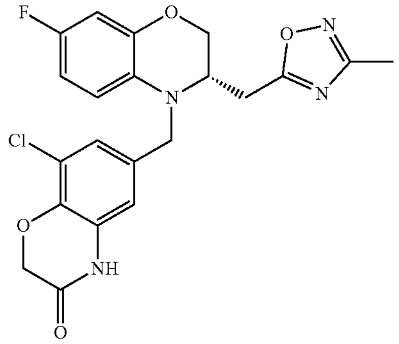

10

Step 1

Intermediate D (500 mg, 2.09 mmol) and intermediate B (920 mg, 2.72 mmol) were dissolved in acetonitrile (10 mL), and sodium iodide (313 mg, 2.09 mmol) and potassium carbonate (867 mg, 6.27 mmol) were added to the reaction solution. The reaction mixture was stirred at 80° C. for 12 h and then filtered. The filtrate was concentrated under reduced pressure, and the crude product was separated by silica gel column chromatography (eluent: petroleum ether/ethyl acetate, 200/1-8/1, V/V) to give compound 10-1. MS-ESI calcd. [M+H]$^+$ 497, found 497.

Step 2

Compound 10-1 (900 mg, 1.81 mmol) was dissolved in acetic acid (10 mL), and iron powder (1.01 g, 18.1 mmol) was added to the reaction solution. The reaction mixture was stirred at 80° C. for 0.5 h and then filtered through diatomite. The filtrate was diluted with ethyl acetate (250 mL) and washed with a saturated sodium bicarbonate solution (250 mL×2) and saturated brine (250 mL). The organic phase was dried over anhydrous sodium sulfate and filtered. The filtrate was concentrated under reduced pressure to give crude compound 10-2. MS-ESI calcd. [M+H]$^+$ 435, found 435.

Step 3

Compound 10-2 (0.500 g, 1.15 mmol) was dissolved in methanol (5 mL), and a solution of lithium hydroxide monohydrate (386 mg, 9.20 mmol) in water (1 mL) was added to the reaction solution. The reaction mixture was stirred at 20° C. for 12 h. Water (20 mL) was added to the reaction mixture, and the resulting mixture was adjusted to pH 4 with 1 M hydrochloric acid and extracted with ethyl acetate (20 mL×2). The organic phases were combined, washed with saturated brine (20 mL), dried over anhydrous sodium sulfate, and filtered. The filtrate was concentrated under reduced pressure to give crude compound 10-3. MS-ESI calcd. [M+H]$^+$ 407, found 407.

Step 4

Compound 10-3 (60.0 mg, 0.148 mmol) was dissolved in N,N-dimethylformamide (2 mL), and 1,1'-carbonyldiimidazole (28.7 mg, 0.177 mmol) was added to the reaction solution. The reaction mixture was stirred at 20° C. for 0.5 h. N-Hydroxyacetamidine (32.3 mg, 0.442 mmol) was then added to the reaction mixture. The reaction mixture was stirred at 20° C. for 0.5 h and then stirred at 80° C. for another 11 h. The reaction mixture was then diluted with water (20 mL) and extracted with ethyl acetate (20 mL×2). The organic phases were combined, washed with saturated brine (50 mL), dried over anhydrous sodium sulfate, and filtered. The filtrate was concentrated under reduced pressure to give a crude product. The crude product was separated by thin layer chromatography (developing solvent: petroleum ether/ethyl acetate/ethanol, 4/3/1, V/V/V) to give compound 10. MS-ESI calcd. [M+H]$^+$ 445, found 445. $^1$H NMR (400 MHz, $CD_3OD$) δ 6.89 (s, 1H), 6.74-6.64 (m, 2H), 6.63-6.52 (m, 2H), 4.63 (s, 2H), 4.34-4.17 (m, 3H), 4.11-4.02 (m, 1H), 3.92-3.82 (m, 1H), 3.05 (d, J=6.8 Hz, 2H), 2.27 (s, 3H) ppm.

Example 11

Synthetic Route:

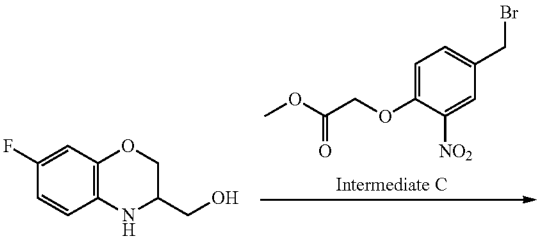

7-2

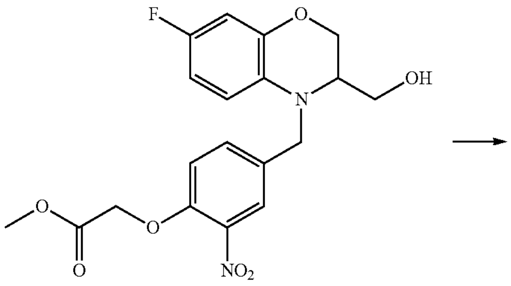

11-1

-continued

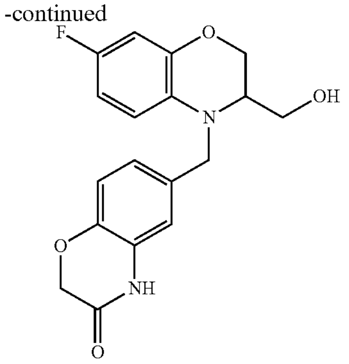

11

Step 1

7-2 (0.2 g, 1.09 mmol), intermediate C (498 mg, 1.64 mmol), sodium iodide (164 mg, 1.09 mmol), potassium carbonate (453 mg, 3.28 mmol), and acetonitrile (3 mL) were added to a reaction flask, and the mixture was purged three times with nitrogen. Under the nitrogen atmosphere, the reaction mixture was heated to 80° C., stirred for reaction for 16 h, and then poured into water (10 mL). The resulting mixture was extracted with ethyl acetate (10 mL×3), and the organic phases were combined, dried over anhydrous sodium sulfate, and filtered. The filtrate was concentrated under reduced pressure to give crude compound 11-1. MS-ESI calcd. $[M+H]^+$ 407, found 407.

Step 2

Compound 11-1 (0.5 g, 1.23 mmol), iron powder (68.7 mg, 1.23 mmol), and acetic acid (5 mL) were added to a reaction flask, and the mixture was purged three times with nitrogen. Under the nitrogen atmosphere, the reaction mixture was heated to 80° C., stirred for reaction for 1 h, and then filtered through diatomite. The filter cake was washed with ethyl acetate (20 mL), and the filtrate was concentrated under reduced pressure. The resulting residue was dissolved in ethyl acetate (10 mL) and washed with water (10 mL×3). The organic phase was dried over anhydrous sodium sulfate and filtered, and the filtrate was concentrated under reduced pressure to give a crude product. The crude product was separated and purified by high performance liquid chromatography (chromatographic column: Phenomenex Gemini-NX C18 75×30 mm×3 mu; mobile phase: 10 mM aqueous ammonium bicarbonate solution-acetonitrile; gradient:acetonitrile: 25%-50%, 6 min) to give compound 11. MS-ESI calcd. $[M+H]^+$ 344, found 344. $^1H$ NMR (400 MHz, DMSO-$d_6$) δ 10.61 (s, 1H), 6.94-6.87 (m, 1H), 6.86-6.79 (m, 2H), 6.65-6.59 (m, 1H), 6.54-6.46 (m, 1H), 6.42-6.34 (m, 1H), 4.94-4.91 (m, 1H), 4.53 (s, 2H), 4.47-4.34 (m, 2H), 3.97-3.92 (m, 1H), 3.50-3.43 (m, 1H), 3.40-3.30 (m, 2H) ppm.

Example 12

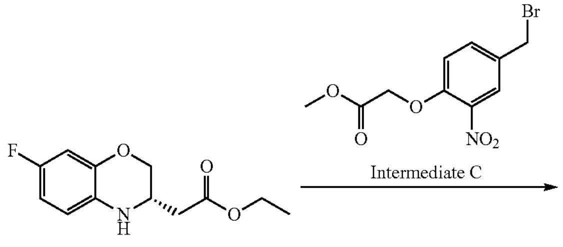

Intermediate D

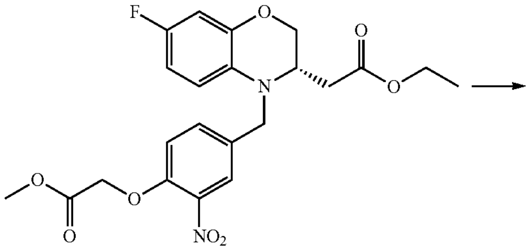

12-1

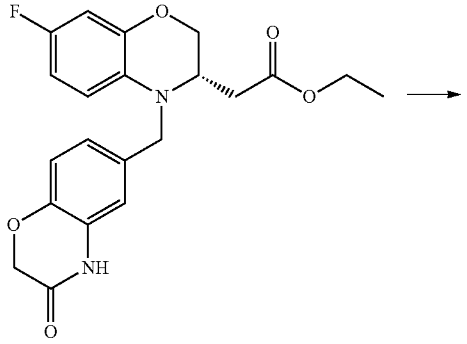

12-2

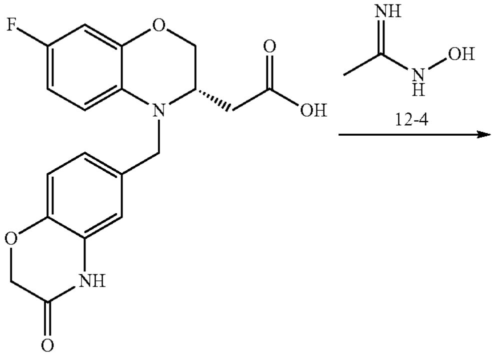

12-3

-continued

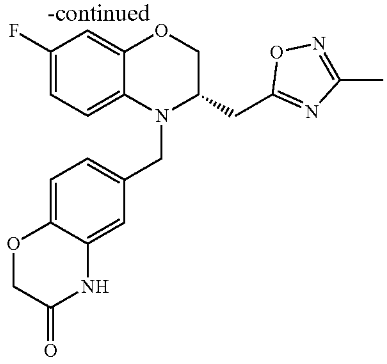

12

Step 1

Intermediate D (720 mg, 3.01 mmol), intermediate C (763 mg, 2.51 mmol), potassium carbonate (1.04 g, 7.52 mmol), sodium iodide (376 mg, 2.51 mmol), and acetonitrile (10 mL) were added to a reaction flask, and the reaction mixture was heated to 80° C. for reaction for 5 h and then filtered. The filtrate was concentrated under reduced pressure to give a crude product. The crude product was separated by silica gel column chromatography (eluent: petroleum ether/ethyl acetate, 20/1-2/1, V/V) to give compound 12-1. MS-ESI calcd. $[M+H]^+$ 463, found 463.

Step 2

Compound 12-1 (1 g, 2.16 mmol), iron powder (1.09 g, 19.5 mmol), and acetic acid (10 mL) were added to a reaction flask, and the reaction mixture was purged three times with nitrogen, heated to 80° C., stirred for reaction for 16 h, and then filtered under reduced pressure. The filtrate was concentrated under reduced pressure. Ethyl acetate (25 mL) was added to the resulting residue, and the mixture was stirred for 0.5 h and washed with a saturated sodium carbonate solution (15 mL). The organic phase was concentrated under reduced pressure to give crude compound 12-2. MS-ESI calcd. $[M+H]^+$ 401, found 401.

Step 3

Compound 12-2 (920 mg, 2.30 mmol) was dissolved in tetrahydrofuran (6 mL) and water (6 mL), and lithium hydroxide (275 mg, 11.5 mmol) was added. The reaction mixture was stirred at 20° C. for reaction for 2 h. Water (30 mL) was added to quench the reaction, and the mixture was extracted with ethyl acetate (20 mL×2). The aqueous phase was adjusted to about pH 4 with a 1 M aqueous hydrochloric acid solution and extracted with ethyl acetate (20 mL×3). The organic phases were combined, dried over anhydrous sodium sulfate, and filtered. The filtrate was concentrated under reduced pressure to give crude compound 12-3.

Step 4

Compound 12-3 (250 μmg, 671 μmol) was dissolved in N,N-dimethylformamide (2.5 mL), and 1,1'-carbonyldiimidazole (131 mg, 806 μmol) was added. The reaction mixture was stirred at 20° C. for reaction for 1 h. 12-4 (149 mg, 2.01 mmol) was added to the reaction mixture, and the reaction mixture was stirred at 20° C. for reaction for 1 h, then heated to 80° C., and stirred for reaction for another 14 h. Water (20 mL) was added to the reaction mixture to quench the reaction, and the mixture was extracted with ethyl acetate (20 mL×2). The organic phases were combined, washed with saturated brine (50 mL), dried over anhydrous sodium sulfate, and filtered. The filtrate was concentrated under reduced pressure to give a crude product. The crude product was separated and purified by silica gel column chromatography (petroleum ether/ethyl acetate, 2/1-1/1, V/V) to give compound 12. MS-ESI calcd. $[M+H]^+$ 411, found 411. $^1H$ NMR (400 MHz, DMSO-$d_6$) δ 10.59 (s, 1H), 6.91-6.83 (m, 1H), 6.82-6.74 (m, 2H), 6.70 (d, J=8.8 Hz, 1H), 6.64-6.59 (m, 2H), 4.53 (s, 2H), 4.41-4.21 (m, 3H), 4.04 (d, J=10.8 Hz, 1H), 3.92 (t, J=6.8 Hz, 1H), 3.07 (d, J=6.8 Hz, 2H), 2.27 (s, 3H) ppm.

Example 13

Synthetic Route:

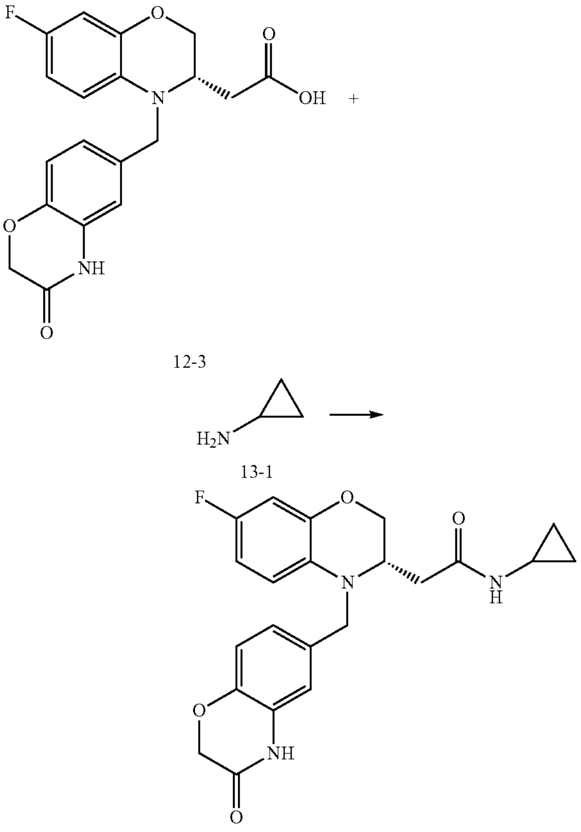

12-3

13-1

13

Compound 12-3 (50 mg, 134 gmol) was dissolved in dichloromethane (1 mL), and 1,1'-carbonyldiimidazole (65 mg, 403 μmol) was added. The reaction mixture was stirred at 25° C. for reaction for 0.5 h. Cyclopropylamine (31 mg, 571 gmol) was added to the reaction mixture, and the reaction mixture was stirred for reaction for another 1.5 h. Water (20 mL) was added to the reaction mixture to quench the reaction, and the mixture was extracted with ethyl acetate (10 mL×3). The organic phases were combined, washed with saturated brine (20 mL), dried over anhydrous sodium sulfate, and filtered. The filtrate was concentrated under reduced pressure to give a crude product. The crude product was separated and purified by preparative high performance liquid chromatography (chromatographic column: Waters Xbridge 150×25 mm×5 μm; mobile phase: 10 mM aqueous ammonium bicarbonate solution-acetonitrile; gradient:acetonitrile: 28%-58%, 8 min) to give compound 13. MS-ESI calcd. [M+H]+ 412, found 412. $^1$H NMR (400 MHz, DMSO-$d_6$) δ 10.60 (s, 1H), 8.01 (d, J=4.0 Hz, 1H), 6.91-6.86 (m, 1H), 6.85-6.79 (m, 2H), 6.64 (dd, J=2.8, 9.6 Hz, 1H), 6.59-6.51 (m, 1H), 6.48-6.42 (m, 1H), 4.53 (s, 2H), 4.42-4.24 (m, 2H), 4.18 (d, J=9.6 Hz, 1H), 4.03 (dd, J=1.8, 10.8 Hz, 1H), 2.64-2.53 (m, 2H), 2.37-2.21 (m, 2H), 0.63-0.55 (m, 2H), 0.39-0.30 (m, 2H) ppm.

Example 14

Synthetic Route:

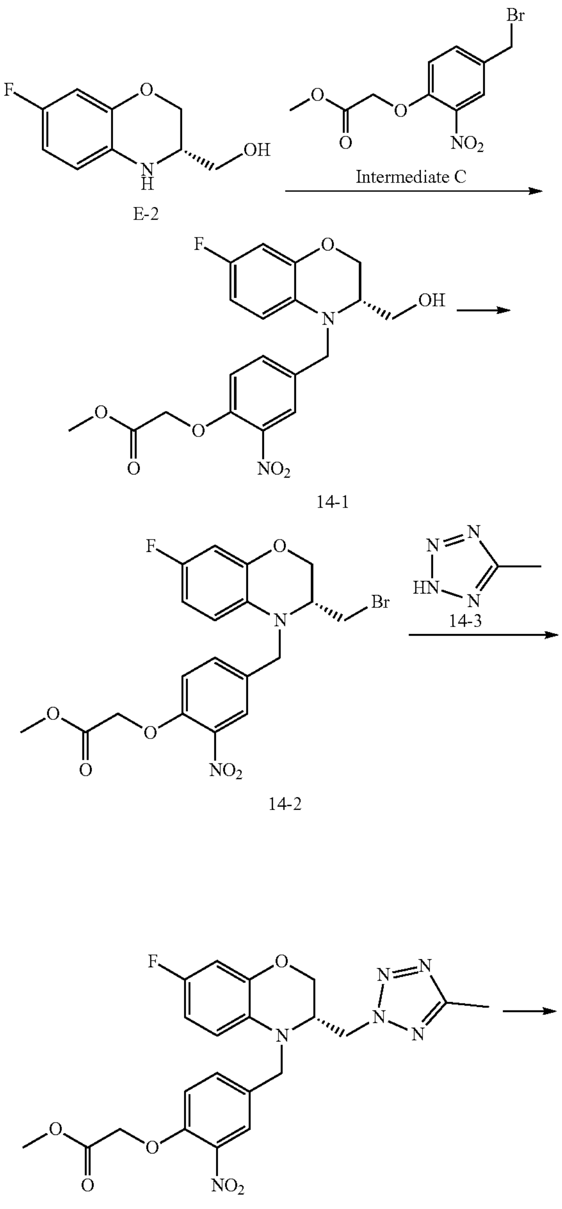

-continued

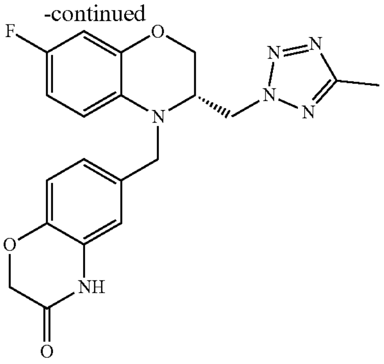

14

Step 1

Compound E-2 (3.00 g, 16.4 mmol) and intermediate C (5.48 g, 18.0 mmol) were dissolved in acetonitrile (40 mL), and sodium iodide (2.45 g, 16.4 mmol) and potassium carbonate (6.79 g, 49.1 mmol) were added. The reaction mixture was stirred at 80° C. for reaction for 12 h and then concentrated under reduced pressure to give a crude product. The crude product was separated and purified by silica gel column chromatography (petroleum ether/ethyl acetate, 8/1-1/2, V/V) to give compound 14-1. MS-ESI calcd. [M+H]+ 407, found 407.

Step 2

Compound 14-1 (6.4 g, 15.8 mmol) and triphenylphosphine (6.2 g, 23.6 mmol) were dissolved in N,N-dimethylformamide (64 mL), and N-bromosuccinimide (4.20 g, 23.6 mmol) was added at 20° C. The reaction mixture was stirred at 50° C. for reaction for 1 h. Water (600 mL) was added to the reaction mixture to quench the reaction, and the mixture was extracted with ethyl acetate (200 mL×2). The organic phases were combined, washed with saturated brine (200 mL×2), dried over anhydrous sodium sulfate, and filtered. The filtrate was concentrated under reduced pressure to give a crude product. The crude product was separated and purified by silica gel column chromatography (petroleum ether/ethyl acetate, 8/1-4/1, V/V) to give compound 14-2. MS-ESI calcd. [M+H]+ 469/471, found 469/471.

Step 3

Compounds 14-2 (200 mg, 426 mol) and 14-3 (108 mg, 1.28 mmol) were dissolved in acetonitrile (4 mL), and sodium carbonate (70.8 mg, 852 mol) was added. The reaction mixture was stirred at 70° C. for reaction for 12 h and then filtered. The filtrate was concentrated under reduced pressure to give a crude product. The crude product was separated and purified by silica gel column chromatography (petroleum ether/ethyl acetate, 1/1, V/V) to give compound 14-4. MS-ESI calcd. [M+H]+ 473, found 473.

Step 4

Compound 14-4 (50 mg, 106 μmol) was dissolved in glacial acetic acid (2 mL), and iron powder (59 mg, 1.06 mmol) was added. The reaction mixture was stirred at 80° C. for reaction for 1 h and then filtered. The filtrate was concentrated under reduced pressure to give a crude product.

The crude product was separated and purified by thin layer chromatography (developing solvent: dichloromethane/methanol, 20/1, V/V) to give compound 14. MS-ESI calcd. $[M+H]^+$ 411, found 411. $^1H$ NMR (400 MHz, $CDCl_3$) δ 6.88-6.83 (m, 1H), 6.80-6.69 (m, 3H), 6.67-6.56 (m, 2H), 4.66 (d, J=7.2 Hz, 2H), 4.55 (s, 2H), 4.31-4.14 (m, 3H), 4.07-3.95 (m, 2H), 2.42 (s, 3H) ppm.

Example 15

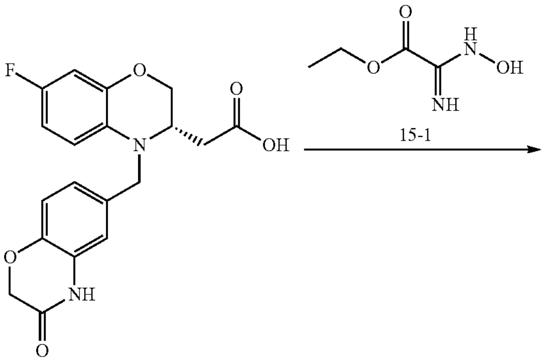

12-3

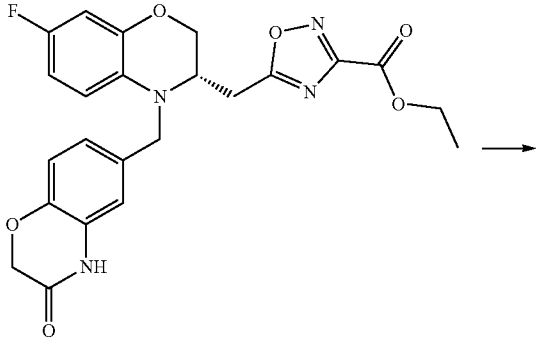

15-2

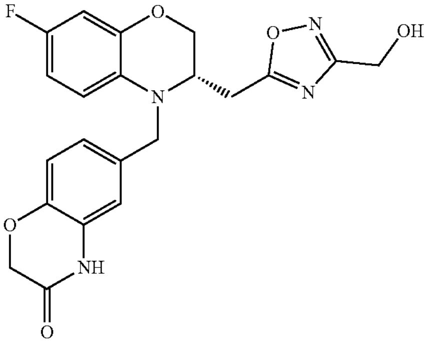

15

Step 1

Compound 12-3 (680 mg, 1.83 mmol) was dissolved in N,N-dimethylformamide (10 mL), and 1,1'-carbonyldiimidazole (355 mg, 2.19 mmol) was added to the reaction solution. The reaction mixture was stirred at 20° C. for 1 h, and then compound 15-1 (723 mg, 5.48 mmol) was added. The reaction mixture was stirred at 20° C. for another 1 h, then heated to 80° C., and stirred for 14 h. Water (20 mL) was added to the reaction mixture, and the resulting mixture was extracted with ethyl acetate (20 mL×2). The organic phases were combined, washed with saturated brine (50 mL), dried over anhydrous sodium sulfate, and filtered. The filtrate was concentrated under reduced pressure. The crude product resulting from the concentration was separated and purified by silica gel column chromatography (petroleum ether/ethyl acetate, 5/1-1/1, V/V) to give compound 15-2. MS-ESI calcd. $[M+H]^+$ 469, found 469.

Step 2

Compound 15-2 (600 mg, 1.28 mmol) was dissolved in tetrahydrofuran (3 mL) and absolute ethanol (15 mL), and sodium borohydride (97.0 mg, 2.56 mmol) was added portionwise to the reaction solution. The reaction mixture was stirred at 25° C. for 2 h, and then a saturated ammonium chloride solution (100 mL) was added. The mixture was then extracted with ethyl acetate (60 mL×3), and the organic phases were combined, washed with saturated brine (50 mL), dried over anhydrous sodium sulfate, and filtered. The filtrate was concentrated under reduced pressure to give a crude product. The crude product was separated and purified by preparative high performance liquid chromatography (chromatographic column: Phenomenex Gemini-NX C18 75×30 mm×3 μm; mobile phase: 0.225% aqueous formic acid solution-acetonitrile; gradient:acetonitrile 40%-50%, 7 min) to give compound 15. MS-ESI calcd. $[M+H]^+$ 427, found 427. $^1H$ NMR (400 MHz, DMSO-$d_6$) δ 10.58 (s, 1H), 6.89-6.85 (m, 1H), 6.81-6.76 (m, 2H), 6.73-6.68 (m, 1H), 6.64-6.59 (m, 2H), 5.71-5.57 (m, 1H), 4.53 (s, 2H), 4.49 (d, J=4.4 Hz, 2H), 4.41-4.34 (m, 1H), 4.33-4.21 (m, 2H), 4.08-4.02 (m, 1H), 3.95 (s, 1H), 3.12 (d, J=6.8 Hz, 2H) ppm.

Example 16

Synthetic Route:

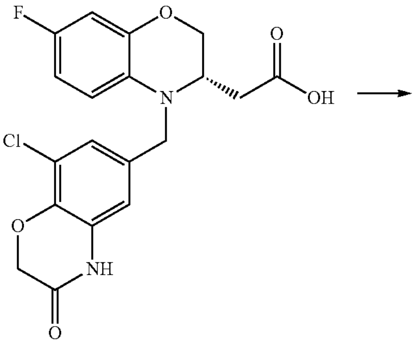

10-3

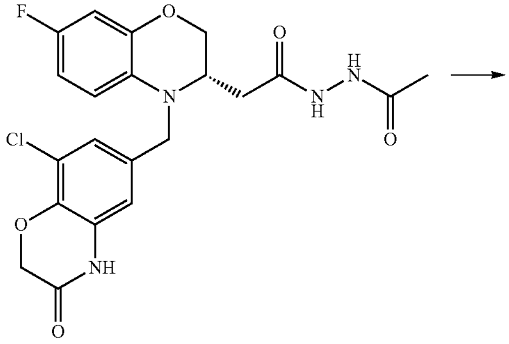

16-1

-continued

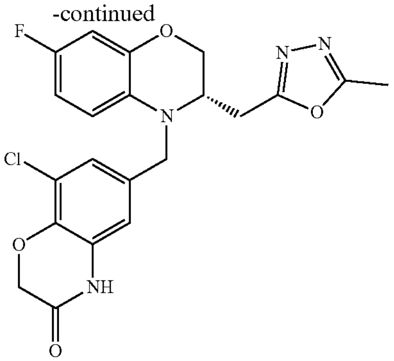

16

Step 1

Compound 10-3 (200 mg, 492 mmol) and acethydrazide (182 mg, 2.46 mmol) were dissolved in ethyl acetate (5 mL), a 50% solution of tri-n-propyl cyclophosphoric anhydride (1.56 g, 2.46 mmol) in ethyl acetate and triethylamine (249 mg, 2.46 mmol) were added to the reaction solution. The reaction mixture was stirred at 20° C. for 0.5 h. Water (20 mL) was added to the reaction mixture, and the resulting mixture was extracted with ethyl acetate (20 mL×2). The organic phases were combined, washed with saturated brine (50 mL), dried over anhydrous sodium sulfate, filtered, and concentrated under reduced pressure to give crude compound 16-1. MS-ESI calcd. $[M+H]^+$ 463, found 463.

Step 2

Compound 16-1 (200 mg, 432 μmol) was dissolved in acetonitrile (3 mL), and N,N-diisopropylethylamine (168 mg, 1.30 mmol) and p-toluenesulfonyl chloride (165 mg, 864 μmol) were added to the reaction solution. The reaction mixture was stirred at 60° C. for 12 h. Water (20 mL) was added to the reaction mixture, and the resulting mixture was extracted with ethyl acetate (20 mL×2). The organic phases were combined, washed with saturated brine (50 mL), dried over anhydrous sodium sulfate, filtered, and concentrated under reduced pressure to give a crude product. The crude product was separated by preparative high performance liquid chromatography (chromatographic column: Waters Xbridge 150×25 mm×10 Wm; mobile phase: 0.225% aqueous formic acid solution-acetonitrile; gradient:acetonitrile 38%-38%, 2 min) to give compound 16. MS-ESI calcd. $[M+H]^+$ 445, found 445. $^1H$ NMR (400 MHz, DMSO-$d_6$) δ 10.84-10.72 (m, 1H), 6.99-6.89 (m, 1H), 6.79-6.67 (m, 2H), 6.67-6.55 (m, 2H), 4.70-4.62 (m, 2H), 4.40-4.21 (m, 3H), 4.14-4.02 (m, 1H), 3.94-3.84 (m, 1H), 3.08-2.92 (m, 2H), 2.42-2.36 (m, 3H) ppm.

Example 17

Synthetic Route:

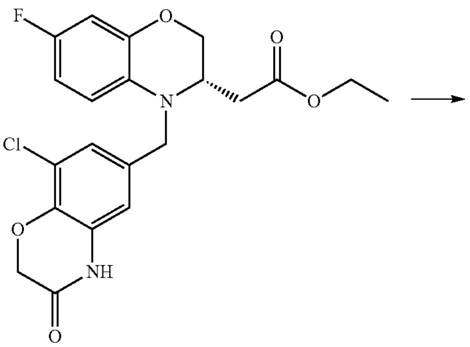

10-2

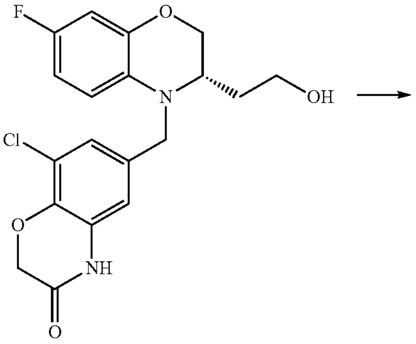

17-1

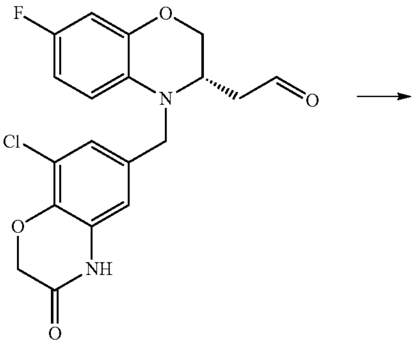

17-2

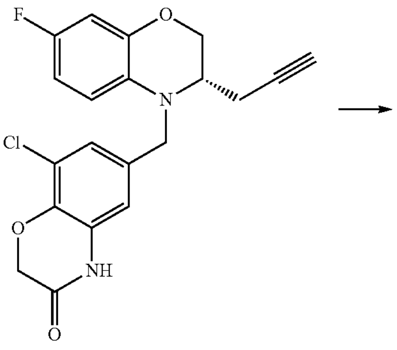

17-3

-continued

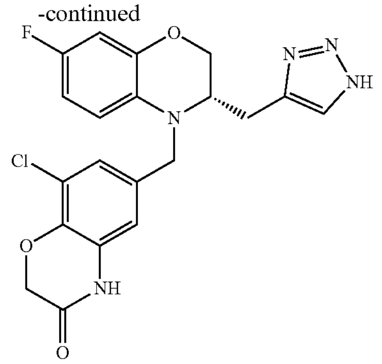

17

Step 1

Lithium aluminum hydride (209 mg, 5.52 mmol) was dissolved in tetrahydrofuran (10 mL), and a solution of compound 10-2 (2.00 g, 4.60 mmol) in tetrahydrofuran (5 mL) was added to the reaction solution under nitrogen atmosphere at 0° C. The reaction mixture was stirred at 20° C. for 12 h. Water (100 mL) was added to the reaction mixture, and the resulting mixture was adjusted to pH 2 with 2 M hydrochloric acid and extracted with ethyl acetate (100 mL×2). The organic phases were combined, washed with saturated brine (100 mL), dried over anhydrous sodium sulfate, filtered, and concentrated under reduced pressure to give a crude product. The crude product was separated by silica gel column chromatography (eluent: petroleum ether/ethyl acetate, 2/1-1/2, V/V) to give compound 17-1. MS-ESI calcd. $[M+H]^+$ 393, found 393.

Step 2

Compound 17-1 (200 mg, 489 μmol) was dissolved in dichloromethane (2 mL), and Dess-Martin periodinane (311 mg, 733 μmol) was added to the reaction solution. The reaction mixture was stirred at 20° C. for 12 h. A saturated sodium bicarbonate solution (30 mL) and a saturated sodium sulfite solution (30 mL) were added to the reaction mixture, and the resulting mixture was extracted with ethyl acetate (50 mL×2). The organic phases were combined, washed with saturated brine (50 mL), dried over anhydrous sodium sulfate, filtered, and concentrated under reduced pressure to give a crude product. The crude product was separated by silica gel column chromatography (eluent: petroleum ether/ethyl acetate, 5/1-1/1, V/V) to give compound 17-2. MS-ESI calcd. $[M+H]^+$ 391, found 391.

Step 3

Compound 17-2 (260 mg, 665 mol) and dimethyl (1-diazo-2-oxopropyl)phosphonate (256 mg, 1.33 mmol) were dissolved in methanol (5 mL), and potassium carbonate (276 mg, 2.00 mmol) was added to the reaction solution. The reaction mixture was stirred at 20° C. for 12 h. Water (20 mL) was added to the reaction mixture, and the resulting mixture was extracted with ethyl acetate (20 mL×2). The organic phases were combined, washed with saturated brine (20 mL), dried over anhydrous sodium sulfate, filtered, and concentrated under reduced pressure to give a crude product. The crude product was separated by thin layer chromatography (developing solvent: petroleum ether/ethyl acetate, 1/1, V/V) to give compound 17-3. MS-ESI calcd. $[M+H]^+$ 387, found 387.

Step 4

Compound 17-3 (200 mg, 517 mol), anhydrous copper sulfate (82.5 mg, 517 mmol), and sodium ascorbate (205 mg, 1.03 mmol) were dissolved in tert-butanol (15 mL) and water (5 mL), and azidotrimethylsilane (179 mg, 1.55 mmol) was added to the reaction solution at 20° C. The reaction mixture was stirred at 90° C. for 12 h. Water (100 mL) was added to the reaction mixture, and the resulting mixture was adjusted to pH 8 with a saturated sodium bicarbonate solution and extracted with ethyl acetate (100 mL×2). The organic phases were combined, washed with saturated brine (100 mL), dried over anhydrous sodium sulfate, filtered, and concentrated under reduced pressure to give a crude product. The crude product was separated by thin layer chromatography (developing solvent: dichloromethane/methanol, 10/1, V/V) to give compound 17. MS-ESI calcd. $[M+H]^+$ 430, found 430. $^1H$ NMR (400 MHz, $CD_3OD$) δ 7.64-7.48 (m, 1H), 7.03-6.88 (m, 1H), 6.83-6.70 (m, 1H), 6.67-6.46 (m, 3H), 4.64 (s, 2H), 4.28 (s, 2H), 4.21-4.13 (m, 1H), 4.09-4.01 (m, 1H), 3.71-3.61 (m, 1H), 3.02-2.88 (m, 2H) ppm.

Example 18

Synthetic Route:

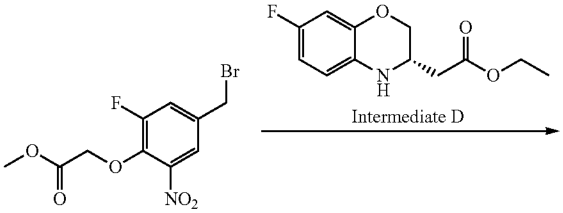

3-5

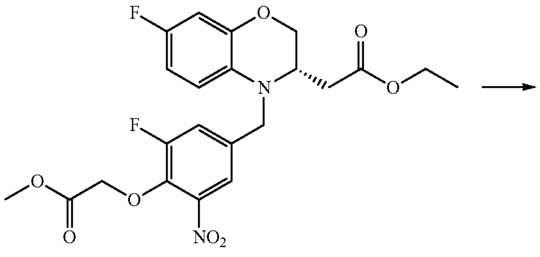

18-1

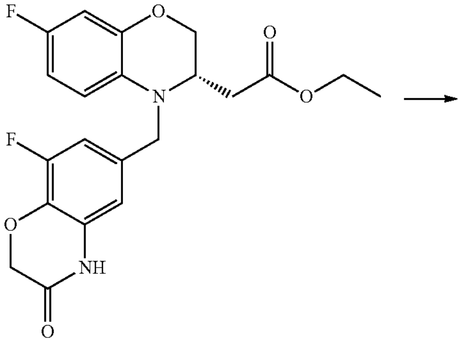

18-2

-continued

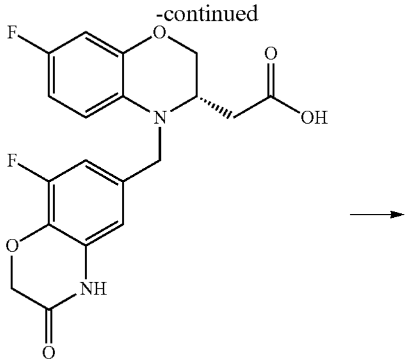

18-3

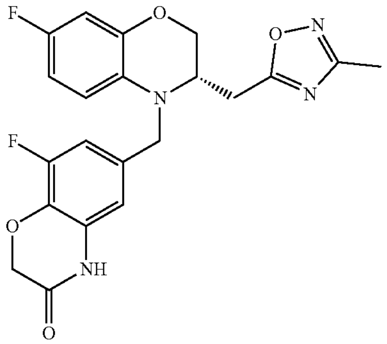

18

Step 1

Compound 3-5 (300 mg, 1.25 mmol) and intermediate D (444 mg, 2.72 mmol) were dissolved in acetonitrile (3 mL), and sodium iodide (188 mg, 1.25 mmol) and potassium carbonate (520 mg, 3.76 mmol) were added to the reaction solution. The reaction mixture was stirred at 80° C. for 2 h and then filtered. The filtrate was concentrated under reduced pressure to give compound 18-1. MS-ESI calcd. $[M+H]^+$ 481, found 481.

Step 2

Compound 18-1 (500 mg, 1.04 mmol) was dissolved in acetic acid (5 mL), and iron powder (581 mg, 10.4 mmol) was added to the reaction solution. The reaction mixture was stirred at 80° C. for 3 h and then filtered through diatomite. The filtrate was concentrated under reduced pressure to give a crude product. The crude product was separated by thin layer chromatography (developing solvent: petroleum ether/ethyl acetate, 1/1, V/V) to give compound 18-2. MS-ESI calcd. $[M+H]^+$ 419, found 419.

Step 3

Compound 18-2 (370 mg, 884 μmol) was dissolved in methanol (3 mL), and a solution of lithium hydroxide monohydrate (297 mg, 7.07 mmol) in water (0.5 mL) was added to the reaction solution. The reaction mixture was stirred at 25° C. for 1 h. Water (20 mL) was added to the reaction mixture, and the resulting mixture was adjusted to about pH 3 with 1 M hydrochloric acid and extracted with ethyl acetate (20 mL×2). The organic phases were combined, washed with saturated brine, dried over anhydrous sodium sulfate, and filtered. The filtrate was concentrated under reduced pressure to give crude compound 18-3. MS-ESI calcd. $[M+H]^+$ 391, found 391.

Step 4

Compound 18-3 (300 μmg, 769 μmol) was dissolved in N,N-dimethylformamide (3 mL), and 1,1'-carbonyldiimidazole (150 mg, 922 μmol) was added to the reaction solution. The reaction mixture was stirred at 20° C. for 0.5 h. N-Hydroxyacetamidine (114 mg, 1.54 mmol) was added to the reaction mixture, and the reaction mixture was stirred at 20° C. for 0.5 h and then stirred at 80° C. for another 11 h. Water (20 mL) was added to the reaction mixture, and the resulting mixture was extracted with ethyl acetate (50 mL×2). The organic phases were combined, washed with saturated brine (50 mL), dried over anhydrous sodium sulfate, filtered, and concentrated under reduced pressure to give a crude product. The crude product was separated by preparative high performance liquid chromatography (chromatographic column: Waters Xbridge 150×25 mm×10 m; mobile phase: 0.225% aqueous formic acid solution-acetonitrile; gradient:acetonitrile 42%-72%, 10 min) to give compound 18. MS-ESI calcd. $[M+H]^+$ 429, found 429. H NMR (400 MHz, DMSO-$d_6$) δ 10.94-10.65 (m, 1H), 6.81-6.67 (m, 2H), 6.67-6.54 (m, 3H), 4.68-4.57 (m, 2H), 4.37-4.21 (m, 3H), 4.13-4.03 (m, 1H), 3.97-3.89 (m, 1H), 3.13-3.01 (m, 2H), 2.31-2.22 (m, 3H) ppm.

Example 19

Synthetic Route:

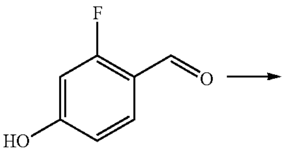

19-1

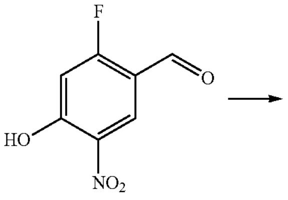

19-2

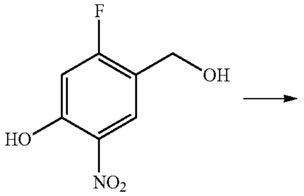

19-3

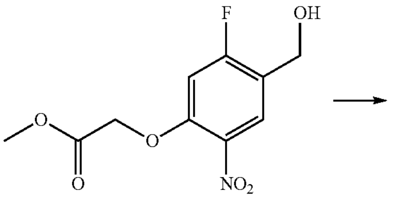

19-4

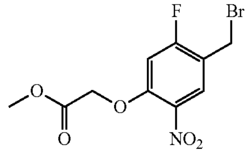

19-5

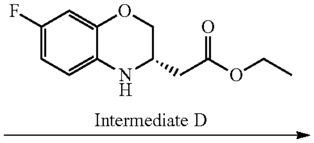

-continued

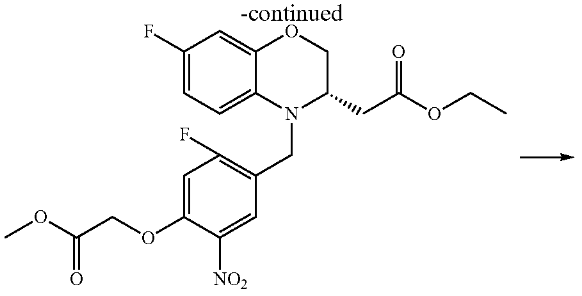

19-6

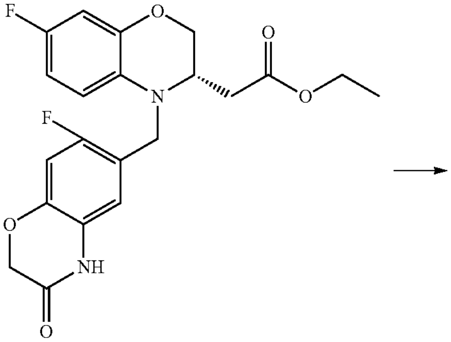

19-7

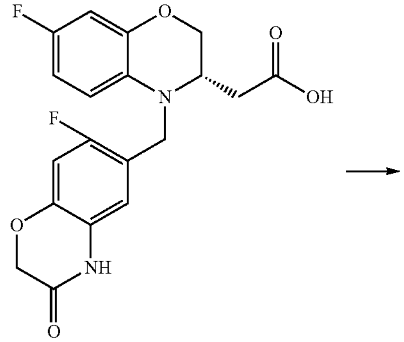

19-8

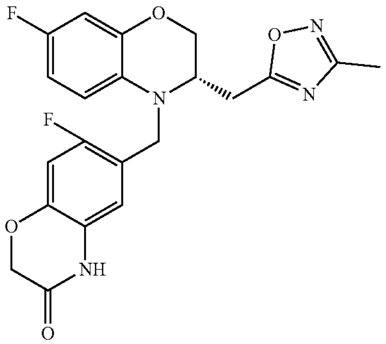

19

Step 1

Compound 19-1 (3.00 g, 21.4 mmol) was dissolved in sulfuric acid (25 mL). At −20° C., a 65% nitric acid solution (4.7 g, 48.5 mmol) was dissolved in sulfuric acid (5 mL), and the resulting solution was added to the above reaction solution. The reaction mixture was stirred at −20° C. for 2 h. 300 mL of ice water was added to the reaction mixture, and the resulting mixture was filtered. The filter cake was collected and dried to give crude compound 19-2.

Step 2

Compound 19-2 (2.10 g, 11.3 mmol) was dissolved in tetrahydrofuran (15 mL), and a solution of sodium borohydride (1.00 g, 26.4 mmol) in water (5 mL) was added to the reaction solution at 20° C. The reaction mixture was stirred at 20° C. for 1 h and then adjusted to about pH 3 with 2 M hydrochloric acid. Water (50 mL) was then added, and the mixture was extracted with ethyl acetate (50 mL×2). The organic phases were combined, washed with saturated brine (50 mL), dried over anhydrous sodium sulfate, and filtered. The filtrate was concentrated under reduced pressure to give crude compound 19-3.

Step 3

Compound 19-3 (1.90 g, 10.2 mmol) and methyl bromoacetate (2.33 g, 15.2 mmol) were dissolved in N,N-dimethylformamide (20 mL), and potassium carbonate (2.11 g, 15.2 mmol) was added to the reaction solution. The reaction mixture was stirred at 80° C. for 0.5 h, then diluted with water (100 mL), and extracted with ethyl acetate (100 mL×2). The organic phases were combined, washed with saturated brine, dried over anhydrous sodium sulfate, and filtered. The filtrate was concentrated under reduced pressure to give crude compound 19-4.

Step 4

Compound 19-4 (2.70 g, 10.4 mmol) was dissolved in dichloromethane (30 mL), and phosphorus tribromide (3.10 g, 11.5 mmol) was added slowly and dropwise to the reaction solution at 0° C. The reaction mixture was stirred at 20° C. for 0.5 h, then diluted with water (100 mL), adjusted to about pH 7 with a saturated sodium bicarbonate solution, and extracted with dichloromethane (100 mL×2). The organic phases were combined, washed with saturated brine, dried over anhydrous sodium sulfate, and filtered. The filtrate was concentrated under reduced pressure to give a crude product. The crude product was separated by silica gel column chromatography (eluent: petroleum ether/ethyl acetate, 20/1-10/1, V/V) to give compound 19-5. MS-ESI calcd. $[M+H]^+$ 322/324, found 322/324.

Step 5

Intermediate D (150 mg, 627 μmol) and compound 19-5 (242 mg, 752 μmol) were dissolved in acetonitrile (3 mL), and sodium iodide (94.0 mg, 627 μmol) and potassium carbonate (260 mg, 1.88 mmol) were added to the reaction solution. The reaction mixture was stirred at 80° C. for 1 h and then filtered. The filtrate was concentrated under reduced pressure to give compound 19-6. MS-ESI calcd. $[M+H]^+$ 481, found 481.

Step 6

Compound 19-6 (400 mg, 833 mol) was dissolved in acetic acid (5 mL), and iron powder (465 mg, 8.33 mmol) was added to the reaction solution. The reaction mixture was stirred at 80° C. for 1 h and then filtered through diatomite. The filtrate was concentrated under reduced pressure. Water (20 mL) and a saturated sodium bicarbonate solution (20 mL) were added to the crude product, and the mixture was extracted with ethyl acetate (50 mL×2). The organic phases were combined, washed with saturated brine, dried over anhydrous sodium sulfate, and filtered. The filtrate was concentrated under reduced pressure to give a crude product. The crude product was separated by thin layer chromatography (developing solvent: petroleum ether/ethyl acetate, 2/1, V/V) to give compound 19-7. MS-ESI calcd. $[M+H]^+$ 419, found 419.

Step 7

Compound 19-7 (250 mg, 598 mol) was dissolved in methanol (3 mL), and a solution of lithium hydroxide monohydrate (201 mg, 4.78 mmol) in water (0.5 mL) was added to the reaction solution. The reaction mixture was stirred at 25° C. for 1 h. Water (20 mL) was added to the reaction mixture, and the resulting mixture was adjusted to about pH 4 with 2 M hydrochloric acid and filtered. The filter cake was concentrated under reduced pressure to give crude compound 19-8. MS-ESI calcd. $[M+H]^+$ 391, found 391.

Step 8

Compound 19-8 (160 mg, 410 μmol) was dissolved in N,N-dimethylformamide (3 mL), and 1,1'-carbonyldiimidazole (79.8 mg, 492 μmol) was added to the reaction solution. The reaction mixture was stirred at 20° C. for 0.5 h. N-Hydroxyacetamidine (60.7 mg, 820 μmol) was added to the reaction mixture, and the reaction mixture was stirred at 20° C. for 0.5 h and then stirred at 80° C. for another 11 h. Water (20 mL) was added to the reaction mixture, and the resulting mixture was extracted with ethyl acetate (50 mL×2). The organic phases were combined, washed with saturated brine (50 mL), dried over anhydrous sodium sulfate, and filtered. The filtrate was concentrated under reduced pressure to give a crude product. The crude product was separated by thin layer chromatography (developing solvent: petroleum ether/ethyl acetate, 1/1, V/V) to give compound 19. MS-ESI calcd. $[M+H]^+$ 429, found 429. $^1H$ NMR (400 MHz, DMSO-$d_6$) δ 10.68-10.42 (m, 1H), 6.93-6.84 (m, 1H), 6.80-6.70 (m, 2H), 6.70-6.58 (m, 2H), 4.60-4.52 (m, 2H), 4.46-4.24 (m, 3H), 4.08-3.99 (m, 1H), 3.98-3.90 (m, 1H), 3.14-3.03 (m, 2H), 2.33-2.19 (m, 3H) ppm.

Example 20

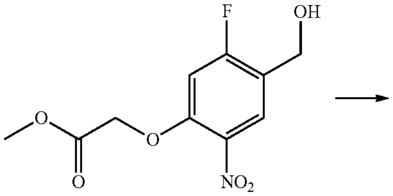

19-4

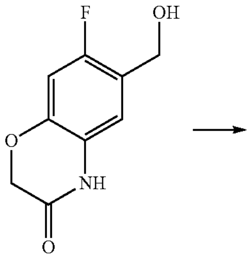

20-1

-continued

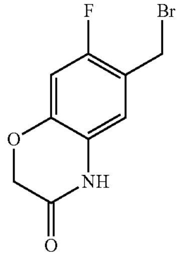

20-2

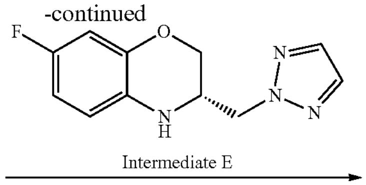

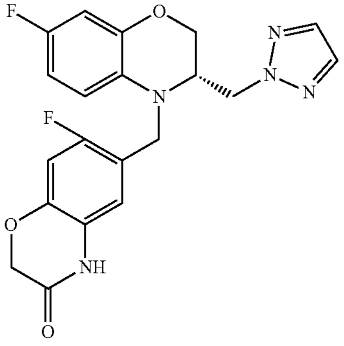

20

Step 1

Compound 19-4 (50.0 g, 833 μmol) and iron powder (86.2 g, 1.54 mmol) were dissolved in ethanol (500 mL), and a solution of ammonium chloride (82.6 g, 1.54 mmol) in water (150 mL) was added to the reaction solution. The reaction mixture was stirred at 80° C. for 3 h and then filtered through diatomite. Water (1 L) was added to the filtrate, and the mixture was extracted with ethyl acetate (1 L×3). The organic phases were combined, washed with saturated brine, dried over anhydrous sodium sulfate, and filtered. The filtrate was concentrated under reduced pressure to give crude compound 20-1. MS-ESI calcd. $[M+H]^+$ 198, found 198.

Step 2

Compound 20-1 (35.0 g, 178 mmol) was dissolved in dichloromethane (400 mL), and phosphorus tribromide (57.7 g, 213 mmol) was added slowly and dropwise to the reaction solution at 0° C. The reaction mixture was stirred at 20° C. for 0.5 h, then diluted with water (400 mL), and extracted with dichloromethane (300 mL×4). The organic phases were combined, washed with saturated brine, dried over anhydrous sodium sulfate, and filtered. The filtrate was concentrated under reduced pressure to give a crude product. Ethyl acetate (600 mL) was added to the crude product, and the mixture was stirred at 25° C. for 30 min and filtered. The filter cake was dried to give compound 20-2. MS-ESI calcd. $[M+H]^+$ 260/262, found 260/262.

Step 3

Compound 20-2 (18.3 g, 70.4 mmol) and intermediate E (11.0 g, 47.0 mmol) were dissolved in acetonitrile (220 mL), and sodium iodide (7.04 g, 47.0 mmol) and sodium bicarbonate (7.89 g, 93.9 mmol) were added to the reaction solution. The reaction mixture was stirred at 75° C. for 12 h and then filtered. The filtrate was concentrated under reduced pressure to give a crude product. The crude product was separated by silica gel column chromatography (eluent: petroleum ether/ethyl acetate, 10/1-1/1, V/V) to give compound 20. MS-ESI calcd. $[M+H]^+$ 414, found 414. $^1H$ NMR (400 MHz, DMSO-$d_6$) δ 10.60-10.43 (m, 1H), 7.89-7.72 (m, 2H), 6.92-6.82 (m, 1H), 6.80-6.69 (m, 2H), 6.69-6.59 (m, 1H), 6.58-6.47 (m, 1H), 4.64-4.44 (m, 4H), 4.38-4.26 (m, 1H), 4.25-4.15 (m, 1H), 4.06-3.95 (m, 2H), 3.90-3.79 (m, 1H) ppm.

Example 21

Synthetic Route:

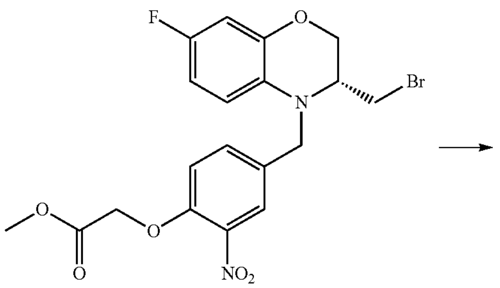

14-2

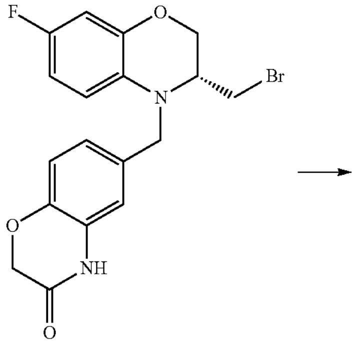

21-1

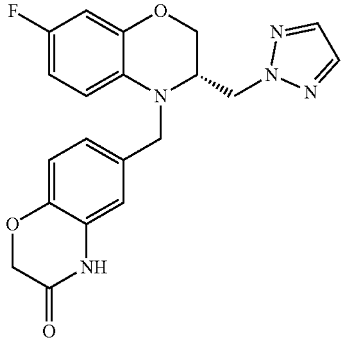

21

Step 1

Compound 14-2 (750 mg, 1.60 mmol) was dissolved in acetic acid (8 mL), and iron powder (893 mg, 16.0 mmol) was added to the reaction solution. The reaction mixture was stirred at 80° C. for 1 h and then filtered through diatomite. The filter cake was washed with ethyl acetate (50 mL). The filtrate was washed with a saturated sodium bicarbonate solution (50 mL×2), washed with a saturated brine (50 mL), dried over anhydrous sodium sulfate, filtered, and concentrated under reduced pressure to give a crude product. The crude product was separated by silica gel column chromatography (eluent: petroleum ether/ethyl acetate, 20/1-5/1, V/V) to give compound 21-1. MS-ESI calcd. $[M+H]^+$ 407/409, found 407/409.

Step 2

Compound 21-1 (200 mg, 491 μmol) and 1H-1,2,3-triazole (170 mg, 18.0 mmol) were dissolved in acetonitrile (2 mL), and sodium iodide (73.6 mg, 491 μmol) and potassium carbonate (204 mg, 1.47 mmol) were added to the reaction solution. The reaction mixture was stirred at 80° C. for 12 h and then filtered. The filtrate was concentrated under reduced pressure, and the crude product resulting from the concentration was separated by thin layer chromatography (developing solvent: petroleum ether/ethyl acetate, 1/1, V/V) to give compound 21. MS-ESI calcd. $[M+H]^+$ 396, found 396. $^1H$ NMR (400 MHz, DMSO-$d_6$) δ 10.66-10.48 (m, 1H), 7.90-7.71 (m, 2H), 6.90-6.81 (m, 1H), 6.78-6.68 (m, 3H), 6.66-6.57 (m, 1H), 6.57-6.49 (m, 1H), 4.63-4.43 (m, 4H), 4.31-4.21 (m, 1H), 4.20-4.11 (m, 1H), 4.07-3.93 (m, 2H), 3.92-3.79 (m, 1H) ppm.

Example 22

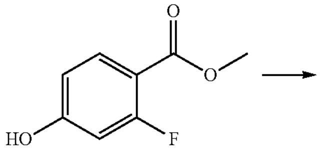

22-1

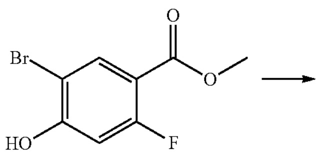

22-2

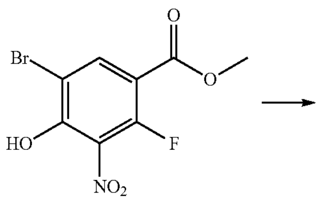

22-3

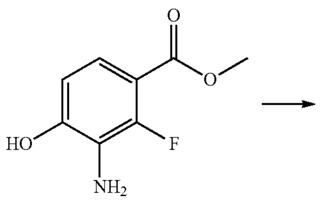

22-4

-continued

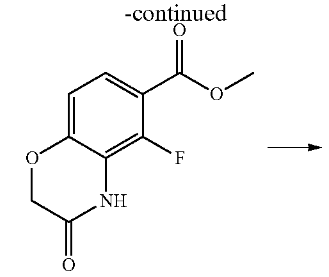

22-5

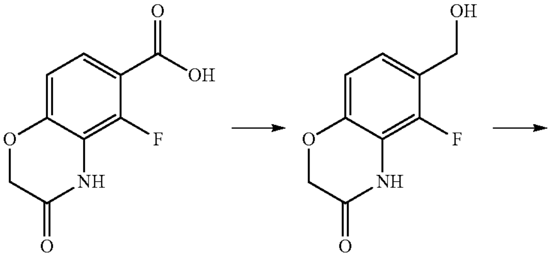

22-6

22-7

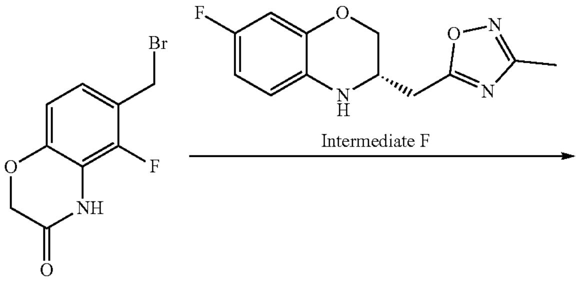

22-8

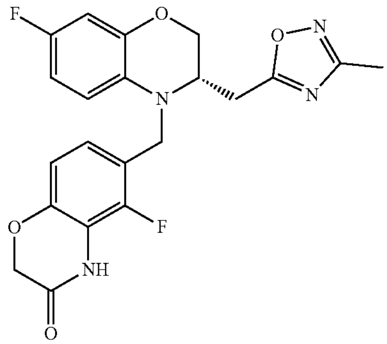

22

Step 1

Compound 22-1 (25.0 g, 147 mmol) was dissolved in acetic acid (400 mL), and a solution of liquid bromine (8.33 mL, 162 mmol) in acetic acid (40 mL) was added to the reaction solution. The reaction mixture was stirred at 20° C. for 12 h and then poured into water (2.5 L). The resulting mixture was filtered, and the resulting filter cake was dried to give crude compound 22-2. MS-ESI calcd. $[M+H]^+$ 249/251, found 249/251.

Step 2

Compound 22-2 (22.5 g, 90.4 mmol) was dissolved in acetic acid (160 mL) and trifluoroacetic acid (80 mL), and nitric acid (8.36 mL, 121 mmol, 65% purity) was added. The mixture was allowed to react at 20° C. for 2 h. Water (500 mL) was added to the reaction mixture, and the resulting mixture was filtered. The filter cake was dried to give crude compound 22-3. MS-ESI calcd. $[M-H]^-$ 292/294, found 292/294.

Step 3

Compound 22-3 (86 g, 292 mmol) was dissolved in ethanol (800 mL), and wet palladium on carbon (15 g, 57.5 mmol, 10% content) was added. The reaction mixture was stirred under hydrogen atmosphere (50 psi) at 25° C. for 16 h and then filtered. The filtrate was concentrated to give crude compound 22-4. MS-ESI calcd. $[M+H]^+$ 186, found 186.

Step 4

Compound 22-4 (54 g, 292 mmol) and potassium carbonate (121 g, 875 mmol) were dissolved in N,N-dimethylformamide (600 mL), and chloroacetyl chloride (25.5 mL, 321 mmol) was added at 0° C. The mixture was allowed to react at 20° C. for 5 h. Water (1.5 L) was added to the reaction mixture, and the resulting mixture was stirred for 10 min and then filtered. The filter cake was dried to give crude compound 22-5. MS-ESI calcd. $[M+H]^+$ 226, found 226.

Step 5

Compound 22-5 (40 g, 178 mmol) was dissolved in methanol (350 mL), and a solution of lithium hydroxide monohydrate (29.8 g, 711 mmol) in water (150 mL) was added to the reaction solution. The reaction mixture was stirred at 20° C. for 4 h. Water (1.5 L) was added to the reaction mixture, and the resulting mixture was adjusted to about pH 1 with concentrated hydrochloric acid and then filtered. The filter cake was dried to give crude compound 22-6. MS-ESI calcd. $[M+H]^+$ 212, found 212.

Step 6

Compound 22-6 (16 g, 75.8 mmol) was dissolved in acetonitrile (400 mL), and 1,1'-carbonyldiimidazole (24.6 g, 152 mmol) was added to the reaction solution. The reaction mixture was stirred at 20° C. for 1 h. A solution of sodium borohydride (5.76 g, 152 mmol) in water (130 mL) was added slowly and dropwise to the reaction mixture, and the resulting mixture was stirred at 20° C. for 2 h and then adjusted to pH 2-3 with concentrated hydrochloric acid. Water (500 mL) was then added, and the mixture was extracted with ethyl acetate (400 mL+300 mL). The organic phases were combined and concentrated to give a residue. The residue was dissolved in a sodium hydroxide solution (1 M, 100 mL), and the resulting solution was adjusted to about pH 7 with hydrochloric acid and filtered. The filter cake was dried to give crude compound 22-7. MS-ESI calcd. $[M+H]^+$ 198, found 198.

Step 7

Compound 22-7 (15 g, 70.0 mmol) was dissolved in dichloromethane (400 mL), and phosphorus tribromide (22.7 g, 84.0 mmol) was added to the reaction solution at 0° C. The reaction mixture was stirred at 20° C. for 1 h. Water (200 mL) was added to the reaction mixture, and the resulting mixture was filtered. The filtrate was separated, and then the organic phases were concentrated to give a residue. The residue was combined with the filter cake, and the mixture was dried to give crude compound 22-8. MS-ESI calcd. $[M+H]^+$ 260/262, found 260/262.

Step 8

Intermediate F (10 g, 40.1 mmol) was dissolved in acetonitrile (200 mL), and potassium carbonate (11.1 g, 80.2 mmol) and sodium iodide (6.01 g, 40.1 mmol) were added to the reaction solution. Compound 22-8 (13.6 g, 52.2 mmol) was then added, and the reaction mixture was stirred at 70° C. for 1 h and then filtered. The filtrate was concentrated under reduced pressure to give a crude product. The crude product was separated by silica gel column chromatography (eluent: petroleum ether/dichloromethane, 3/1-0/1, V/V) to give an oil. The oil was stirred with ethyl acetate/n-heptane (2 V/15 V) for 30 min and then filtered. The filter cake was dried to give compound 22. MS-ESI calcd. $[M+H]^+$ 429, found 429. $^1H$ NMR (400 MHz, $CD_3OD$) δ 6.87-6.82 (m, 2H), 6.73-6.70 (m, 1H), 6.62-6.58 (m, 2H), 4.60 (s, 2H), 4.37-4.26 (m, 3H), 4.03-3.99 (m, 1H), 3.88-3.84 (m, 1H), 3.01 (d, J=7.2 Hz, 2H), 2.27 (s, 3H).

Example 23

Synthetic Route:

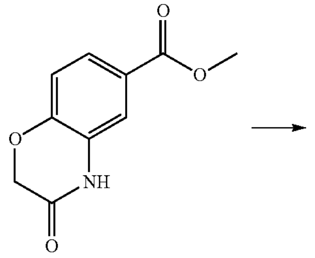

23-1

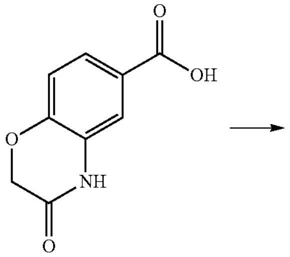

23-2

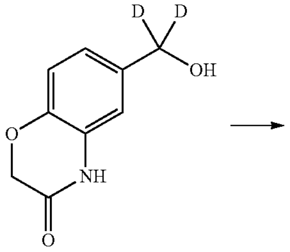

23-3

-continued

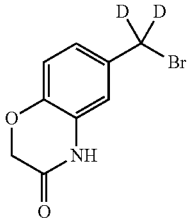

23-4

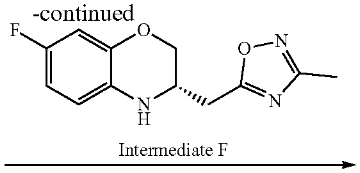

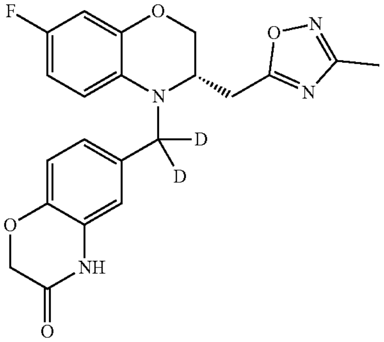

23

Step 1

Compound 23-1 (1 g, 4.83 mmol) was dissolved in a mixed solution of tetrahydrofuran (10 mL), water (10 mL) and methanol (10 mL), and lithium hydroxide (1.16 g, 48.3 mmol) was added to the reaction solution. The reaction mixture was stirred at 25° C. for 1 h. Water (50 mL) was added to the reaction mixture, and the resulting mixture was extracted with ethyl acetate (50 mL×2). The aqueous phase was adjusted to about pH 4 with 1 M hydrochloric acid solution and extracted with ethyl acetate (50 mL×2). The organic phases were combined, washed with saturated brine (100 mL), dried over anhydrous sodium sulfate, and filtered. The filtrate was concentrated under reduced pressure to give crude compound 23-2. MS-ESI calcd. $[M+H]^+$ 194, found 194.

Step 2

Compound 23-2 (500 mg, 2.59 mmol) was dissolved in acetonitrile (10 mL), and 1,1'-carbonyldiimidazole (839 mg, 5.18 mmol) was added to the reaction solution. The reaction mixture was stirred at 20° C. for 0.5 h. A solution of sodium borodeuteride (195 mg, 5.18 mmol) in water (5 mL) was then added to the reaction mixture, and the mixture was stirred at 20° C. for 1 h. Water (50 mL) was added to the reaction mixture, and the resulting mixture was adjusted to about pH 4 with a 1 M hydrochloric acid solution and extracted with ethyl acetate (50 mL×2). The organic phases were combined, washed with saturated brine (100 mL), dried over anhydrous sodium sulfate, and filtered. The filtrate was concentrated under reduced pressure to give crude compound 23-3. MS-ESI calcd. $[M+H]^+$ 182, found 182.

Step 3

Compound 23-3 (100 mg, 0.55 mmol) was dissolved in anhydrous dichloromethane (3 mL), and a phosphorus tribromide solution (164 mg, 0.60 mmol) was added slowly and dropwise to the reaction solution at 0° C. The reaction mixture was stirred at 25° C. for 2 h. Ice water (50 mL) was added to the reaction mixture, and the resulting mixture was extracted with ethyl acetate (40 mL×3). The organic phases were combined, washed with saturated brine (50 mL), dried over anhydrous sodium sulfate, and filtered. The filtrate was concentrated under reduced pressure to give crude compound 23-4.

Step 4

Compound 23-4 (102 mg, 0.42 mmol) and intermediate F (69 mg, 0.28 mmol) were dissolved in acetonitrile (1.5 mL), and sodium iodide (42 mg, 0.42 mmol) and anhydrous potassium carbonate (115 mg, 0.84 mmol) were added to the reaction solution. The reaction mixture was stirred at 80° C. for 16 h, then filtered through diatomite, and concentrated under reduced pressure. The crude product was separated by silica gel column chromatography (petroleum ether/ethyl acetate, 20/1-2/1, V/V) to give compound 23. MS-ESI calcd. $[M+H]^+$ 413, found 413. $^1H$ NMR (400 MHz, DMSO-$d_6$) δ 10.59 (s, 1H), 6.91-6.85 (m, 1H), 6.82-6.75 (m, 2H), 6.70 (d, J=8.8 Hz, 1H), 6.65-6.58 (m, 2H), 4.53 (s, 2H), 4.36-4.24 (m, 1H), 4.11-3.97 (m, 1H), 3.96-3.86 (m, 1H), 3.07 (d, J=6.8 Hz, 2H), 2.27 (s, 3H) ppm.

Example 24

Synthetic Route:

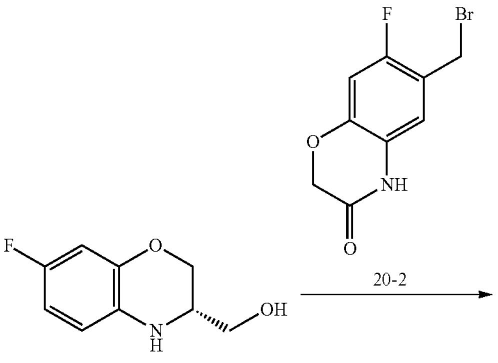

E-2

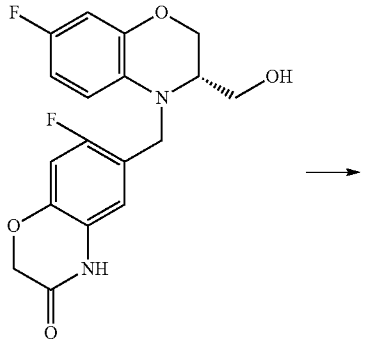

24-1

-continued

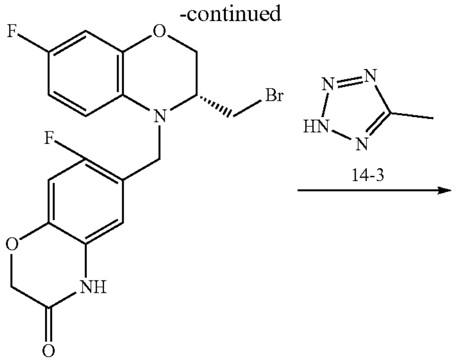

24-2

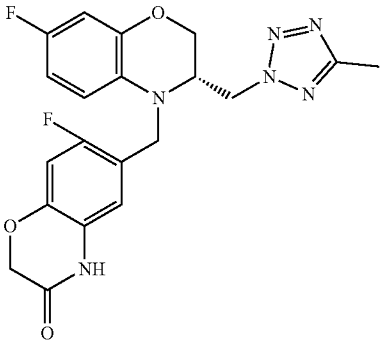

24

Step 1

Compound E-2 (0.40 mg, 2.18 mmol) and compound 20-2 (0.68 g, 2.62 mmol) were dissolved in acetonitrile (15 mL), and sodium iodide (327 mg, 2.18 mmol) and anhydrous sodium carbonate (0.91 g, 6.55 mmol) were added to the reaction solution. The reaction mixture was stirred at 80° C. for 16 h and then filtered through diatomite. The filtrate was concentrated under reduced pressure to give a crude product, which was then separated by silica gel column chromatography (petroleum ether/ethyl acetate, 20/1-2/1, V/V) to give compound 24-1. MS-ESI calcd. $[M+H]^+$ 363, found 363.

Step 2

Compound 24-1 (1.06 g, 2.31 mmol) was dissolved in N,N-dimethylformamide (20 mL), and triphenylphosphine (0.91 g, 3.47 mmol) was added to the reaction solution. N-Bromosuccinimide (0.62 g, 3.47 mmol) was added portionwise at 0° C., and the reaction mixture was stirred at 50° C. for 1 h. Water (100 mL) was added to the reaction mixture, and the resulting mixture was extracted with ethyl acetate (100 mL×2). The organic phases were combined, washed with saturated brine (200 mL), dried over anhydrous sodium sulfate, and filtered. The filtrate was concentrated under reduced pressure to give a crude product. The crude product was separated by silica gel column chromatography (petroleum ether/ethyl acetate, 200/1-5/1, V/V) to give compound 24-2.

Step 3

Compound 24-2 (100 mg, 0.24 mmol) and compound 14-3 (59.3 mg, 0.71 mmol) were dissolved in acetonitrile (3 mL), and anhydrous sodium carbonate (39.0 mg, 0.47 mmol) was added to the reaction solution. The reaction mixture was stirred at 20° C. for 2 h. Water (30 mL) was added to the reaction mixture, and then the resulting mixture was extracted with ethyl acetate (20 mL×2). The organic phases were combined, washed with saturated brine (50 mL), dried over anhydrous sodium sulfate, filtered, and concentrated under reduced pressure to give a crude product. The crude product was subjected to silica gel column chromatography (petroleum ether/ethyl acetate, 5/1-1/1, V/V) to give compound 24. MS-ESI calcd. $[M+H]^+$ 429, found 429. $^1H$ NMR (400 MHz, DMSO-$d_6$) δ 10.55 (s, 1H), 6.87 (d, J=10.6 Hz, 1H), 6.79-6.74 (m, 1H), 6.72-6.62 (m, 3H), 4.71 (d, J=6.0 Hz, 1H), 4.66-4.59 (m, 1H), 4.56 (s, 2H), 4.37-4.26 (m, 2H), 4.10-3.97 (m, 3H), 2.40 (s, 3H) ppm.

Example 25

Synthetic Route:

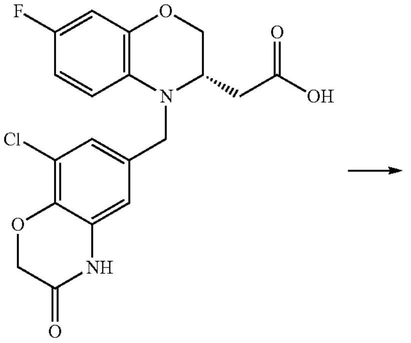

10-3

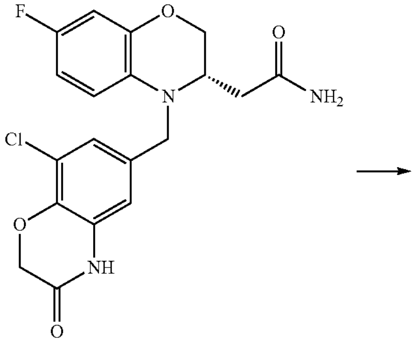

25-1

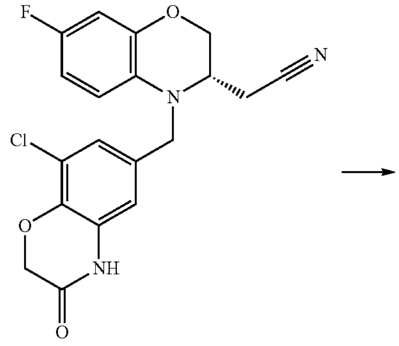

25-2

-continued

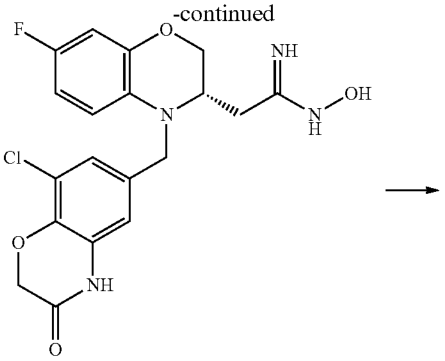

25-3

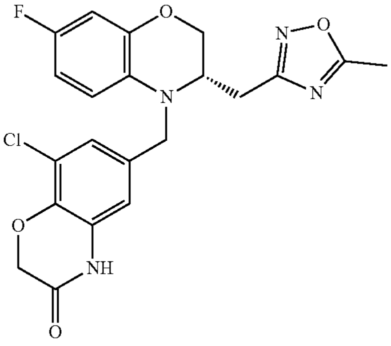

25

Step 1

Compound 10-3 (830 mg, 2.04 mmol) and 4-methylmorpholine (289 mg, 2.86 mmol, 314 μL) were dissolved in tetrahydrofuran (8 mL), and isobutyl chloroformate (334 mg, 2.45 mmol, 322 μL) was added. Ammonium hydroxide (511 mg, 4.08 mmol, 561 μL, 28% purity) was then added, and the reaction mixture was stirred at 0° C. for reaction for 1 h and then concentrated under reduced pressure to give a crude product. The crude product was separated by silica gel column chromatography (dichloromethane/methanol, 100:1-20:1, V/V) to give compound 25-1. MS-ESI calcd. $[M+H]^+$ 406, found 406.

Step 2

Palladium dichloride (60.3 mg, 340 μmol) was added to a mixed solution of compound 25-1 (460 mg, 1.13 mmol) in acetonitrile (5 mL) and water (5 mL), and the reaction mixture was stirred at 50° C. for reaction for 5 h and then concentrated under reduced pressure. The resulting crude product was separated by silica gel column chromatography (dichloromethane/methanol, 100:1-20:1, V/V) to give compound 25-2.

Step 3

Compound 25-2 (440 mg, 1.13 mmol) and hydroxylamine hydrochloride (315 mg, 4.54 mmol) were dissolved in ethanol (10 mL), and triethylamine (689 mg, 6.81 mmol, 948 μL) was added. The reaction mixture was stirred at 80° C. for reaction for 3 h and then concentrated under reduced pressure to give a crude product. The crude product was separated by silica gel column chromatography (dichloromethane/methanol, 100:1-10:1, V/V) to give compound 25-3. MS-ESI calcd. [M+H]$^+$ 421, found 421.

Step 4

Compound 25-3 (120 mg, 285 mol) and ethyl acetate (75.4 mg, 855 mol, 83.8 μL) were dissolved in dimethyl sulfoxide (2 mL), and sodium hydroxide (34.2 mg, 855 μmol) was added. The reaction mixture was stirred at 15° C. for reaction for 2 h, then diluted with water (20 mL), and extracted with ethyl acetate (10 mL×3). The organic phases were combined, washed with saturated brine (20 mL), dried over anhydrous sodium sulfate, and filtered. The filtrate was concentrated under reduced pressure to give a crude product. The crude product was separated by preparative high performance liquid chromatography (chromatographic column: Phenomenex Gemini-NX C18 75×30 mm×3 Wm; mobile phase: 10 mM aqueous ammonium bicarbonate solution-acetonitrile; gradient:acetonitrile 32%-62%, 8 min) to give compound 25. MS-ESI calcd. [M+H]$^+$ 445, found 445. $^1$H NMR (400 MHz, $CD_3OD$) δ 6.95-6.91 (m, 1H), 6.77-6.73 (m, 1H), 6.68-6.52 (m, 3H), 4.65 (s, 2H), 4.36-4.21 (m, 3H), 4.07 (dd, J=2.0, 11.0 Hz, 1H), 3.83-3.74 (m, 1H), 2.96-2.82 (m, 2H), 2.50 (s, 3H) ppm.

Example 26

Synthetic Route:

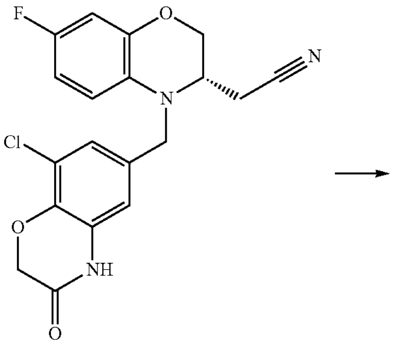

25-2

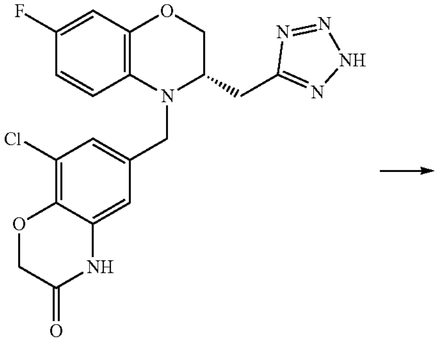

26-1

-continued

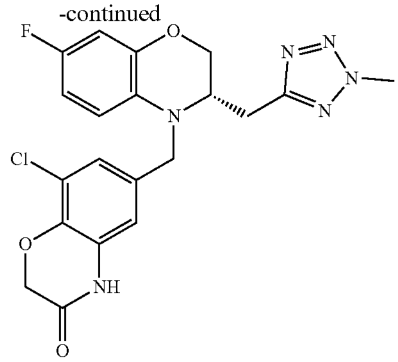

26

Step 1

Compound 25-2 (200 mg, 516 mol), azidotrimethylsilane (238 mg, 2.06 mmol, 271 μL), and dibutyltin oxide (20 mg, 80.3 mol) were dissolved in toluene (3 mL), and the reaction solution was stirred under nitrogen atmosphere at 10° C. for reaction for 14 h. A saturated aqueous KF solution (20 mL) was first added to the reaction solution, and the mixture was stirred for at least one hour. Saturated sodium bicarbonate (50 mL) was then added, and the mixture was extracted with ethyl acetate (20 mL×3). The organic phases were combined and concentrated under reduced pressure to give a crude product. The crude product was separated by silica gel column chromatography (petroleum ether/ethyl acetate (2:1)-dichloromethane/methanol (20:1), V/V) to give compound 26-1. MS-ESI calcd. [M+H]$^+$ 431, found 431.

Step 2

Compound 26-1 (50 mg, 116 μmol), iodomethane (165 mg, 1.16 mmol, 72.3 μL), and triethylamine (58.7 mg, 580 μmol, 80.8 μL) were dissolved in acetonitrile (1 mL), and the reaction solution was stirred at 85° C. for reaction for 0.5 h and then concentrated under reduced pressure to give a crude product. The crude product was separated by thin layer chromatography (developing solvent: dichloromethane/methanol, 10/1, V/V) to give compound 26. MS-ESI calcd. [M+H]$^+$ 445, found 445. $^1$H NMR (400 MHz, $CDCl_3$) δ 9.51 (s, 1H), 6.89 (s, 1H), 6.69-6.59 (m, 2H), 6.56-6.45 (m, 2H), 4.69 (s, 2H), 4.32-4.21 (m, 6H), 4.09 (dd, J=2.0, 11.0 Hz, 1H), 3.84-3.71 (m, 1H), 3.18-3.05 (m, 2H) ppm.

Example 27

Synthetic Route:

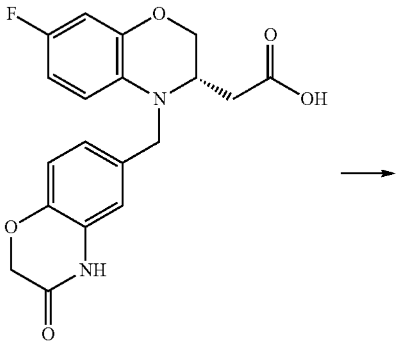

12-3

-continued

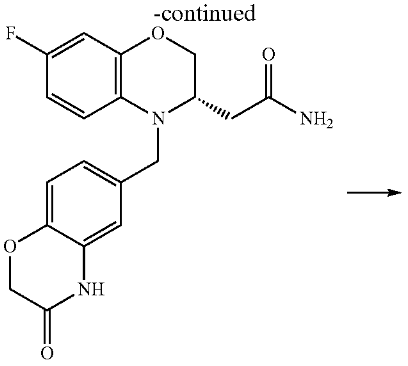

27-1

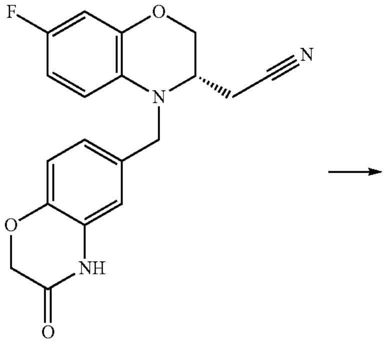

27-2

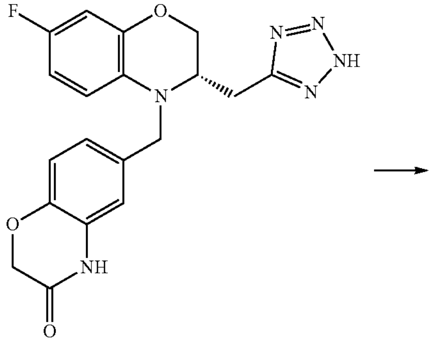

27-3

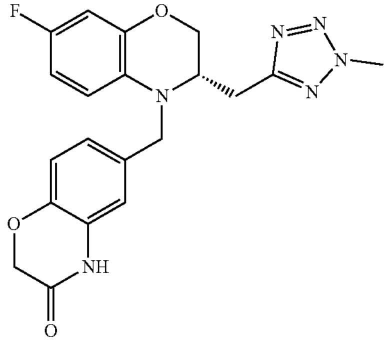

27

Step 1

Compound 12-3 (220 mg, 591 mol) and 4-methylmorpholine (83.7 mg, 827 mmol, 91.0 μL) were dissolved in tetrahydrofuran (6 mL), and isobutyl chloroformate (96.8 mg, 709 μmol, 93.1 μL) was added. Ammonium hydroxide (148 mg, 1.18 mmol, 163 μL, 28% purity) was then added, and the reaction mixture was stirred at 0° C. for reaction for 1 h and then concentrated under reduced pressure to give a crude product. The crude product was separated by silica gel column chromatography (dichloromethane/methanol, 100:1-20:1, V/V) to give compound 27-1. MS-ESI calcd. $[M+H]^+$ 372, found 372.

Step 2

Palladium dichloride (37.2 mg, 210 μmol) was added to a mixed solution of compound 27-1 (260 mg, 1.13 mmol) in acetonitrile (5 mL) and water (5 mL), and the reaction mixture was stirred at 50° C. for reaction for 11 h and then concentrated under reduced pressure to give a crude product. The crude product was separated by silica gel column chromatography (dichloromethane/methanol, 100:1-20:1, V/V) to give compound 27-2. MS-ESI calcd. $[M+H]^+$ 354, found 354.

Step 3

Compound 27-2 (230 mg, 651 mol), azidotrimethylsilane (300 mg, 2.60 mmol, 342 μL), and dibutyltin oxide (110 mg, 442 μmol) were dissolved in toluene (5 mL), and the reaction solution was stirred under nitrogen atmosphere at 80° C. for reaction for 30 h. A saturated aqueous KF solution (20 mL) was first added to the reaction solution, and the mixture was stirred for at least one hour. A saturated sodium bicarbonate solution (50 mL) was then added, and the mixture was extracted with ethyl acetate (20 mL×3). The organic phases were combined and concentrated under reduced pressure to give a crude product. The crude product was separated by silica gel column chromatography (petroleum ether/ethyl acetate (2:1)-dichloromethane/methanol (20:1), V/V) to give compound 27-3. MS-ESI calcd. $[M+H]^+$ 397, found 397.

Step 4

Compound 27-3 (200 mg, 505 mol) and (trimethylsilyl) diazomethane (2 M, 706 μmol, 353 μL) were dissolved in tetrahydrofuran (2 mL) and methanol (0.5 mL), and the reaction solution was stirred at 10° C. for reaction for 0.5 h and then concentrated under reduced pressure to give a crude product. The crude product was separated by thin layer chromatography (developing solvent: dichloromethane/methanol, 10/1, V/V) to give compound 27. MS-ESI calcd. $[M+H]^+$ 411, found 411. $^1$H NMR (400 MHz, $CDCl_3$) δ 8.04 (s, 1H), 6.96-6.89 (m, 1H), 6.88-6.82 (m, 1H), 6.73-6.60 (m, 2H), 6.60-6.48 (m, 2H), 4.61 (s, 2H), 4.36-4.24 (m, 6H), 4.17-3.98 (m, 1H), 3.92-3.70 (m, 1H), 3.22-3.08 (m, 2H) ppm.

Example 28

Synthetic Route:

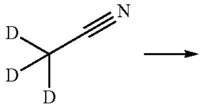

28-1

-continued

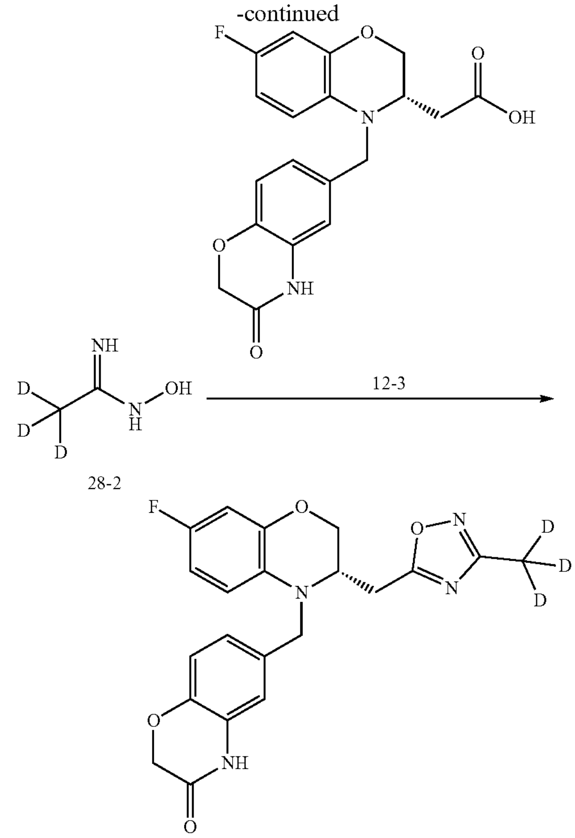

28-2

28

Step 1

Sodium methoxide (400 mg, 7.41 mmol) was added to a solution of hydroxylamine hydrochloride (500 mg, 7.20 mmol) in methanol (5 mL), and the reaction mixture was stirred at 0° C. for one hour. Compound 28-1 (430 mg, 9.77 mmol, 0.51 mL) was then added, and the reaction mixture was heated to 15° C., stirred for reaction for 15 h, then heated to 40° C., and stirred for reaction for another 4 h. The reaction mixture was concentrated under reduced pressure to give a crude product, and ethyl acetate (50 mL×3) was added to the crude product. The organic phases were combined and concentrated under reduced pressure to give crude compound 28-2.

Step 2

Compound 12-3 (300 µmg, 806 µmol) was dissolved in N,N-dimethylformamide (3 mL), and 1,1'-carbonyldiimidazole (157 mg, 967 µmol) was added. The reaction mixture was stirred at 15° C. for reaction for 1 h. 28-2 (182 mg, 2.36 mmol) was added to the reaction mixture, and the reaction mixture was stirred at 15° C. for reaction for 1 h, then heated to 90° C., and stirred for reaction for another 64 h. The reaction solution was concentrated under reduced pressure to give a crude product. The crude product was separated and purified by thin layer chromatography (developing solvent: petroleum ether/ethyl acetate, 1/2, V/V) to give compound 28. MS-ESI calcd. $[M+H]^+$ 414, found 414. $^1H$ NMR (400 MHz, DMSO-$d_6$) δ 10.59 (s, 1H), 6.92-6.83 (m, 1H), 6.83-6.75 (m, 2H), 6.74-6.67 (m, 1H), 6.65-6.57 (m, 2H), 4.53 (s, 2H), 4.40-4.21 (m, 3H), 4.04 (dd, J=2.2, 11.0 Hz, 1H), 3.98-3.86 (m, 1H), 3.08 (d, J=6.8 Hz, 2H) ppm.

Example 29

Synthetic Route:

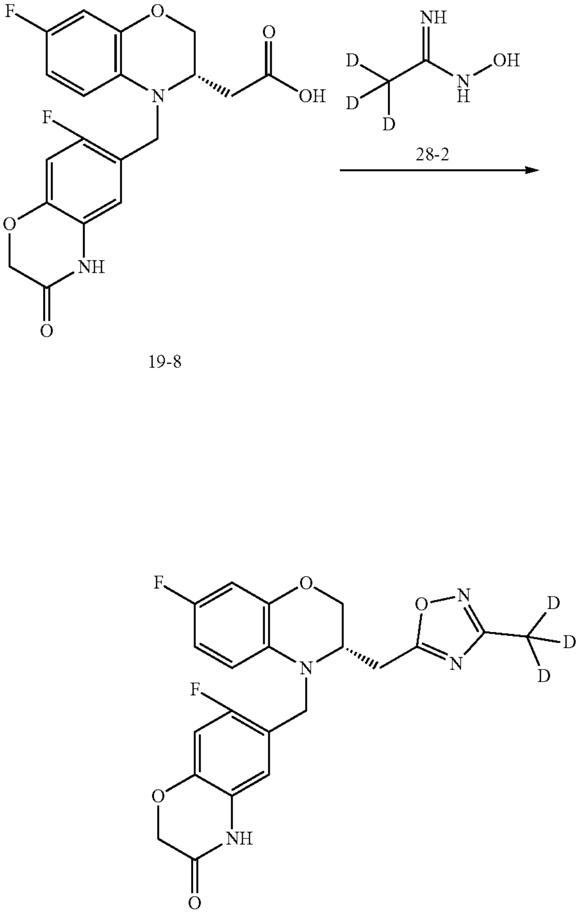

19-8

29

Step 1

Compound 19-8 (95 mg, 243 µmol) was dissolved in N,N-dimethylformamide (1 mL), and 1,1'-dicarbonylimidazole (48 mg, 296 µmol) was added. The reaction mixture was stirred at 15° C. for reaction for 1 h. Compound 28-2 (60 mg, 778 mol) was then added, and the reaction mixture was stirred at 15° C. for reaction for 1 h and then heated to 90° C. for reaction for another 12 h. The reaction mixture was concentrated under reduced pressure to give a crude product. The crude product was separated by silica gel column chromatography (petroleum ether/ethyl acetate, 1:2, V/V) to give compound 29. MS-ESI calcd. $[M+H]^+$ 432, found 432. $^1H$ NMR (400 MHz, DMSO-$d_6$) δ 10.54 (s, 1H), 6.88 (d, J=10.8 Hz, 1H), 6.79-6.69 (m, 2H), 6.69-6.51 (m, 2H), 4.56 (s, 2H), 4.46-4.37 (m, 1H), 4.37-4.24 (m, 2H), 4.02 (dd, J=2.0, 11.0 Hz, 1H), 3.98-3.71 (m, 1H), 3.18-2.99 (m, 2H) ppm.

Example 30

Synthetic Route:

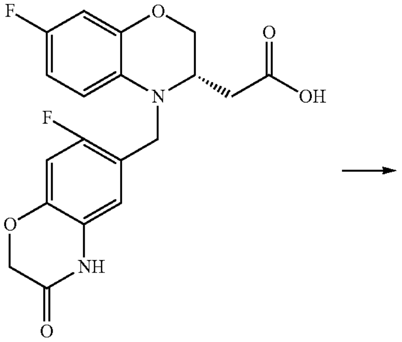

19-8

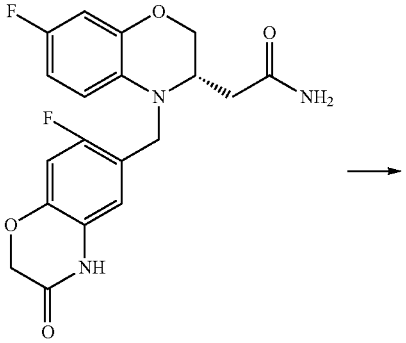

30-1

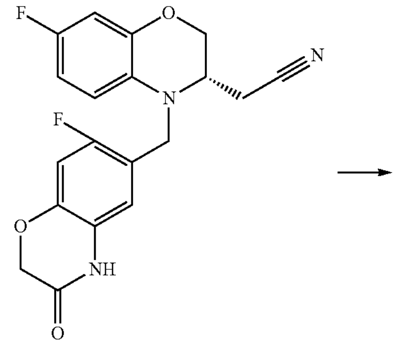

30-2

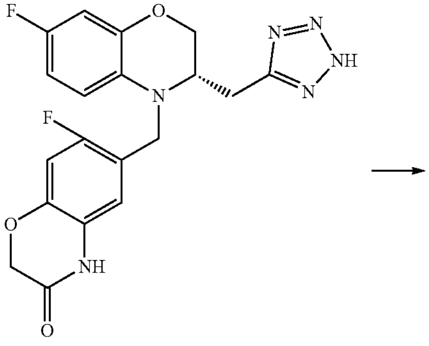

30-3

-continued

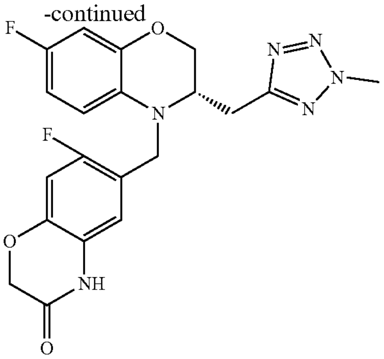

30

Step 1

Compound 19-8 (250 mg, 640 μmol) and 4-methylmorpholine (129 mg, 1.27 mmol, 140 μL) were dissolved in tetrahydrofuran (5 mL), and isobutyl chloroformate (130 mg, 952 μmol, 125 μL) was added. Ammonium hydroxide (241 mg, 1.93 mmol, 265 μL, 28% purity) was then added, and the reaction mixture was stirred at 0° C. for reaction for 2 h and then diluted with ethyl acetate (20 mL). The organic phase was washed with a 10% aqueous citric acid solution (10 mL), a 10% sodium bicarbonate solution (10 mL) and saturated brine (10 mL) in sequence, and then concentrated under reduced pressure to give crude compound 30-1. MS-ESI calcd. $[M-H]^-$ 388, found 388.

Step 2

Palladium dichloride (45.5 mg, 257 μmol) was added to a mixed solution of compound 30-1 (200 mg, 514 mol) in acetonitrile (0.5 mL) and water (0.5 mL), and the reaction mixture was stirred at 50° C. for reaction for 1 h and then extracted with ethyl acetate (20 mL×3). The organic phases were combined, washed with saturated brine (20 mL), dried over anhydrous sodium sulfate, and filtered. The filtrate was concentrated under reduced pressure to give a crude product. The crude product was separated by silica gel column chromatography (dichloromethane/methanol, 100:1-20:1, V/V) to give compound 30-2.

Step 3

Compound 30-2 (200 mg, 539 mol), azidotrimethylsilane (263 mg, 2.17 mmol, 300 μL), and dibutyltin oxide (20 mg, 80.3 mol) were dissolved in toluene (5 mL), and the reaction solution was stirred under nitrogen atmosphere at 100° C. for reaction for 14 h. A saturated aqueous KF solution (20 mL) was first added to the reaction solution, and the mixture was stirred for at least one hour. Saturated sodium bicarbonate (50 mL) was then added, and the mixture was extracted with ethyl acetate (20 mL×3). The organic phases were combined and concentrated under reduced pressure to give a crude product. The crude product was separated by silica gel column chromatography (dichloromethane/methanol, 100:1-20:1, V/V) to give compound 30-3. MS-ESI calcd. $[M+H]^+$ 415, found 415.

Step 4

Compound 30-3 (180 mg, 434 mol) and (trimethylsilyl) diazomethane (2 M, 608 μmol, 304 μL) were dissolved in tetrahydrofuran (4 mL) and methanol (1 mL), and the reaction solution was stirred at 10° C. for reaction for 2 h. Water (20 mL) was added to the reaction mixture to quench the reaction, and the resulting mixture was extracted with ethyl acetate (20 mL×2). The organic phases were combined, washed with saturated brine (30 mL), dried over anhydrous sodium sulfate, and concentrated under reduced pressure to give a crude product. The crude product was separated by thin layer chromatography (developing solvent: dichloromethane/methanol, 10/1, V/V) to give compound 30. MS-ESI calcd. $[M+H]^+$ 429, found 429. $^1H$ NMR (400 MHz, $CDCl_3$) δ 9.23-8.93 (m, 1H), 6.73-6.67 (m, 2H), 6.64-6.59 (m, 1H), 6.56-6.51 (m, 2H), 4.60-4.54 (m, 2H), 4.42-4.21 (m, 6H), 4.11-4.00 (m, 1H), 3.85-3.74 (m, 1H), 3.16-3.09 (m, 2H) ppm.

Example 31

Synthetic Route:

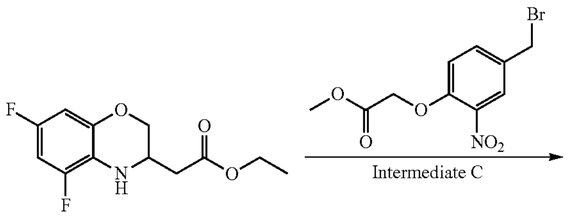

5-4

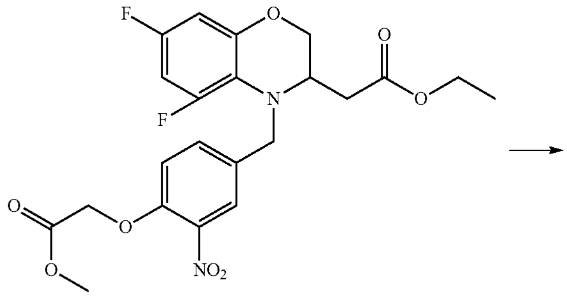

31-1

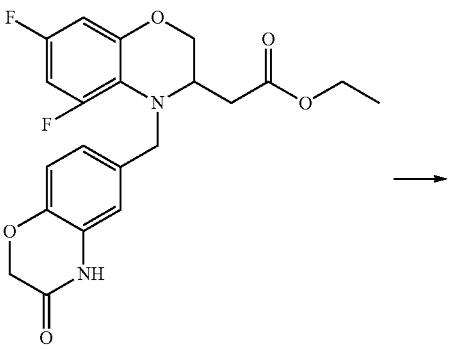

31-2

-continued

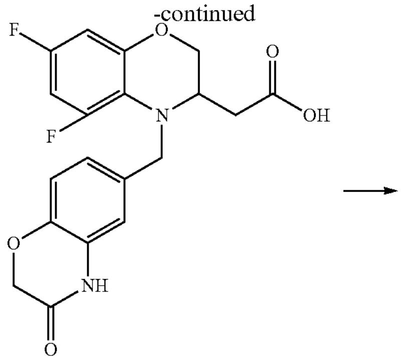

31-3

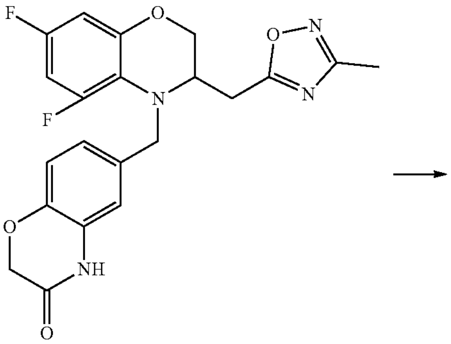

31-4

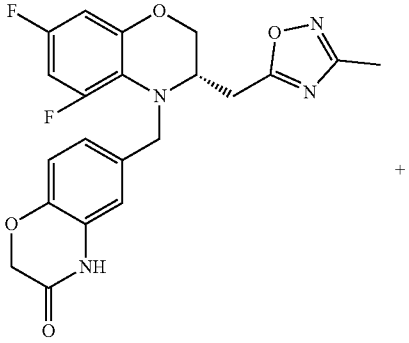

31a or 31b

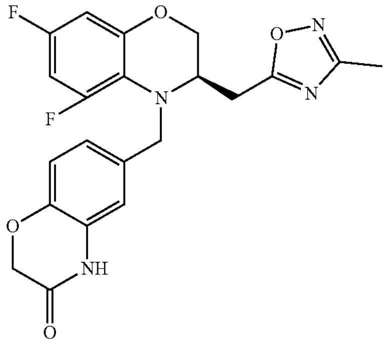

31b or 31a

Step 1

Compound 5-4 (1.00 g, 3.89 mmol) and compound intermediate C (1.42 g, 4.67 mmol) were dissolved in acetonitrile (20 mL), and sodium iodide (583 mg, 3.89 mmol) and potassium carbonate (1.61 g, 11.66 mmol) were added to the reaction solution. The reaction mixture was stirred at 80° C.

for 12 h and then filtered. The filtrate was concentrated under reduced pressure to give compound 31-1. MS-ESI calcd. $[M+H]^+$ 481, found 481.

Step 2

Compound 31-1 (2.00 g, 4.16 mmol) was dissolved in acetic acid (20 mL), and iron powder (2.33 g, 41.63 mmol) was added to the reaction solution. The reaction mixture was stirred at 80° C. for 12 h and then filtered through diatomite. The filtrate was concentrated under reduced pressure, and the crude product was separated by silica gel column chromatography (eluent: petroleum ether/ethyl acetate, 6/1-2/1) to give compound 31-2. MS-ESI calcd. $[M+H]^+$ 419, found 419.

Step 3

Compound 31-2 (900 mg, 2.15 mmol) was dissolved in methanol (10 mL), and a solution of lithium hydroxide monohydrate (903 mg, 21.51 mmol) in water (2 mL) was added to the reaction solution. The reaction mixture was stirred at 25° C. for 12 h and then adjusted to pH 2 with 12 M hydrochloric acid. Water (50 mL) was added, and the mixture was extracted with ethyl acetate (50 mL×2). The organic phases were combined, washed with saturated brine (200 mL), dried over anhydrous sodium sulfate, filtered, and concentrated under reduced pressure to give compound 31-3. MS-ESI calcd. $[M+H]^+$ 391, found 391.

Step 4

Compound 31-3 (400 mg, 1.02 mmol) was dissolved in N,N-dimethylformamide (2 mL), and 1,1-carbonyldiimidazole (199 mg, 1.23 mmol) was added to the reaction solution. The reaction mixture was stirred at 20° C. for 0.5 h. N-Hydroxyacetamidine (152 mg, 2.05 mmol) was added to the reaction mixture, and the reaction mixture was stirred at 20° C. for 0.5 h and then stirred at 80° C. for another 15 h. Water (50 mL) was added to the reaction mixture, and the resulting mixture was extracted with ethyl acetate (50 mL×2). The organic phases were combined, washed with saturated brine (200 mL), dried over anhydrous sodium sulfate, filtered, and concentrated under reduced pressure to give a crude product. The crude product was separated by preparative high performance liquid chromatography (chromatographic column: Waters Xbridge 150×25 mm×10 μm; mobile phase: 0.225% aqueous formic acid solution-acetonitrile; gradient:acetonitrile 42%-72%) to give compound 31-4. MS-ESI calcd. $[M+H]^+$ 429, found 429.

Step 5

Compound 31-4 was separated by SFC (separation column: DAICEL CHIRALPAK AD 250 mm×30 mm×10 Wm; mobile phase: supercritical $CO_2$-solution of 0.1% ammonium hydroxide in isopropanol; gradient: solution of 0.1% ammonium hydroxide in isopropanol 25%-25%) to give compounds 31b (first main peak) and 31a (second main peak). The compounds were then tested for e.e. value by SFC (chromatographic column: Chiralcel AD-3 50 mm×4.6 mm×3 M; mobile phase: supercritical $CO_2$-solution of 0.05% diethylamine in ethanol; gradient: solution of 0.05% diethylamine in ethanol: 5%-40%).

Compound 31a: e.e. %=98%, RT=1.569 min. MS-ESI calcd. $[M+H]^+$ 429, found 429; $^1H$ NMR (400 MHz, DMSO-$d_6$) δ 10.63 (s, 1H), 6.96-6.85 (m, 1H), 6.84-6.79 (m, 1H), 6.76 (s, 1H), 6.74-6.68 (m, 2H), 4.54 (d, J=3.2 Hz, 2H), 4.29 (d, J=10.8 Hz, 1H), 4.16-3.94 (m, 2H), 3.71 (d, J=14.4 Hz, 1H), 3.52-3.41 (m, 1H), 2.93-2.81 (m, 1H), 2.69-2.60 (m, 1H), 2.19 (s, 3H).

Compound 31b: e.e. %=100%, RT=1.336 min. MS-ESI calcd. $[M+H]^+$ 429, found 429; $^1H$ NMR (400 MHz, DMSO-$d_6$) δ 10.63 (s, 1H), 6.96-6.85 (m, 1H), 6.84-6.79 (m, 1H), 6.76 (s, 1H), 6.74-6.68 (m, 2H), 4.54 (d, J=3.2 Hz, 2H), 4.29 (d, J=10.8 Hz, 1H), 4.16-3.94 (m, 2H), 3.71 (d, J=14.4 Hz, 1H), 3.52-3.41 (m, 1H), 2.93-2.81 (m, 1H), 2.69-2.60 (m, 1H), 2.19 (s, 3H).

Example 32

Synthetic Route:

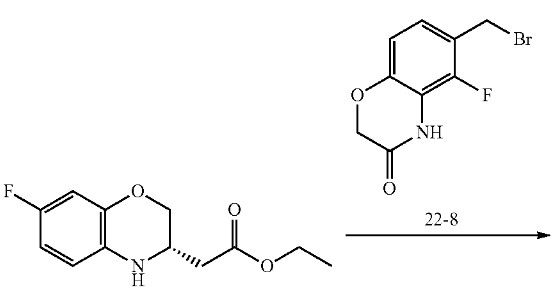

Intermediate D

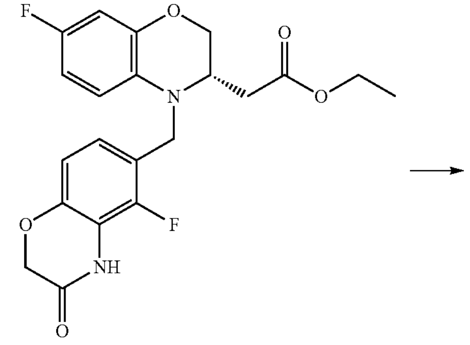

32-1

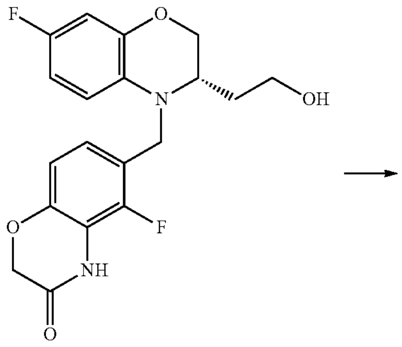

32-2

-continued

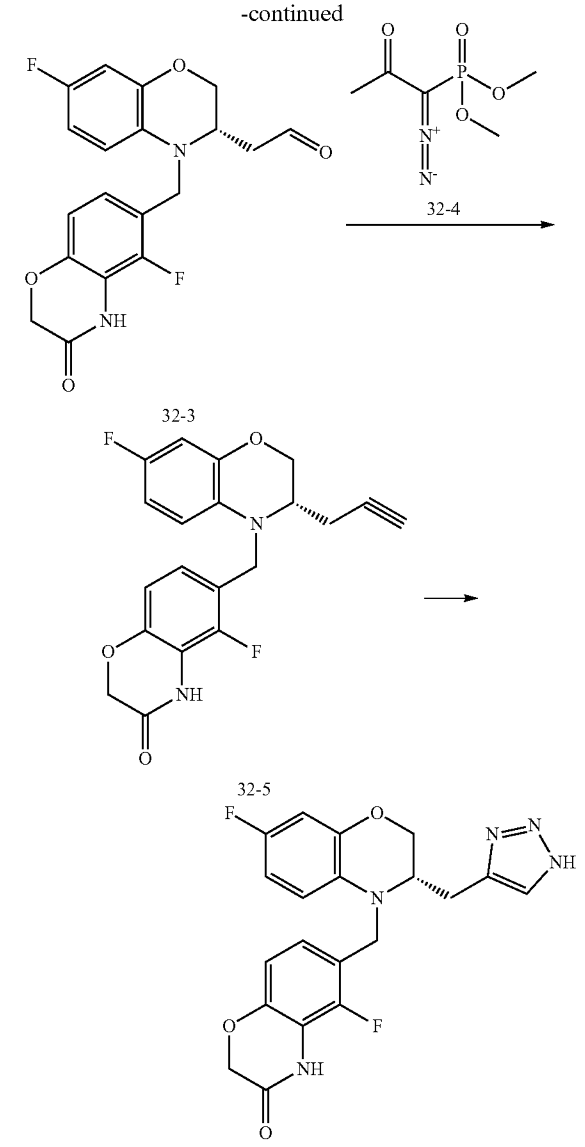

32-3

32-4

32-5

32

Step 1

Intermediate D (3 g, 12.54 mmol) and compound 22-8 (3.59 g, 13.79 mmol) were dissolved in acetonitrile (50 mL), and sodium iodide (1.88 g, 12.54 mmol) and potassium carbonate (5.20 g, 37.62 mmol) were added to the reaction solution. The reaction mixture was stirred at 80° C. for 12 h, then concentrated under reduced pressure, diluted with water (50 mL), and extracted with ethyl acetate (50 mL×3). The organic phases were combined, washed with saturated brine (30 mL×3), dried over anhydrous sodium sulfate, and filtered. The filtrate was concentrated under reduced pressure to give a crude product. The product was separated by silica gel column chromatography (eluent: petroleum ether/ethyl acetate, 1/0-3/1) to give compound 32-1. MS-ESI calcd. $[M+H]^+$ 419, found 419.

Step 2

Lithium aluminum hydride (68.58 mg, 1.81 mmol) was dissolved in anhydrous tetrahydrofuran (5 mL), and a solution of compound 32-1 (0.63 g, 1.51 mmol) in anhydrous tetrahydrofuran (5 mL) was added to the reaction solution at 0° C. under nitrogen atmosphere. The reaction mixture was stirred at 20° C. for 1 h. After the reaction was completed, a saturated aqueous ammonium chloride solution (20 mL) was added to quench the reaction, and the mixture was diluted with water (30 mL) and extracted with ethyl acetate (50 mL×3). The organic phases were combined, washed with saturated brine (30 mL×3), dried over anhydrous sodium sulfate, filtered, and concentrated under reduced pressure to give compound 32-2. MS-ESI calcd. $[M+H]^+$ 377, found 377.

Step 3

Compound 32-2 (550 mg, 1.46 mmol) was dissolved in dichloromethane (10 mL), and DMP (929.76 mg, 2.19 mmol) was added to the reaction solution. The reaction mixture was stirred at 20° C. for 1 h. After the reaction was completed, a saturated aqueous sodium sulfite solution (20 mL) was added to the reaction mixture to quench the reaction. The mixture was then adjusted to pH 8 with a saturated aqueous sodium bicarbonate solution, diluted with water (30 mL), and extracted with dichloromethane (50 mL×3). The organic phases were combined, washed with saturated brine (30 mL×3), dried over anhydrous sodium sulfate, filtered, and concentrated under reduced pressure to give compound 32-3. MS-ESI calcd. $[M+H]^+$ 375, found 375.

Step 4

Compound 32-3 (460 mg, 1.23 mmol) and compound 32-4 were dissolved in methanol (10 mL), and potassium carbonate (509.5 mg, 3.69 mmol) was added to the reaction solution. The reaction mixture was stirred at 20° C. for 1 h. After the reaction was completed, water (20 mL) was added to the reaction mixture, and the resulting mixture was extracted with ethyl acetate (50 mL×3). The organic phases were combined, washed with saturated brine (30 mL×3), and dried over anhydrous sodium sulfate. The filtrate was concentrated under reduced pressure, and the crude product was separated by silica gel column chromatography (eluent: petroleum ether/ethyl acetate, 1/0-3/1) to give compound 32-5. MS-ESI calcd. $[M+H]^+$ 371, found 371.

Step 5

Compound 32-5 (150 mg, 405.02 μmol), anhydrous copper sulfate (64.65 mg, 405.02 μmol), and sodium ascorbate (160.48 mg, 810.05 μmol) were dissolved in tert-butanol (10 mL) and water (4 mL), and the mixed solution was purged three times with nitrogen. Under the nitrogen atmosphere, (trimethylsilyl)diazomethane (139.99 mg, 1.22 mmol) was added at 20° C. The reaction mixture was stirred at 90° C. for 12 h. After the reaction was completed, ammonium hydroxide (2 mL) was added at 25° C., and the mixed solution was stirred at 25° C. for another 30 min. Water (20 mL) was then added, and the resulting mixture was extracted with ethyl acetate (50 mL×3). The organic phases were combined, washed with saturated brine (30 mL×2), and dried over anhydrous sodium sulfate. The filtrate was concentrated under reduced pressure to give a crude product. The crude product was separated by high performance liquid chromatography (chromatographic column: Unisil 3-100 C18 Ultra 150×25 mm×3 mu; mobile phase: 0.225% aqueous formic acid solution-acetonitrile; gradient:acetonitrile 26%-56%) to give compound 32. MS-ESI calcd. $[M+H]^+$ 414, found 414. $^1H$ NMR (400 MHz, DMSO-$d_6$) δ 10.62-11.35 (m, 1H), 7.62 (s, 1H), 6.80-6.89 (m, 1H), 6.74 (d, J=8.6 Hz, 1H), 6.66-6.71 (m, 1H), 6.57-6.63 (m, 2H), 4.59 (s, 2H), 4.41-4.50 (m, 1H), 4.27-4.34 (m, 1H), 4.14 (m, 1H), 3.95 (m, 1H), 3.66-3.73 (m, 1H), 2.79-2.92 (m, 2H).

Example 33

Synthetic Route:

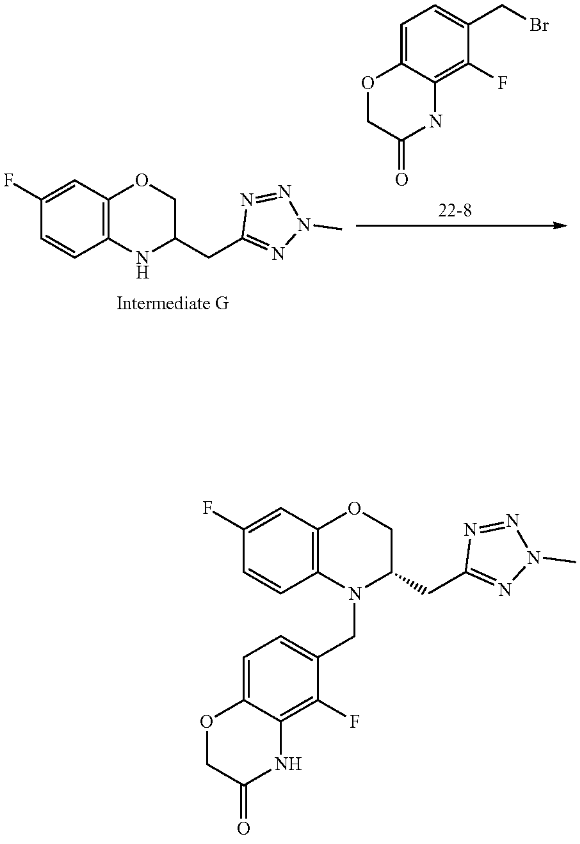

33

Intermediate G (200 mg, 802 μmol) and compound 22-8 (313 mg, 1.20 mmol) were dissolved in acetonitrile (4 mL), and sodium iodide (120 mg, 802 μmol) and potassium carbonate (333 mg, 2.41 mmol) were added to the reaction solution. The reaction mixture was stirred at 80° C. for 12 h and then filtered. The filtrate was concentrated under reduced pressure to give a crude product. The crude product was separated by thin layer chromatography (developing solvent: petroleum ether/ethyl acetate, 1/1, V/V) to give a compound. The compound was then separated by preparative high performance liquid chromatography (chromatographic column: Phenomenex Luna C18 150×25 mm×10 Wm; mobile phase: 0.225% aqueous formic acid solution-acetonitrile; gradient:acetonitrile 34%-64%) to give compound 33. MS-ESI calcd. $[M+H]^+$ 429, found 429. $^1H$ NMR (400 MHz, $CD_3OD$) δ 6.88-6.65 (m, 3H), 6.64-6.46 (m, 2H), 4.60 (s, 2H), 4.32 (s, 2H), 4.29-4.17 (m, 4H), 4.08-3.92 (m, 1H), 3.85-3.73 (m, 1H), 3.01 (m, 2H).

Example 34

Synthetic Route:

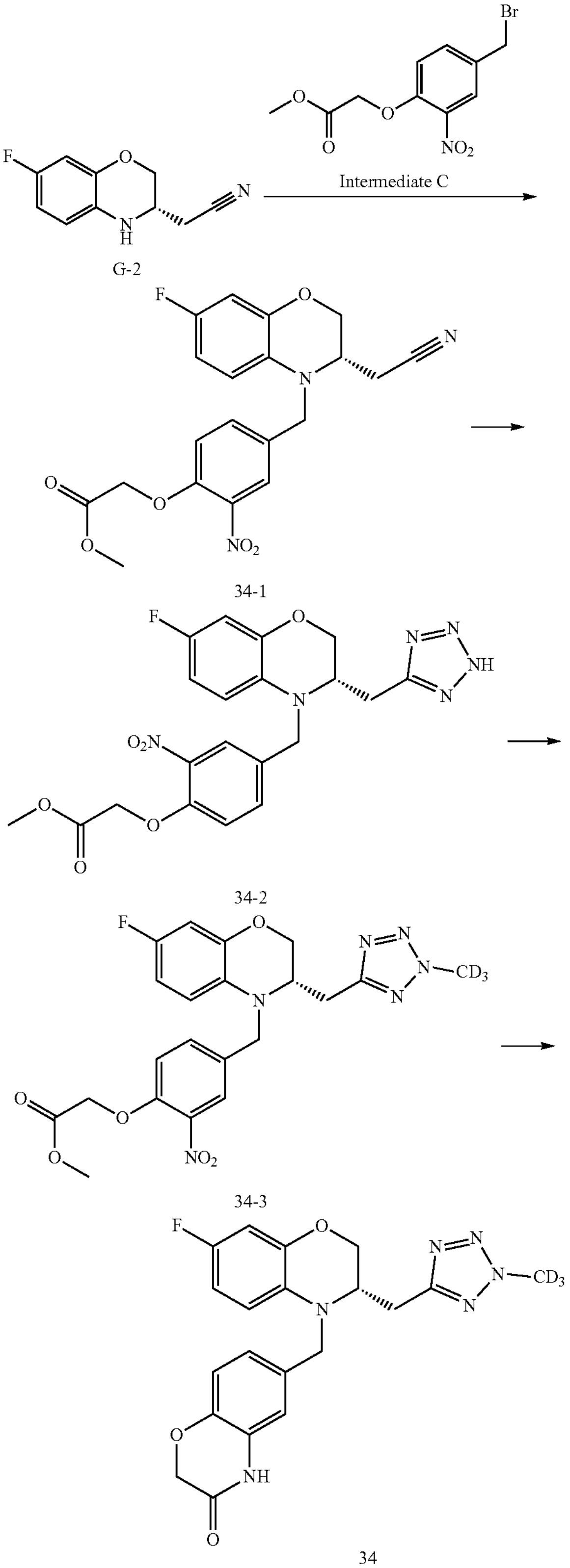

34

Step 1

Compound G-2 (750 mg, 3.90 mmol) was dissolved in acetonitrile (20 mL), and sodium iodide (585 mg, 3.90 mmol), sodium bicarbonate (983 mg, 11.71 mmol) and intermediate C (1.78 g, 5.85 mmol) were added to the reaction solution. The reaction mixture was stirred at 80° C. for 12 h and then filtered. The filtrate was concentrated under reduced pressure to give a crude product. The crude product was separated by silica gel column chromatography (eluent: petroleum ether/ethyl acetate, 5/1-1/1, V/V) to give compound 34-1. MS-ESI calcd. $[M+Na]^+$438, found 438.

Step 2

Compound 34-1 (1.20 g, 2.89 mmol) and dibutyltin oxide (321 mg, 1.29 mmol) were dissolved in toluene (15 mL), and azidotrimethylsilane (1.40 g, 11.56 mmol, 1.60 mL) was added to the reaction solution at 25° C. under nitrogen atmosphere. The reaction mixture was stirred under nitrogen atmosphere at 100° C. for reaction for 12 h. An aqueous saturated potassium fluoride solution (50 mL) was first added to the reaction mixture, and the mixture was stirred for at least one hour. A saturated sodium bicarbonate solution (30 mL) was then added, and the mixture was extracted with ethyl acetate (50 mL×3). The organic phases were combined and concentrated under reduced pressure to give a crude product. The crude product was separated by silica gel column chromatography (eluent: petroleum ether/ethyl acetate, 10/1-1/2, V/V) to give compound 34-2. MS-ESI calcd. $[M+H]^+$ 459, found 459.

Step 3

Compound 34-2 (450 mg, 982 μmol) and potassium carbonate (204 mg, 1.47 mmol) were dissolved in tetrahydrofuran (5 mL), and deuterated iodomethane (209 mg, 1.47 mmol) was added to the reaction solution. The reaction mixture was stirred at 25° C. for reaction for 12 h, then diluted with water (50 mL), and extracted with ethyl acetate (50 mL×2). The organic phases were combined, washed with saturated brine, dried over anhydrous sodium sulfate, and filtered. The filtrate was concentrated under reduced pressure to give compound 34-3. MS-ESI calcd. $[M+H]^+$ 476, found 476.

Step 4

Compound 34-3 (400 mg, 841 mol) was dissolved in acetic acid (5 mL), and iron powder (376 mg, 6.73 mmol) was added to the reaction solution. The reaction mixture was stirred at 80° C. for 12 h and then filtered through diatomite. The filtrate was concentrated under reduced pressure to give a crude product. The crude product was separated by preparative high performance liquid chromatography (chromatographic column: Phenomenex Luna 150×25 mm×10 μm; mobile phase: 0.225% aqueous formic acid solution-acetonitrile; gradient:acetonitrile 33%-63%) to give compound 34. MS-ESI calcd. $[M+H]^+$ 414, found 414. H NMR (400 MHz, $CDCl_3$) δ 8.19 (s, 1H), 6.96-6.88 (m, 1H), 6.88-6.82 (m, 1H), 6.73-6.62 (m, 2H), 6.56-6.48 (m, 2H), 4.65-4.55 (m, 2H), 4.35-4.21 (m, 3H), 4.11-4.03 (m, 1H), 3.82-3.70 (m, 1H), 3.20-3.06 (m, 2H).

Example 35

Synthetic Route:

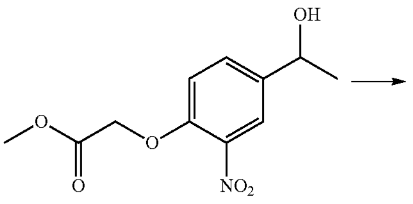

6-3

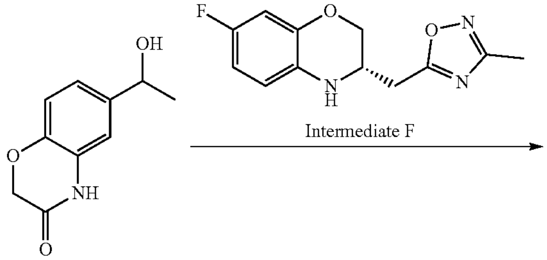

35-1

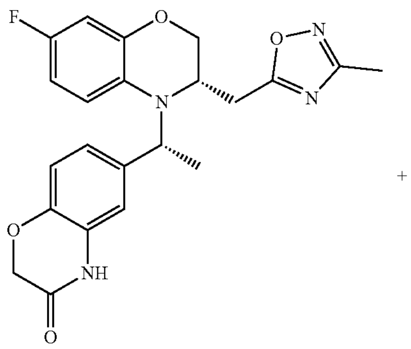

35a or 35b

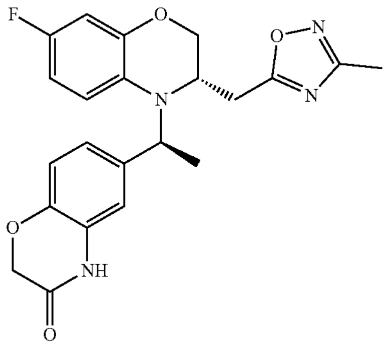

35b or 35a

Step 1

Compound 6-3 (3 g, 11.14 mmol) was dissolved in ethanol (10 mL) and water (5 mL), and reduced iron powder (4.98 g, 89.14 mmol) and ammonium chloride (4.77 g, 89.14 mmol) were added to the reaction solution. The reaction mixture was stirred at −80° C. for 3 h. After the reaction was completed, the reaction mixture was filtered.

Water (30 mL) was added to the filtrate, and the mixture was extracted with ethyl acetate (30 mL×2) and washed with saturated brine (30 mL). The organic phases were combined and concentrated under reduced pressure to give a crude product. The crude product was separated and purified by silica gel column chromatography (eluent: petroleum ether/ethyl acetate, 100/1-1/1, V/V) to give 35-1. MS-ESI calcd. $[M-H]^-$ 192, found 192.

Step 2

Compound 35-1 (1.00 g, 4.01 mmol) and intermediate F (1.16 g, 6.02 mmol) were dissolved in 1,2-dichloroethane (20 mL), and hypophosphorous acid (52.2 mg, 802 μmol) was added to the reaction solution. The reaction mixture was stirred at 80° C. for 16 h and then filtered. The filtrate was concentrated under reduced pressure to give a crude product. The crude product was separated by preparative high performance liquid chromatography (chromatographic column: Phenomenex Luna 250×50 mm×10 M; mobile phase: 0.1% ammonium hydroxide solution-ethanol; gradient: 35%-65%, 20 min) to give a compound. The compound was then separated by SFC (separation column: Agela Innoval ODS-2 250 mm×100 mm×10 mu; mobile phase: supercritical $CO_2$-solution of 0.1% ammonium hydroxide in ethanol; gradient: solution of 0.1% ammonium hydroxide in ethanol 30%-30%) to give compounds 35a (first main peak) and 35b (second main peak). The compounds were then tested for e.e. value by SFC (chromatographic column: Chiralcel OD-3 50 mm×4.6 mm×3 μm; mobile phase: supercritical $CO_2$-solution of 0.05% diethylamine in ethanol; gradient: solution of 0.05% diethylamine in ethanol: 5%-40%).

Compound 35a: e.e. %=98%, RT=1.344 min. $^1H$ NMR (400 MHz, DMSO-$d_6$) δ 10.55 (s, 1H), 6.99-6.89 (m, 1H), 6.86 (d, J=8.2 Hz, 1H), 6.80-6.62 (m, 4H), 4.93-4.75 (m, 1H), 4.53 (s, 2H), 4.09 (d, J=10.4 Hz, 1H), 3.88 (m, 1H), 3.29-3.21 (m, 1H), 3.08-2.97 (m, 1H), 2.94-2.83 (m, 1H), 2.31 (s, 3H), 1.32 (d, J=7.0 Hz, 3H). MS-ESI calcd. $[M+H]^+$ 425, found 425.

Compound 35b: e.e. %=98%, RT=1.515 min. $^1H$ NMR (400 MHz, DMSO-$d_6$) δ 10.58 (s, 1H), 7.23-7.08 (m, 1H), 6.97-6.82 (m, 3H), 6.80-6.68 (m, 2H), 5.03-4.89 (m, 1H), 4.65-4.45 (m, 2H), 4.23 (d, J=10.6 Hz, 1H), 3.93-3.67 (m, 2H), 2.92-2.74 (m, 1H), 2.59-2.53 (m, 1H), 2.19 (s, 3H), 1.34 (m, 3H). MS-ESI calcd. $[M+H]^+$ 425, found 425.

Example 36

Synthetic Route:

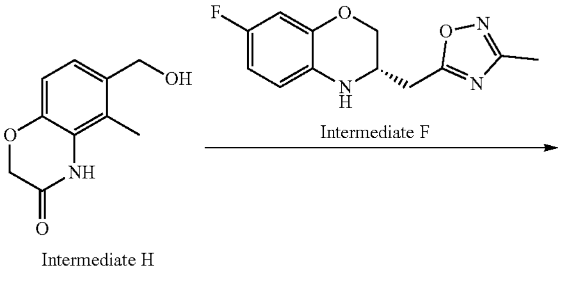

-continued

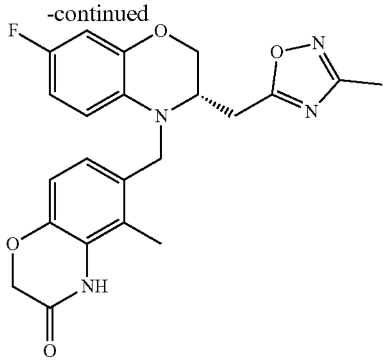

36

Intermediate H (200 mg, 1.04 mmol) and intermediate F (387 mg, 1.55 mmol) were dissolved in 1,2-dichloroethane (5 mL), and hypophosphorous acid (67.3 mg, 1.04 mmol) was added to the reaction solution. The reaction mixture was stirred at 80° C. for 12 h and then concentrated under reduced pressure to give a crude product. The crude product was separated by thin layer chromatography (developing solvent: dichloromethane/methanol, 15/1, V/V) to give a compound. The compound was then separated by preparative high performance liquid chromatography (chromatographic column: Phenomenex Luna 150×25 mm×10 mu; mobile phase: 0.225% aqueous formic acid solution-acetonitrile; gradient:acetonitrile 42%-72%, 10 min) to give compound 36. MS-ESI calcd. $[M+H]^+$ 425, found 425. $^1H$ NMR (400 MHz, DMSO-$d_6$) δ 10.24 (s, 1H), 6.84-6.57 (m, 5H), 4.49 (d, J=1.8 Hz, 2H), 4.37-4.14 (m, 3H), 4.12-3.99 (m, 1H), 3.72 (m, 1H), 3.09-2.96 (m, 2H), 2.24 (s, 3H), 2.12 (s, 3H).

Example 37

Synthetic Route:

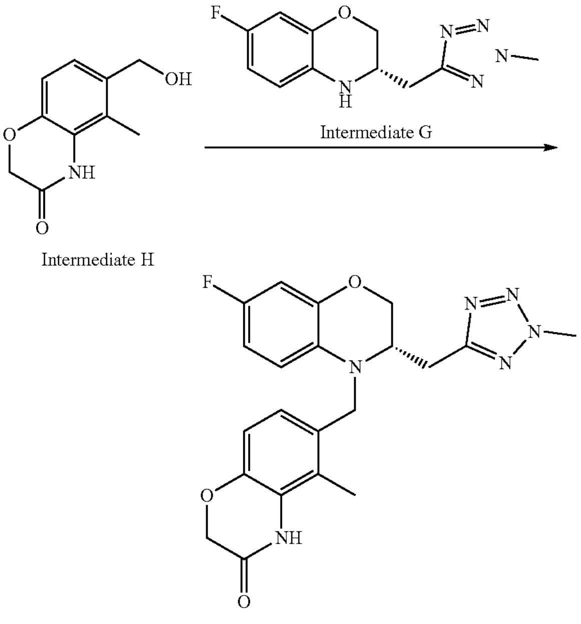

37

Intermediate H (200 mg, 802 μmol) and intermediate G (233 mg, 1.20 mmol) were dissolved in 1,2-dichloroethane (5 mL), and hypophosphorous acid (52.2 mg, 802 mol) was added to the reaction solution. The reaction mixture was stirred at 80° C. for 24 h and then concentrated under reduced pressure to give a crude product. The crude product was separated by thin layer chromatography (developing solvent: petroleum ether/ethyl acetate, 1/1, V/V) to give a compound. The compound was then separated by preparative high performance liquid chromatography (chromatographic column: Phenomenex Luna 150×25 mm×10 Wm; mobile phase: 0.225% aqueous formic acid solution-acetonitrile; gradient:acetonitrile 38%-68%) to give compound 37. MS-ESI calcd. $[M+H]^+$ 425, found 425. H NMR (400 MHz, DMSO-$d_6$) δ 10.25 (s, 1H), 6.82-6.66 (m, 3H), 6.66-6.55 (m, 2H), 4.49 (d, J=1.2 Hz, 2H), 4.36 (d, J=15.6 Hz, 1H), 4.26 (s, 3H), 4.22-4.12 (m, 2H), 4.07-3.97 (m, 1H), 3.70-3.58 (m, 1H), 3.13-2.88 (m, 2H), 2.16-2.04 (m, 3H).

Example 38

Synthetic Route:

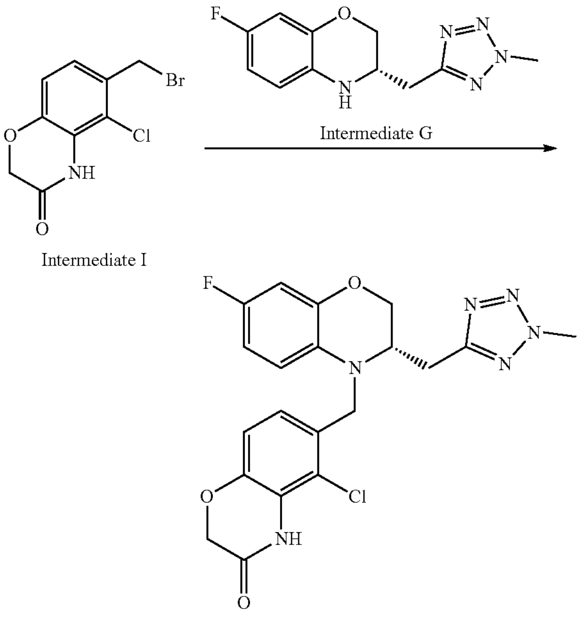

38

Intermediate I (50.0 mg, 181 μmold) an intermediate G (54.1 mg, 217 μmol) were dissolved in acetonitrile (3 mL), and sodium iodide (27.1 mg, 181 μmol) and potassium carbonate (75.0 mg, 542 μmol) were added to the reaction solution. The reaction mixture was stirred at 80° C. for 12 h and then filtered. The filtrate was concentrated under reduced pressure, and the crude product was separated by thin layer chromatography (developing solvent: petroleum ether/ethyl acetate, 1/1, V/V) to give a compound. The compound was then separated by preparative high performance liquid chromatography (chromatographic column: Phenomenex Luna 150×25 mm×10 mu; mobile phase: 0.225% aqueous formic acid solution-acetonitrile; gradient: acetonitrile 39%-69%, 10 min) to give compound 38. MS-ESI calcd. $[M+H]^+$ 445, found 445. $^1$H NMR (400 MHz, DMSO-$d_6$) δ 10.49 (s, 1H), 6.93-6.87 (m, 1H), 6.87-6.78 (m, 1H), 6.76-6.66 (m, 1H), 6.66-6.54 (m, 1H), 6.53-6.42 (m, 1H), 4.67-4.55 (m, 2H), 4.46-4.33 (m, 1H), 4.31-4.20 (m, 5H), 4.14-4.06 (m, 1H), 3.82 (m, 1H), 3.14-2.94 (m, 2H).

Example 39

Synthetic Route:

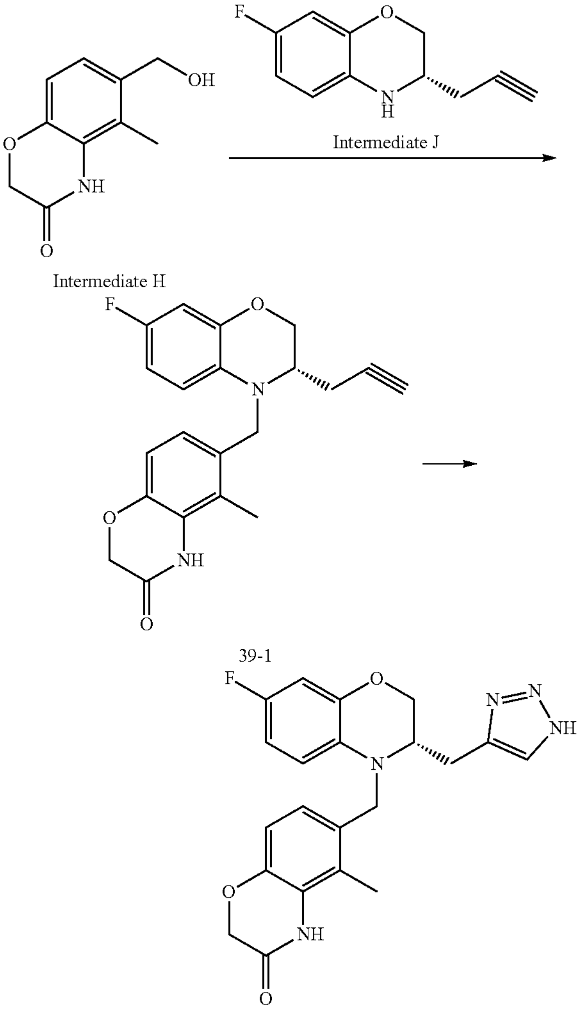

39

Step 1

Intermediate H (500 mg, 2.59 mmol) and intermediate J (594 mg, 3.11 mmol) were dissolved in 1,2-dichloroethane (20 mL), and hypophosphorous acid (168 mg, 2.59 mmol) was added to the reaction solution. The reaction mixture was stirred at 80° C. for 24 h and then concentrated under reduced pressure to give a crude product, which was then separated and purified by silica gel column chromatography (eluent: petroleum ether/ethyl acetate, 10/1-2/1, V/V) to give compound 39-1. MS-ESI calcd. $[M+H]^+$ 367, found 367.

Step 2

Compound 39-1 (270 mg, 737 μmol), sodium ascorbate (292 mg, 1.47 mmol), and anhydrous copper sulfate (118 mg, 737 μmol) were dissolved in tert-butanol (20 mL) and water (8 mL), and azidotrimethylsilane (255 mg, 2.21 mmol) was added to the reaction solution at 20° C. under nitrogen atmosphere. The reaction mixture was stirred at 90° C. for 12 h, then diluted with water (50 mL) and ammonium hydroxide (20 mL), and extracted with ethyl acetate (50 mL×2). The organic phases were combined, washed with saturated brine (100 mL), dried over anhydrous sodium sulfate, and filtered. The filtrate was concentrated under reduced pressure to give a crude product. The crude product was separated by preparative high performance liquid chromatography (chromatographic column: Phenomenex Luna 150×25 mm×10 m; mobile phase: 0.225% aqueous formic acid solution-acetonitrile; gradient:acetonitrile 29%-59%) to give compound 39. MS-ESI calcd. $[M+H]^+$ 410, found 410. $^1H$ NMR (400 MHz, DMSO-$d_6$) δ 10.31-10.12 (m, 1H), 7.66-7.47 (m, 1H), 6.72 (br s, 2H), 6.71-6.63 (m, 1H), 6.63-6.55 (m, 1H), 6.54-6.45 (m, 1H), 4.54-4.45 (m, 2H), 4.45-4.36 (m, 1H), 4.28-4.15 (m, 1H), 4.15-4.04 (m, 1H), 4.04-3.93 (m, 1H), 3.56-3.52 (m, 1H), 2.98-2.74 (m, 2H), 2.20-2.08 (m, 3H).

Example 40

Synthetic Route:

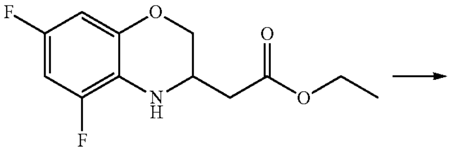

5-4

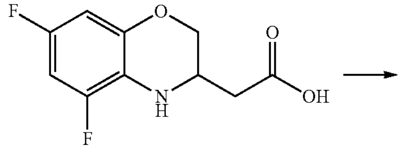

40-1

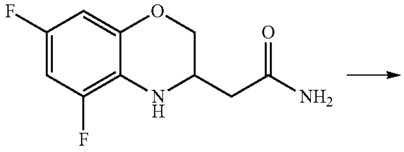

40-2

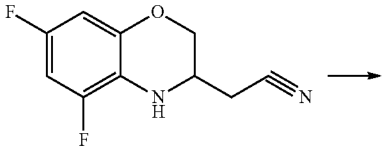

40-3

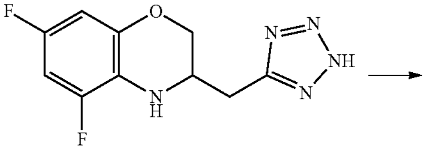

40-4

-continued

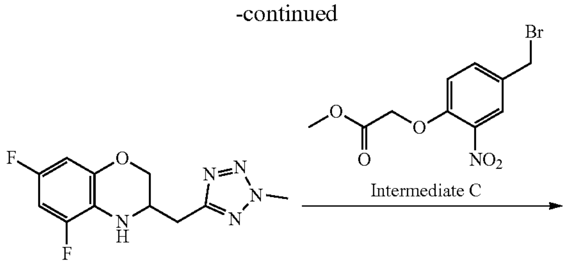

40-5

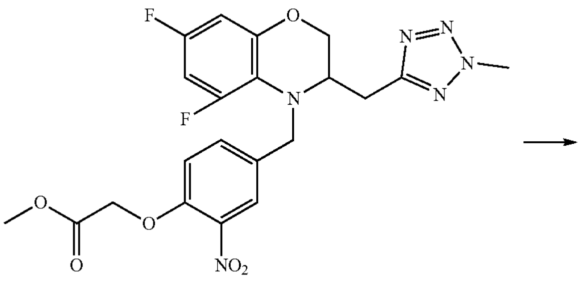

40-6

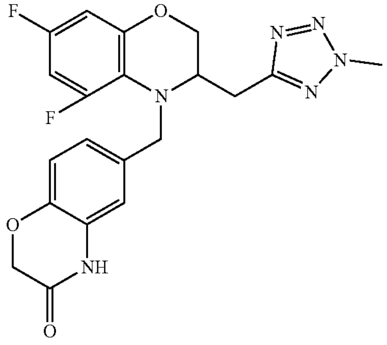

40

Step 1

Compound 5-4 (5.5 g, 21.38 mmol) was dissolved in methanol (60 mL), and a solution of lithium hydroxide monohydrate (1.35 g, 32.07 mmol) in water (15 mL) was added to the reaction solution. The reaction mixture was stirred at 20° C. for 12 h. After the reaction was completed, the reaction mixture was concentrated under reduced pressure to remove the methanol, then diluted with water (50 mL), adjusted to pH 4 with an aqueous hydrochloric acid solution (2 M), and extracted with ethyl acetate (50 mL×2). The organic phases were combined, washed with a saturated sodium chloride solution (30 mL), dried over anhydrous sodium sulfate, filtered, and concentrated under reduced pressure to give compound 40-1. MS-ESI calcd. $[M+H]^+$ 230, found 230.

Step 2

Compound 40-1 (4.66 g, 20.33 mmol) was dissolved in N,N-dimethylformamide (50 mL), and 1,1'-carbonyldiimidazole (4.95 g, 30.05 mol) was added to the reaction solution. The reaction mixture was stirred at 25° C. for 30 min. Ammonium chloride (3.26 g, 61 mmol) and DIPEA (7.88 g, 61 mmol) were then added to the reaction mixture, and the reaction mixture was stirred at 25° C. for 12 h. After the reaction was completed, the reaction mixture was diluted with water (250 mL) and extracted with ethyl acetate (200 mL×2). The organic phases were combined, dried over anhydrous sodium sulfate, and filtered. The reaction solution was concentrated under reduced pressure to give a crude product. The crude product was separated by silica gel column chromatography (eluent: petroleum ether/ethyl acetate-ethyl acetate/methanol, 5/1-20/1, V/V) to give a compound, which was then separated to give compound 40-2. MS-ESI calcd. [M+H]+ 229, found 229.

Step 3

Compound 40-2 (6.58 g, 28.83 mmol) was dissolved in acetonitrile (70 mL) and water (70 mL), and palladium dichloride (2.56 g, 14.42 mmol) was added to the reaction solution. The reaction mixture was stirred at 50° C. for 12 h. After the reaction was completed, the reaction mixture was diluted with water (150 mL) and extracted with ethyl acetate (150 mL×2). The organic phases were combined, dried over anhydrous sodium sulfate, and filtered. The reaction solution was concentrated under reduced pressure to give a crude product. The crude product was separated by silica gel column chromatography (eluent: petroleum ether/ethyl acetate, 10/1-3/1, V/V) to give a compound, which was then separated to give compound 40-3. MS-ESI calcd. [M+H]+ 211, found 211.

Step 4

Compound 40-3 (0.73 g, 3.47 mmol) was dissolved in toluene (20 mL), and azidotrimethylsilane (1.60 g, 13.89 mmol) and dibutyltin oxide (899.20 mg, 3.61 mmol) were added to the reaction solution. The reaction mixture was purged with nitrogen and stirred under the nitrogen atmosphere at 100° C. for 2.5 h. After the reaction was completed, an aqueous potassium fluoride solution (100 mL) was added, and the mixture was stirred for 1 h and then extracted with ethyl acetate (50 mL) and water (20 mL). The organic phases were combined, washed with a saturated sodium chloride solution (50 mL), dried over anhydrous sodium sulfate, filtered, and concentrated under reduced pressure to give compound 40-4. MS-ESI calcd. [M+H]+ 254, found 254.

Step 5

Compound 40-4 (1.4 g, 5.53 mmol) was dissolved in methanol (16 mL) and tetrahydrofuran (3 mL), and (trimethylsilyl)diazomethane (2 M, 8.85 mL) was added to the reaction solution. The reaction mixture was stirred at 5° C. for 12 h. After the reaction was completed, the mixture was extracted with ethyl acetate (30 mL) and water (30 mL). The organic phases were combined, washed with a saturated sodium chloride solution (50 mL), dried over anhydrous sodium sulfate, filtered, and concentrated under reduced pressure to give a crude product. The crude product was subjected to silica gel column chromatography (petroleum ether/ethyl acetate: 10/1-2/1, V/V) to give compound 40-5. MS-ESI calcd. [M+H]+ 268, found 268.

Step 6

Compound 40-5 (300 mg, 1.12 mmol) and intermediate C (682.76 mg, 2.25 mmol) were dissolved in acetonitrile (10 mL), and sodium iodide (336.54 mg, 2.25 mmol) and sodium bicarbonate (282.93 mg, 3.37 mmol) were added to the reaction solution. The reaction mixture was stirred at 80° C. for 12 h and then filtered. The filtrate was concentrated under reduced pressure to give compound 40-6. MS-ESI calcd. [M+H]+ 491, found 491.

Step 7

Compound 40-6 (1 g, 2.04 mmol) was dissolved in acetic acid (15 mL), and iron powder (1.51 g, 27.0 mmol) was added to the reaction solution. The reaction mixture was stirred at 80° C. for 12 h and then filtered. The filtrate was concentrated under reduced pressure to give a crude product. The crude product was separated by preparative high performance liquid chromatography (chromatographic column: Phenomenex Luna C18 250×50 mm×10 Wm; mobile phase: 0.225% aqueous formic acid solution-acetonitrile; gradient: acetonitrile 35%-65%, 20 min) to give compound 40. MS-ESI calcd. [M+H]+ 429, found 429. $^1$H NMR (400 MHz, $CD_3Cl$) δ=8.48 (s, 1H), 6.89-6.75 (m, 2H), 6.67 (d, J=1.2 Hz, 1H), 6.56-6.43 (m, 2H), 4.63 (d, J=4.4 Hz, 2H), 4.35 (s, 1H), 4.27 (s, 1H), 4.21 (s, 3H), 3.97-3.90 (m, 1H), 3.59 (d, J=14.4 Hz, 1H), 3.40 (br t, J=7.6 Hz, 1H), 2.93-2.75 (m, 2H).

Example 41

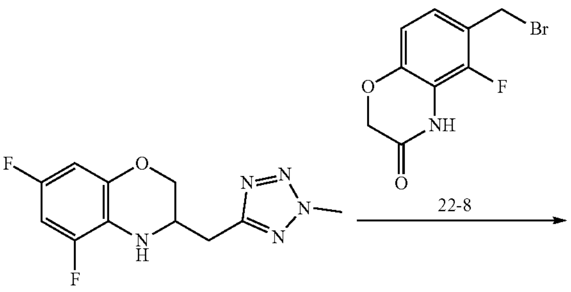

40-5

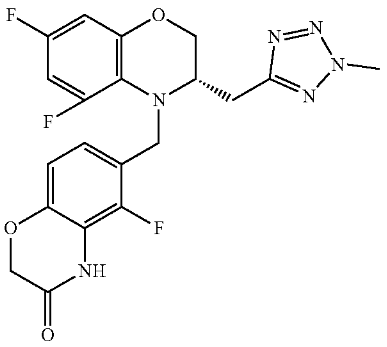

+

41a or 41b

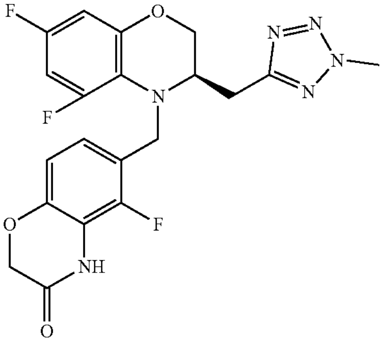

41b or 41a

Compound 40-5 (280 mg, 1.05 mmol) and compound 22-8 (817.45 mg, 3.14 mmol) were dissolved in acetonitrile (10 mL), and sodium iodide (314.10 mg, 2.10 mmol) and sodium bicarbonate (264.07 mg, 3.14 mmol) were added to the reaction solution. The reaction mixture was stirred at 80° C. for 12 h. The reaction solution was filtered, the filtrate was concentrated under reduced pressure to give a crude product, which was separated by preparative high performance liquid chromatography (chromatographic column: Phenomenex Synergi Max-RP 250×0 mm×10 Wm; mobile phase: 0.225% aqueous formic acid solution-acetonitrile; gradient: 40%-65%, 21 min) to give compounds 41a (first main peak) and 41b (second main peak). The compounds were then tested for e.e. value by SFC (chromatographic column: Chiralpak AS-3 50×4.6 mm I.D., 3 μm; mobile phase: supercritical $CO_2$-solution of 0.05% DEA in methanol; gradient: solution of 0.05% DEA in methanol: 5%-40%).

Compound 41a: e.e. %=100%, RT=1.214 min. $^1$H NMR (400 MHz, $CD_3Cl$) δ=8.30 (br s, 1H), 6.88 (t, J=8.2 Hz, 1H), 6.67 (d, J=8.6 Hz, 1H), 6.56-6.44 (m, 2H), 4.66 (d, J=0.8, 2H), 4.28-4.09 (m, 5H), 4.06-3.97 (m, 1H), 3.94-3.87 (m, 1H), 3.47 (br t, J=7.6 Hz, 1H), 2.97-2.75 (m, 2H). MS-ESI calcd. $[M+H]^+$ 447, found 447.

Compound 41b: e.e. %=100%, RT=1.517 min. $^1$H NMR (400 MHz, $CD_3Cl$) δ=8.30 (br s, 1H), 6.88 (t, J=8.2 Hz, 1H), 6.67 (d, J=8.6 Hz, 1H), 6.56-6.44 (m, 2H), 4.66 (d, J=0.8, 2H), 4.28-4.09 (m, 5H), 4.06-3.97 (m, 1H), 3.94-3.87 (m, 1H), 3.47 (br t, J=7.6 Hz, 1H), 2.97-2.75 (m, 2H). MS-ESI calcd. $[M+H]^+$ 447, found 447.

Example 42

Synthetic Route:

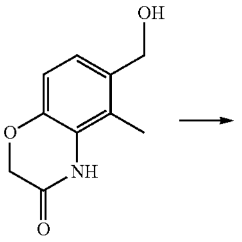

Intermediate H

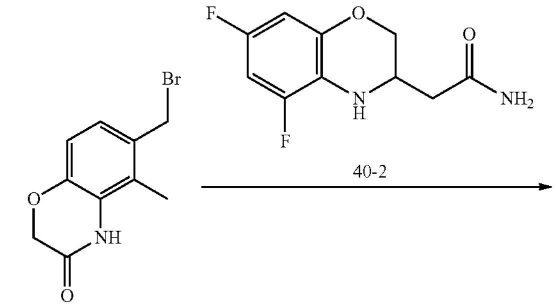

42-1

40-2

-continued

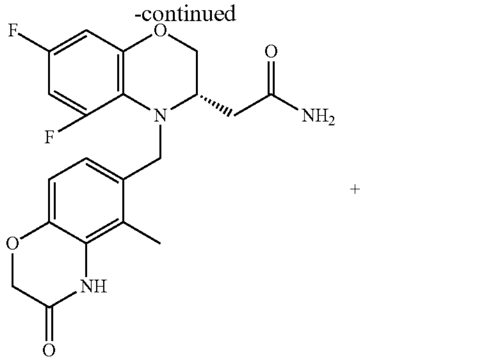

+

42a or 42b

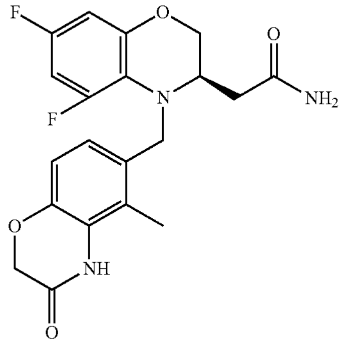

42b or 42a

Step 1

Intermediate H (14 g, 72.46 mmol) was dissolved in toluene (200 mL), and the reaction solution was stirred at 45° C. for 0.5 h. Phosphorus tribromide (33.35 g, 123.19 mmol) was added slowly and dropwise to the reaction solution, and the reaction mixture was stirred at 100° C. for 1 h. Water (1000 mL) was added to the reaction mixture, and the resulting mixture was stirred for 30 min and then filtered. The filter cake was dried to give compound 42-1. $^1$H NMR (400 MHz, MeOD) δ=6.94 (d, J=8.0 Hz, 1H), 6.78 (d, J=8.0 Hz, 1H), 4.50-4.41 (m, 4H), 2.23 (s, 3H).

Step 2

Compound 42-1 (8.42 g, 32.87 mmol) and compound 40-2 (7.5 g, 32.87 mmol) were dissolved in acetonitrile (90 mL), and sodium iodide (4.93 g, 32.87 mmol) and potassium carbonate (13.63 g, 98.60 mmol) were added to the reaction solution. The reaction mixture was stirred at 80° C. for 3 h and then filtered. The filtrate was concentrated under reduced pressure, and the resulting crude product was concentrated. Methanol and water (methanol/water, 1/1, V/V, 65 mL) were added to the crude product, and the mixture was stirred at room temperature for 10 min and then filtered to give a filter cake. The filter cake was dried to give a compound, which was then separated by SFC (chromatographic column: DAICEL CHIRALPAKIG (250 mm×50 mm×10 um); mobile phase: supercritical $CO_2$-solution of 0.1% ammonium hydroxide in ethanol; gradient: 50%-50%) to give compounds 42a (first main peak) and 42b (second main peak). The compounds were then tested for e.e. value by SFC (chromatographic column: Chiralpak AS-3 50×4.6 mm I.D., 3 μm; mobile phase: supercritical $CO_2$-solution of 0.05% DEA in ethanol; gradient: solution of 0.05% DEA in ethanol: 5%-40%).

Compound 42a: e.e. %=100%, RT=0.800 min. $^{1}$H NMR (400 MHz, DMSO-$d_6$) δ=10.21 (s, 1H), 7.24 (s, 1H), 7.06 (d, J=8.4 Hz, 1H), 6.91-6.75 (m, 3H), 6.72-6.60 (m, 1H), 4.51 (s, 2H), 4.23-3.90 (m, 4H), 3.38-3.26 (m, 3H), 2.24 (s, 3H). MS-ESI calcd. $[M+H]^+$ 404, found 404.

Compound 42b: e.e. %=100%, RT=1.129 min. $^{1}$H NMR (400 MHz, DMSO-$d_6$) δ=10.21 (s, 1H), 7.24 (s, 1H), 7.06 (d, J=8.4 Hz, 1H), 6.91-6.75 (m, 3H), 6.72-6.60 (m, 1H), 4.51 (s, 2H), 4.23-3.90 (m, 4H), 3.38-3.26 (m, 3H), 2.24 (s, 3H). MS-ESI calcd. $[M+H]^+$ 404, found 404.

Example 43

Synthetic Route:

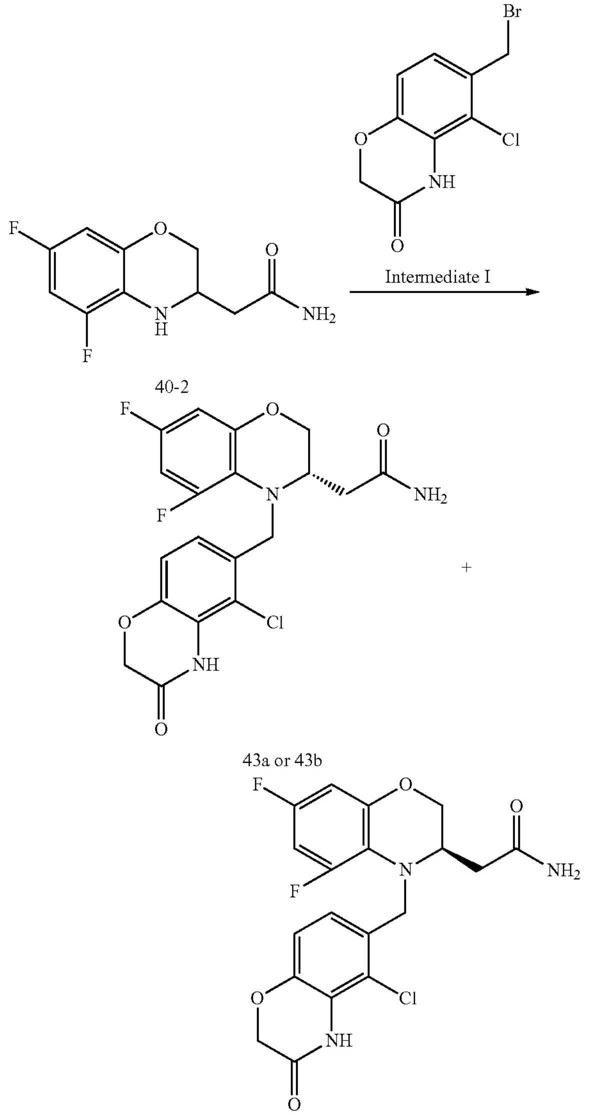

40-2

43a or 43b 43b or 43a

Compound 40-2 (204.25 mg, 895.07 μmol) and intermediate I (275 mg, 994.52 μmol) were dissolved in acetonitrile (10 mL), and potassium carbonate (412.35 mg, 2.98 mmol) and sodium iodide (149.07 mg, 994.52 mol) were added to the reaction solution. The reaction mixture was stirred at 85° C. for 2 h and then filtered. The filtrate was extracted and concentrated under reduced pressure to give a crude product, which was then separated by preparative high performance liquid chromatography (chromatographic column: Phenomenex Luna C18 150×25 mm×10 mu; mobile phase: 0.225% aqueous formic acid solution-acetonitrile; gradient:acetonitrile 34%-64%, 10 min) to give a compound. The compound was then separated by SFC (separation column: DAICEL CHIRALPAK AY-H 250 mm×30 mm×10 μm; mobile phase: supercritical $CO_2$-solution of 0.1% ammonium hydroxide in ethanol; gradient: solution of 0.1% ammonium hydroxide in ethanol 60%-60%) to give compounds 43a (first main peak) and 43b (second main peak). The compounds were then tested for e.e. value by SFC (chromatographic column: Chiralpak AY-3 50 mm×4.6 mm×3 Wm; mobile phase: supercritical $CO_2$-solution of 0.05% diethanolamine in isopropanol and acetonitrile; gradient: 40% solution of 0.05% diethylamine in isopropanol and acetonitrile).

Compound 43a: e.e. %=100%, RT=0.497 min. $^{1}$H NMR (400 MHz, DMSO-$d_6$) δ=10.45 (s, 1H), 7.30-7.23 (m, 2H), 7.00 (d, J=8.0 Hz, 1H), 6.86-6.78 (m, 2H), 6.67 (d, J=10.0 Hz, 1H), 4.61 (s, 2H), 4.27-4.23 (m, 1H), 4.16-4.12 (m, 2H), 3.95-3.90 (m, 1H), 3.43-3.40 (m, 1H), 2.19-2.07 (m, 2H). MS-ESI calcd. $[M+H]^+$ 424, found 424.

Compound 43b: e.e. %=99.74%, RT=1.555 min. $^{1}$H NMR (400 MHz, DMSO-$d_6$) δ=10.45 (s, 1H), 7.29-7.22 (m, 2H), 7.00 (d, J=8.4 Hz, 1H), 6.86-6.78 (m, 2H), 6.68-6.66 (m, 1H), 4.61 (s, 2H), 4.27-4.23 (m, 1H), 4.15-4.12 (m, 2H), 3.92-3.89 (m, 1H), 3.41-3.40 (m, 1H), 2.15-2.11 (m, 2H). MS-ESI calcd. $[M+H]^+$ 424, found 424.

Activity Assay

Experimental Example 1: In Vitro Evaluation of MR Antagonistic Activity

Purpose of Experiment: to assay the MR antagonistic activity of the compounds

Experimental Materials

A DMEM medium purchased from BI; fetal bovine serum purchased from Biosera; an HEK293/Gal4/MR cell line provided by Wuhan Heyan Biomedical Technology Co., Ltd.; Bright Glo purchased from Promega; and an EnVision multi-marker analyzer (PerkinElmer).

Procedures

MR cells were seeded in a white 96-well plate, with 80 mL of cell suspension containing 40000 cells added to each well. The cell plate was incubated in a $CO_2$ incubator overnight.

The compounds to be tested were serially 5-fold diluted to the 8th concentration point with a multi-channel pipette, and the compound concentration ranged from 2 mmol to 0.026 mol. 38 μL of the medium was added to an intermediate plate, and the compound was added to corresponding wells of the intermediate plate at 2 μL/well. After well mixing, the compound solution was transferred to the cell plate at 10 μL/well, and the cell plate was incubated in a $CO_2$ incubator for 1 h. Aldosterone was diluted to 10 nmol with a medium, i.e., 20 μL of aldosterone with a concentration of 1 μmol was added to 1980 μL of the medium. After well mixing, 10 μL of the aldosterone solution was added to each well of the cell plate except the positive control wells. The cell plate was incubated in a $CO_2$ incubator for 24 h. The final concentration of the compound ranged from 10 μmol to 0.128 nmol, and the final concentration of aldosterone was 1 nmol. After the incubation was completed, the cell supernatant was discarded, and the Bright Glo reagent was added to the cell plate at 100 μL/well. Readings were taken immediately on the EnVision multi-marker analyzer.

Data Analysis

The original data were converted to inhibition rates using the following equation: % inhibition=((RFU$_{cmpd}$−AVER (RFU$_{Neg.Ctrl}$))/((AVER(RFU$_{Pos.Ctrl}$)−AVER(RFU$_{Neg.Ctrl}$))× 100%. Compound curves were fitted by log(inhibitor) vs. response-Variable slope of Graphpad Prism 5. $IC_{50}$ values were calculated by the software using the following formula: Y=Bottom+(Top−Bottom)/(1+10^((Log IC50−X)×HillSlope)).

The Experimental Results are Shown in Table 1.

TABLE 1

Results of MR antagonistic activity assay

| Compound | $IC_{50}$ (nM) for MR |
|---|---|
| 2 | 372 |
| 4 | 289 |
| 5 | 325 |
| 6 | 273 |
| 7 | 519 |
| 8a | 130 |
| 9 | 403 |
| 10 | 15 |
| 12 | 27 |
| 14 | 78 |
| 15 | 107 |
| 18 | 62 |
| 19 | 66 |
| 20 | 27 |
| 21 | 50 |
| 22 | 9 |
| 23 | 29 |
| 24 | 32 |
| 25 | 72 |
| 26 | 32 |
| 27 | 80 |
| 28 | 35 |
| 29 | 22 |
| 30 | 68 |
| 31a | 80 |
| 32 | 50.8 |
| 33 | 11 |
| 34 | 130 |
| 35a | 251.1 |
| 35b | 76.6 |
| 36 | 13.7 |
| 37 | 43.9 |
| 38 | 22.6 |
| 42a | 29.14 |
| 43a | 18.03 |

Experimental conclusion: The compounds of the present application have good antagonistic activity on mineralocorticoid receptors.

Experimental Example 2: Pharmacokinetic Evaluation

Experimental Materials

SD rats (male, 7-9 weeks old, Beijing Vital River Laboratory Animal Technology Co., Ltd.)

Procedures

Pharmacokinetic characteristics of the compounds after intravenous injection (IV) and oral administration (PO) in rodents were tested by a standard scheme. The rats were subjected to intravenous injection and oral administration once in the experiment. The vehicle for the intravenous injection was water. The vehicle for the intravenous injection was a clear solution of 80% polyethylene glycol 400/20% water, and the vehicle for the oral administration was a homogeneous suspension of 99.9% (0.5% HPMC:Solutol HS15=95:5)/0.1% Tween 80. Four male SD rats were used in this project. Two rats were subjected to intravenous injection, and plasma samples were collected at 0 h (before administration) and 0.083, 0.25, 0.5, 1, 2, 4, 8 and 24 h (after administration); the other two rats were subjected to oral intragastric administration, and plasma samples were collected at 0 h (before administration) and 0.25, 0.5, 1, 2, 4, 8, and 24 h (after administration). Whole blood samples within 24 h were collected. All blood samples were immediately transferred to labeled commercial centrifuge tubes containing K2-EDTA. After blood sample collection, the plasma supernatant was taken by centrifugation at 3200 g at 4° C. for 10 min, immediately placed in dry ice, and then stored at −60° C. or a lower temperature for LC-MS/MS analysis. Plasma concentration-time data were analyzed by a non-compartmental model using a WinNonlin software package (Version 6.3 and above), and pharmacokinetic parameters such as peak concentration ($C_{max}$), clearance (CL), tissue distribution (Vdss), area under plasma concentration-time curve ($AUC_{0-last}$), bioavailability (F) and the like were calculated.

The experimental results are shown in Table 2.

TABLE 2

Pharmacokinetic evaluation results of compounds of examples disclosed herein in rats

| Compound | Dose of administration | Bioavailability F (%) | Peak concentration $C_{max}$ (nM) | Tissue distribution Vdss (L/kg) | Clearance CL (mL/min/kg) | Area under plasma concentration-time curve $AUC_{0-last}$ PO (nM · hr) |
|---|---|---|---|---|---|---|
| Compound 36 | IV (1 mg/kg), PO (100 mg/kg) | 64.9 | 5625 | 6.96 | 82.6 | 29875 |
| Compound 37 | IV (1 mg/kg), PO (100 mg/kg) | 141.8 | 18900 | 4.75 | 47.9 | 115969 |
| Compound 42a | IV (1 mg/kg), PO (10 mg/kg) | 34.6 | 2740 | 1.57 | 24.4 | 5933 |

Experimental conclusion: The compounds of the present application have good pharmacokinetic properties.

Experimental Example 3: In Vivo Efficacy Study in Rats with Unilateral Nephrectomy

Experimental Materials

SD rats (male, Beijing Vital River Laboratory Animal Technology Co., Ltd.)

Procedures

SD male rats were acclimatized for 2-3 days before being subjected to right nephrectomy, and during this period, the rats were fed with ordinary feed and drinking water. After a one-week recovery period, the rats were grouped according to body weight. After grouping, osmotic pumps were implanted subcutaneously, aldosterone was injected with a concentration of 3 mg/mL (dissolved in 0.15% DMSO/prepared with sterile water) (Yuanye Biotech S30644-5 mg) at a flow rate of 0.75 μg/hr (Alzet model 2004), and the rats were fed with 6% NaCl high-salt feed (customized by Beijing Keao Xieli Feed Co., Ltd.) and 0.3% KCl drinking water (Yuanye Biotech S24120). The osmotic pumps were implanted subcutaneously while oral administration was performed at a dose specified at grouping. The vehicle (0.5% hydroxypropyl methyl cellulose:polyethylene glycol stearate 15=95:5 (v/v, containing 0.1% Tween 80)) was administered orally to the control group. The oral administrations were conducted once daily over 4 consecutive weeks. Body weights were measured and recorded daily.

Experimental conclusion: The compounds of the present application have remarkable protection effects on the kidney and can effectively reduce the ratio of albumin to creatinine in rat urine.

The invention claimed is:

1. A compound of formula (II), a stereoisomer thereof or a pharmaceutically acceptable salt thereof:

(II)

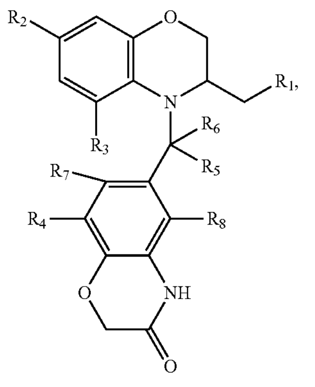

wherein $R_1$ is selected from the group consisting of $R_{11}$ and $R_{12}$;

$R_{11}$ is selected from the group consisting of —$OR_a$, —C(=O)$NR_bR_c$, and —S(=O)$_2C_{1-4}$ alkyl, wherein the $C_{1-4}$ alkyl is optionally substituted with 1, 2, or 3 $R_{aa}$;

$R_{12}$ is selected from 5-membered heteroaryl, wherein the 5-membered heteroaryl is optionally substituted with 1, 2, or 3 $R_d$;

$R_2$, $R_3$, and $R_4$ are each independently selected from the group consisting of H, F, Cl, Br, I, —CN, —$NH_2$, —OH, and $C_{1-4}$ alkyl;

$R_5$ and $R_6$ are each independently selected from the group consisting of H, D, F, Cl, Br, and $C_{1-4}$ alkyl, wherein the $C_{1-4}$ alkyl is optionally substituted with 1, 2, or 3 $R_{ab}$;

$R_7$ and $R_8$ are each independently selected from the group consisting of H, F, Cl, Br, I, —CN, —$NH_2$, —OH, and $C_{1-4}$ alkyl;

$R_a$, $R_b$, and $R_c$ are each independently selected from the group consisting of H, $C_{1-4}$ alkyl, and $C_{3-4}$ cycloalkyl, wherein the $C_{1-4}$ alkyl and the $C_{3-4}$ cycloalkyl are each independently and optionally substituted with 1, 2, or 3 R;

each $R_d$ is independently selected from the group consisting of H, F, Cl, Br, I, —CN, —$NH_2$, —OH, and $C_{1-4}$ alkyl, wherein the $C_{1-4}$ alkyl is optionally substituted with 1, 2, or 3 $R_{ac}$;

$R_{aa}$, $R_{ab}$, and $R_{ac}$ are each independently selected from the group consisting of D, F, Cl, Br, I, —CN, —$NH_2$, and —OH;

each R is independently selected from the group consisting of F, Cl, Br, I, —CN, —$NH_2$, and —OH; and the "hetero" in the 5-membered heteroaryl means 1, 2, 3, or 4 heteroatoms or heteroatom groups each independently selected from the group consisting of —O—, —NH—, —S—, and —N—.

2. The compound, the stereoisomer thereof or the pharmaceutically acceptable salt thereof according to claim 1, wherein $R_a$ is selected from H.

3. The compound, the stereoisomer thereof or the pharmaceutically acceptable salt thereof according to claim 1, wherein $R_b$ and Re are each independently selected from the group consisting of H, —$CH_3$, —$CH_2CH_3$, and

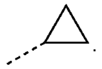

4. The compound, the stereoisomer thereof or the pharmaceutically acceptable salt thereof according to claim 1, wherein each $R_d$ is independently selected from the group consisting of H, F, Cl, Br, and $C_{1-4}$ alkyl, wherein the $C_{1-4}$ alkyl is optionally substituted with 1, 2, or 3 $R_{ac}$;

or each $R_d$ is independently selected from the group consisting of H, F, Cl, Br, and —$CH_3$, wherein the —$CH_3$ is optionally substituted with 1, 2, or 3 $R_{ac}$;

or each $R_d$ is independently selected from the group consisting of H, F, Cl, Br, —$CH_3$,

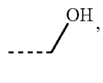, and 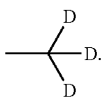

5. The compound, the stereoisomer thereof or the pharmaceutically acceptable salt thereof according to claim 1, wherein $R_{11}$ is selected from the group consisting of —OH, —C(=O)$NH_2$, —C(=O)$NHCH_3$, —C(=O)$NHCH_2CH_3$,

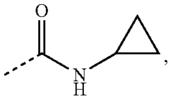, and —S(=O)$_2CH_3$.

6. The compound, the stereoisomer thereof or the pharmaceutically acceptable salt thereof according to claim 1, wherein $R_{12}$ is selected from the group consisting of

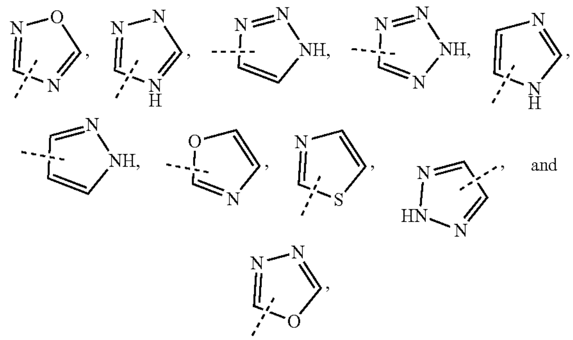

and wherein the

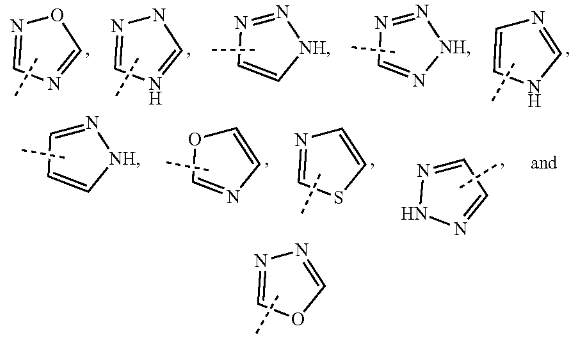

and are each independently and optionally substituted with 1, 2, or 3 $R_d$;

or $R_{12}$ is selected from the group consisting of

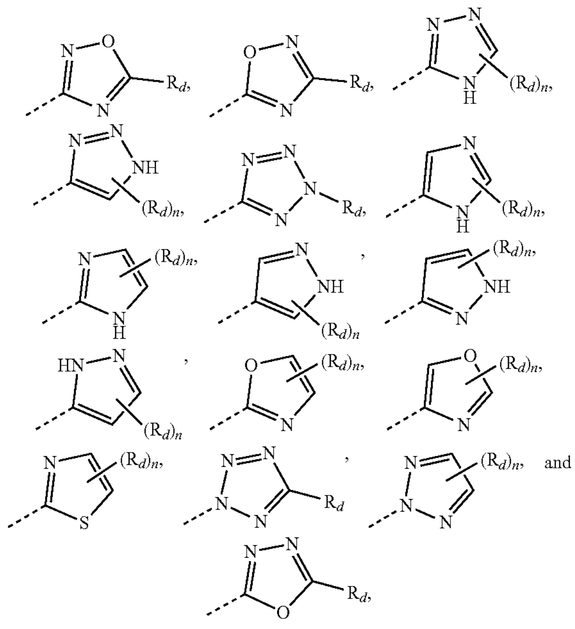

and wherein n is selected from the group consisting of 1, 2, and 3;

or $R_{12}$ is selected from the group consisting of

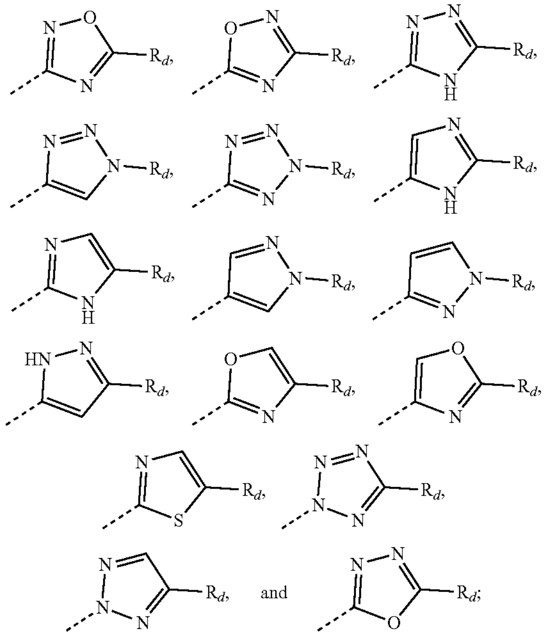

and or $R_{12}$ is selected from the group consisting of

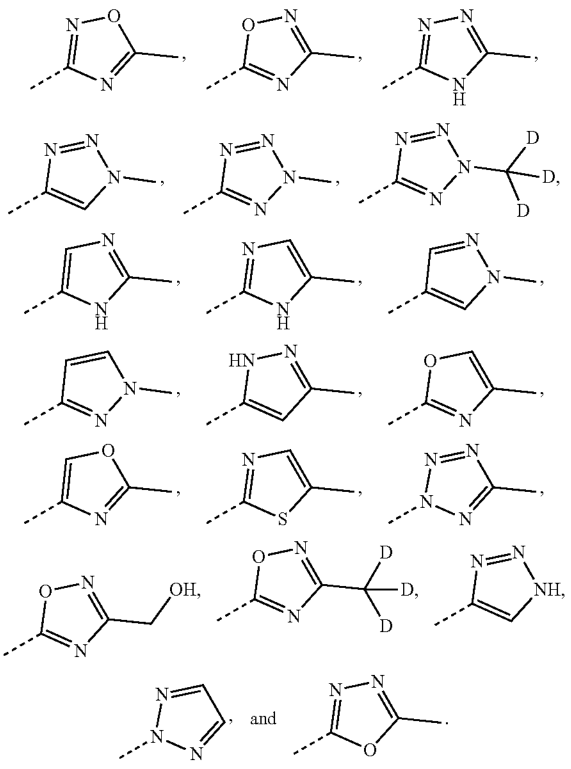

and

7. The compound, the stereoisomer thereof or the pharmaceutically acceptable salt thereof according to claim 1, wherein $R_1$ is selected from the group consisting of —OH, —C(=O)$NH_2$, —C(=O)$NHCH_3$, —C(=O)$NHCH_2CH_3$,

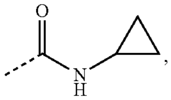,

—$S(=O)_2CH_3$,

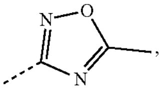, 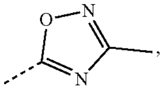, 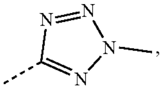,

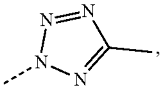, 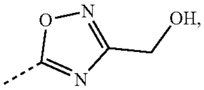

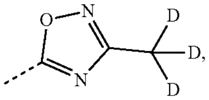 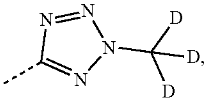 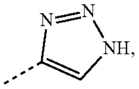

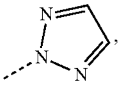, and 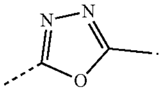.

8. The compound, the stereoisomer thereof or the pharmaceutically acceptable salt thereof according to claim 1, wherein $R_2$ and $R_3$ are each independently selected from the group consisting of H, F, and Cl.

9. The compound, the stereoisomer thereof or the pharmaceutically acceptable salt thereof according to claim 1, wherein $R_4$ is selected from the group consisting of H, F, Cl, and $C_{1-4}$ alkyl;

or $R_4$ is selected from the group consisting of H, F, Cl, and —$CH_3$.

10. The compound, the stereoisomer thereof or the pharmaceutically acceptable salt thereof according to claim 1, wherein $R_5$ and $R_6$ are each independently selected from the group consisting of H, D, and $C_{1-4}$ alkyl, wherein the $C_{1-4}$ alkyl is optionally substituted with 1, 2, or 3 $R_{ab}$;

or $R_5$ and $R_6$ are each independently selected from the group consisting of H, D, and —$CH_3$.

11. The compound, the stereoisomer thereof or the pharmaceutically acceptable salt thereof according to claim 1, wherein $R_7$ is selected from the group consisting of H and F.

12. The compound, the stereoisomer thereof or the pharmaceutically acceptable salt thereof according to claim 1, wherein Rs is selected from the group consisting of H, F, Cl, and $C_{1-4}$ alkyl;

or Rs is selected from the group consisting of H, F, Cl, and —$CH_3$.

13. Compounds of the following formulas, stereoisomers thereof or pharmaceutically acceptable salts thereof:

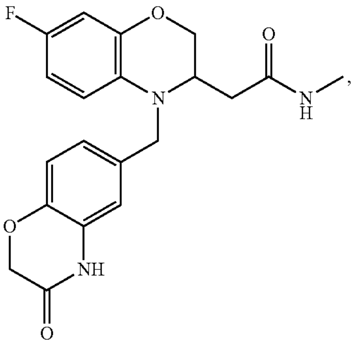,

-continued

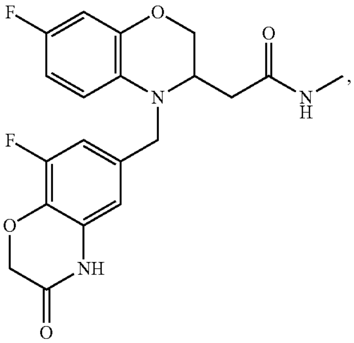,

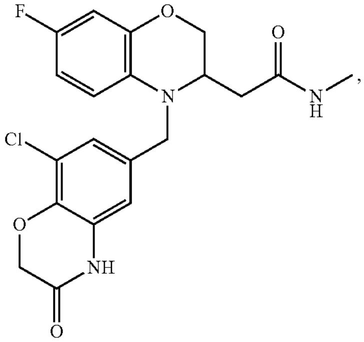,

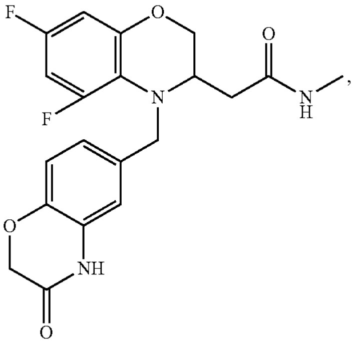,

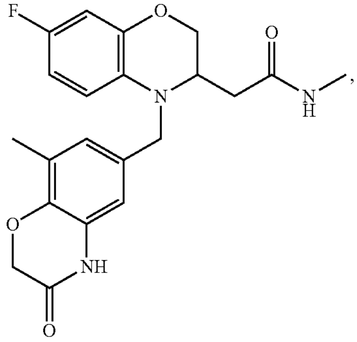,

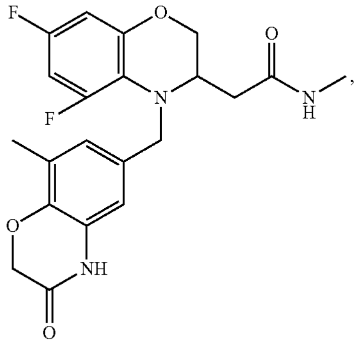,

-continued
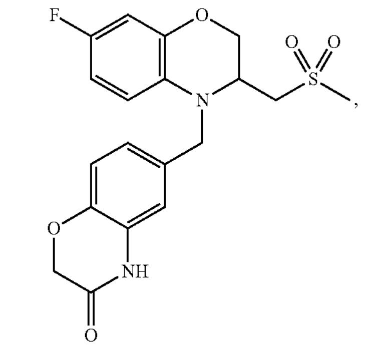
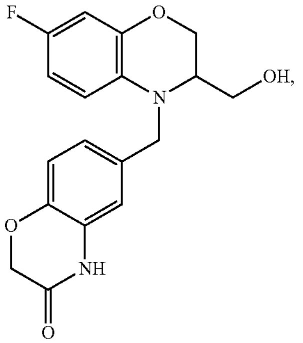
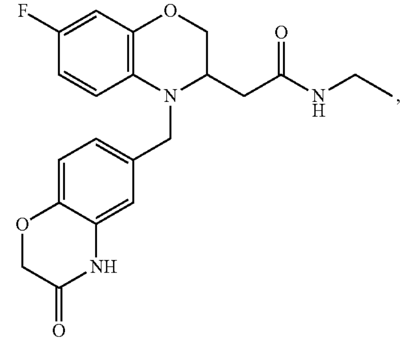
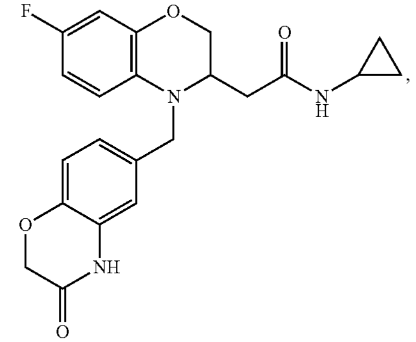
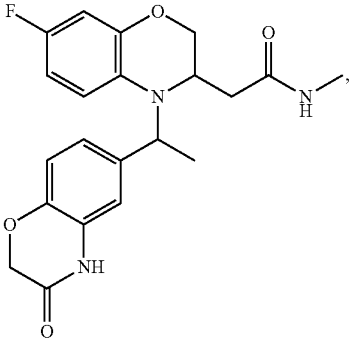
-continued
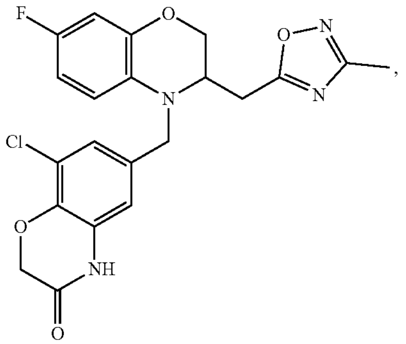
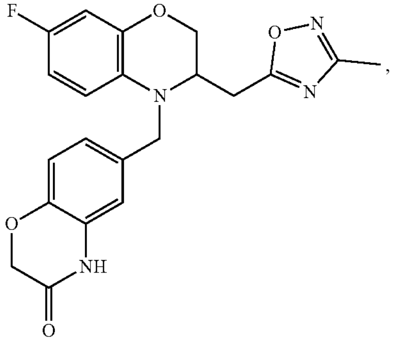
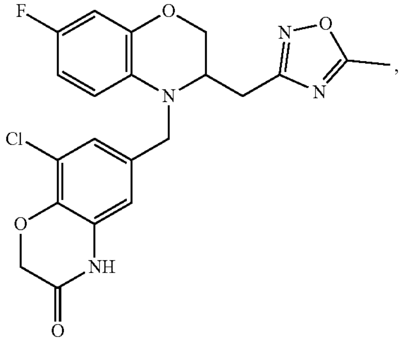
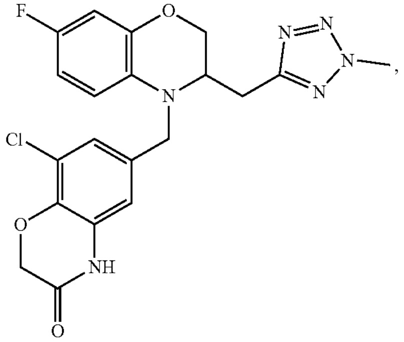
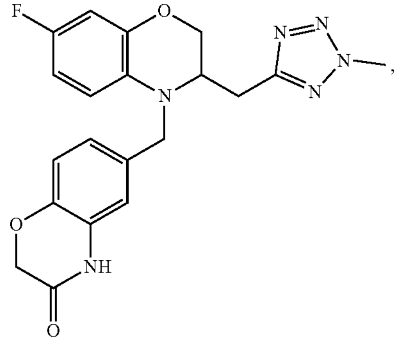

-continued
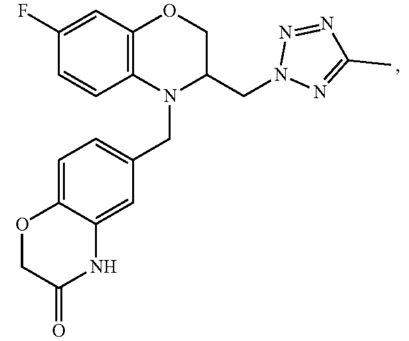
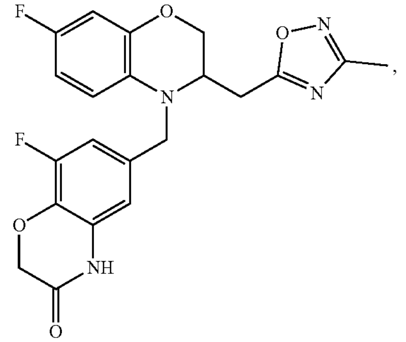
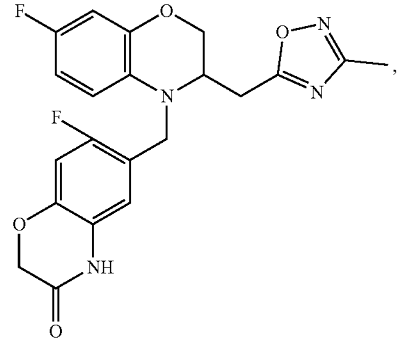
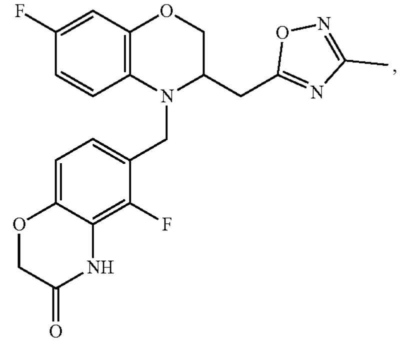
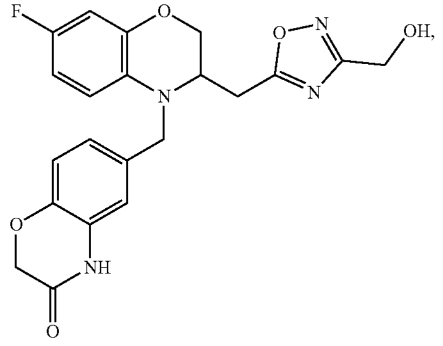
-continued
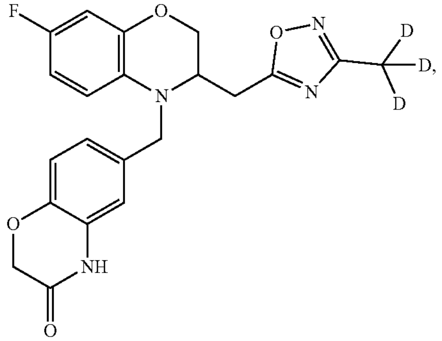
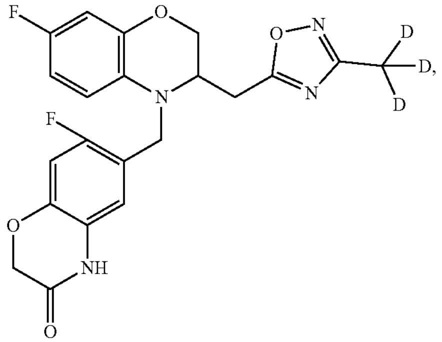
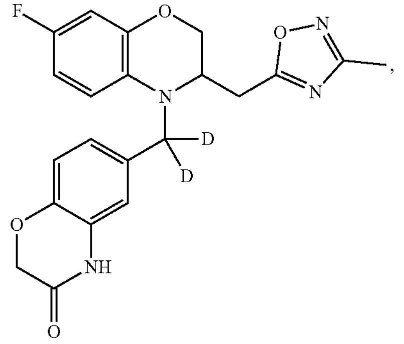
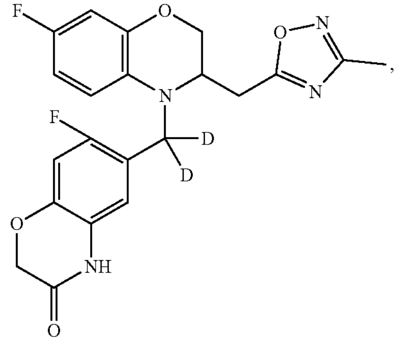
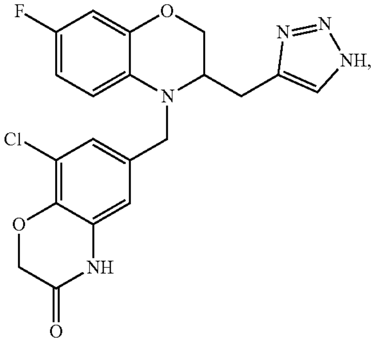

-continued
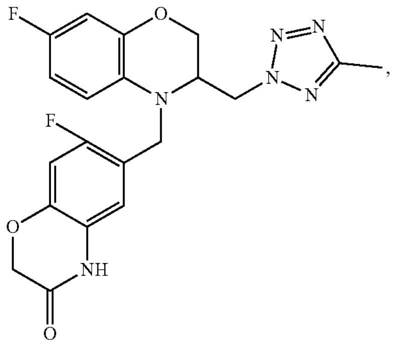
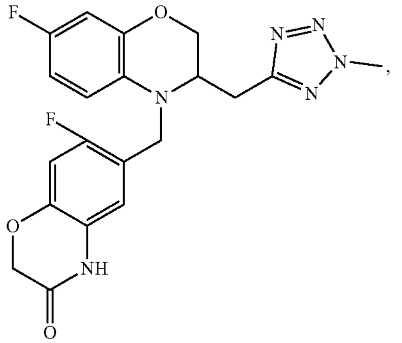
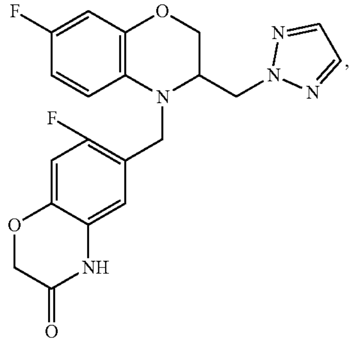
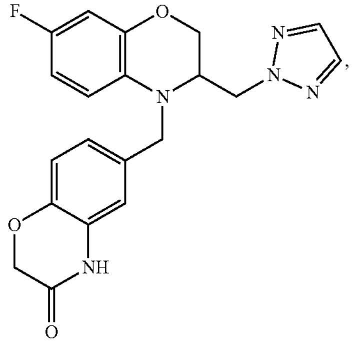
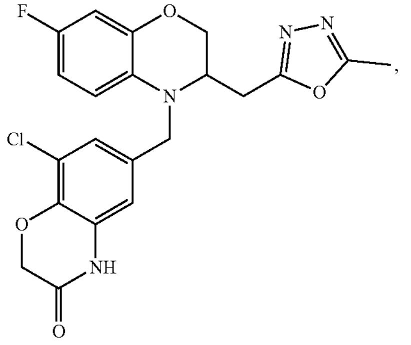
-continued
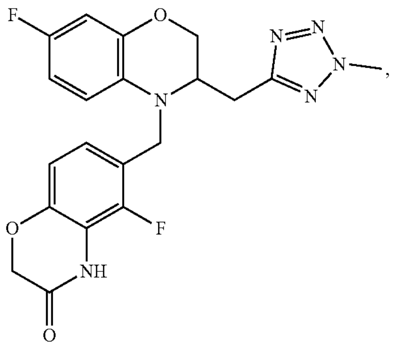
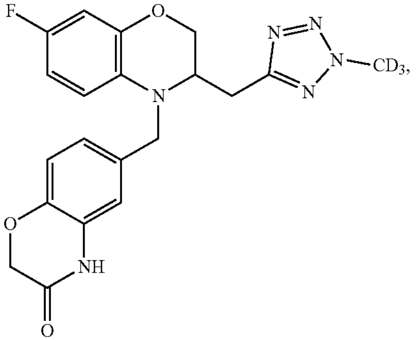
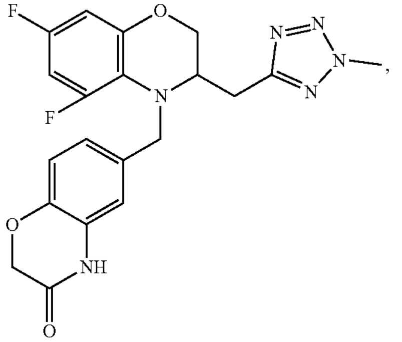
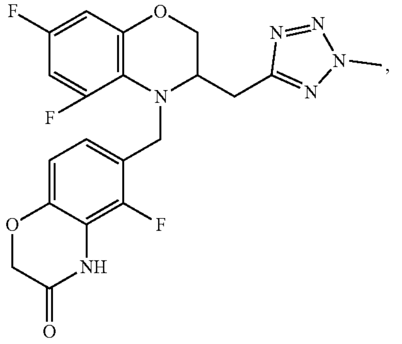
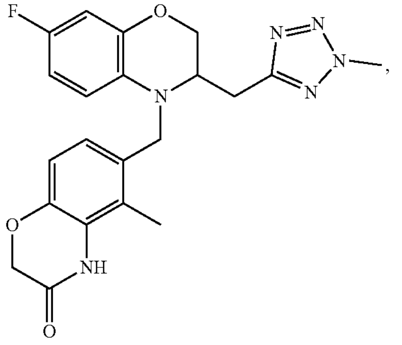

-continued
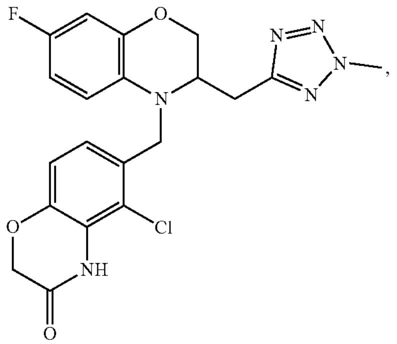
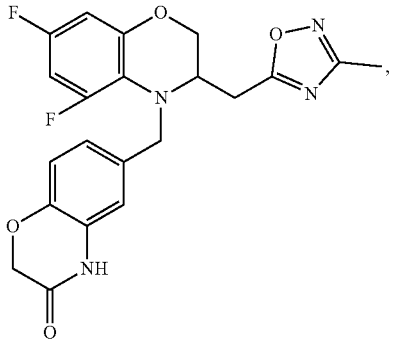
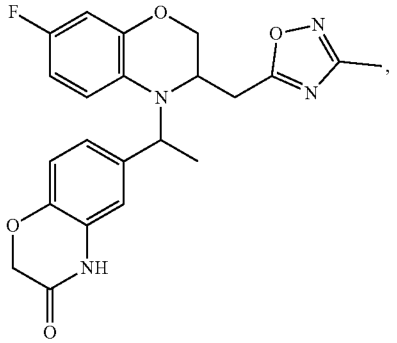
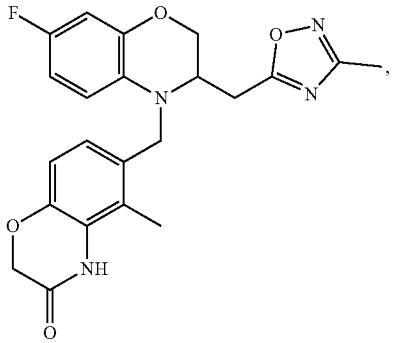
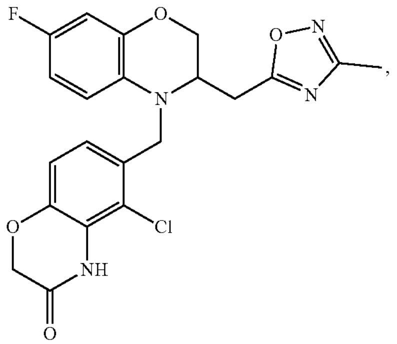
-continued
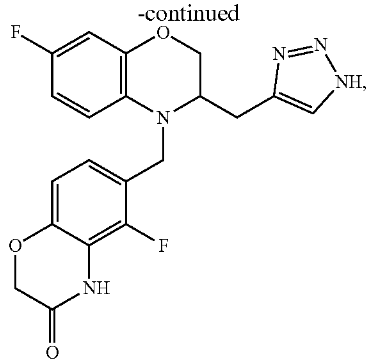
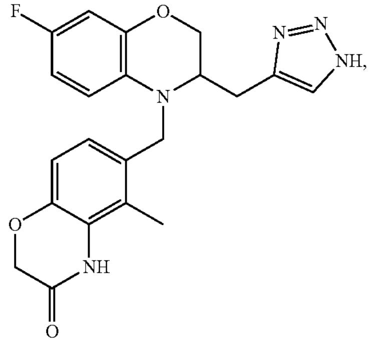
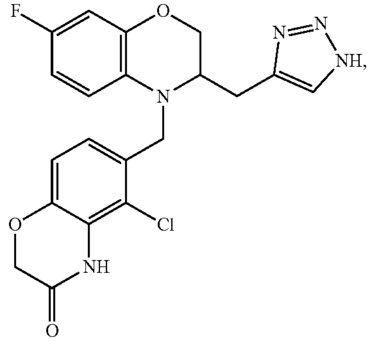
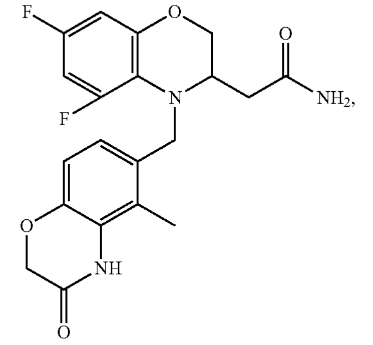
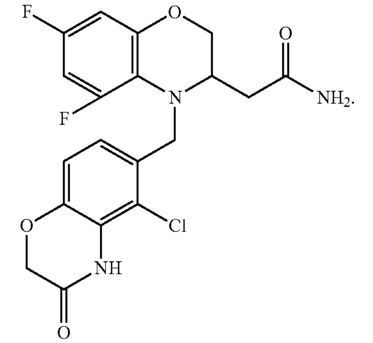 [SMILES: NC(=O)CC1COc2cc(F)cc(F)c2N1Cc1ccc2c(c1Cl)NC(=O)CO2]

14. A pharmaceutical composition, comprising a therapeutically effective amount of the compound, the stereoisomer thereof or the pharmaceutically acceptable salt thereof according to claim 1 and a pharmaceutically acceptable carrier.

15. A method for treating a mineralocorticoid receptor antagonist-related disease, comprising administering an effective amount of the compound, the stereoisomer thereof or the pharmaceutically acceptable salt thereof according to claim 1 to a subject in need thereof.

16. The method for treating a mineralocorticoid receptor antagonist-related disease according to claim 15, wherein the mineralocorticoid receptor antagonist-related disease is selected from diabetic nephropathy.

17. A compound of formula (I), a stereoisomer thereof or a pharmaceutically acceptable salt thereof:

(I)

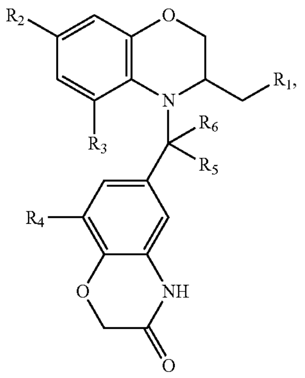

wherein $R_1$ is selected from the group consisting of $R_{11}$ and $R_{12}$;

$R_{11}$ is selected from the group consisting of —$OR_a$, —C(=O)$NR_bR_c$, and —S(=O)$_2C_{1-4}$ alkyl, wherein the $C_{1-4}$ alkyl is optionally substituted with 1, 2, or 3 $R_{aa}$;

$R_{12}$ is selected from 5-membered heteroaryl, wherein the 5-membered heteroaryl is optionally substituted with 1, 2, or 3 $R_d$;

$R_2$, $R_3$, and $R_4$ are each independently selected from the group consisting of H, F, Cl, Br, I, —CN, —$NH_2$, —OH, and $C_{1-4}$ alkyl;

$R_5$ and $R_6$ are each independently selected from the group consisting of H, F, Cl, Br, and $C_{1-4}$ alkyl, wherein the $C_{1-4}$ alkyl is optionally substituted with 1, 2, or 3 $R_{ab}$;

$R_a$, $R_b$, and $R_c$ are each independently selected from the group consisting of H, $C_{1-4}$ alkyl, and $C_{3-4}$ cycloalkyl, wherein the $C_{1-4}$ alkyl and the $C_{3-4}$ cycloalkyl are each independently and optionally substituted with 1, 2, or 3 R;

each $R_d$ is independently selected from the group consisting of H, F, Cl, Br, I, —CN, —$NH_2$, —OH, and $C_{1-4}$ alkyl, wherein the $C_{1-4}$ alkyl is optionally substituted with 1, 2, or 3 $R_{ac}$;

$R_{aa}$, $R_{ab}$, and $R_{ac}$ are each independently selected from the group consisting of F, Cl, Br, I, —CN, —$NH_2$, and —OH;

each R is independently selected from the group consisting of F, Cl, Br, I, —CN, —$NH_2$, and —OH; and the "hetero" in the 5-membered heteroaryl means 1, 2, 3, or 4 heteroatoms or heteroatom groups each independently selected from the group consisting of —N—, —O—, —S—, and —NH—.

18. The compound, the stereoisomer thereof or the pharmaceutically acceptable salt thereof according to claim 1 selected from:

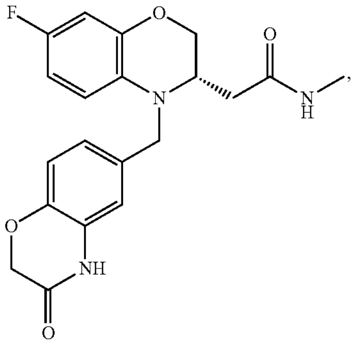

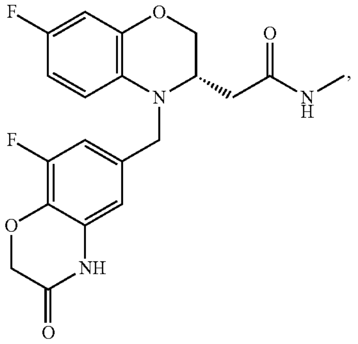

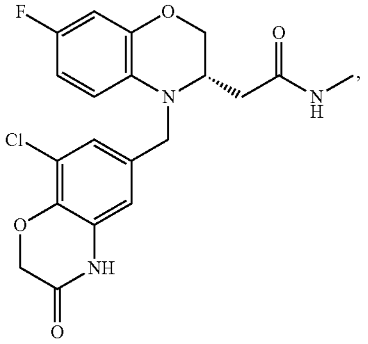

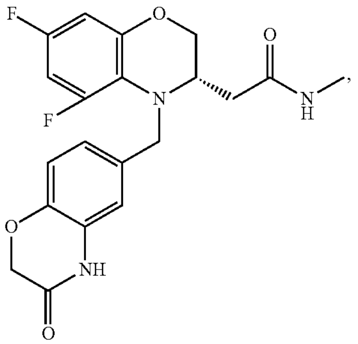

-continued
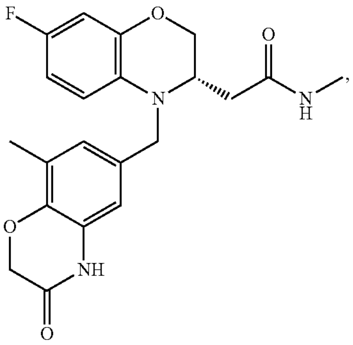
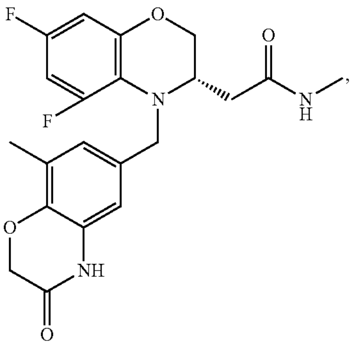
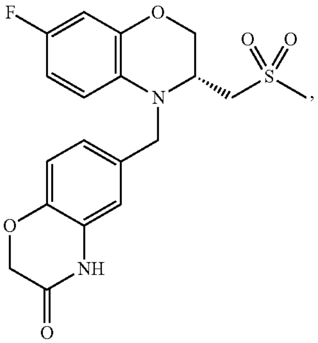
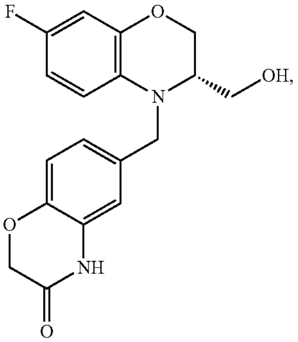
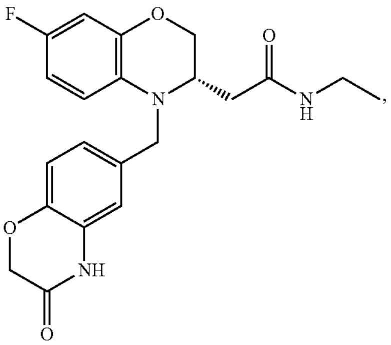
-continued
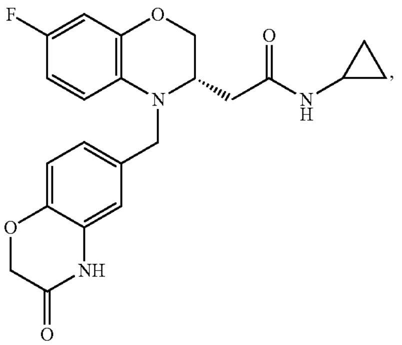
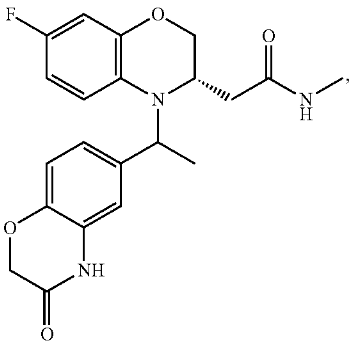
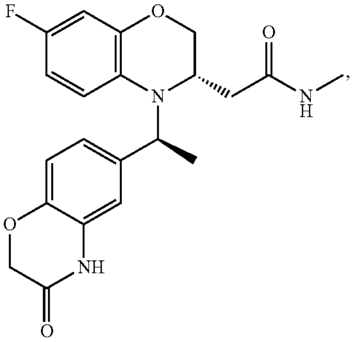
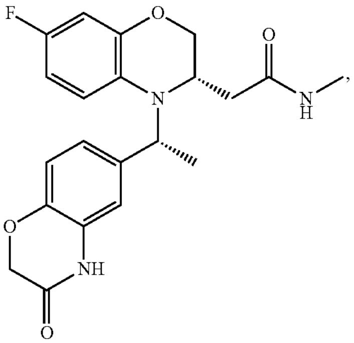
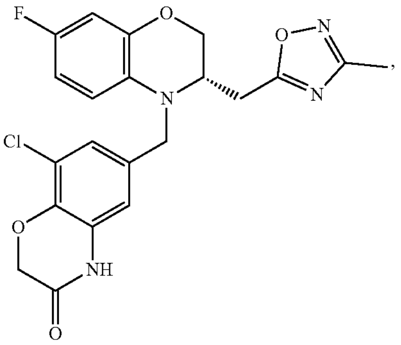

-continued
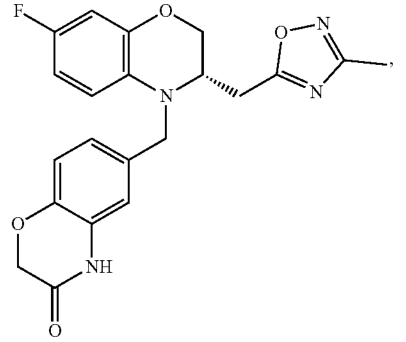
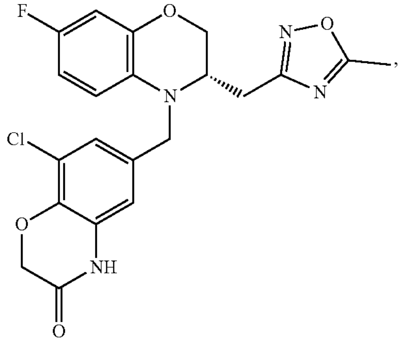
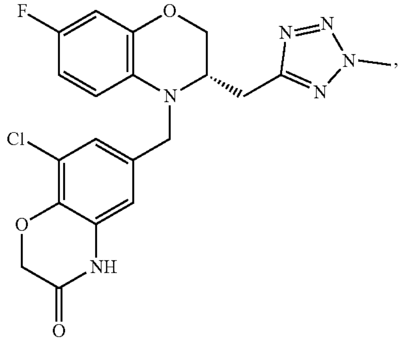
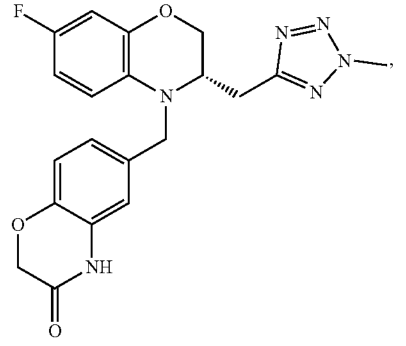
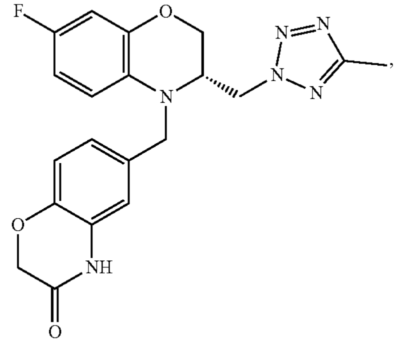
-continued
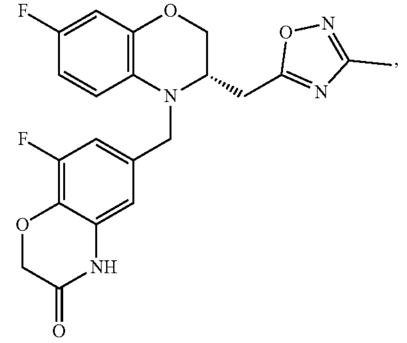
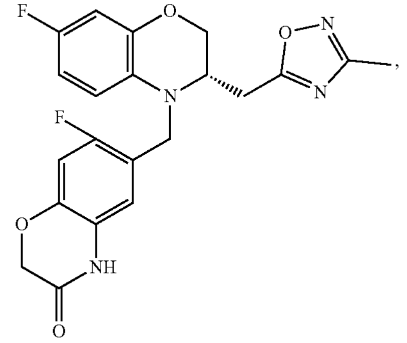
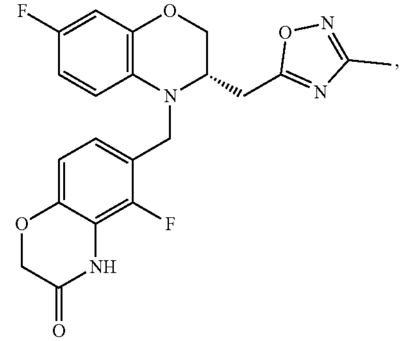
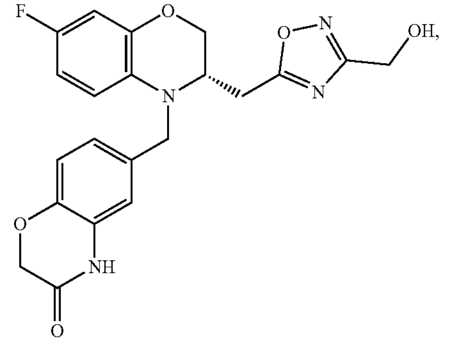
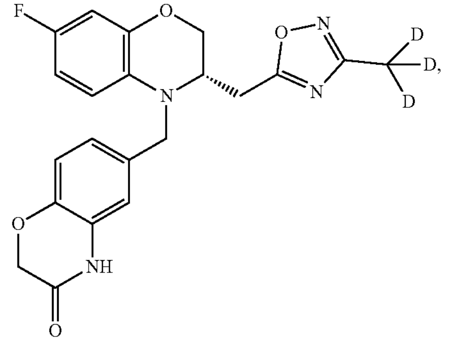

-continued
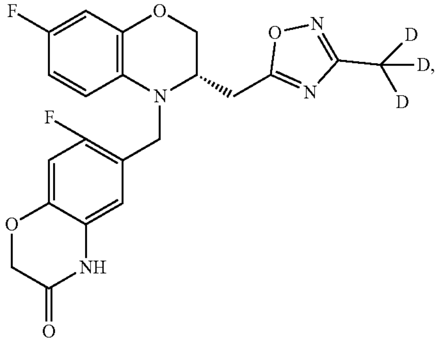
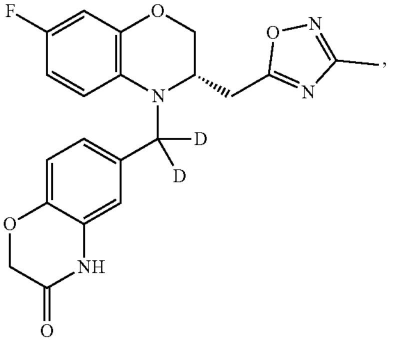
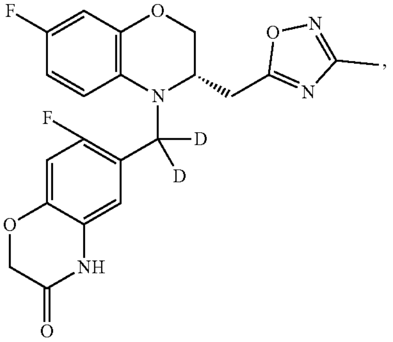
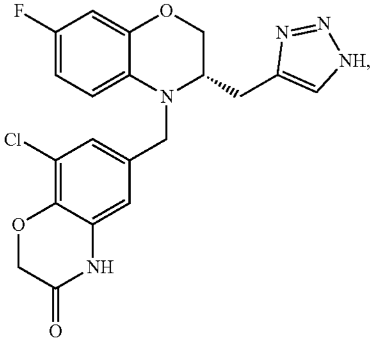
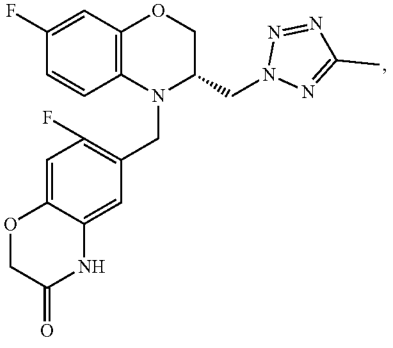
-continued
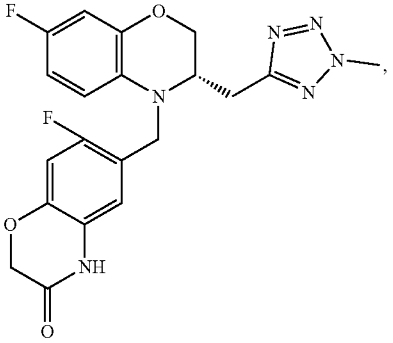
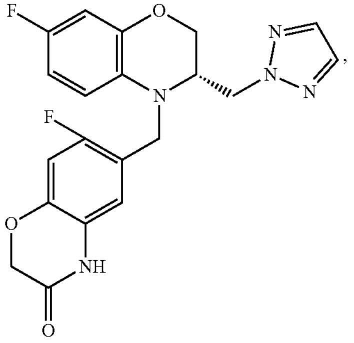
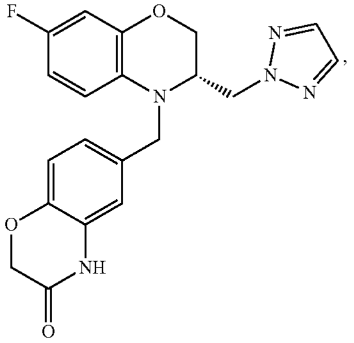
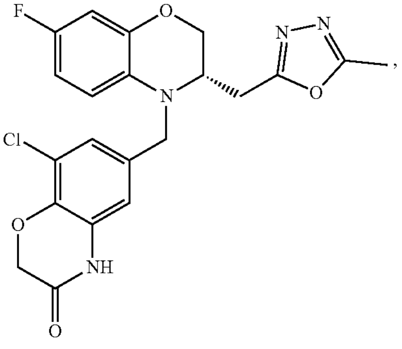
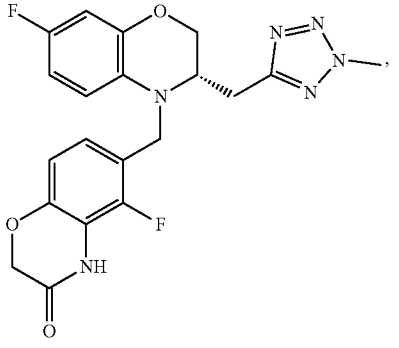

-continued
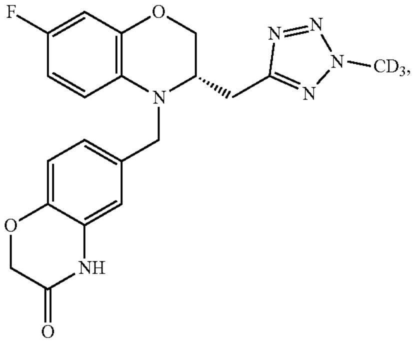
,
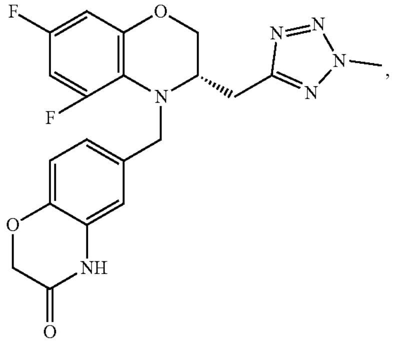
,
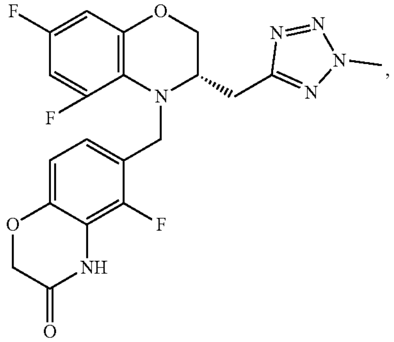
,
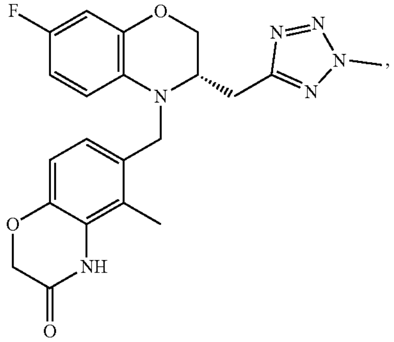
,
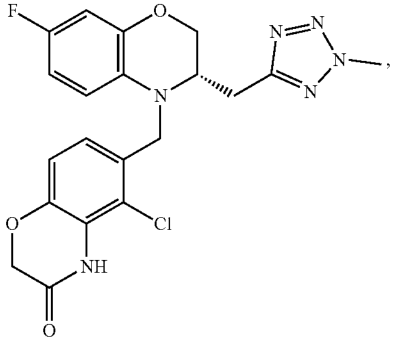
,
-continued
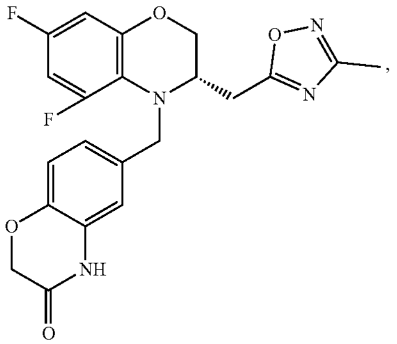
,
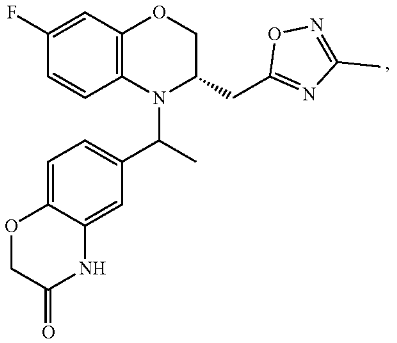
,
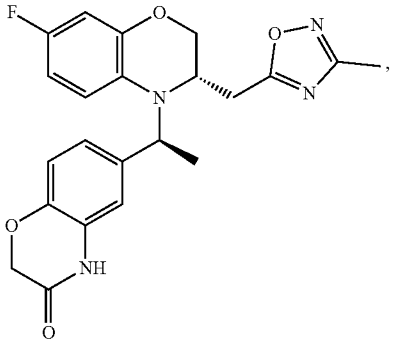
,
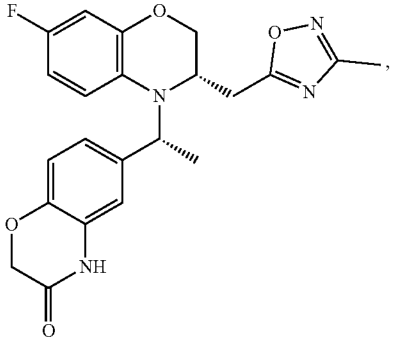
,
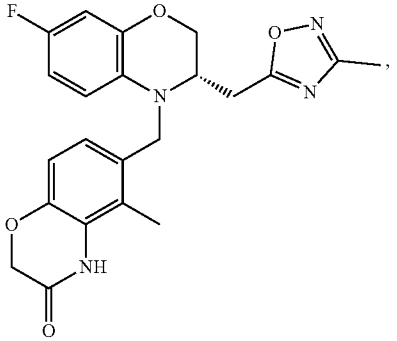
, -continued
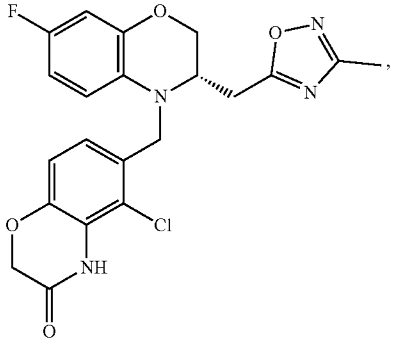
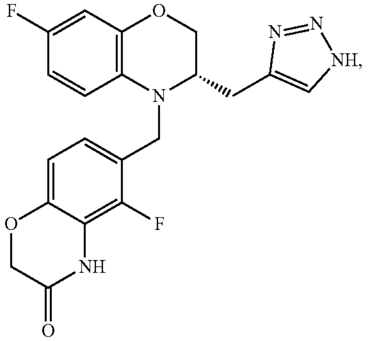
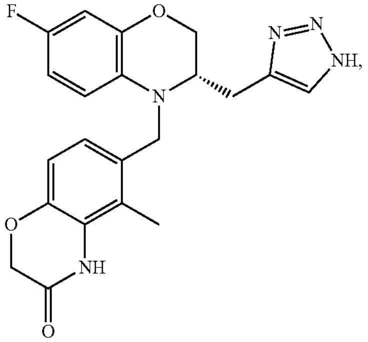
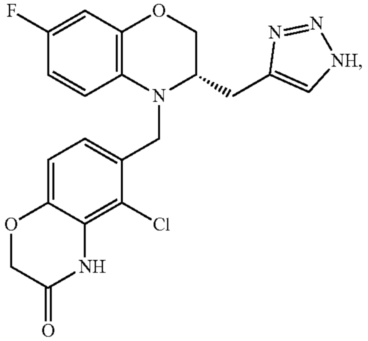
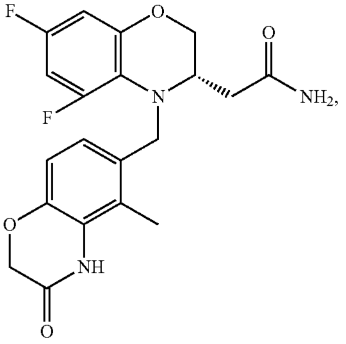
and
-continued
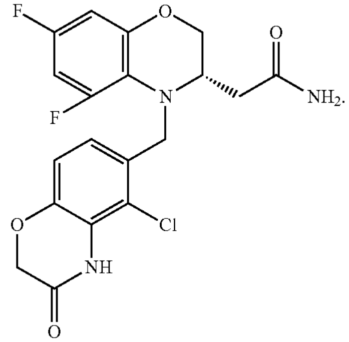
19. The compound, the stereoisomer thereof or the pharmaceutically acceptable salt thereof according to claim 1 selected from:
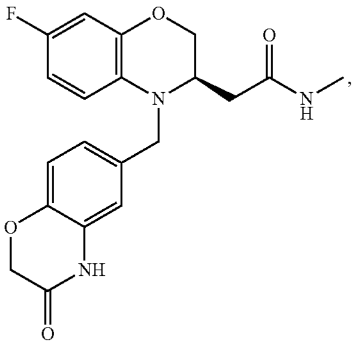
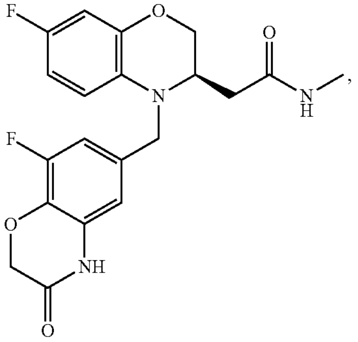
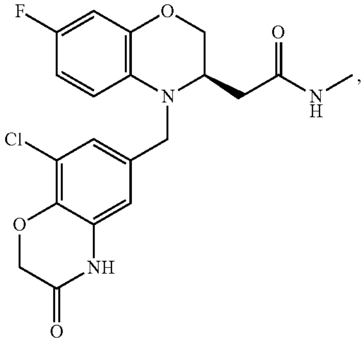

-continued
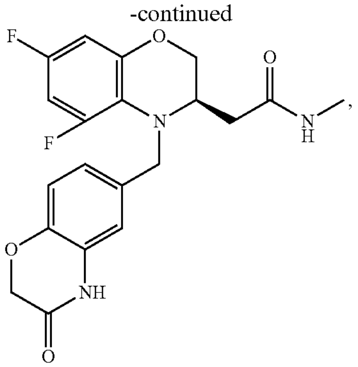
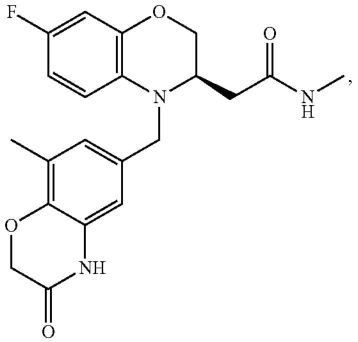
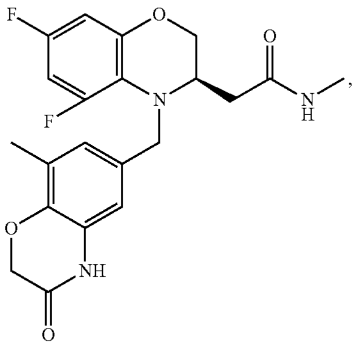
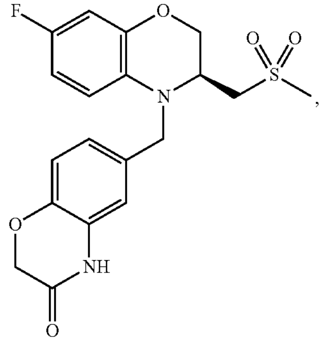
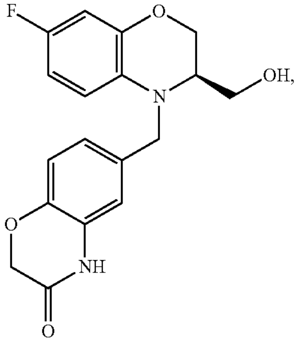
-continued
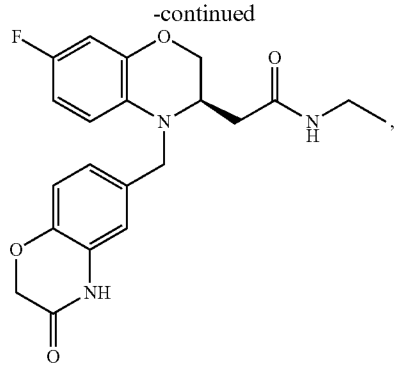
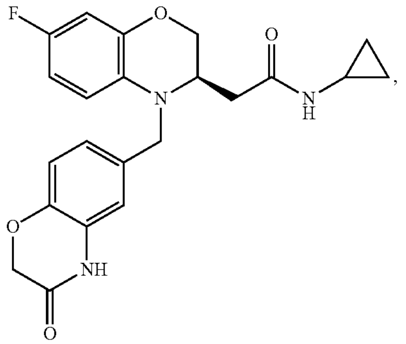
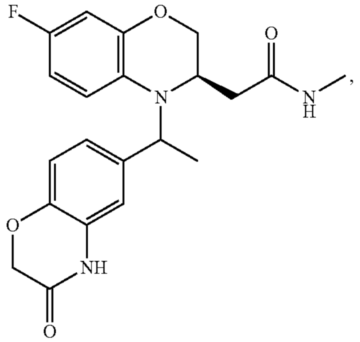
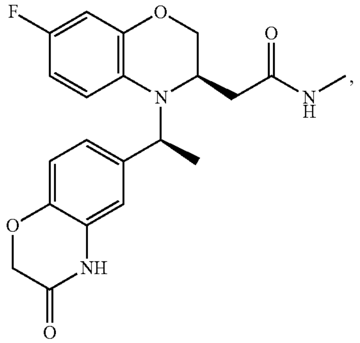
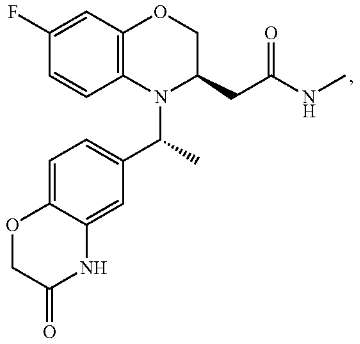

-continued
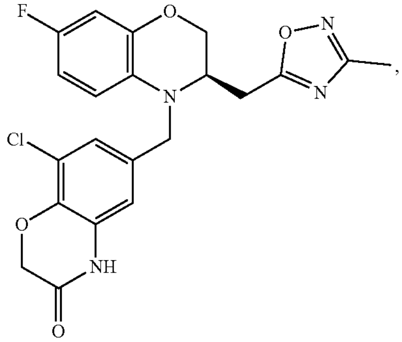
,
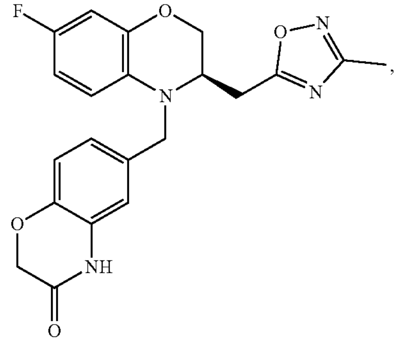
,
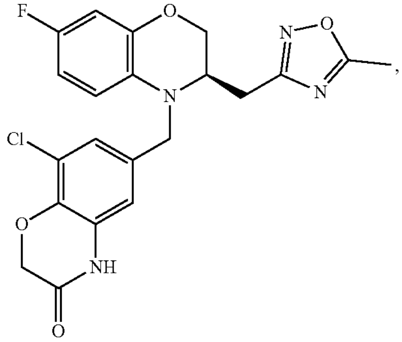
,
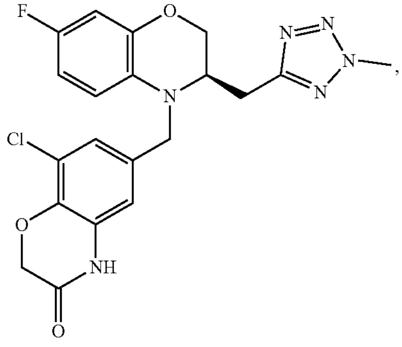
,
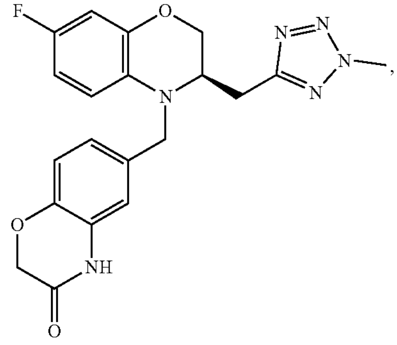
,
-continued
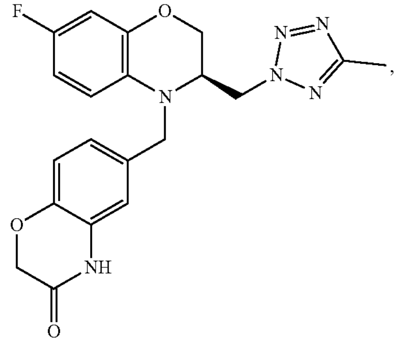
,
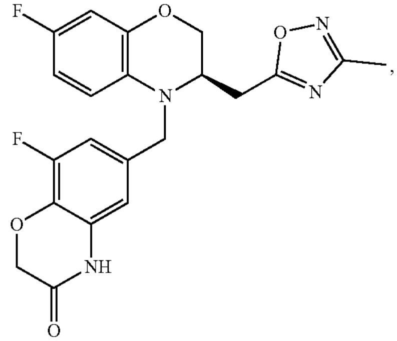
,
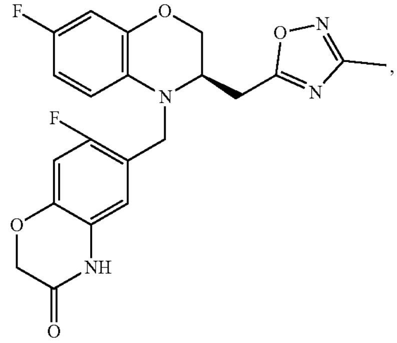
,
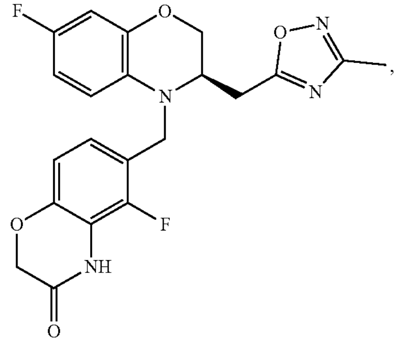
,
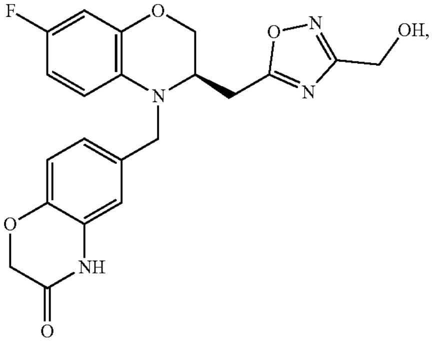
, -continued
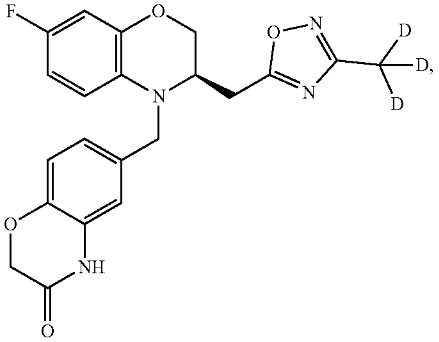
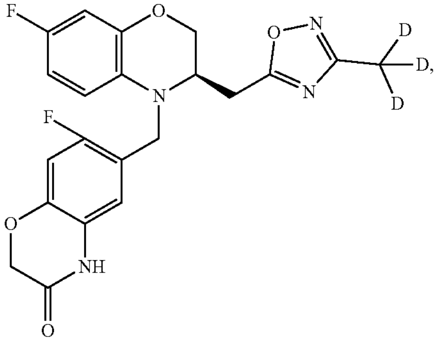
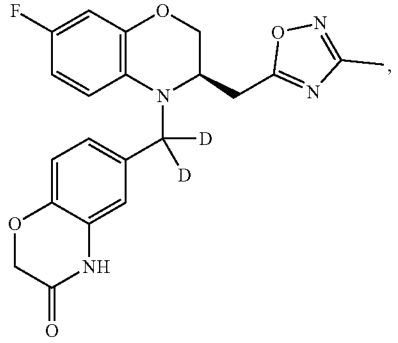
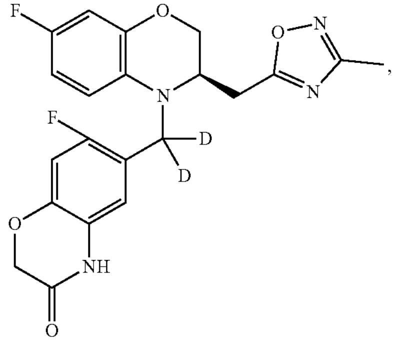
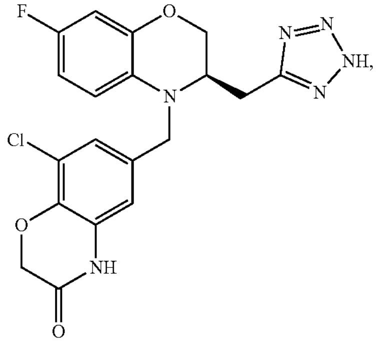
-continued
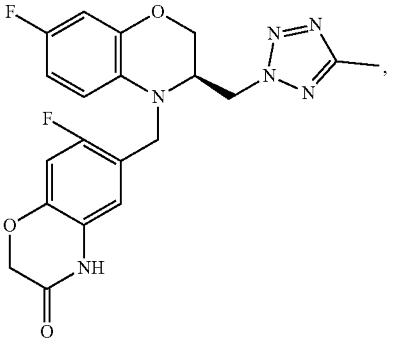
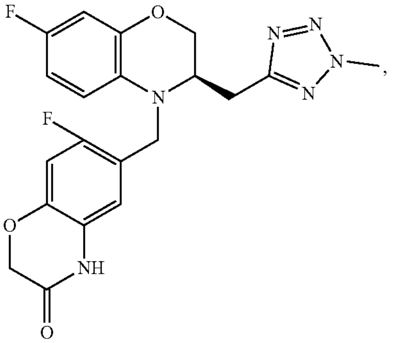
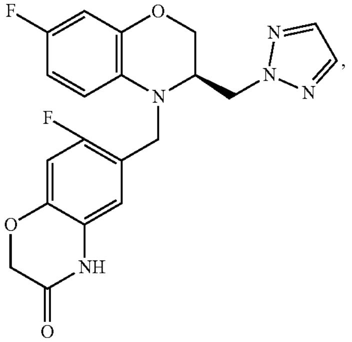
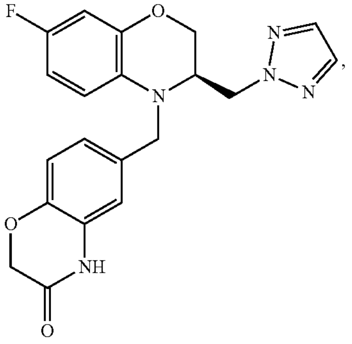
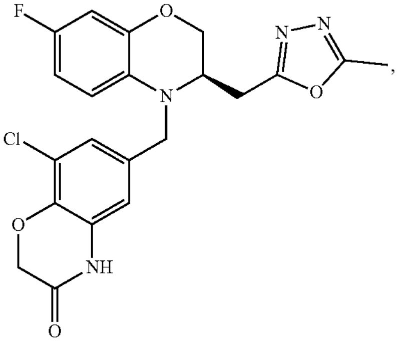

-continued
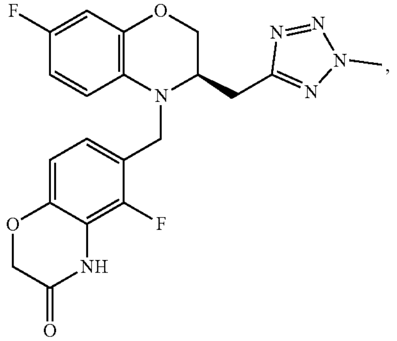
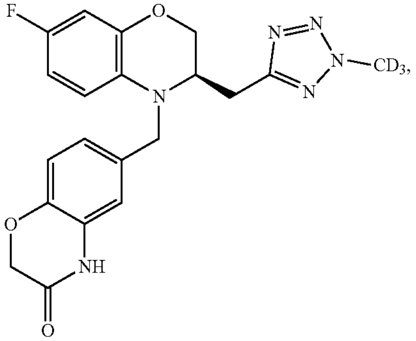
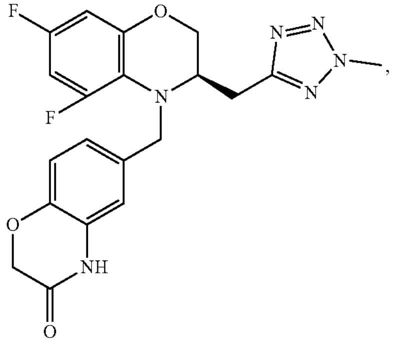
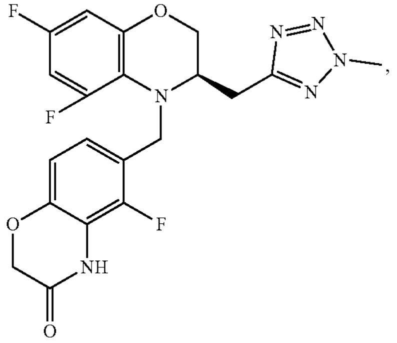
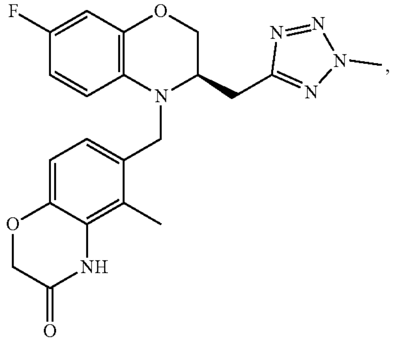
-continued
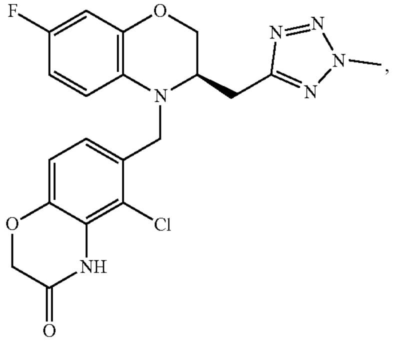
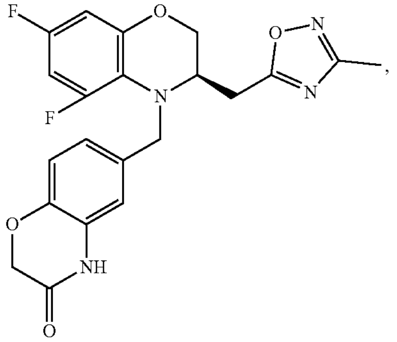
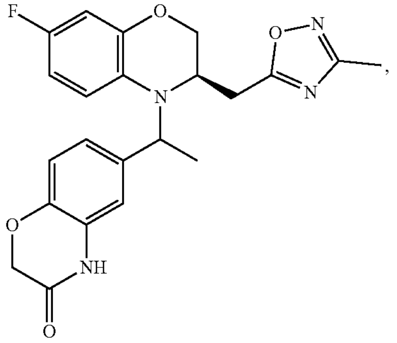
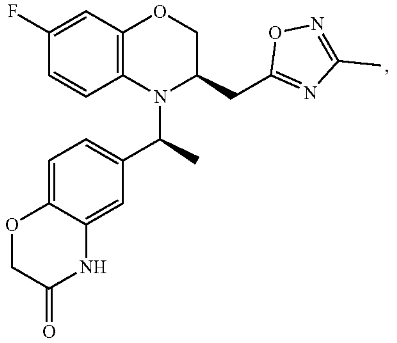
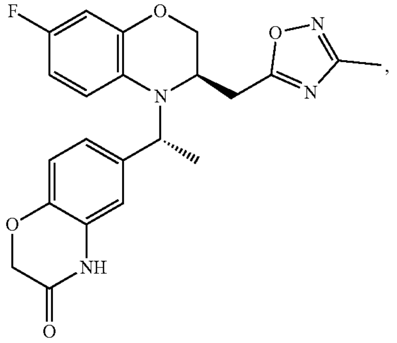

-continued
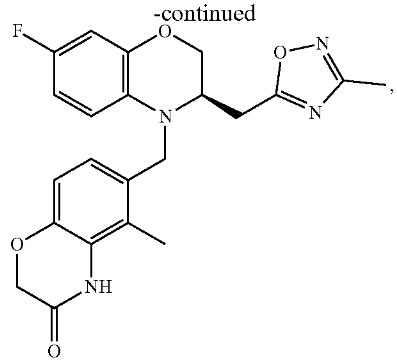
,
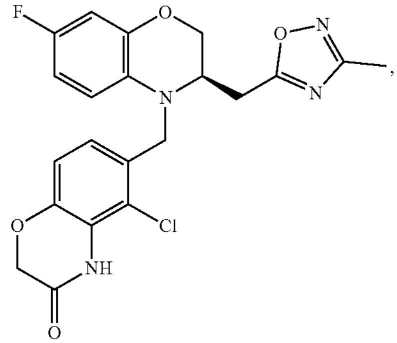
,
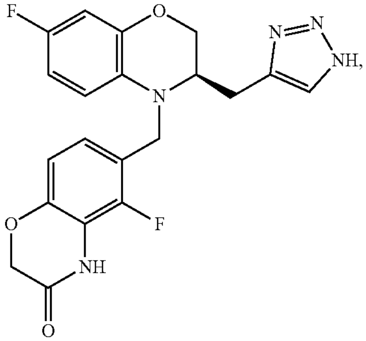
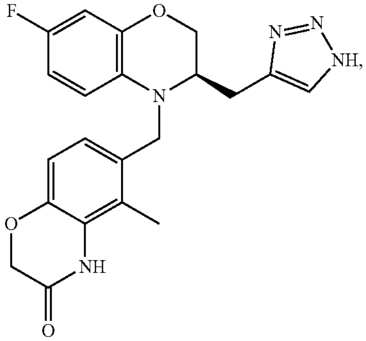
-continued
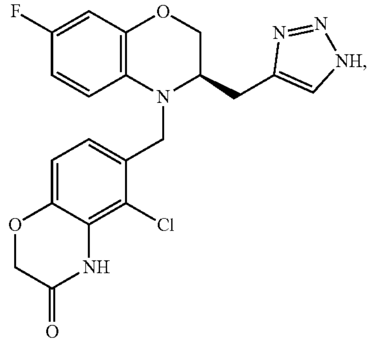
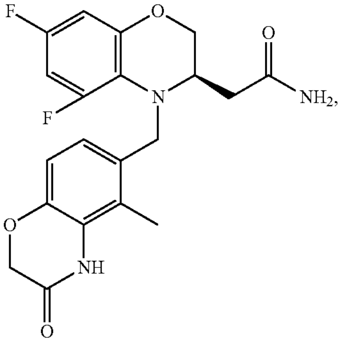
and
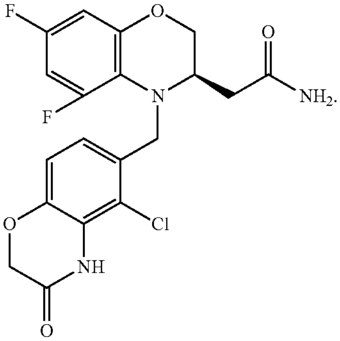
* * * * *